(12) United States Patent
Ahmad et al.

(10) Patent No.: US 8,563,583 B2
(45) Date of Patent: Oct. 22, 2013

(54) PYRIDONE ANALOGS USEFUL AS MELANIN CONCENTRATING HORMONE RECEPTOR-1 ANTAGONISTS

(75) Inventors: Saleem Ahmad, Wall, NJ (US); William N. Washburn, Titusville, NJ (US); Andres S. Hernandez, Lawrenceville, NJ (US); Jeffrey A. Robl, Newtown, PA (US); Khehyong Ngu, Pennington, NJ (US); Zhenghua Wang, Monmouth Junction, NJ (US)

(73) Assignee: Bristol-Myers Squibb Company, Princeton, NJ (US)

(*) Notice: Subject to any disclaimer, the term of this patent is extended or adjusted under 35 U.S.C. 154(b) by 67 days.

(21) Appl. No.: 13/255,129

(22) PCT Filed: Mar. 9, 2010

(86) PCT No.: PCT/US2010/026626
§ 371 (c)(1),
(2), (4) Date: Sep. 7, 2011

(87) PCT Pub. No.: WO2010/104830
PCT Pub. Date: Sep. 16, 2010

(65) Prior Publication Data
US 2011/0319449 A1 Dec. 29, 2011

Related U.S. Application Data

(60) Provisional application No. 61/158,554, filed on Mar. 9, 2009.

(51) Int. Cl.
*A61K 31/44* (2006.01)
*C07D 213/78* (2006.01)

(52) U.S. Cl.
USPC ............ 514/335; 514/345; 546/301; 546/261

(58) Field of Classification Search
USPC .......................... 514/335, 345; 546/301, 261
See application file for complete search history.

(56) References Cited

U.S. PATENT DOCUMENTS

| | | | |
|---|---|---|---|
| 2007/0093509 A1 | 4/2007 | Washburn et al. | |
| 2007/0208046 A1 | 9/2007 | Otake et al. | |
| 2008/0085884 A1 | 4/2008 | Armour et al. | |
| 2009/0011994 A1* | 1/2009 | Stein et al. | 514/12 |

FOREIGN PATENT DOCUMENTS

| | | |
|---|---|---|
| WO | WO2007/142217 A1 | 12/2007 |
| WO | WO2008/041090 A1 | 4/2008 |

OTHER PUBLICATIONS

Kishino et al. CAS: 148: 54903, 2007.*
Borowsky, B. et al., "Antidepressant, anxiolytic and anorectic effects of a melanin-concentrating hormone-1 receptor antagonist", Nature Medicine, vol. 8(8), pp. 825-830 (2002).
Gehlert, D. et al., "Preclinical Evaluation of Melanin-Concentrating Hormone Receptor 1 Antagonism for the Treatment of Obesity and Depression", The J. Of Pharmacology and Experimental Therapeutics, vol. 329(2), pp. 429-438 (2009).
Kokkotou, E. et al., "Melanin-concentrating hormone as a mediator of intestinal inflammation", PNAS, vol. 105(30), pp. 10613-10618 (2008).
Kowalski, T. et al., "Melanin-concentrating hormone-1 receptor antagonism decreases feeding by reducing meal size", European J. of Pharmacology, vol. 497, pp. 41-47 (2004).
Takekawa, S. et al., "T-226296: a novel, orally active and selective melanin-concentrating hormone receptor antagonist", European J. of Pharmacology, vol. 438, pp. 129-135 (2002).

* cited by examiner

*Primary Examiner* — Rei-tsang Shiao
(74) *Attorney, Agent, or Firm* — Maureen S. Gibbons; Jing G. Sun

(57) ABSTRACT

MCHR1 antagonists are provided having the following Formula I:

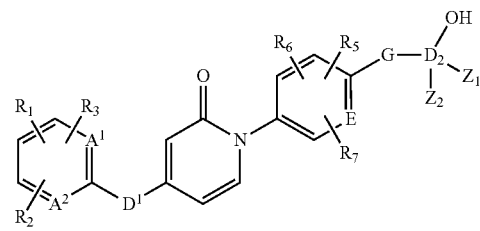

wherein all of the variables are defined herein. Such compounds are useful for the treatment of MCHR1 mediated diseases, such as obesity, diabetes, IBD, depression, and anxiety.

21 Claims, No Drawings

PYRIDONE ANALOGS USEFUL AS MELANIN CONCENTRATING HORMONE RECEPTOR-1 ANTAGONISTS

CROSS-REFERENCE TO RELATED APPLICATIONS

The present application is a 371 application of PCT/US2010/026626 filed Mar. 9, 2010, which claims priority benefit of U.S. provisional application Ser. No. 61/158,554, filed Mar. 9, 2009, each of which is incorporated by reference herein.

FIELD OF THE INVENTION

The present invention relates to pyridone compounds which act as melanin concentrating hormone receptor-1 (MCHR1) antagonists, pharmaceutical compositions containing such compounds, and methods for using such compounds for the treatment of MCHR1 mediated diseases such as diabetes, obesity and inflammatory bowel disease.

BACKGROUND

Several lines of pharmacological and genetic evidence support the role of Melanin Concentrating Hormone Receptor-1 (hereafter "MCHR1") as a modulator of food intake and body weight. Central administration of MCH increases food intake and body weight in both rats and mice. Chronic ICV infusion of MCH causes increased food intake and ultimately obesity in mice, while infusion of an MCH peptide antagonist blocks MCH-induced food intake and results in weight loss and decreased feeding in diet-induced obese mice.

The expression of both the MCH peptide and receptor are modulated by nutritional status. MCH mRNA is upregulated both in hyperphagic obese mice (ob/ob), and fasted animals. Targeted disruption of the gene for MCH peptide results in hypophagia and leanness. Disruption of the MCHR1 gene causes leanness, altered metabolism, and hyperlocomotion accompanied by mild hyperphagia. Conversely, over-expression of MCH peptide results in hyperphagia, obesity and diabetes. Small molecule MCHR1 antagonists have been shown to cause weight loss in rodent weight and feeding models after both oral and intraperitoneal administration; Eur. J. Pharmacol., 438:129-135 (2002), Nat. Med., 8:825-830 (2002), Eur. J. Pharmacol., 497:41-47 (2004).

MCHR1 has also been reported to play a key role in the pathogenesis of acute experimental colitis and possibly human TBD (inflammatory bowel disease). It has been shown that immunoneutralization is an effective treatment for TNBS-induced colitis. Kokkotou, E. et al., "Melanin-concentrating hormone as a mediator of intestinal inflammation", PNAS, 105(30):10613-10618 (Jul. 29, 2008).

In addition, MCH and MCHR1 has also been reported to play a role in the endocrine and behavioral responses to stress. Treatment of rats and mice with MCHR antagonists produce a robust anti-depressant and anti-anxiolytic effect. (JPET DOI:10.1124/jpet.108.143362)

Small molecule MCHR1 antagonists have been reported in the literature. See, for example, United States Patent Application Publication No. US 2009/0011994, which discloses compounds having the following Formula:

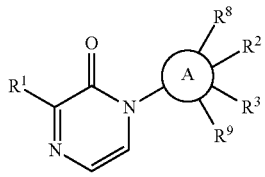

wherein

is a phenylene ring or a heteroaryl ring which is a monocyclic ring or a bicyclic ring which contains one or two nitrogen atoms or one oxygen atom;

$R^1$ is Z—Y—X—, wherein

X is O, S,

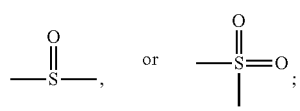

X is O, S,

Y is a bond, a 3- to 6-membered cycloalkyl, or an alkyl chain; and

Z is aryl such as phenyl and naphthyl, or heteroaryl such as pyridinyl, pyridimidinyl, pyrazinyl, benzimidazolyl, benzothiazolyl, benzoxazolyl, or other "heteroaryl"; $R^2$ is -E-G-(J)$_m$, with m being an integer from 1 to 3;

E is O, S, or a bond; G is lower alkyl, phenylalkyl, cycloalkyl, cycloalkylalkyl, alkylcycloalkyl, cycloalkoxy, alkylcycloalkoxy, or cycloalkoxyalkyl;

each J is independently hydrogen, hydroxyl, CN, —SO$_2$R$^7$, —SR$^7$, —SOR$^7$, lower alkyl, lower alkoxy, CF$_3$, CF$_3$O—, —COOR$^5$ (wherein R$^5$ is H, C$_{1-3}$ alkyl, or cycloalkyl), or —CO—NR$^{5a}$R$^6$ wherein R$^{5a}$ and R$^6$ are each independently selected from H, C$_{1-3}$ alkyl, or cycloalkyl, or R$^{5a}$ and R$^6$ taken together can be propanediyl, butanediyl or pentanediyl to form with the N atom to which they are attached a 4-, 5- or 6-membered cyclic amine, such as azetidinyl, pyrrolidinyl, piperidinyl, morpholinyl, or piperazinyl, optionally substituted with substituents as set out for "heterocyclo";

R$^7$ is lower alkyl;

R$^3$ is C$_{1-6}$ alkyl, cycloalkyl, C$_{1-6}$ alkoxy, halogen, hydrogen, —S—C$_{1-6}$ alkyl, CN, CF$_3$O, or CF$_3$;

and wherein R$^2$ and R$^3$ can be taken together to form a 5- to 7-membered ring which is saturated, unsaturated, or partially unsaturated and may include an E heteroatom, which is O, or 0, 1 or 2 N atoms, which ring is substituted with one or two of —O-G-(J)$_m$ groups, wherein at least one J is OH, and optionally other substituents as set out for "alkyl", "aryl", or "heteroaryl", such as alkyl and/or OH;

with the proviso that where

is a phenylene ring, E-G and R³ are not identical unsubstituted lower alkoxy groups, and when G is lower alkyl and J is H, R³ is not hydrogen; and R⁸ and R⁹ are each independently hydrogen, halogen, or lower alkyl;

including esters thereof, prodrugs thereof, solvates thereof, and all stereoisomers thereof.

Specific examples include compounds having the following structures:

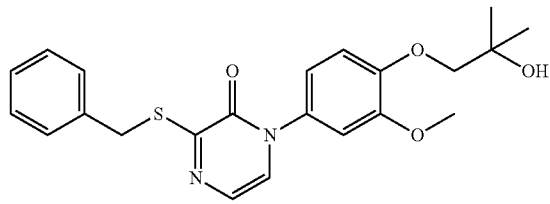 [SMILES: COc1cc(-n2ccnc(SCc3ccccc3)c2=O)ccc1OCC(C)(C)O]

3-(benzylthio)-1-(4-(2-hydroxy-2-methylpropoxy)-3-methoxyphenyl)pyrazin-2(1H)-one

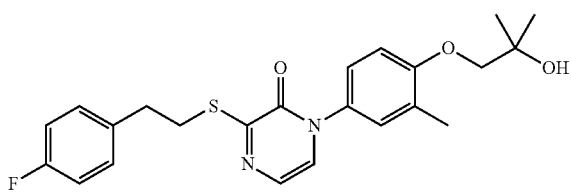 [SMILES: Cc1cc(-n2ccnc(SCCc3ccc(F)cc3)c2=O)ccc1OCC(C)(C)O]

3-(4-fluorophenethylthio)-1-(4-(2-hydroxy-2-methyl propoxy)-3-methylphenyl)pyrazin-2(1H)-one United States Patent Application Publication No. US 2007/0093509 also discloses small molecule inhibitors of MCHR1 having the following Formula:

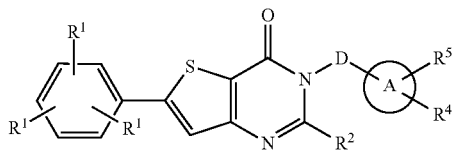

wherein,

A is selected from the group consisting of phenyl and a monocyclic heteroaryl;

D is selected from the group consisting of $CH_2$ and a direct bond;

$R^1$ is independently selected from the group consisting of hydrogen, halogen, lower alkyl, lower cycloalkyl, $CF_3$, $OR^6$ and $SR^6$;

$R^2$ is selected from the group consisting of hydrogen and lower alkyl;

$R^4$ is selected from the group consisting of hydroxyl or $G-D^2-Z_n$;

n is an integer from 1 to 3;

$R^5$ is selected from the group consisting of hydrogen, halogen, lower alkyl, lower cycloalkyl, $CF_3$, $SR^6$, lower alkoxy, lower cycloalkoxy, CN, $CONR^7R^7$, $SOR^6$, $SO_2R^6$, $NR^7COR^7$, $NR^7CO_2R^7$, $CO_2R^6$, heteroaryl, $NR^7SO_2R^6$ and $COR^6$;

G is selected from the group consisting of O, S and $CR^7R^7$;

$D^2$ is selected from the group consisting of a direct bond, lower alkyl, lower cycloalkyl and a 4 to 6-membered non-basic heterocycle;

Z is selected from the group consisting of hydrogen, hydroxyl, lower alkoxy, lower cycloalkoxy, $OCONR^7R^7$, CN, $CONR^7R^7$, $SOR^6$, $SO_2R^6$, $NR^7COR^7$, $NR^7CO_2R^7$, $CO_2R^6$, heteroaryl, $NR^6SO_2R^6$ and $COR^6$;

$R^6$ is independently selected from the group consisting of lower alkyl and lower cycloalkyl; and $R^7$ is independently selected from the group consisting of hydrogen, lower alkyl and lower cycloalkyl, wherein two $R^7$ and the atom to which they are attached may optionally form a ring of 4 to 7 atoms.

Other reported MCHR1 antagonists include those disclosed in the following published patent applications:

US 2008/0085884 (Pfizer), for example:

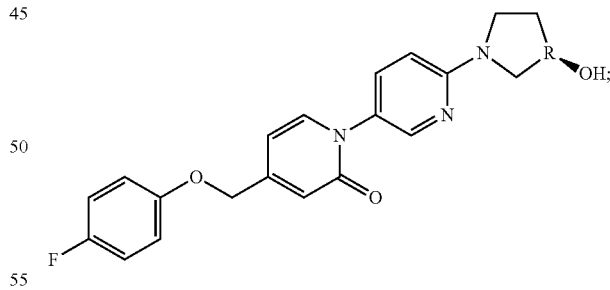

US 2007/0208046 (Banyu), for example:

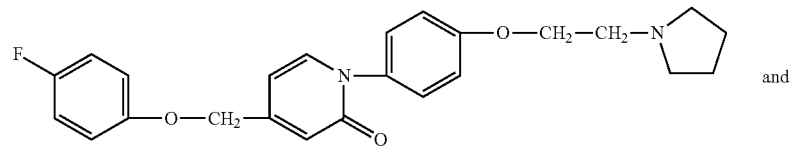

and

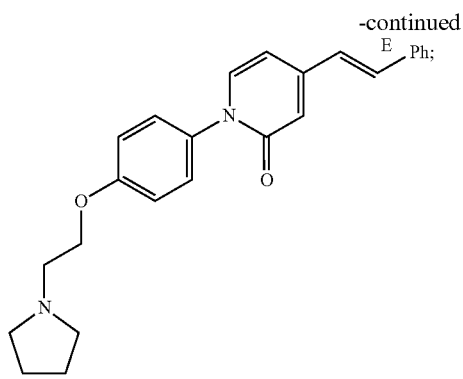

and WO 2007142217 (Banyu), disclosing, for example:

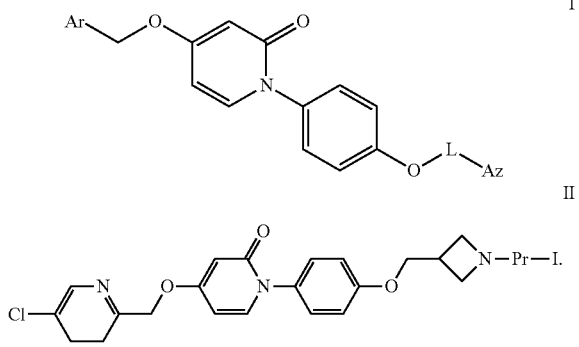

There is a need in the art for novel MCHR1 antagonists that are useful as pharmaceuticals, for example, in the treatment of obesity and inflammatory bowel disease.

SUMMARY OF THE INVENTION

The following invention is directed to novel MCHR1 antagonists, methods for using them for the treatment of disease states such as obesity and inflammatory bowel disease, pharmaceutical compositions comprising such antagonists, and pharmaceutical combinations. The present invention is directed to compounds having the following Formula I, including pharmaceutically acceptable salts and prodrugs thereof:

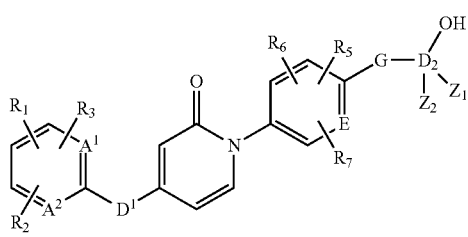

wherein, $A^1$ and $A^2$ are independently C or N;

E is C or N;

$D^1$ is a bond, $-CR^8R^9X-$, $-XCR^8R^9-$, $-CHR^8CHR^9-$, $-CR^{10}=CR^{10'}-$, $C\equiv C-$, or 1,2-cyclopropyl;

X is O, S, $SO_2$ or $-NR^{11}$;

$R^1$, $R^2$, and $R^3$ are independently selected from the group consisting of hydrogen, halogen, $-CN$, substituted or unsubstituted $C_1$ to $C_4$ alkyl, substituted or unsubstituted $C_3$ to $C_5$ cycloalkyl, substituted or unsubstituted $C_3$ to $C_5$ cycloalkoxy, $-CF_3$, $-OCF_3$, $-OCHF_2$, $-OCF_2CHF_2$, $-OR^{12}$, substituted or unsubstituted phenyl and $-SR^{12}$;

G is O or S;

$D^2$ is substituted or unsubstituted $C_2$ to $C_4$ alkyl, substituted or unsubstituted $C_3$ to $C_5$ cycloalkyl, substituted or unsubstituted $C_3$ to $C_5$ cycloalkoxy, substituted or unsubstituted $C_2$ to $C_3$ alkyl-$C_3$ to $C_5$ cycloalkyl, substituted or unsubstituted $C_1$ to $C_3$ alkyl-$C_3$ to $C_5$ cycloalkoxy;

$Z_1$ and $Z_2$ are independently hydrogen, halogen, substituted or unsubstituted $C_1$ to $C_3$ alkyl, substituted or unsubstituted $C_3$ to $C_5$ cycloalkyl, $-OCH_3$, substituted or unsubstituted $C_3$ to $C_5$ cycloalkoxy, halo, $-CH_2SO_2$-alkyl, hydroxyalkyl, $-CF_3$, $-OCONR^{14}R^{14'}$, $-CN$, $-CONR^{14}R^{14'}$, $-SOR^{12}$, $-SO_2R^{12}$, $-NR^{14}COR^{14'}$, $-NR^{14}CO_2R^{14'}$, $-CO_2R^{12}$, $NR^{14}SO_2R^{12}$ or $-COR^{12}$ provided that if $Z_1$ is $-CH_3$ and one of $R_1$, $R_2$, or $R_3$ is F, then $Z_2$ cannot be H;

$R^5$, $R^6$, and $R^7$ are independently selected from the group consisting of hydrogen, halogen, substituted or unsubstituted $C_1$ to $C_4$ alkyl, substituted or unsubstituted $C_3$ to $C_5$ cycloalkyl, substituted or unsubstituted $C_3$ to $C_5$ cycloalkoxy, $-CF_3$, $-SR^{12}$, $-OCH_3$, $-OCH_2CH_3$, $-OCH_2OMe$, $-CN$, $-CONR^{14}R^{14'}$, $SOR^{12}$, $SO_2R_{12}$, $NR^{14}COR^{14'}$, $NR^{14}CO_2R^{12}$, $CO_2R^{12}$, $NR^{14}SO_2R^{12}$ and $-COR^{12}$;

$R^8$, $R^9$, $R^{10}$, $R^{10'}$, $R^{11}$ are independently hydrogen or $-CH_3$;

$R^{12}$ is substituted or unsubstituted $C_1$ to $C_4$ alkyl, substituted or unsubstituted $C_3$ to $C_5$ cycloalkyl or phenyl;

$R^{14}$ and $R^{14'}$ are independently H, substituted or unsubstituted $C_1$ to $C_3$ alkyl, substituted or unsubstituted $C_3$ to $C_5$ cycloalkyl or $R^{14}$ and $R^{14'}$ together with the N to which they are attached form a ring having 4 to 7 atoms; and wherein the prodrugs of Formula I are selected from the group consisting of amino acid esters, monoesters of dicarboxylic acids and monoesters of phosphoric acid and incorporate the hydroxyl group that is attached to D.

DETAILED DESCRIPTION OF THE INVENTION

The present invention is directed to compounds, including all stereoisomers, salts, solvates, prodrugs, isotopes, and pharmaceutically acceptable forms thereof according to Formula I. Additionally, the present application provides pharmaceutical compositions containing at least one compound according to Formula I and optionally at least one additional therapeutic agent. Finally, the present application provides methods for treating a patient suffering from an MCHR-1 modulated disease or disorder such as, for example, obesity, diabetes, depression, anxiety or intestinal inflammation by administration of a therapeutically effective dose of a compound according to Formula I.

The present invention is directed to compounds according to Formula I, or a prodrug or pharmaceutically acceptable salt thereof:

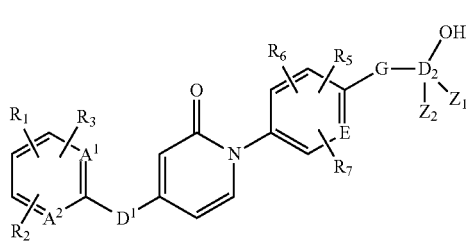

I wherein, $A^1$ and $A^2$ are independently C or N;

E is C or N;

$D^1$ is a bond, —$CR^8R^9X$—, —$XCR^8R^9$—, —$CHR^8CHR^9$—, —$CR^{10}$—$CR^{10'}$—, —C≡C—, or 1,2-cyclopropyl;

X is O, S, $SO_2$ or —$NR^{11}$;

$R^1$, $R^2$, and $R^3$ are independently selected from the group consisting of hydrogen, halogen, substituted or unsubstituted $C_1$ to $C_4$ alkyl, substituted or unsubstituted $C_3$ to $C_5$ cycloalkyl, —$CF_3$, —$OCF_3$, —$OR^{12}$, substituted or unsubstituted phenyl and —$SR^{12}$;

G is O or S;

$D^2$ is substituted or unsubstituted $C_2$ to $C_4$ alkyl, substituted or unsubstituted $C_3$ to $C_5$ cycloalkyl, substituted or unsubstituted $C_3$ to $C_5$ cycloalkoxy, substituted or unsubstituted $C_2$ to $C_3$ alkyl-$C_3$ to $C_5$ cycloalkyl, substituted or unsubstituted $C_1$ to $C_3$ alkyl-$C_3$ to $C_5$ cycloalkoxy;

$Z_1$ and $Z_2$ are independently hydrogen, halogen, substituted or unsubstituted $C_1$ to $C_3$ alkyl, substituted or unsubstituted $C_3$ to $C_5$, cycloalkyl, —$OCH_3$, substituted or unsubstituted $C_3$ to $C_5$ cycloalkoxy, halo, —$CF_3$, —$OCONR^{14}R^{14'}$, —CN, —$CONR^{14}R^{14'}$, —$SOR^{12}$, —$SO_2R^{12}$, —$NR^{14}COR^{14'}$, —$NR^{14}CO_2R^{14'}$, —$CO_2R^{12}$, $NR^{14}SO_2R^{12}$ or —$COR^{12}$ provided that if $Z_1$ is —$CH_3$ and one of $R_1$, $R_2$, or $R_3$ is F, then $Z_2$ cannot be H;

$R^5$, $R^6$, and $R^7$ are independently selected from the group consisting of hydrogen, halogen, substituted or unsubstituted $C_1$ to $C_4$ alkyl, substituted or unsubstituted $C_3$ to $C_5$ cycloalkyl, substituted or unsubstituted $C_3$ to $C_5$ cycloalkoxy, $CF_3$, —$SR^{12}$, —$OCH_3$, —$OCH_2CH_3$, —CN, —$CONR^{14}R^{14'}$, $SOR^{12}$, $SO_2R^{12}$, $NR^{14}COR^{14'}$, $NR^{14}CO_2R^{12}$, $CO_2R^{12}$, $NR^{14}SO_2R^{12}$ and —$COR^{12}$;

$R^8$, $R^9$, $R^{10}$, $R^{10'}$, $R^{11}$ are independently hydrogen or —$CH_3$;

$R^{12}$ is substituted or unsubstituted $C_1$ to $C_4$ alkyl or substituted or unsubstituted $C_3$ to $C_5$ cycloalkyl;

$R^{14}$ and $R^{14'}$ are independently H, substituted or unsubstituted $C_1$ to $C_3$ alkyl, substituted or unsubstituted $C_3$ to $C_5$ cycloalkyl or $R^{14}$ and $R^{14'}$ together with the N to which they are attached form a ring having 4 to 7 atoms; and wherein the prodrugs of Formula I are selected from the group consisting of amino acid esters, monoesters of dicarboxylic acids and monoesters of phosphoric acid and incorporate the hydroxyl group that is attached to D.

According to one preferred embodiment of the present invention, $R^1$, $R^2$, and $R^3$ are each independently H, halo, lower alkoxy, —$C_2F_5$, —$OCF_3$ or $CF_3$.

According to one preferred embodiment of the present invention, G is a

According to one preferred embodiment of the present invention, $D^2$ is —$CH_2C$— or —$CH_2$-cyclobutyl-.

According to one preferred embodiment of the present invention, D1 is —$CR^8R^9X$—, —$XCR^8R^9$—, —$CR^{10}$=$CR^{10}$—, or —C≡C— and X is O, S, —$SO_2$ or —$NR^{11}$—.

According to one preferred embodiment of the present invention, $Z^1$ and $Z^2$ are each —$CH_3$.

According to one preferred embodiment of the present invention, $Z^1$ and $Z^2$ are each —F.

According to one preferred embodiment of the present invention, $Z^1$ is H and $Z^2$ is cyclopropyl.

According to one preferred embodiment of the present invention, compounds of the present invention have the following Formula Ia, and include pharmaceutically acceptable salts and prodrugs thereof:

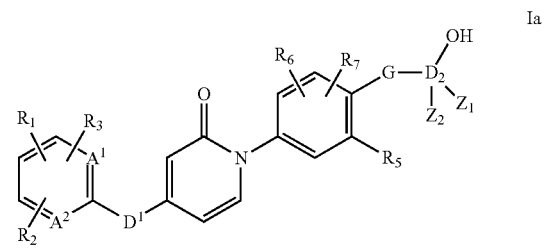

Ia wherein, $R_1$, $R_2$, and $R_3$ are independently H, halo, or $CF_3$;

$A^1$ is C or N;

$A^2$ is C;

$D^1$ is a bond, —$CR^8R^9X$—, —$XCR^8R^9$—, —$CHR^8CHR^9$—, or —$CR^{10}$=$CR^{10'}$—;

X is O, S, $SO_2$, NH;

$R^5$, $R^6$, and $R^7$ are independently H, —$CH_3$ and —$OCH_3$;

$R^8$, $R^9$, $R^{10}$, and $R^{11}$, are H;

G is O or S;

$D^2$ is —$CH_2C$— or —$CH_2$-cyclobutyl;

$Z^1$ and $Z^2$ are both —$CH_3$ or $Z^1$ is H and $Z^2$ is cyclopropyl, or $Z_1$ and $Z_2$ are both F; and wherein the prodrugs of Formula I are selected from the group consisting of amino acid esters, monoesters of dicarboxylic acids and monoesters of phosphoric acid and incorporate the hydroxyl group that is attached to D.

According to another aspect of the present invention, pharmaceutical compositions that are useful for the treatment of obesity and obesity related illnesses are provided, comprising a therapeutically effective amount of a compound according to Formula I, as defined herein, together with a pharmaceutically acceptable carrier or diluent.

According to one aspect of the present invention, methods are provided for treating a patient suffering from an MCHR1 modulated disease or disorder such as, for example, obesity, diabetes, depression, anxiety or intestinal inflammation such as inflammatory bowel disease, colitis or Crohn's disease by administration of a therapeutically effective dose of a compound according to Formula I, optionally in combination with other therapeutic agents, such as those described below.

The present invention is further directed to methods for treating diabetes comprising administering to a patient in need of such treatment a pharmaceutically effective amount of a compound according to Formula I, optionally in combination with a further anti-diabetic agent as described herein.

The present invention is further directed to the use of a compound according to Formula I in the manufacture of a medicament for the treatment of obesity.

The present invention is further directed to the use of compound according to Formula I in the manufacture of a medicament for the treatment of diabetes.

The present invention is further directed to the use of a compound according to Formula I in the manufacture of a medicament for the treatment of inflammatory bowel disease.

The present invention is further directed to the use of a compound according to Formula I in the manufacture of a medicament for the treatment of depression.

The present invention is further directed to the use of a compound according to Formula I in the manufacture of a medicament for the treatment of anxiety.

According to one aspect of the present invention, pharmaceutical combinations are provided, comprising a compound according to Formula I and at least one additional therapeutic agent selected from the group consisting of an acetyl-cholinesterase inhibitor; a muscarinic receptor-1 agonist, a nicotinic agonist, a glutamic acid receptor (AMPA and NMDA) modulator, a nootropic agent, an agent for Alzheimer's disease, an agent for treatment of Parkinson's disease, antihyperlipidemia agent, an anti-obesity agent; anti-diabetic agent, appetite suppressant; HDL-raising agent, cognition enhancing agent, an agent used to treat neurodegeneration, an agent used to treat bowel disorders, an anti-inflammatory agent; anti-anxiety agent; an anti-depressant; and an anti-sleep disorder agent.

DEFINITIONS

Unless otherwise indicated, the term alkyl as employed herein alone or as part of another group includes both straight and branched chain hydrocarbons containing the terms "alkyl" and "alk" as employed herein alone or as part of another group includes both straight and branched chain hydrocarbons. Preferred alkyl groups of the present invention include methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof and may also be substituted with groups including halo, preferably F, Br, Cl or I or $CF_3$, alkyl, alkoxy, aryl, aryloxy, aryl(aryl) or diaryl, arylalkyl, arylalkyloxy, alkenyl, alkynyl, cycloalkyl, cycloalkenyl, cycloalkylalkyl, cycloalkylalkyloxy, hydroxy, hydroxyalkyl, acyl, alkanoyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl and/or alkylthio.

Preferred alkyl groups of the present invention include $C_1$, $C_2$, $C_3$ and $C_4$ alkyl groups that are optionally substituted with F, such as —$CF_3$, —$C_2F_5$, or —$C_3F_7$.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, any one of which may optionally be a Spiro substituted cycloalkyl, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

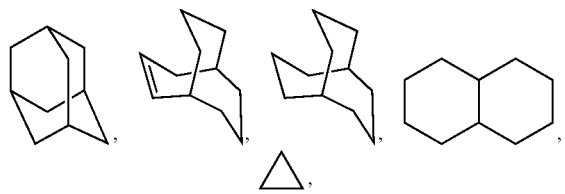

any of which groups may be optionally substituted with substituents such as halogen, alkyl, alkoxy, hydroxy, aryl, aryloxy, arylalkyl, cycloalkyl, alkylamido, alkanoylamino, oxo, acyl, arylcarbonylamino, nitro, cyano, thiol and/or alkylthio and/or any of the alkyl substituents. Preferred "cycloalkyl" groups of the present invention include $C_3$ to $C_5$ carbon atoms, such as cyclopropyl, or cyclobutyl, or cyclopentyl.

Unless otherwise indicated, the term "cycloalkoxy" as employed herein alone or as part of another group, represents a 4-, 5- or 6-membered saturated ring containing an oxygen in the ring and includes

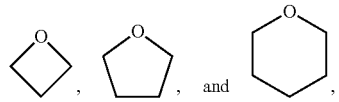

and which may be optionally substituted with 1 or 2 of any of the substituents as set out for cycloalkyl.

The term alkylcycloalkyl, wherein the number of carbon atoms may be specified, e.g., "$C_2$ to $C_3$ alkyl-$C_3$ to $C_5$ cycloalkyl" refers to a group bonded through the cycloalkyl portion. For example, "$C_1$ alkyl-$C_6$ cycloalkyl" refers to the group

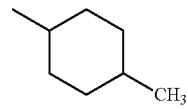

while the term "cycloalkylalkyl" refers to a cycloalkyl group bonded through the alkyl portion, such as

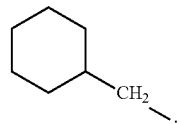

The term "alkylcycloalkoxy" refers to a group bonded to the rest of the molecule via the cycloalkoxy portion.

The terms "heterocyclo", "heterocyclyl" or "heterocyclic" as used herein, alone or as part of another group, represents an unsubstituted or substituted stable 4 to 7-membered monocyclic ring system which may be saturated or unsaturated, and which consists of carbon atoms, with one to four heteroatoms selected from nitrogen, oxygen or sulfur, and wherein the nitrogen and sulfur heteroatoms may optionally be oxidized, and the nitrogen heteroatom may optionally be quaternized.

The heterocyclic ring may be attached at any heteroatom or carbon atom which results in the creation of a stable structure. Examples of such heterocyclic groups include, but is not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinyl sulfoxide, thiamorpholinyl sulfone, or oxadiazolyl or other heterocycles described in Katritzky, A. R. et al., eds., *Comprehensive Heterocyclic Chemistry: The Structure, Reactions, Synthesis and Uses of Heterocyclic Compounds*, Pergamon Press, New York, N.Y. (1984); and Katritzky, A. R. et al., eds., *Comprehensive Heterocyclic Chemistry II: A Review of the Literature* 19824995, Elsevier Science, Inc., Tarrytown, N.Y. (1996); and references therein. The heterocycloalkyl may optionally be substituted with at least one of F, Br, Cl or I or CF$_3$, alkyl, alkoxy, aryl, aryloxy, aryl(aryl) or diaryl, arylalkyl, arylalkyloxy, alkenyl, alkynyl, cycloalkyl, cycloalkenyl, cycloalkylalkyl, cycloalkylalkyloxy, hydroxy, hydroxyalkyl, acyl, alkanoyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl and/or alkylthio.

The term "halogen" or "halo" as used herein alone or as part of another group refers to chlorine, bromine, fluorine, and iodine, with chlorine or fluorine being preferred.

The term "aryl" herein alone or as part of another group refers to monocyclic or bicyclic aromatic rings, e.g., phenyl, substituted phenyl and the like, as well as groups which are fused, e.g., napthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. Aryl groups may optionally be substituted with one or more groups including, but not limited to halogen, alkyl, alkenyl, cycloalkyl, heterocycloalkyl, alkoxy, haloalkoxy, haloalkyl, hydroxy, carboxy, carbamoyl, alkyloxycarbonyl, nitro, alkenyloxy, trifluoromethyl, amino, cycloalkyl, aryl, heteroaryl, cyano, alkyl S(O)$_m$ (m=0, 1, 2), or thiol and/or any of the alkyl substituents set out herein.

Unless otherwise indicated, the term "heteroaryl" as used herein alone or as part of another group refers to a 5- or 6-membered aromatic ring which includes 1, 2, 3 or 4 hetero atoms such as nitrogen, oxygen or sulfur. Such rings may be fused to an aryl, cycloalkyl, heteroaryl or heterocyclyl and include possible N-oxides as described in Katritzky, A. R. et al., eds. *Comprehensive Heterocyclic Chemistry: The Structure, Reactions, Synthesis and Uses of Heterocyclic Compounds*, Pergamon Press, New York, N.Y. (1984); and Katritzky, A. R. et al., eds., *Comprehensive Heterocyclic Chemistry, II: A Review of the Literature* 1982-1995, Elsevier Science, Inc., Tarrytown, N.Y. (1996); and references therein. Further, "heteroaryl", as defined herein, may optionally be substituted with one or more substituents such as the substituents included above in the definition of "substituted alkyl" and "substituted aryl". Examples of heteroaryl groups include the following:

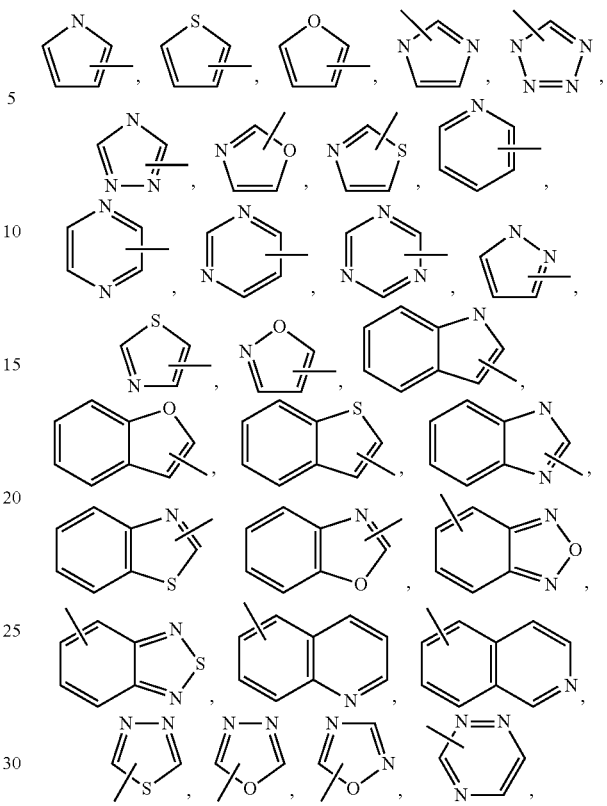

and the like.

Unless otherwise indicated, the term "lower alkoxy", "alkoxy", "aryloxy" or "aralkoxy" as employed herein alone or as part of another group includes any of the above alkyl, aralkyl or aryl groups linked to an oxygen atom.

Methods of Use

According to one embodiment of the present invention, methods are provided for treating obesity in a patient in need of such treatment, which includes the step of administering a therapeutically effective amount of at least one compound according to Formula I alone or in combination with one or more additional anti-obesity agents, wherein the obesity agent is selected from those described herein.

According to one embodiment of the present invention, methods are provided for treating diabetes, especially Type II diabetes, which includes the step of administering a therapeutically effective amount of at least one compound according to Formula I alone or in combination with one or more additional anti-diabetic agents to a patient in need of such treatment, wherein the anti-diabetic agent is described herein.

According to one embodiment of the present invention, methods for treating depression are provided, which includes the step of administering a therapeutically effective amount of at least one compound according to Formula I or in combination with one or more additional antidepressants to a patient in need of such treatment.

According to one embodiment of the present invention, methods are provided for treating anxiety, which includes the step of administering to a patient in need of such treatment a therapeutically effective amount of a compound having Formula I or in combination with one or more additional anti-anxiety agents.

According to another embodiment of the present invention, methods are provided for treating intestinal inflammatory conditions, such as inflammatory bowel disease (IBD), colitis and Crohn's disease (CD) in a patient in need of such treatment which includes the step of administering a therapeutically effective amount of a compound of Formula I or in combination with one or more additional anti-inflammatory agents.

Utility

The compounds of the present invention can be administered to mammals, preferably humans, for the treatment of a variety of conditions and disorders, including, but not limited to metabolic and eating disorders as well as conditions associated with metabolic disorders (e.g., obesity, diabetes, arteriosclerosis, hypertension, polycystic ovary disease, cardiovascular disease, osteoarthritis, dermatological disorders, impaired glucose hemostasis, insulin resistance, hypercholesterolemia, hypertriglyceridemia, choletithiasis, dislipidemic conditions, bulimia nervosa and compulsive eating disorders); sleep disorders; and psychiatric disorders, such as depression, anxiety, schizophrenia, substance abuse, cognition-enhancement and Parkinson's disease; and inflammatory diseases such as inflammatory bowel disease, colitis and/or Crohn's disease.

The compounds described in the present invention could be used to enhance the effects of cognition-enhancing agents, such as acetylcholinesterase inhibitors (e.g., tacrine), muscarinic receptor-1 agonists (e.g., milameline), nicotinic agonists, glutamic acid receptor (AMPA and NMDA) modulators, and neurotropic agents (e.g., piracetam, levetiracetam). Examples of suitable therapies for treatment of Alzheimer's disease and cognitive disorders for use in combination with the compounds of the present invention include donepezil, tacrine, revastigraine, 5HT6, gamma secretase inhibitors, beta secretase inhibitors, SK channel blockers, Maxi-K blockers, and KCNQs blockers.

The compounds described in the present invention could be used to enhance the effects of agents used in the treatment of Parkinson's Disease. Examples of agents used to treat Parkinson's Disease include: levadopa with or without a COMT inhibitor, antiglutamatergic drugs (amantadine, riluzole), alpha-2 adrenergic antagonists such as idazoxan, opiate antagonists, such as naltrexone, other dopamine agonists or transporter modulators, such as ropinirole, or pramipexole or neurotrophic factors such as glial derived neurotrophic factor (GDNF).

Dosage Forms

The compounds of the present invention can be administered in oral dosage form The dosage form for said pharmaceutical composition includes such oral dosage forms as granules, powders, tablets, capsules, syrups, emulsions, suspensions, etc. and such non-oral dosage forms as injections (e.g., subcutaneous, intravenous, intramuscular and intraperitoneal injections), drip infusions, external application forms (e.g., nasal spray preparations, transdermal preparations, ointments, etc.), and suppositories (e.g., rectal and vaginal suppositories).

These dosage forms can be manufactured by the per se known technique conventionally used in pharmaceutical procedures. The specific manufacturing procedures are as follows.

To manufacture an oral dosage form, an excipient (e.g., lactose, sucrose, starch, mannitol, etc.), a disintegrator (e.g., calcium carbonate, carboxymethylcellulose calcium, etc.), a binder (e.g., a-starch, gum arabic, carboxymethylcellulose, polyvinylpyrrolidone, hydroxypropylcellulose, etc.), and a lubricant (e.g., talc, magnesium stearate, polyethylene glycol 6000, etc.), for instance, are added to the active component or components and the resulting composition is compressed. Where necessary, the compressed product is coated, by the per se known technique, for masking the taste or for enteric dissolution or sustained release. The coating material that can be used includes, for instance, ethylcellulose, hydroxymethylcellulose, polyoxyethylene glycol, cellulose acetate phthalate, hydroxypropylmethylcellulose phthalate, and EUDRAGIT® (Rohm & Haas, Germany, methacrylic-acrylic copolymer).

Injections can be manufactured typically by the following procedure. The active component or components are dissolved, suspended or emulsified in an aqueous vehicle (e.g., distilled water, physiological saline, Ringer's solution, etc.) or an oily vehicle (e.g., vegetable oil such as olive oil, sesame oil, cottonseed oil, corn oil, etc. or propylene glycol) together with a dispersant, e.g., Tween 80 (Atlas Powder, U.S.A.), HCO 60 (Nikko Chemicals), polyethylene glycol, carboxymethylcellulose, sodium alginate, etc.), a preservative (e.g., methyl p-hydroxybenzoate, propyl p-hydroxybenzoate, benzyl alcohol, chlorobutanol, phenol, etc.), an isotonizing agent (e.g., sodium chloride, glycerol, sorbitol, glucose, inverted sugar, etc.) and other additives. If desired, a solubilizer (e.g., sodium salicylate, sodium acetate, etc.), a stabilizer (e.g., human serum albumin), a soothing agent (e.g., benzalkonium chloride, procaine hydrochloride, etc.) and other additives can also be added.

A dosage form for external application can be manufactured by processing the active component or components into a solid, semi-solid or liquid composition. To manufacture a solid composition, for instance, the active component or components, either as they are or in admixture with an excipient (e.g., lactose, mannitol, starch, microcrystalline cellulose, sucrose, etc.), a thickener (e.g., natural gums, cellulose derivatives, acrylic polymers, etc.), etc., are processed into powders. The liquid composition can be manufactured in substantially the same manner as the injections mentioned above. The semi-solid composition is preferably provided in a hydrous or oily gel form or an ointment form. These compositions may optionally contain a pH control agent (e.g., carbonic acid, phosphoric acid, citric acid, hydrochloric acid, sodium hydroxide, etc.), and a preservative (e.g., p-hydroxybenzoic acid esters, chlorobutanol, benzalkonium chloride, etc.), among other additives.

Suppositories can be manufactured by processing the active component or components into an oily or aqueous composition, whether solid, semi-solid or liquid. The oleaginous base that can be used includes, for instance, higher fatty acid glycerides [e.g., cacao butter, Witepsols (Dinamit-Nobel), etc.], medium-chain fatty acids [e.g., Migriols (Dinamit-Nobel), etc.], vegetable oils (e.g., sesame oil, soybean oil, cotton-seed oil, etc.), etc. The water-soluble base includes, for instance, polyethylene glycols propylene glycol, etc. The hydrophilic base includes, for instance, natural gums, cellulose derivatives, vinyl polymers, and acrylic polymers, etc.

Dosages

The dosage of the pharmaceutical composition of the present invention may be appropriately determined with reference to the dosages recommended for the respective active components and can be selected appropriately according to the recipient, the recipient's age and body weight, current clinical status, administration time, dosage form, method of administration, and combination of the active components, among other factors. For example, the dosage of the insulin sensitivity enhancer for an adult can be selected from the clinical oral dose range of 0.01 to 10 mg/kg body weight (preferably 0.05 to 10 mg/kg body weight, more preferably 0.05 to 5 mg/kg body weight) or the clinical parenteral dose range of 0.005 to 10 mg/kg body weight (preferably 0.01 to 10 mg/kg body weight, more preferably 0.01 to 1 mg/kg body weight). The other active component or components having different modes of action for use in combination can also be used in dose ranges selected by referring to the respective recommended clinical dose ranges.

The proportions of the active components in the pharmaceutical composition of the present invention can be appropriately selected according to the recipient, the recipient's age and body weight, current clinical status, administration time, dosage form, method of administration, and combination of active components, among other factors.

Pharmaceutical Combinations

The present invention includes within its scope pharmaceutical compositions comprising a therapeutically effective amount of at least one of the compounds of Formula I, together with a pharmaceutically acceptable carrier or diluent. Compounds of the present invention can be used alone or in pharmaceutical combinations comprising other suitable therapeutic agents useful in the treatment of the aforementioned disorders including anti-obesity agents, anti-diabetic agents, appetite suppressants, lipid-lowering agents, HDL-raising agents, cognition enhancing agents, agents used to treat neurodegeneration, agents used to treat bowel disorders, anti-inflammatory agents, anti-anxiety agents, and anti-depressants.

The pharmaceutical combinations of the present invention can be formulated in combination, or separately by mixing the respective active components either together or independently with a physiologically acceptable carrier, excipient, binder, diluent, etc. When the active components are formulated independently, the respective formulations can be extemporaneously admixed using a diluent or the like and administered or can be administered independently of each other, either concurrently or at staggered times to the same subject. So, such other therapeutic agent(s) may be administered prior to, simultaneously with, or following the administration of the melanin-concentrating hormone receptor (MCHR) antagonists in accordance with the invention.

Examples of suitable anti-obesity agents for use in combination with the compounds of the present invention include melanocortin receptor (MC4R) agonists, cannabinoid receptor modulators, endocannabinoid synthesis modulators, GPR119 agonists, inhibitors of fat absorption, growth hormone secretagogue receptor (GHSR) antagonists, galanin receptor modulators, orexin antagonists, SGLT2 inhibitors, DPP4 inhibitors, triple monoamine reuptake inhibitors, CCK agonists, GLP-1 agonists, and other Pre-proglucagon-derived peptides; NPY1 or NPYS antagonist, NPY2 and NPY4 modulators, corticotropin releasing factor modulators, histamine receptor-3 (H3) modulators, aP2 inhibitors, PPAR gamma modulators, PPAR delta modulators, acetyl-CoA carboxylase (ACC) inhibitors, steroyl Co-A desaturase-1 (SCD-1) inhibitors, 11-β-HSD-1 inhibitors, adinopectin receptor modulators; beta 3 adrenergic agonists, thyroid receptor beta modulators, lipase inhibitors, serotonin receptor agonists, monoamine reuptake inhibitors or releasing agents, anorectic agents, CNTF (ciliary neurotrophic factor), BDNF (brain-derived neurotrophic factor), leptin and leptin receptor modulators, cannabinoid-1 receptor inverse agonists/neutral antagonists, DGAT inhibitors, opiate antagonists, and amylin receptor modulators.

Preferred antiobesity agents include SGLT2 inhibitors, such as those disclosed in U.S. Pat. No. 6,414,126. Most preferred anti-obesity agents include dapagliflozin and lipase inhibitors, such as orlistat, or monoamine reuptake inhibitors or releasing agents, such as fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol.

Examples of suitable anti-diabetic agents for use in combination with the compounds of the present invention include: oral antihypergycernic agents, insulin secretagogues or insulin sensitizers, which may include biguanides, sulfonyl ureas, glucosidase inhibitors, aldose reductase inhibitors, PPAR γ agonists such as thiazolidinediones, PPAR α agonists (such as fibric acid derivatives), PPAR δ antagonists or agonists, PPAR α/γ dual agonists, 11-β-HSD-1 inhibitors, dipeptidyl peptidase IV (DP4) inhibitors, SGLT2 inhibitors, glucokinase inhibitors, glycogen phosphorylase inhibitors, and/or meglitinides, as well as insulin, and/or glucagon-like peptide-1 (GLP-1), GLP-1 agonist, a PTP-1B inhibitor (protein tyrosine phosphatase-1B inhibitor), and/o a histone deacetylase modulator such as a SIRT1 activator.

The compounds of the present invention may be employed in combination with anti-hyperlipidemia agents, or agents used to treat arteriosclerosis. An example of an hypolipidemic agent would be a fabric acid derivatives, bile acid sequestrants, nicotinic acid, aspirin, poly(diallylmethylamine) derivatives, quaternary amine poly(diallyldimethylammonium chloride) and ionenes and other known serum cholesterol lowering agents. Hypolipidemic agents include ACAT inhibitors, an upregulator of LDL receptor activity, and cholesterol absorption inhibitors.

Lipid agent or lipid-modulating agents include cholesteryl transfer protein inhibitors (CETP) The hypolipidemic agent may be an ileal $Na^+$/bile acid cotransporter inhibitor such as disclosed in *Drugs of the Future*, 24:425-430 (1999). The ATP citrate lyase inhibitor which may be employed in the combination of the invention may include, for example, those disclosed in U.S. Pat. No. 5,447,954.

The other lipid agent also includes a phytoestrogen compounds, a beta-lactam cholesterol absorption inhibitor, a PPAR α-agonist and/or an FXR agonist; an LDL catabolism promoter, a sodium-proton exchange inhibitor; an LDL-receptor inducer or a steroidal glycoside; an anti-oxidant, an antihomocysteine agent, a cholesterol absorption inhibitor, an HMG-CoA synthase inhibitor, or a lanosterol demethylase inhibitor, a sterol regulating element binding protein-I (SREBP-1).

MCHRI antagonists could be useful in treating other diseases associated with obesity, including sleep disorders. Therefore, the compounds described in accordance with the present invention could be used in combination with therapeutics for treating sleep disorders. Examples of suitable therapies for treatment of sleeping disorders for use in combination with the compounds of the present invention include melatonin analogs, melatonin receptor antagonists, ML 1 B agonists, GABA receptor modulators; NMDA receptor modulators, histamine-3 (H3) receptor modulators, dopamine agonists and orexia receptor modulators.

MCHR1 antagonists may reduce or ameliorate substance abuse or addictive disorders. Therefore, combination of MCHR1 modulators with agents used to treat addictive disorders may reduce the dose requirement or improve the efficacy of current addictive disorder therapeutics. Examples of agents used to treat substance abuse or addictive disorders are: selective serotonin reuptake inhibitors (SSRI), methadone, buprenorphine, nicotine and bupropion.

MCHR1 antagonists may reduce anxiety or depression; therefore, the compounds described in accordance with the present invention may be used in combination with anti-anxiety agents or antidepressants. Examples of suitable anti-anxiety agents for use in combination with the compounds of the present invention include benzodiazepines, 5HT1A receptor agonists, and corticotropin releasing factor (CRF) antagonists.

Examples of suitable classes of anti-depressants for use in combination with the compounds of the present invention include norepinephrine reuptake inhibitors (tertiary and secondary amine tricyclics), selective serotonin reuptake inhibitors (SSRIs), monoamine oxidase inhibitors, reversible inhibitors of monoamine oxidase (RIMAs), serotonin and norepinephrine reuptake inhibitors (SNRIs) (venlafaxine), corticotropin releasing factor (CRF) receptor antagonists, alpha-adrenoreceptor antagonists, and atypical antidepressants.

The combination of a conventional antipsychotic drug with a MCHR1 antagonist could also enhance symptom reduction in the treatment of psychosis or mania. Further, such a combination could enable rapid symptom reduction, reducing the need for chronic treatment with antipsychotic agents. Such a combination could also reduce the effective antipsychotic dose requirement, resulting in reduced probability of developing the motor dysfunction typical of chronic antipsychotic treatment.

Examples of suitable antipsychotic agents for use in combination with the compounds of the present invention include the phenothiazines thioxanthine, heterocyclic dibenzazepines, butyrophenone, diphenylbutylpiperidine (pimozide) and indolone (molindolone) classes of antipsychotic agents. Other antipsychotic agents with potential therapeutic value in combination with the compounds in the present invention include loxapine, sulpiride and risperidone.

Combination of the compounds in the present invention with conventional antipsychotic drugs could also provide an enhanced therapeutic effect for the treatment of schizophrenic disorders, as described above for manic disorders. As used here, schizophrenic disorders include paranoid, disorganized, catatonic, undifferentiated and residual schizophrenia, schizophreniform disorder, schizoaffective disorder, delusional disorder, brief psychotic disorder and psychotic disorder not specified. Examples of suitable antipsychotic drugs for combination with the compounds in the present invention include the antipsychotics mentioned above, as well as dopamine receptor antagonists, muscarinic receptor agonists, 5HT2A receptor antagonists and 5HT2A/dopamine receptor antagonists or partial agonists (e.g., olanzepine, aripiprazole, risperidone, ziprasidone).

Methods of Preparation

The compounds of the present invention can be prepared in a number of ways well known to one skilled in the art of organic synthesis using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The novel compounds of Formula I may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One skilled in the art of organic synthesis understands that the functionality present on various portions of the edict molecule must be compatible with the reagents and reactions proposed. Not all compounds of Formula I falling into a given class may be compatible with some of the reaction conditions required in some of the methods described. Such restrictions to the substituents, which are compatible with the reaction conditions, will be readily apparent to one skilled in the art and alternate methods must be used.

It will be understood that $R^4$ may be present in its final form throughout the synthesis or can be introduced at any point in the following synthetic sequences particularly if $R^4$ contains an hydroxyl. Specifically, $R^4$ may be carried along as a truncated moiety $R^{4'}$ such as GH that may be protected as a SEM ether, SEM thioether, BOC amine or etc. and then elongated whenever appropriate. Likewise compounds of Formula I for which $D^1$ is $SOCH_2$ or $SO_2CH_2$ can be prepared by treatment of compounds of Formula I where $D^1$ is $SCH_2$ with one or two equivalents respectively of an oxidant such as m-chloroperbenzoic acid in a solvent such as $CH_2Cl_2$.

Scheme 1 below portrays a generalized reaction sequence for the synthesis of compounds of Formula IA for which $A^1$ and $A^2$ are $CR^1$ and $D^1$ is $OCH_2$, $SCH_2$ or $NR^5CH_2$. Compounds of Formula IV can be synthesized by copper (II) catalyzed coupling of compound II with boronic acids of general Formula III by procedures reported at *Tetrahedron Lett.*, 42:3415 (2001). Compound II is either commercially available or easily prepared by esterification of the corresponding acid.

Compounds of Fothiula V can be obtained from compounds of Formula IV by employing a reducing agent such as $LiBH_4$ in a solvent such as THF. Compound of Formula VI can be obtained from compounds of Formula V by treatment with carbon tetabromide/triphenylphosphine in a solvent such as $CH_2Cl_2$.

Compounds of Formula IA can be obtained by alkylating commercially available compounds of Formula VII with compounds of Formula VI. In the case where X is oxygen or sulfur, this may be achieved by stirring Compounds of Formula VII with a base such as NaH, $K_2CO_3$ or $Cs_2CO_3$ in a solvent such DMF or MeCN for 30 min prior to addition of compounds of Formula VI. In the case where X is $NR^5$, the condensation was promoted with a base such as DBU in a solvent such as DMF.

Scheme 1

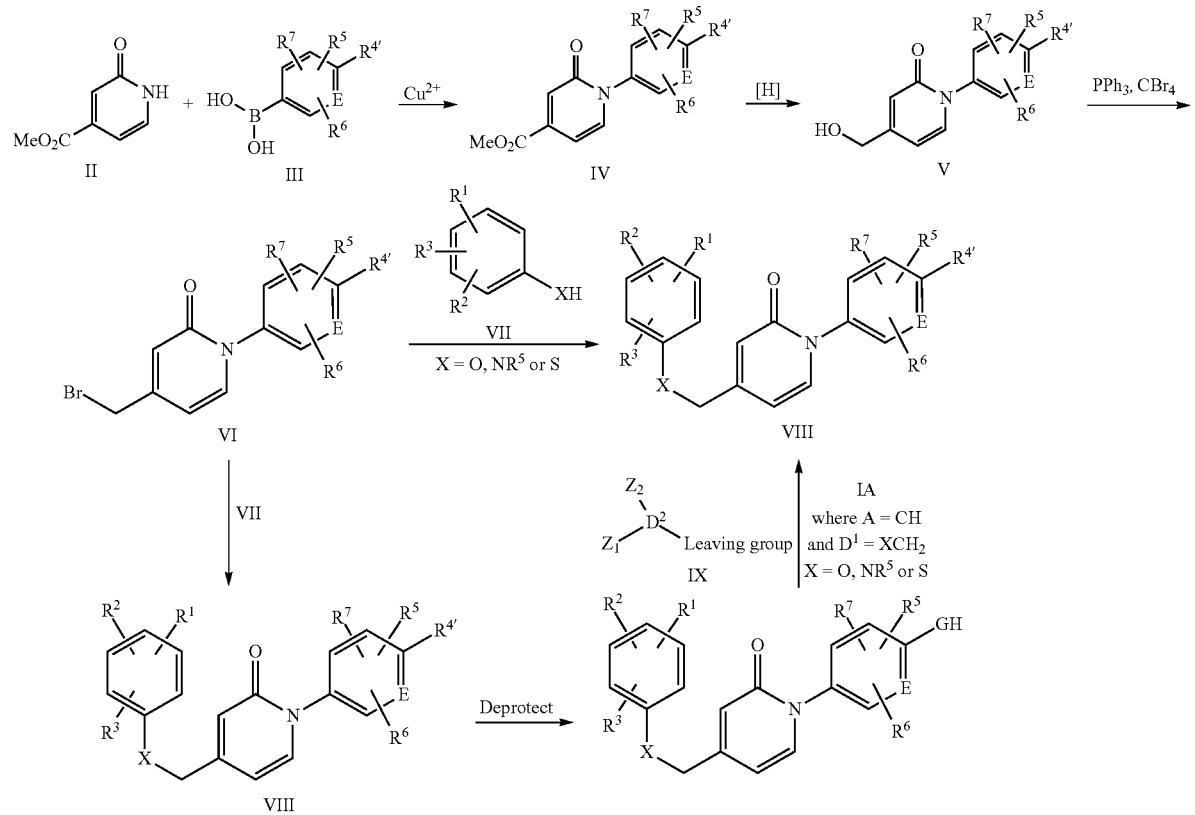

For those instances for which $R^{4'}$ of compounds of formula VIII is protected $R^4$, deprotection completes the synthesis of IA. For those cases where $R^{4'}$ is protected GH, deprotection followed by alkylation with compounds of Formula IX using methods known to those skilled in the arts completes the conversion to compounds of Formula IA. Reaction sequences to effect this transformation but are not restricted to include condensation with an epoxide in a solvent such as 80% MeCN/H$_2$O containing Na$_2$CO$_3$ or by alkylation with an α-haloketone in a solvent such as DMF in the presence of a base such as Cs$_2$CO$_3$ followed by reduction with NaBH$_4$.

Scheme 2 below portrays a generalized reaction sequence for the synthesis of compounds of Formula IB for which, in compounds of Formula I, A$^1$ and/or A$^2$ are nitrogen. Compounds of Formula X can be obtained by deprotection of compounds of Formula V. Compounds of Formula XI may be obtained upon alkylation of compounds of Formula X with compounds of Formula IX to generate compounds of Foimula XI. Compounds of IB where X is oxygen can be obtained by subsequent condensation of compounds of Formula XI with readily available compounds of Formula XII in solvent such as DMF containing a catalyst such as Pd(OAc)$_2$ and ligand such as racemic 2-(di-t-butylphosphino)-1,1'-binaphthyl and a base such as Cs$_2$CO$_3$.

Compounds of Formula TB where X is sulfur can be prepared from alcohols of Formula XI by conversion to thiols of Formula XI using known methods entailing for example activation of the primary alcohol of XI by conversion to the mesylate, reaction with thioacetate and hydrolysis to generate thiols of Formula XI which upon condensation with compounds of Formula XII is converted to compounds of Founula IB where X is sulfur. In a similar manner compounds of Formula IB where X is NR" can be prepared upon conversion of the primary hydroxyl of XI to an NHR$^{11}$ followed by condensation with compounds of Formula XII.

Scheme 2

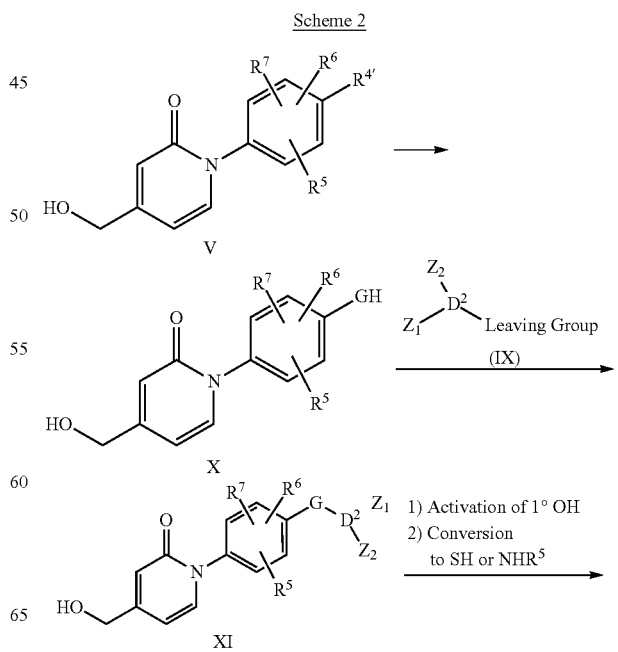

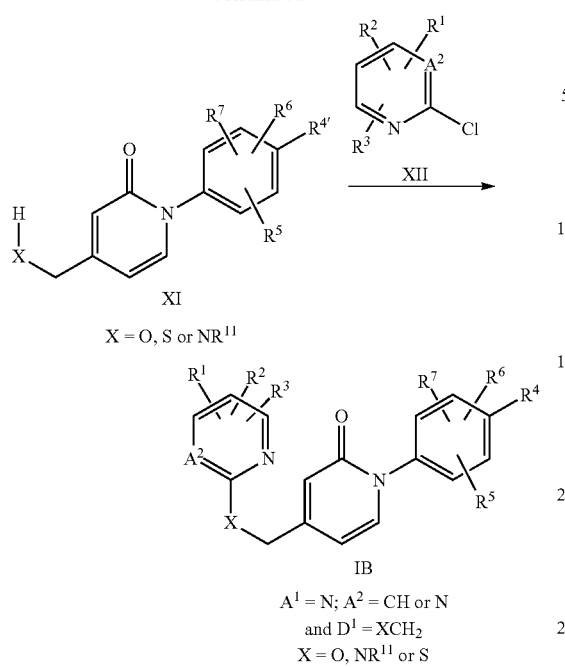

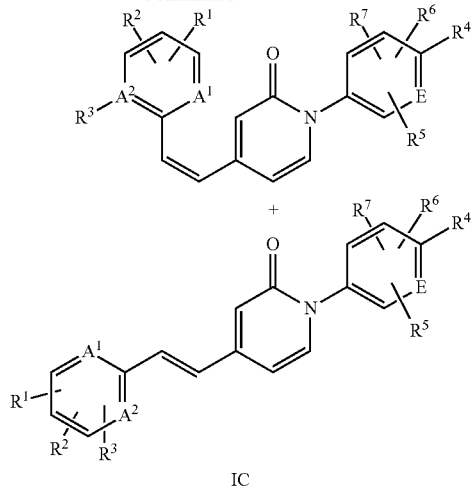

Scheme 4 below portrays a generalized reaction sequence for the synthesis of compounds of Formula ID wherein $D^1$ is $CH_2O$, $CH_2S$ or $CH_2NR^{11}$. Compounds of Formula XVII can be prepared from the commercially available pyridone XV via N-arylation with compounds either of Foimula III or of Foiniula XVI. Treatment of XV with aryl or heteroaryl bromides XVI in the presence of catalytic amounts of Cu(I) iodide, potassium phosphate and an amine ligand (e.g., N1,N2-dimethylcyclohexane-1,2-diamine, N1,N2-dimethylethylenediamine) in solvents such as dioxane or DMF at 50 to 150° C. affords XVII. Alternatively, XVII can be prepared by coupling compounds of Formula XV with aryl or heteroaryl boronic acids III in the presence of catalytic amounts of $CuOAc_2$ and an amine (e.g., triethylamine, N1,N1,N2,N2-tetramethylethylenediamine) or pyridine in solvents such as DCM, MeOH etc. Compounds of Fomumula XVIII can be prepared by debenzylation of compounds of Formula XVII with $H_2$ gas in the presence of a catalyst such PdJC in a solvent such as EtOH or MeOH. Alkylation of compounds of Formula XVIII in a solvent such as DMF, NMP or THF in the presence of a base such as an alkali metal carbonate with compounds of Formula XIX where the leaving group is a halide or sulfate etc generates compounds of Formula ID where $D^1$ is $CH_2O$. Compounds of Formula ID where $D^1$ is $CH_2S$ or $CH_2NR^{11}$ can be respectively prepared by reacting compounds of formula XX with thiols of Formula XXI or amines of Formula XXIII in a solvent such as DMF or THF containing a base such as $Na_2CO_3$ or $K_2CO_3$ as described in Scheme 1 to generate compounds of Formula XXII and XXIV followed by N-arylation as previously described.

Scheme 3 below portrays a generalized reaction sequence for the synthesis of compounds of Founula IC wherein $D^1$ is vinyl. Compounds of Formula XIII can be prepared upon heating compounds of Founula VI with triphenylphosphine in a solvent such as toluene. Sequential treatment of compounds of Formula XIII with a strong base such as n-butyl lithium in a solvent such as THF followed by addition of a compound of Formula XIV followed by deprotection and subsequent reaction with compounds of Formula IX generates compounds of Formula IC as mixture of cis and trans isomers which can be separated by reverse phase chromatography.

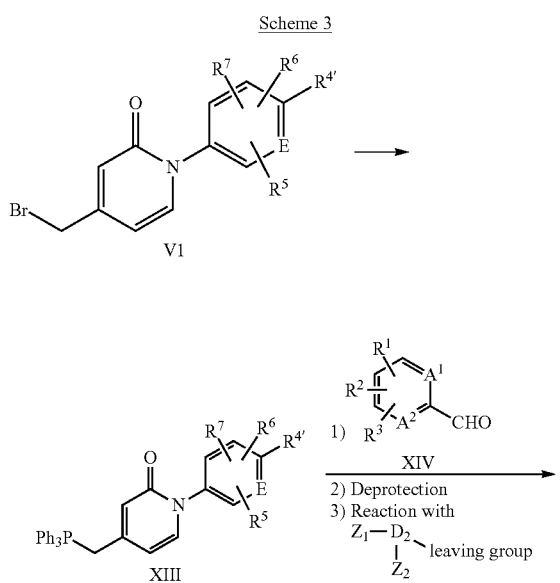

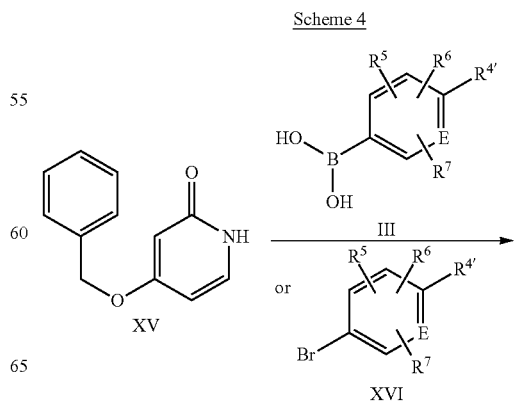

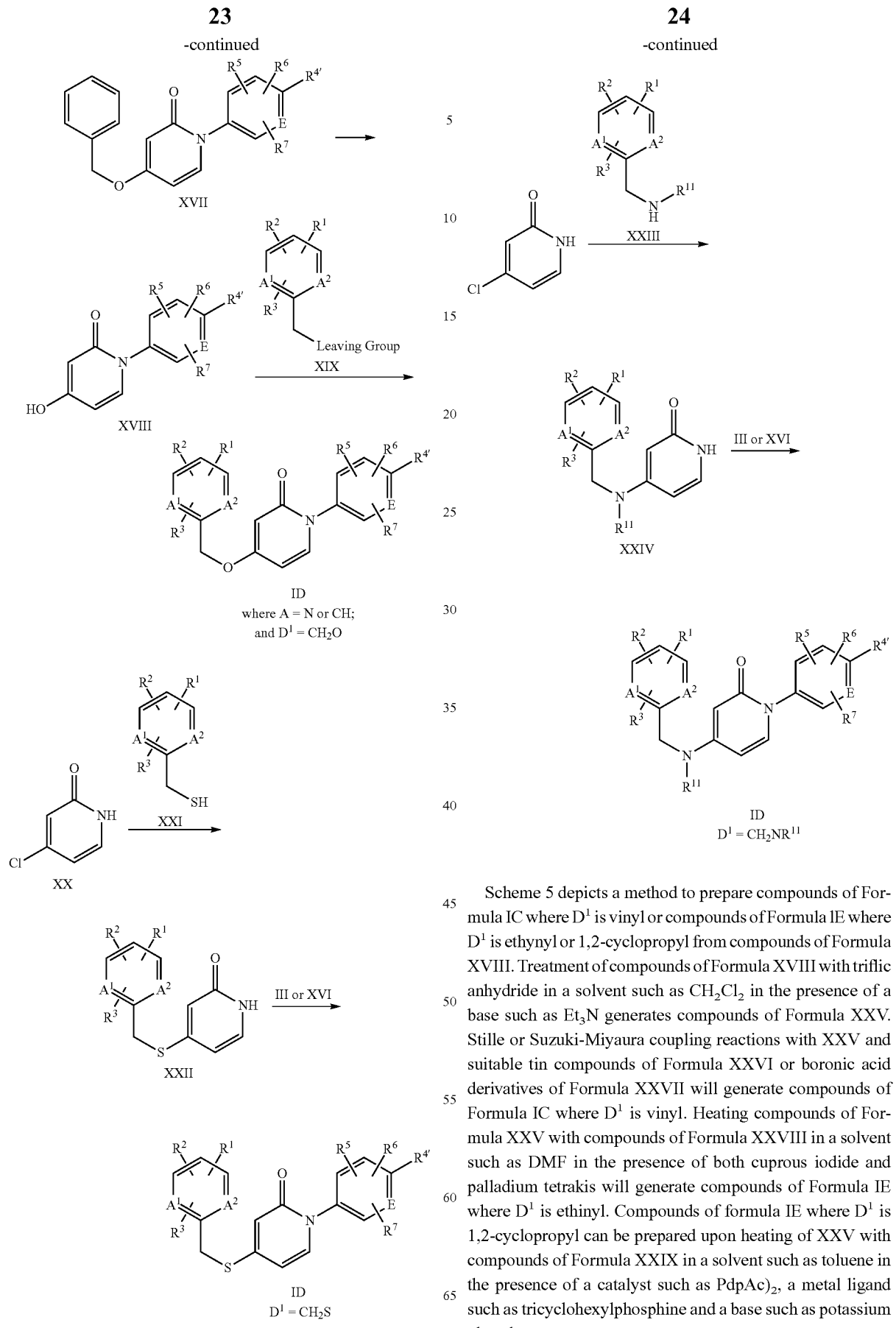

Scheme 5 depicts a method to prepare compounds of Formula IC where $D^1$ is vinyl or compounds of Formula IE where $D^1$ is ethynyl or 1,2-cyclopropyl from compounds of Formula XVIII. Treatment of compounds of Formula XVIII with triflic anhydride in a solvent such as $CH_2Cl_2$ in the presence of a base such as $Et_3N$ generates compounds of Formula XXV. Stille or Suzuki-Miyaura coupling reactions with XXV and suitable tin compounds of Formula XXVI or boronic acid derivatives of Formula XXVII will generate compounds of Formula IC where $D^1$ is vinyl. Heating compounds of Formula XXV with compounds of Formula XXVIII in a solvent such as DMF in the presence of both cuprous iodide and palladium tetrakis will generate compounds of Formula IE where $D^1$ is ethynyl. Compounds of formula IE where $D^1$ is 1,2-cyclopropyl can be prepared upon heating of XXV with compounds of Formula XXIX in a solvent such as toluene in the presence of a catalyst such as $PdpAc)_2$, a metal ligand such as tricyclohexylphosphine and a base such as potassium phosphate

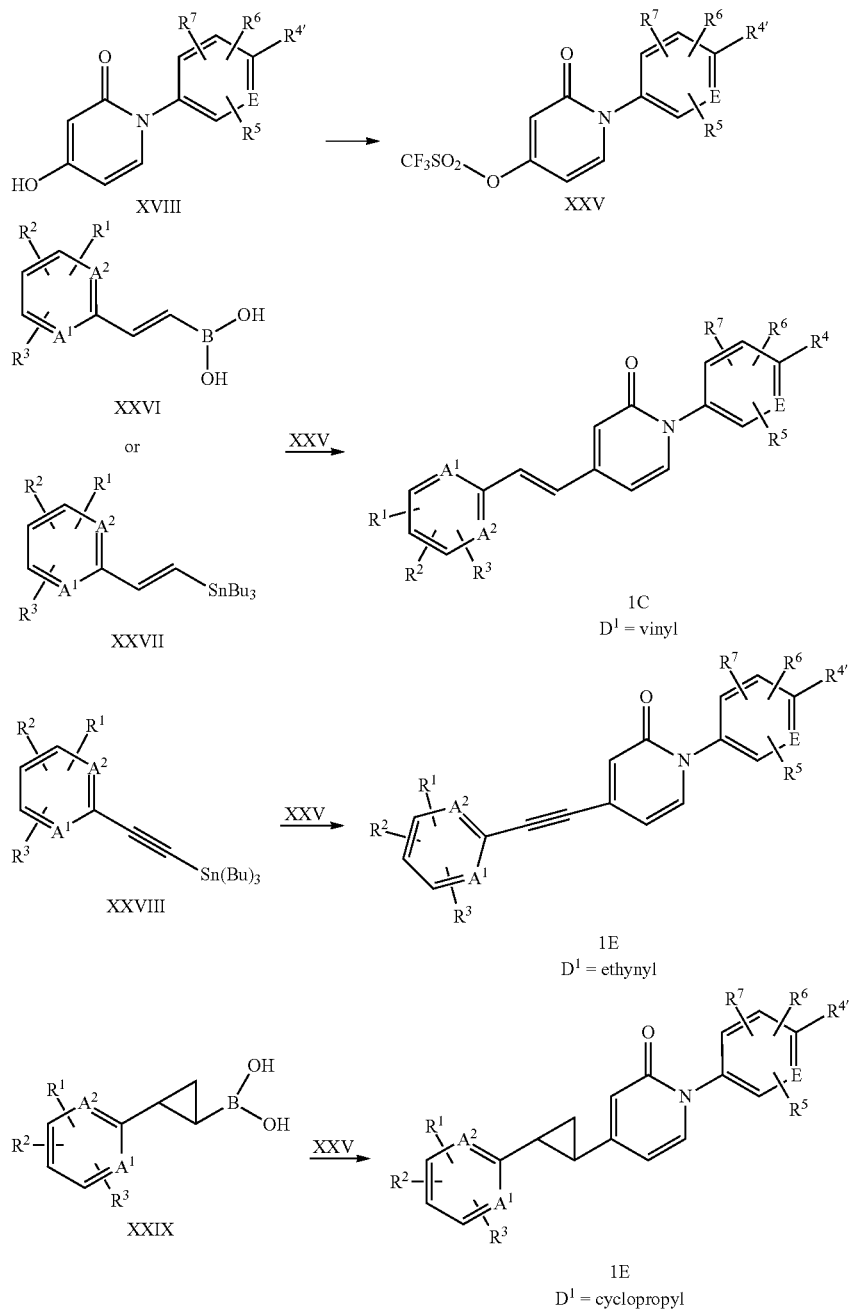

Scheme 6 below portrays a generalized reaction sequence for the synthesis of compounds of Formula 1F where $D^1$ is a bond. N-arylation of compound of Formula XX to generate compounds of Formula XXX can be achieved by stirring of XX with aryl boronic acids of Formula III in the presence of a catalyst such as Cu(II) acetate in a solvent such as 10% MeOH/CH$_2$Cl$_2$ containing a base such as pyridine.

Compounds of Formula XXX can be converted to compounds of Formula 1F upon being heated with stirring in a solvent such as DMF containing aryl boronic acids of Formula XXXI, a catalyst such as palladium tetrakis and a base such as tribasic potassium phosphate.

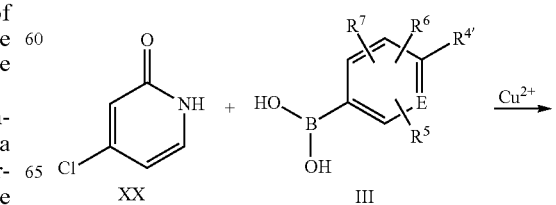

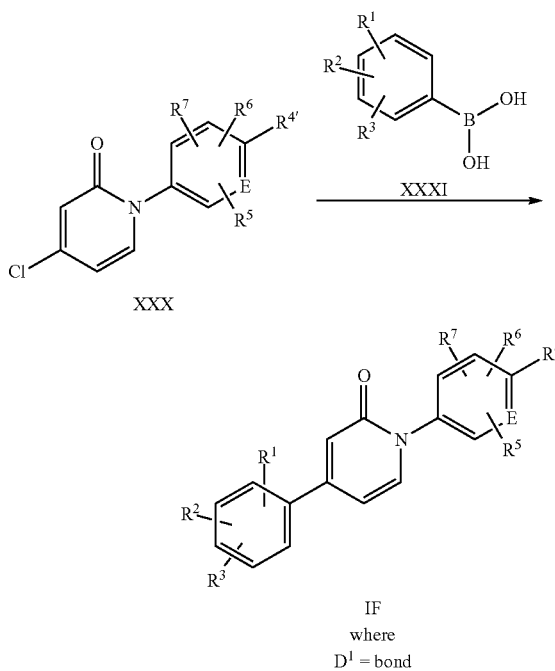
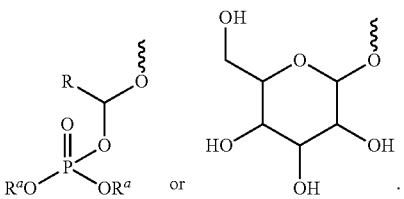

IF
where
$D^1$ = bond

Prodrugs, Salts and Stereoisomers

The term "prodrug" encompasses both the term "prodrug esters" and the term "prodrug ethers". The term "prodrug esters" as employed herein includes esters and carbonates formed by reacting one or more hydroxyls of compounds of the present invention with either alkyl, alkoxy, or aryl substituted acylating agents or phosphorylating agent employing procedures known to those skilled in the art to generate acetates, pivalates, methylcarbonates, benzoates, amino acid esters, phosphates and the like.

Examples of such prodrug esters include

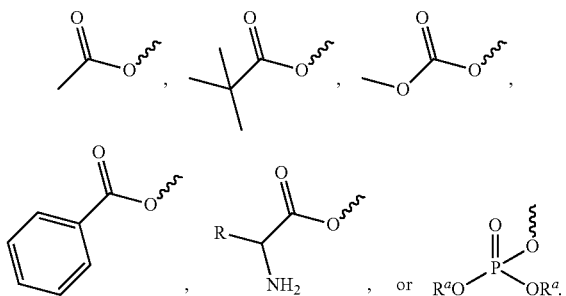

Preferred prodrug esters are those prepared from monobasic carboxylic acids, such as acetic, pivalic, benzoic or amino acids or monoesters of dibasic carboxylic acids such as carbonic acid, oxalic, malonic, succinic, and glutaric acids, or monoesters of phosphoric acid.

The term "prodrug ethers" include both phosphate acetals and O-glucosides. Representative examples of such prodrug ethers include In the above formulae, R is alkyl or H and $R^a$ is H, alkyl, or benzyl.

The compounds of Formula I can be present as salts, which are also within the scope of this invention. Pharmaceutically acceptable (i.e., non-toxic, physiologically acceptable) salts are preferred. If the compounds of Formula I have, for example, at least one basic center, they can form acid addition salts. These are formed, for example, with strong inorganic acids, such as mineral acids, for example sulfuric acid, phosphoric acid or a hydrohalic acid, with organic carboxylic acids, such as alkanecarboxylic acids of 1 to 4 carbon atoms, for example acetic acid, which are unsubstituted or substituted, for example, by halogen as chloroacetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methyl- or p-toluene-sulfonic acid. Corresponding acid addition salts can also be formed having, if desired, an additionally present basic center. The compounds of Formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or trilower alkylamine, for example ethyl, tert-butyl, diethyl, diisopropyl, triethyl, tributyl or dimethyl-propylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds of Formula I or their pharmaceutically acceptable salts, are also included.

Preferred salts of the compounds of Formula I which contain a basic group include monohydrochloride, hydrogensulfate, methanesulfonate, phosphate, nitrate or acetate.

Preferred salts of the compounds of Formula I which contain an acid group include sodium, potassium and magnesium salts and pharmaceutically acceptable organic amines.

All stereoisomers of the compound of the instant application are contemplated, either in admixture or in pure or substantially pure form. The compound of the present application can have asymmetric centers at any of the carbon atoms including any one of the R substituents. Consequently, compound of Formula can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

Abbreviations

The following abbreviations are employed herein:
Ph=phenyl
Bn=benzyl
t-Bu=tertiary butyl
Me=methyl
NBS=N-bromosuccinimide
NCS=N-chlorosuccinimide
EDC=1-(3-dimethylaminopropyl)-3-ethylcarbodiimide HCl
DIC=2-dimethylaminoisopropyl chloride HCl
PyBop=purum
BOP-Cl=bis(2-oxo-3-oxazolidinyl)-phosphinic chloride
MCPBA=
OTs=Otosyl
OMs=Omesyl
Tf=triflate
AIBN=2,2'-azobisisobutyronitrile
Et=ethyl
TMS=trimethylsilyl
TBS=tert-butyldimethylsilyl
THF=tetrahydrofuran
$Et_2O$=diethyl ether
EtOAc=ethyl acetate
DMF=dimethyl formamide
MeOH=methanol
EtOH=ethanol
i-PrOH=isopropanol
HOAc or AcOH acetic acid
TFA=trifluoroacetic acid
i-$Pr_2$NEt=diisopropylethylamine
$Et_3$N=triethylamine
DMAP=4-dimethylaminopyridine
$NaBH_4$=sodium borohydride
n-BuLi=n-butyllithium
Pd/C=palladium on carbon
KOH=potassium hydroxide
NaOH=sodium hydroxide
LiOH=lithium hydroxide
$K_2CO_3$=potassium carbonate
$NaHCO_3$=sodium bicarbonate
Palladium tetrakis=palladium tetrakis(triphenylphosphine)
Ar=argon
$N_2$=nitrogen
min=minute(s)
h or hr=hour(s)
L=liter
mL=milliliter
μL=microliter
g=gram(s)
mg=milligram(s)
mol=moles
mmol=millimole(s)
meq=milliequivalent
RT=room temperature
sat or sat'd=saturated
aq.=aqueous
TLC=thin layer chromatography
HPLC=high performance liquid chromatography
LC/MS=high performance liquid chromatography/mass spectrometry
MS or Mass Spec=mass spectrometry
NMR=nuclear magnetic resonance
mp=melting point

EXAMPLES

The present invention is illustrated by but not restricted to the examples contained in Tables A-M. The tables also indicate for each example which of nine synthetic methods was employed as well as which of seven analytical methods was utilized. Detailed synthetic procedures as well as analytical HPLC conditions, solvent and column are described in the section after the Tables

TABLE A

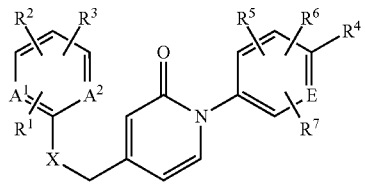

| Ex. No. | Structure | Synthetic Procedure Used | HPLC Method ($t_R$ Min.) | MS (M + H) | NMR Data |
|---|---|---|---|---|---|
| A-1 | 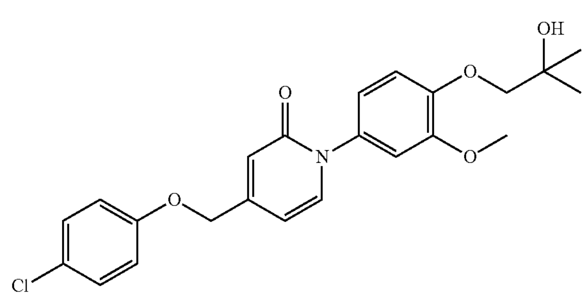 [SMILES: COc1cc(-n2ccc(COc3ccc(Cl)cc3)cc2=O)ccc1OCC(C)(C)O] | #1 | #6 5.0 min. | 430 | $^1$H NMR (CDCl$_3$, 400 MHz) δ 1.36 (s, 6H), 3.86 (2s, 5H), 4.95 (s, 2H), 6.36 (dd, J = 7.0, 1.8 Hz, 1H), 6.78 (s, 1H), 6.84-6.93 (m, 4H), 6.97 (d, J = 8.4 Hz, 1H), 7.26 (d, J = 2.6 Hz, 2H), 7.38 (d, J = 7.0 Hz, 1H). |

TABLE A-continued

| Ex. No. | Structure | Synthetic Procedure Used | HPLC Method ($t_R$ Min.) | MS (M + H) | NMR Data |
|---|---|---|---|---|---|
| A-2 | 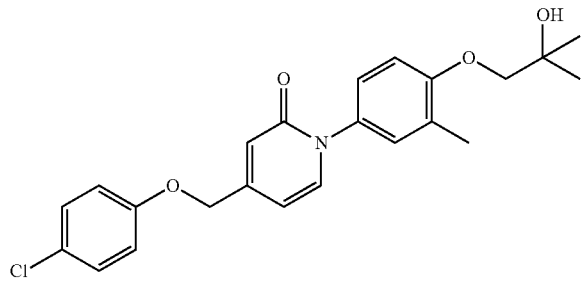 [SMILES: Cc1cc(-n2ccc(COc3ccc(Cl)cc3)cc2=O)ccc1OCC(C)(C)O] | #2 | #6 6.0 min. | 414 | $^1$H NMR (CDCl$_3$, 400 MHz) δ 1.38 (s, 6H), 2.30 (s, 3H), 3.84 (s, 2H), 4.96 (s, 2H), 6.41 (dd, J = 7.0, 1.8 Hz, 1H), 6.84 (s, 1H), 6.89 (m, 3H), 7.10-7.18 (m, 2H), 7.24-7.31 (m, 2H), 7.39 (d, J = 7.0 Hz, 1H). |
| A-3 | 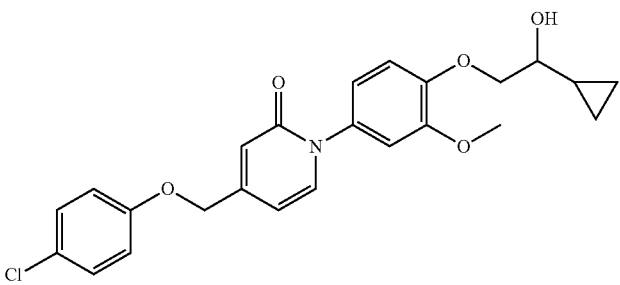 [SMILES: COc1cc(-n2ccc(COc3ccc(Cl)cc3)cc2=O)ccc1OCC(O)C1CC1] | #3 | #6 5.18 min. | 442 | $^1$H NMR (CDCl$_3$, 400 MHz) δ 0.24-0.36 (m, 1H), 0.40-0.49 (m, 1H), 0.50-0.68 (m, 2H), 0.90-1.04 (m, 1H), 3.35 (m, 1H), 3.86 (s, 3H), 4.03 (d, J = 8.4 Hz, 1H), 4.20 (dd, J = 9.7, 3.1 Hz, 1H), 4.93 (s, 2H), 6.30 (d, J = 7.0 Hz, 1H), 6.72 (s, 1H), 6.83-6.95 (m, 4H), 7.01 (d, J = 8.4 Hz, 1H), 7.26 (d, J = 9.2 Hz, 2H), 7.35 (d, J = 7.0 Hz, 1H). |
| A-4 | 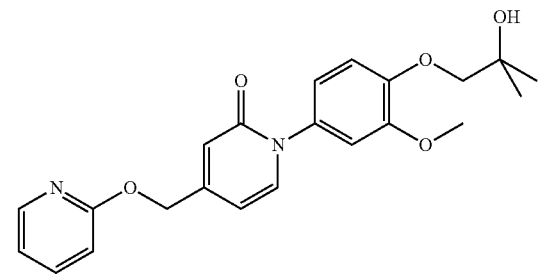 [SMILES: COc1cc(-n2ccc(COc3ccccn3)cc2=O)ccc1OCC(C)(C)O] | #4 | #6 3.07 min. | 397 | $^1$H NMR (CDCl$_3$, 400 MHz) δ 8.16 (m, 1H), 7.62 (m, 1H), 7.31 (d, J = 7.1 Hz, 1H), 6.91 (m, 5H), 6.72 (s, 1H), 6.28 (dd, J = 7.1 and 2.2 Hz, 1H), 5.29 (s, 2H), 3.85 (s, 5H), 1.33 (s, 6H). |
| A-5 | 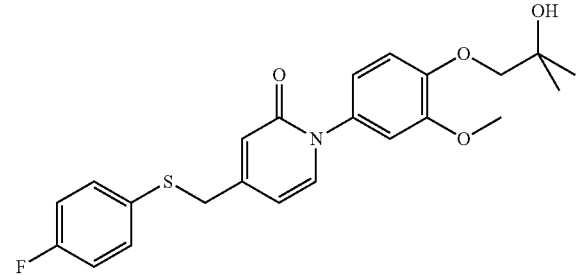 | #5 | #6 3.52 min. | 430 | $^1$H NMR (CDCl$_3$, 400 MHz) δ 7.34 (m, 2H), 7.31 (d, J = 7.1 Hz, 1H), 7.01 (m, 2H), 6.95 (d, J = 8.8 Hz, 1H), 6.88 (d, J = 2.6 Hz, 1H), 6.83 (m, 1H), 6.46 (s, 1H), 6.32 (dd, J = 7.1 and 2.2 Hz, 1H), 3.84 (m, 7H), 1.33 (s, 6H). |

TABLE A-continued

| Ex. No. | Structure | Synthetic Procedure Used | HPLC Method ($t_R$ Min.) | MS (M + H) | NMR Data |
|---|---|---|---|---|---|
| A-6 | 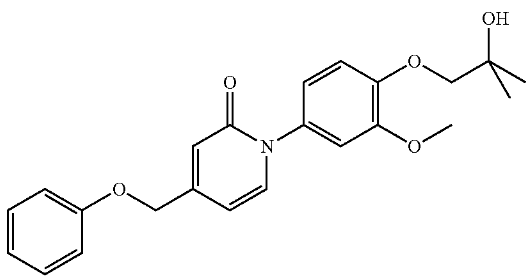 [SMILES: COc1cc(-n2ccc(COc3ccccc3)cc2=O)ccc1OCC(C)(C)O] | #1 | #6 3.93 min. | 396 | $^1$H NMR (CDCl$_3$, 400 MHz) δ 1.36 (s, 6H), 3.86 (2s, 5H), 5.01 (s, 2H), 6.52 (d, J = 7.0 Hz, 1H), 6.86 (dd, J = 8.4, 2.2 Hz, 1H), 6.91 (m, 2H), 6.96 (s, 1H), 6.97 (d, J = 8.4 Hz, 2H), 7.02 (t, J = 7.5 Hz, 1H), 7.32 (t, J = 8.4 Hz, 2H), 7.42 (d, J = 7.0 Hz, 1H). |
| A-7 | 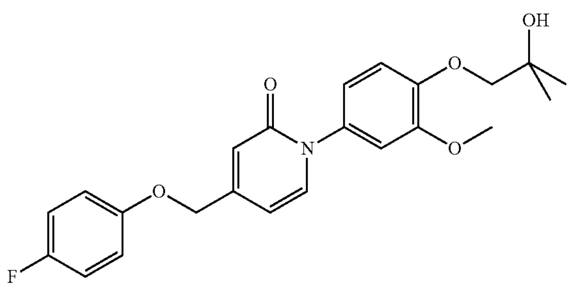 [SMILES: COc1cc(-n2ccc(COc3ccc(F)cc3)cc2=O)ccc1OCC(C)(C)O] | #1 | #6 3.46 min. | 414. | $^1$H NMR (CDCl$_3$, 400 MHz) δ 1.36 (s, 6H), 3.86 (2s, 5H), 4.95 (s, 2H), 6.43 (dd, J = 7.0, 1.8 Hz, 1H), 6.80-6.94 (m, 5H), 6.95-7.06 (m, 3H), 7.40 (d, J = 7.0 Hz, 1H). HPLC-(Zorbax): Rt 3.46 min, purity = 98%. |
| A-8 | 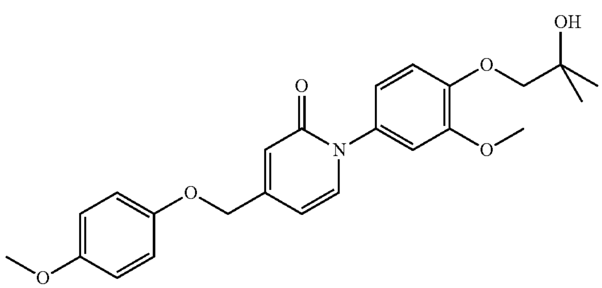 [SMILES: COc1ccc(OCc2ccn(-c3ccc(OCC(C)(C)O)c(OC)c3)c(=O)c2)cc1] | #1 | #6 3.81 min. | 426. | $^1$H NMR (CDCl$_3$, 400 MHz) δ 1.35 (s, 6H), 3.78 (s, 3H), 3.86 (2s, 5H), 4.91 (s, 2H), 6.35 (d, J = 1.7 Hz, 1H), 6.75 (s, 1H), 6.82-6.91 (m, 6H), 6.97 (d, J = 8.4 Hz, 1H), 7.35 (d, J = 7.0 Hz, 1H). |
| A-9 | 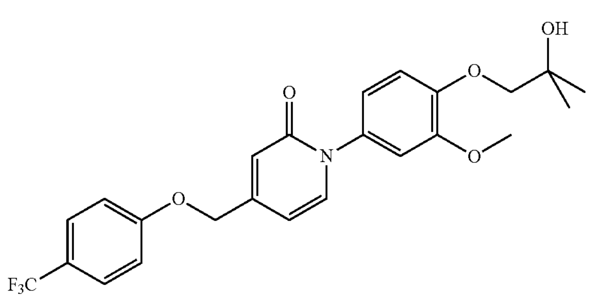 [SMILES: COc1cc(-n2ccc(COc3ccc(C(F)(F)F)cc3)cc2=O)ccc1OCC(C)(C)O] | #1 | #6 5.19 min. | 464 | $^1$H NMR (CDCl$_3$, 400 MHz) δ 1.37 (s, 6H), 3.86 (2s, 5H), 5.05 (s, 2H), 6.49 (dd, J = 7.0, 1.8 Hz, 1H), 6.87 (dd, J = 8.4, 2.2 Hz, 1H), 6.90 (s, 1H), 6.91 (s, 1H), 6.97 (d, J = 8.4 Hz, 1H), 7.04 (d, J = 8.8 Hz, 2H), 7.45 (d, J = 7.0 Hz, 1H), 7.59 (d, J = 8.4 Hz, 2H). |

TABLE A-continued

| Ex. No. | Structure | Synthetic Procedure Used | HPLC Method ($t_R$ Min.) | MS (M + H) | NMR Data |
|---|---|---|---|---|---|
| A-10 | 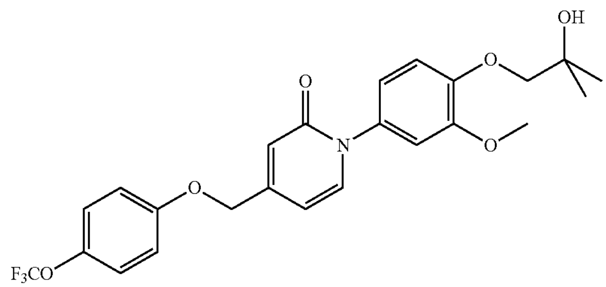 [SMILES: COc1cc(-n2ccc(COc3ccc(OC(F)(F)F)cc3)cc2=O)ccc1OCC(C)(C)O] | #1 | #6 5.51 min. | 480. | $^1$H NMR (CDCl$_3$, 400 MHz) δ 1.36 (s, 6H), 3.86 (2s, 5H), 4.97 (s, 2H), 6.37 (dd, J = 7.0, 1.8 Hz, 1H), 6.79 (1H, s), 6.84-6.89 (m, 1H), 6.91 (d, J = 2.7 Hz, 1H), 6.93-7.00 (m, 3H), 7.18 (d, J = 8.8 Hz, 2H), 7.39 (d, J = 7.0 Hz, 1H). |
| A-11 | 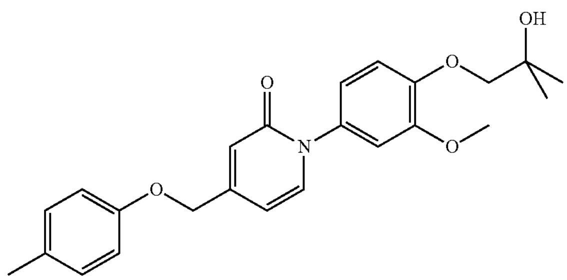 [SMILES: COc1cc(-n2ccc(COc3ccc(C)cc3)cc2=O)ccc1OCC(C)(C)O] | #1 | #6 4.77 min. | 410 | $^1$H NMR (CDCl$_3$, 400 MHz) δ 1.35 (s, 6H), 2.30 (s, 3H), 3.85 (s, 5H), 4.95 (s, 2H), 6.40 (d, J = 7.0 Hz, 1H), 6.79 (s, 1H), 6.85 (d, J = 8.4 Hz, 1H), 6.86 (d, J = 8.8 Hz, 2H), 6.91 (d, J = 2.2 Hz, 1H), 6.96 (d, J = 8.35 Hz, 1H), 7.11 (d, J = 8.4 Hz, 2H), 7.36 (d, J = 7.0 Hz, 1H). |
| A-12 | 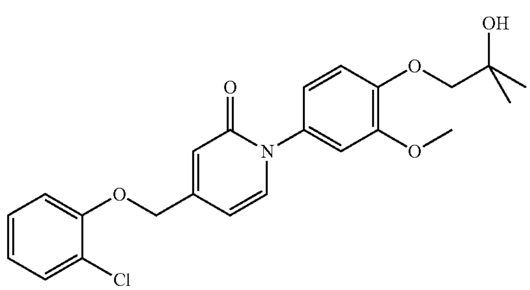 [SMILES: COc1cc(-n2ccc(COc3ccccc3Cl)cc2=O)ccc1OCC(C)(C)O] | #1 | #6 4.62 min. | 430 | $^1$H NMR (CDCl$_3$, 400 MHz) δ 1.35 (s, 6H), 3.86 (2s, 5H), 5.03 (s, 2H), 6.41 (dd, J = 7.03, 1.8 Hz, 1H), 6.76 (s, 1H), 6.84-6.89 (m, 1H), 6.90-7.00 (m, 4H), 7.23 (m, 1H), 7.36 (d, J = 7.5 Hz, 1H), 7.41 (d, J = 7.5 Hz, 1H) |
| A-13 | 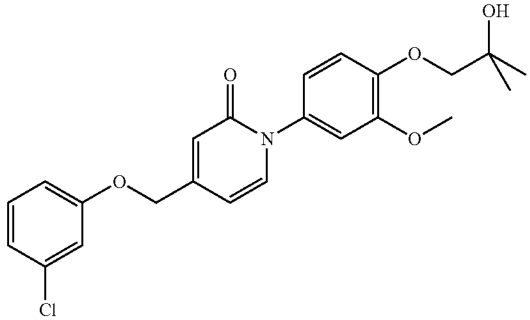 [SMILES: COc1cc(-n2ccc(COc3cccc(Cl)c3)cc2=O)ccc1OCC(C)(C)O] | #1 | #6 4.93 min. | 430 | $^1$H NMR (CDCl$_3$, 400 MHz) δ 1.35 (s, 6H), 2.17 (s, 1H), 3.85 (s, 2H), 3.86 (s, 3H), 4.94 (s, 2H), 6.29 (d, J = 7.0 Hz, 1H), 6.71 (s, 1H), 6.86 (m, 2H), 6.92 (d, J = 2.64 Hz, 1H), 6.93-7.02 (m, 3H), 7.23 (t, J = 8.1 Hz, 1H), 7.35 (d, J = 7.0 Hz, 1H). |

TABLE A-continued

| Ex. No. | Structure | Synthetic Procedure Used | HPLC Method ($t_R$ Min.) | MS (M + H) | NMR Data |
|---|---|---|---|---|---|
| A-14 | 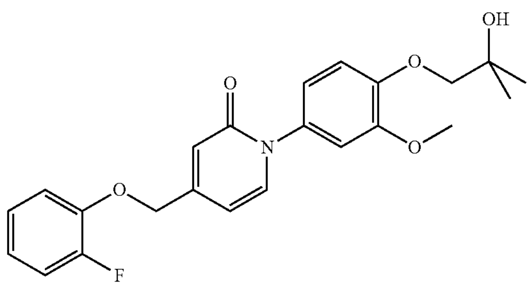 [SMILES: COc1cc(-n2ccc(COc3ccccc3F)cc2=O)ccc1OCC(C)(C)O] | #1 | #6 3.80 min. | 414 | $^1$H NMR (CDCl$_3$, 400 MHz) δ 1.36 (s, 6H), 3.86 (2s, 5H), 5.03 (s, 2H), 6.41 (d, = 7.5 Hz, 1H), 6.77 (s, 1H), 6.86 (dd, J = 8.4, 2.2 Hz, 1H), 6.91 (d, J = 2.2 Hz, 1H), 6.93-7.02 (m, 3H), 7.10 (m, 2H), 7.37 (d, J = 7.0 Hz, 1H). |
| A-15 | 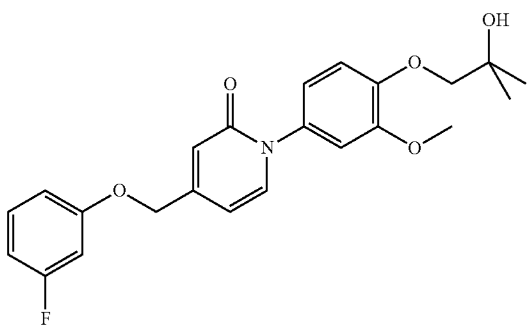 [SMILES: COc1cc(-n2ccc(COc3cccc(F)c3)cc2=O)ccc1OCC(C)(C)O] | #1 | #6 3.58 min. | 414 | $^1$H NMR (CDCl$_3$, 400 MHz) δ ppm 1.36 (s, 6H), 3.86 (2s, 5H), 4.96 (s, 2H), 6.34 (d, J = 7.0 Hz, 1H), 6.64-6.80 (m, 4H), 6.87 (d, J = 8.35 Hz, 1H), 6.91 (s, 1H), 6.97 (d, J = 8.4 Hz, 1H), 7.26 (m, 1H), 7.37 (d, J = 7.0 Hz, 1H). |
| A-16 | 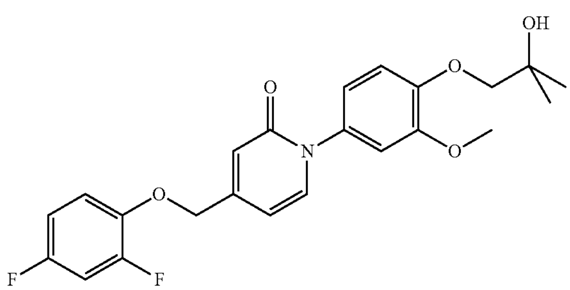 [SMILES: COc1cc(-n2ccc(COc3ccc(F)cc3F)cc2=O)ccc1OCC(C)(C)O] | #1 | #6 3.61 min. | 432 | $^1$H NMR (CDCl$_3$, 400 MHz) δ 1.36 (s, 6H), 3.86 (2s, 5H), 5.01 (s, 2H), 6.47 (dd, J = 7.0, 1.8 Hz, 1H), 6.76-7.00 (7H, m), 7.42 (1H, d, J = 7.0 Hz). |
| A-17 | 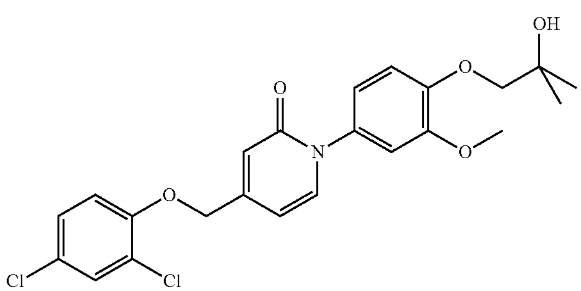 [SMILES: COc1cc(-n2ccc(COc3ccc(Cl)cc3Cl)cc2=O)ccc1OCC(C)(C)O] | #1 | #6 5.23 min. | 464 | $^1$H NMR (CDCl$_3$, 400 MHz) δ ppm 1.37 (s, 6H), 3.86 (2s, 5H), 5.05 (s, 2H), 6.56 (d, J = 5.71 Hz, 1H), 6.87 (d, J = 8.79 Hz, 2H), 6.90 (s, 1H), 6.91(s, 1H), 6.98 (d, J = 8.4 Hz, 1H), 7.21 (dd, J = 8.79, 2.2 Hz, 1H), 7.43 (d, J = 2.2 Hz, 1H), 7.45 (d, J = 7.0 Hz, 1H). |

TABLE A-continued

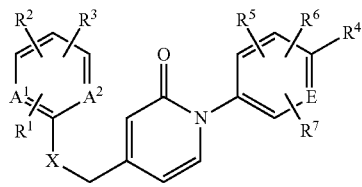

| Ex. No. | Structure | Synthetic Procedure Used | HPLC Method ($t_R$ Min.) | MS (M + H) | NMR Data |
|---|---|---|---|---|---|
| A-18 | 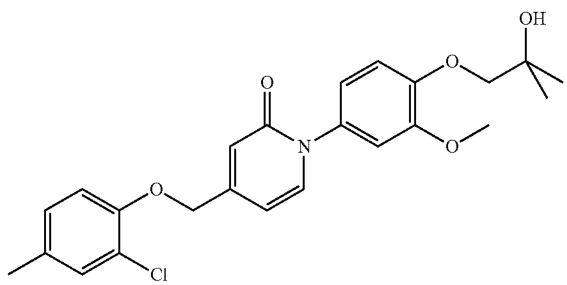 [SMILES: COc1cc(-n2ccc(COc3ccc(C)cc3Cl)cc2=O)ccc1OCC(C)(C)O] | #1 | #6 5.65 min. | 444 | $^1$H NMR (CDCl$_3$, 400 MHz) δ ppm 1.36 (s, 6H), 2.29 (s, 3H), 3.85 (2s, 5H), 5.01 (s, 2H), 6.45-6.50 (m, 1H), 6.80 (s, 1H), 6.83 (d, J = 8.4 Hz, 1H), 6.87 (d, J = 2.2 Hz, 1H), 6.91 (d, J = 2.2 Hz, 1H), 6.97 (d, J = 8.35 Hz, 1H), 6.99-7.04 (m, 1H), 7.23 (d, J = 1.8 Hz, 1H), 7.39 (d, J = 7.0 Hz, 1H). |
| A-19 | 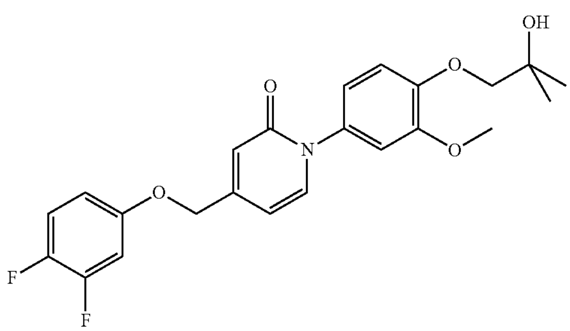 [SMILES: COc1cc(-n2ccc(COc3ccc(F)c(F)c3)cc2=O)ccc1OCC(C)(C)O] | #1 | #6 3.77 min. | 432 | $^1$H NMR (CDCl$_3$, 400 MHz) δ ppm 1.37 (s, 6H), 3.86 (2s, 5H), 4.95 (s, 2H), 6.46 (dd, J = 7.0, 1.8 Hz, 1H), 6.67 (dd, J = 9.2, 1.8 Hz, 1H), 6.79 (m, 1H), 6.85 (d, J = 2.2 Hz, 2H), 6.91 (d, J = 2.2 Hz, 1H), 6.98 (d, J = 8.4 Hz, 1H), 7.11 (1H, q, J = 9.23 Hz), 7.44 (d, J = 7.0 Hz, 1H). |
| A-20 | 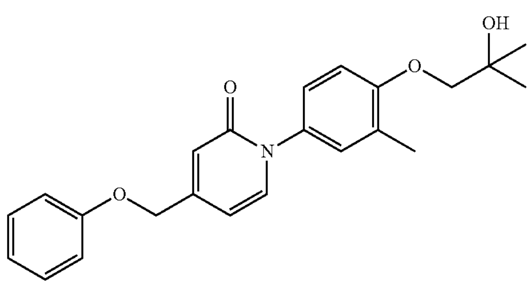 [SMILES: Cc1cc(-n2ccc(COc3ccccc3)cc2=O)ccc1OCC(C)(C)O] | #1 | #6 5.16 min. | 380 | $^1$H NMR (CDCl$_3$, 400 MHz) δ 1.38 (s, 6H), 2.29 (s, 3H), 3.83 (s, 2H), 4.98 (s, 2H), 6.43 (d, J = 7.0 Hz, 1H), 6.84 (s, 1H), 6.88 (d, J = 7.9 Hz, 1H), 6.96 (d, J = 7.9 Hz, 2H), 7.0 (t, J = 6.81 Hz, 1H), 7.11-7.19 (m, 2H), 7.32 (m, 2H), 7.37 (d, J = 7.0 Hz, 1H). |
| A-21 | 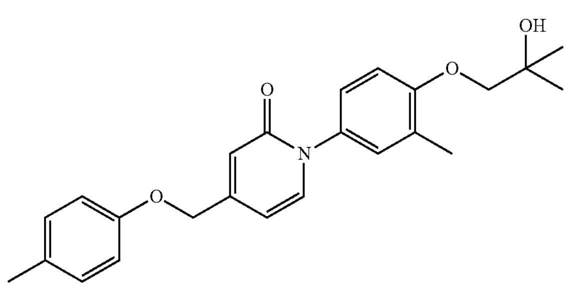 [SMILES: Cc1ccc(OCc2ccn(-c3ccc(OCC(C)(C)O)c(C)c3)c(=O)c2)cc1] | #1 | #6 5.98 min. | 394 | $^1$H NMR (CDCl$_3$, 400 MHz) δ ppm 1.38 (s, 6H), 2.29 (s, 3H), 2.30 (s, 3H), 3.82 (s, 2H), 4.94 (s, 2H), 6.38 (d, J = 7.0 Hz, 1H), 6.79 (s, 1H), 6.86 (m, 3H), 7.06-7.18 (m, 4H), 7.34 (d, J = 7.0 Hz, 1H). |

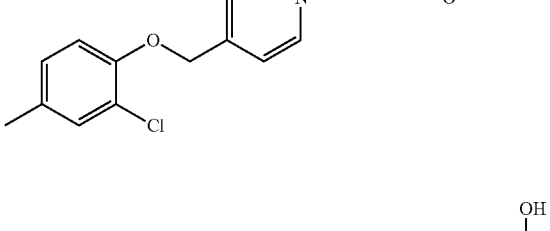
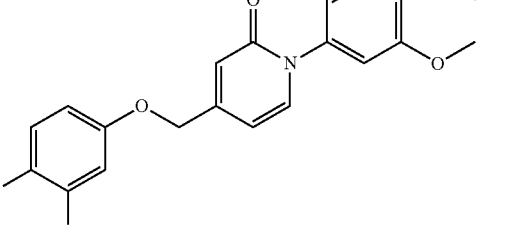
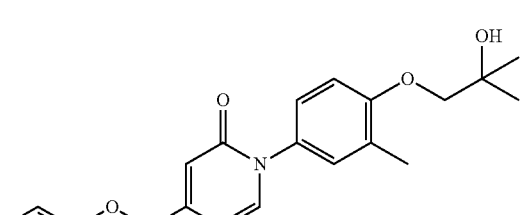
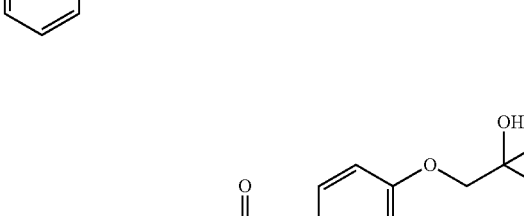

TABLE A-continued

| Ex. No. | Structure | Synthetic Procedure Used | HPLC Method ($t_R$ Min.) | MS (M + H) | NMR Data |
|---|---|---|---|---|---|
| A-22 | 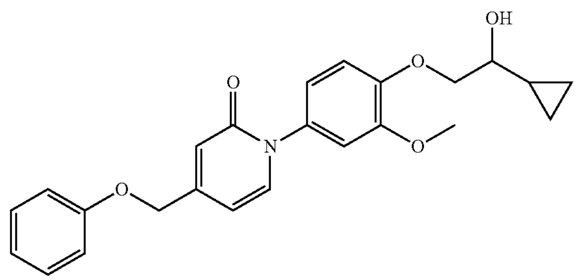 [SMILES: COc1cc(-n2ccc(COc3ccccc3)cc2=O)ccc1OCC(O)C1CC1] | #3 | #6 4.23 min. | 408 | $^1$H NMR (CDCl$_3$, 400 MHz) δ 0.25-0.35 (m, 1H), 0.40-0.50 (m, 1H), 0.50-0.68 (m, 2H), 0.90-1.04 (m, 1H), 3.35 (m, 1H), 3.86 (s, 3H), 4.03 (d, J = 8.4 Hz, 1H), 4.20 (dd, J = 9.7, 2.6 Hz, 1H), 4.96 (s, 2H), 6.33 (dd, J = 7.0, 1.7 Hz, 1H), 6.75 (s, 1H), 6.84-6.90 (m, 1H), 6.92 (d, J = 2.2 Hz, 1H), 6.96 (d, J = 7.9, 2H), 7.00 (m, 2H), 7.28-7.38 (m, 3H). |
| A-23 | 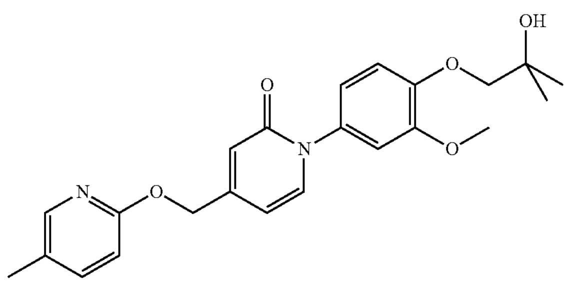 [SMILES: COc1cc(-n2ccc(COc3ccc(C)cn3)cc2=O)ccc1OCC(C)(C)O] | #4 | #7 3.24 min. | 411 | $^1$H NMR (400 MHz, Chloroform-D) δ 7.94 (s, 1H), 7.43 (m, 1H), 7.30 (d, J = 7.1 Hz, 1H), 6.96 (d, J = 8.8 Hz, 1H), 6.90 (d, J = 2.7 Hz, 1H), 6.85 (m, 1H), 6.76 (d, J = 8.2 Hz, 1H), 6.70 (s, 1H), 6.25 (dd, J = 7.1 and 1.7 Hz, 1H), 5.25 (s, 2H), 3.85 (s, 5H), 2.26 (s, 3H), 1.35 (s, 6H). |
| A-24 | 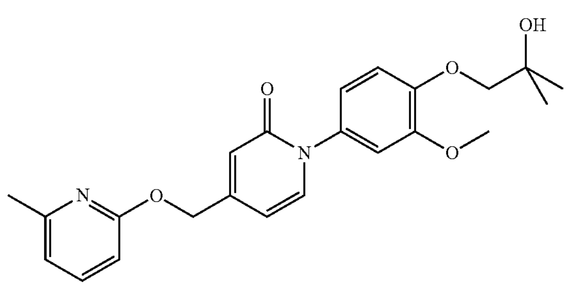 [SMILES: COc1cc(-n2ccc(COc3cccc(C)n3)cc2=O)ccc1OCC(C)(C)O] | #4 | #7 3.01 min. | 411 | $^1$H NMR (400 MHz, Chloroform-D) δ 7.50 (m, 1H), 7.30 (d, J = 7.1 Hz, 1H), 6.96 (d, J = 8.8 Hz, 1H), 6.91 (d, J = 2.2 Hz, 1H), 6.86 (m, 1H), 6.76 (d, J = 7.0 Hz, 1H), 6.72 (s, 1H), 6.63 (d, J = 8.3 Hz, 1H), 6.30 (dd, J = 7.1 and 1.8 Hz, 1H), 5.28 (s, 2H), 3.85 (s, 5H), 2.40 (s, 3H), 1.35 (s, 6H). |
| A-25 | 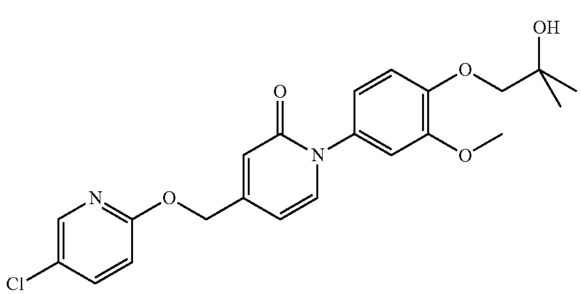 [SMILES: COc1cc(-n2ccc(COc3ccc(Cl)cn3)cc2=O)ccc1OCC(C)(C)O] | #4 | #7 3.56 Min. | 431 | $^1$H NMR (400 MHz, Chloroform-D) δ 8.01 (d, J = 2.6 Hz, 1H), 7.59 (m, 1H), 7.31 (d, J = 7.1 Hz, 1H), 6.96 (d, J = 8.8 Hz, 1H), 6.90 (d, J = 2.2 Hz, 1H), 6.83 (m, 2H), 6.68 (s, 1H), 6.25 (dd, J = 7.1 and 1.7 Hz, 1H), 5.25 (s, 2H), 3.85 (s, 5H), 1.35 (s, 6H). |

TABLE A-continued

| Ex. No. | Structure | Synthetic Procedure Used | HPLC Method ($t_R$ Min.) | MS (M + H) | NMR Data |
|---|---|---|---|---|---|
| A-26 | 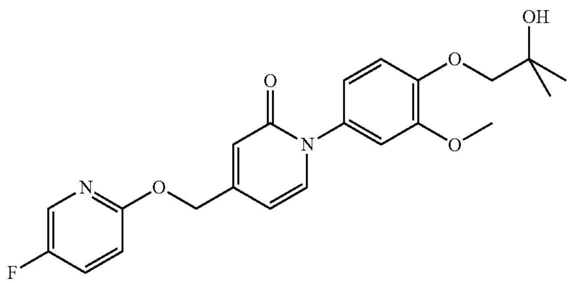 [SMILES: COc1cc(-n2ccc(COc3ccc(F)cn3)cc2=O)ccc1OCC(C)(C)O] | #4 | #7 3.29 min. | 415 | ¹H NMR (400 MHz, Chloroform-D) δ 8.00 (d, J = 3.1 Hz, 1H), 7.39 (m, 1H), 7.31 (d, J = 7.0 Hz, 1H), 6.96 (d, J = 8.8 Hz, 1H), 6.91 (d, J = 2.2 Hz, 1H), 6.84 (m, 2H), 6.69 (s, 1H), 6.25 (dd, J = 7.0 and 1.7 Hz, 1H), 5.24 (s, 2H), 3.85 (s, 5H), 1.35 (s, 6H). |
| A-27 | 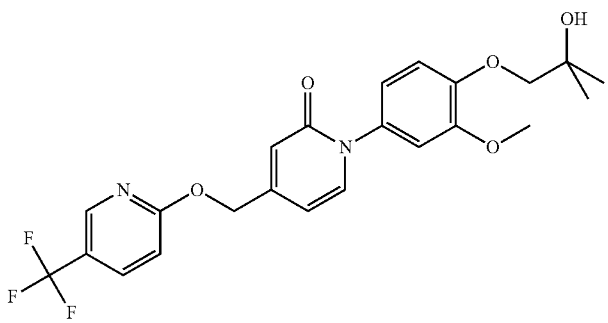 [SMILES: COc1cc(-n2ccc(COc3ccc(C(F)(F)F)cn3)cc2=O)ccc1OCC(C)(C)O] | #4 | #7 3.65 min. | 465 | ¹H NMR (400 MHz, Chloroform-D) δ 8.44 (m, 1H), 7.86 (m, 1H), 7.47 (d, J = 7.0 Hz, 1H), 6.96 (m, 3H), 6.90 (d, J = 2.6 Hz, 1H), 6.87 (m, 1H), 6.56 (dd, J = 7.0 and 1.8 Hz, 1H), 5.42 (s, 2H), 3.86 (s, 2H), 3.87 (s, 3H), 1.38 (s, 6H). |
| A-28 | 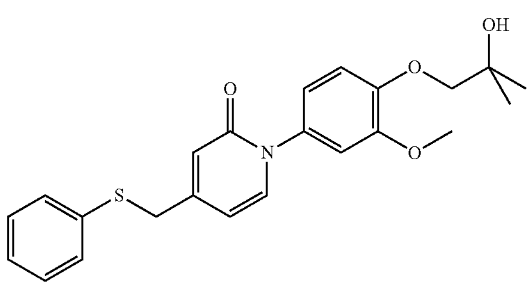 [SMILES: COc1cc(-n2ccc(CSc3ccccc3)cc2=O)ccc1OCC(C)(C)O] | #5 | #7 3.49 min. | 412 | ¹H NMR (400 MHz, Chloroform-D) δ 7.31 (m, 6H), 6.95 (d, J = 8.8 Hz, 1H), 6.88 (d, J = 2.2 Hz, 1H), 6.83 (dd, J = 2.2 and 8.8 Hz, 1H), 6.55 (s, 1H), 6.35 (dd, J = 7.0 and 2.2 Hz, 1H), 3.93 (s, 2H), 3.85 (s, 2H), 3.84 (s, 3H), 1.33 (s, 6H). |
| A-29 | 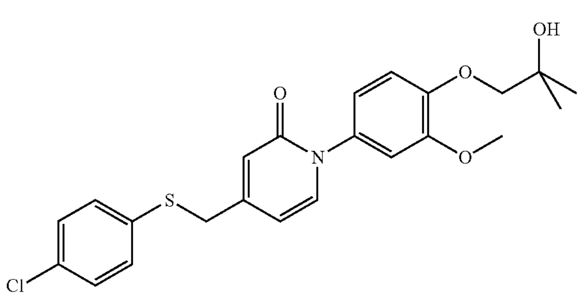 [SMILES: COc1cc(-n2ccc(CSc3ccc(Cl)cc3)cc2=O)ccc1OCC(C)(C)O] | #5 | #7 3.73 min. | 446 | ¹H NMR (400 MHz, Chloroform-D) δ 7.27 (m, 4H), 6.95 (d, J = 8.4 Hz, 1H), 6.88 (d, J = 2.6 Hz, 1H), 6.82 (m, 1H), 6.54 (s, 1H), 6.33 (dd, J = 7.1 and 2.2 Hz, 1H), 3.90 (s, 2H), 3.85 (s, 2H), 3.84 (s, 3H), 1.33 (s, 6H). |

TABLE A-continued

| Ex. No. | Structure | Synthetic Procedure Used | HPLC Method ($t_R$ Min.) | MS (M + H) | NMR Data |
|---|---|---|---|---|---|
| A-30 | 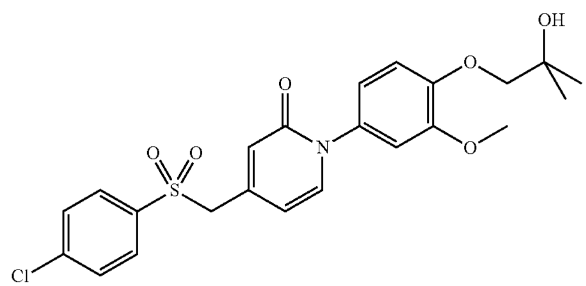 [SMILES: COc1cc(-n2ccc(CS(=O)(=O)c3ccc(Cl)cc3)cc2=O)ccc1OCC(C)(C)O] | m-CPBA oxidation of Ex A-5 | #7 3.05 min. | 478 | $^1$H NMR (CDCl$_3$, 400 MHz) δ 7.79 (d, J = 8.8 Hz, 2H), 7.55 (d, J = 8.8 Hz, 2H), 7.33 (d, J = 7.0 Hz, 1H), 6.96 (d, J = 8.4 Hz, 1H), 6.87 (d, J = 2.6 Hz, 1H), 6.84 (m, 1H), 6.29 (m, 2H), 4.17 (s, 2H), 3.86 (s, 3H), 3.85 (s, 2H), 1.33 (s, 6H). |
| A-32 | 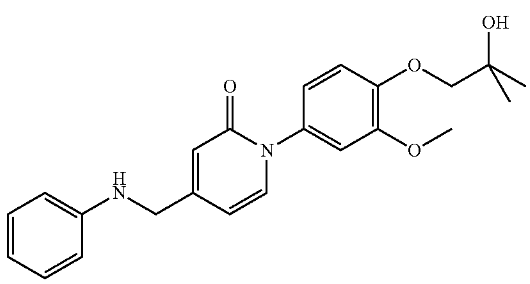 | #5 | #7 3.09 min. | 395 | $^1$H NMR (400 MHz, Chloroform-D) δ 7.28 (d, J = 7.0 Hz, 1H), 7.18 (m, 2H), 6.96 (d, J = 8.4 Hz, 1H), 6.90 (d, J = 2.6 Hz, 1H), 6.85 (m, 1H), 6.72 (m, 1H), 6.65 (s, 1H), 6.61 (d, J = 7.5 Hz, 2H), 6.25 (dd, J = 7.0 and 1.8 Hz, 1H), 4.24 (s, 2H), 3.84 (s, 5H), 1.35 (s, 6H). |
| A-33 | 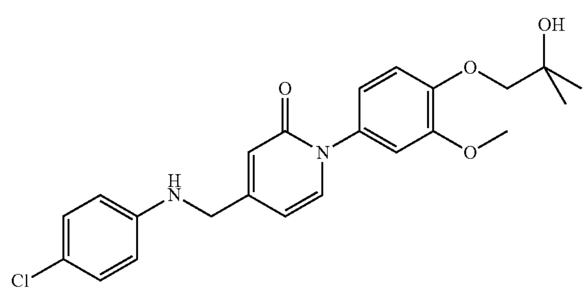 [SMILES: COc1cc(-n2ccc(CNc3ccc(Cl)cc3)cc2=O)ccc1OCC(C)(C)O] | #5 | #7 3.47 min. | 429 | $^1$H NMR (400 MHz, Chloroform-D) δ 7.38 (d, J = 7.0 Hz, 1H), 7.14 (d, J = 8.8 Hz, 2H), 6.97 (d, J = 8.8 Hz, 1H), 6.85 (m, 2H), 6.81 (s, 1H), 6.52 (d, J = 8.8 Hz, 2H), 6.42 (m, 1H), 4.28 (s, 2H), 3.85 (s, 5H), 1.36 (s, 6H). |
| A-34 | 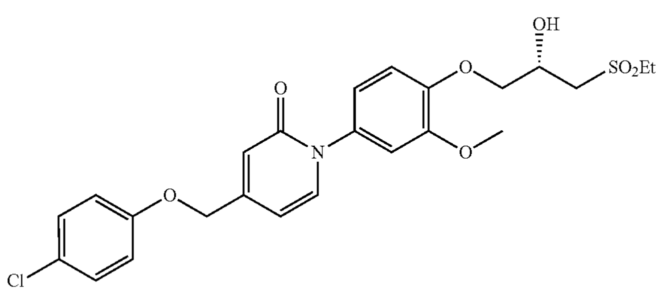 | #10 | #7 3.40 min | 508 | 1H NMR (CDCl3, 400 MHz) δ 7.34 (d, J = 7.2 Hz, 1H), 7.26 (m, 3H), 7.00 (d, J = 8.4 Hz, 1H), 6.93 (d, J = 2.6 Hz, 1H), 6.88 (m, 3H), 6.71 (s, 1H), 6.30 (m, 1H), 4.93 (s, 2H), 4.60 (m, 1H), 4.08 (m, 2H), 3.86 (s, 3H), 3.33 (m, 2H), 1.44 (t, J = 7.5 Hz, 3H) |

TABLE A-continued

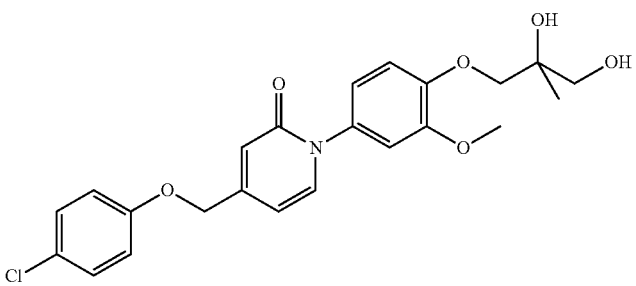 [SMILES: COc1cc(-n2ccc(COc3ccc(Cl)cc3)cc2=O)ccc1OCC(C)(O)CO]

| Ex. No. | Structure | Synthetic Procedure Used | HPLC Method ($t_R$ Min.) | MS (M + H) | NMR Data |
|---|---|---|---|---|---|
| A-35 | (4-chlorophenoxymethyl pyridinone with 3-methoxy-4-(2-hydroxy-2-methyl-3-hydroxypropoxy)phenyl) | #11 | #7 3.43 min | 446 | 1H NMR (CDCl3, 400 MHz) δ 7.31 (d, J = 7.2 Hz, 1H), 7.26 (m, 2H), 6.92 (m, 5H), 6.70 (s, 1H), 6.29 (m, 1H), 4.93 (s, 2H), 4.05 (m, 2H), 3.86 (s, 3H), 3.67 (m, 2H), 1.25 (s, 3H) |
| A-36 | (4-chlorophenoxymethyl pyridinone with 3-methyl-4-(2-hydroxy-2-methyl-3-hydroxypropoxy)phenyl) | #11 | #7 3.67 min | 430 | 1H NMR (CDCl3, 400 MHz) δ 7.31 (d, J = 7.2 Hz, 1H), 7.26 (m, 2H), 7.14 (m, 2H), 6.88 (m, 3H), 6.70 (s, 1H), 6.26 (m, 1H), 4.92 (s, 2H), 3.96 (m, 2H), 3.65 (m, 2H), 2.26 (s, 3H), 1.33 (s, 3H) |

TABLE B

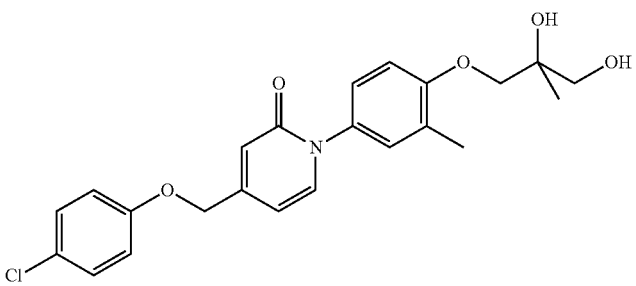 [SMILES: Cc1cc(-n2ccc(COc3ccc(Cl)cc3)cc2=O)ccc1OCC(C)(O)CO]

| Ex. No. | $R^1$ | $R^5$ | Synthetic Procedure Used | HPLC Method ($t_R$ Min.) | MS (M + H) | NMR Data |
|---|---|---|---|---|---|---|
| B-1 | CF$_3$O | OMe | #9 | #5 0.95 min | 450 | 1H NMR (400 MHz, Chloroform-D) δ 7.65 (2 H, d, J = 8.88 Hz), 7.43 (1 H, d, J = 7.49 Hz), 7.34 (2 H, d, J = 8.05 Hz), 6.97-7.02 (2 H, m), 6.93 (1 H, dd), 6.85 (1 H, s), 6.48 (1 H, dd), 3.89 (3 H, s), 3.88 (2 H, s), 1.37 (6 H, s). |
| B-2 | CF$_3$ | OMe | #9 | #5 0.94 min | 434 | 1H NMR (400 MHz, Chloroform-D) δ 7.72-7.79 (4 H, m), 7.46 (1 H, d, J = 6.94 Hz), 6.97-7.03 (2 H, m), 6.88-6.95 (2 H, m), 6.50 (1 H, dd), 3.89 (3 H, s), 3.88 (2 H, s), 1.37 (6 H, s). |
| B-3 | Ph | OMe | #9 | #5 0.99 min | 442 | $^1$H NMR (400 MHz, CHLOROFORM-d) δ ppm 7.73 (3 H, s), 7.64-7.68 (2 H, m), 7.37-7.55 (5 H, m), 6.92-7.03 (4 H, m), 6.58 (1 H, dd), 3.90 (3 H, s), 3.88 (2 H, s), 1.37 (6 H, s) |

TABLE B-continued

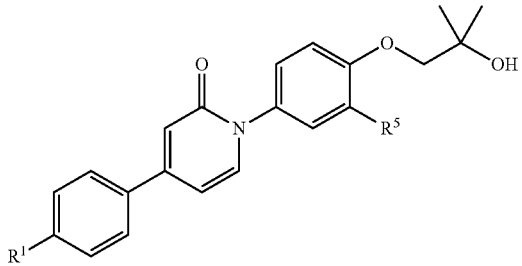

| Ex. No. | R¹ | R⁵ | Synthetic Procedure Used | HPLC Method ($t_R$ Min.) | MS (M + H) | NMR Data |
|---|---|---|---|---|---|---|
| B-4 | i-PrO | OMe | #9 | #5 0.93 min | 424 | ¹H NMR (400 MHz, CHLOROFORM-d) δ ppm 7.58 (2 H, d, J = 8.78 Hz), 7.39 (1 H, d), 6.95-7.03 (4 H, m), 6.90-6.94 (1 H, m), 6.87 (1 H, s), 6.53 (1 H, dd), 4.59-4.68 (1 H, m), 3.88 (3 H, s), 3.88 (2 H, s), 1.40 (3 H, s), 1.38 (3 H, s), 1.37 (6 H, s) |
| B-5 | PhO | OMe | #9 | #5 0.99 min | | ¹H NMR (400 MHz, CHLOROFORM-d) δ ppm 7.61 (2 H, d, J = 8.78 Hz), 7.37-7.46 (3 H, m), 7.15-7.23 (1 H, m), 7.10 (4 H, d, J = 8.78 Hz), 6.97-7.03 (2 H, m), 6.94 (2 H, dd, J = 4.39, 2.13 Hz), 6.57 (1 H, dd), 3.89 (3 H, s), 3.88 (2 H, s), 1.37 (6 H, s) |
| B-6 | CHF₂—CF₂O | OMe | #12 | #5 0.92 min | 482 | ¹H NMR (400 MHz, CHLOROFORM-d) δ ppm 7.63-7.67 (2 H, m), 7.43 (1 H, d, J = 7.26 Hz), 7.34 (2 H, d, J = 8.58 Hz), 6.97-7.03 (2 H, m), 6.90-6.96 (1 H, m), 6.87 (1 H, d, J = 1.76 Hz), 6.49 (1 H, dd, J = 7.26, 1.98 Hz), 5.80-6.11 (1 H, m), 3.89 (3 H, s), 3.88 (2 H, s), 1.37 (6 H, s) |
| B-7 | c-PrO | OMe | #12 | #5 0.91 min | 422 | ¹H NMR (500 MHz, CHLOROFORM-d) δ ppm 7.57-7.61 (2 H, m), 7.38 (1 H, d, J = 7.21 Hz), 7.13-7.18 (2 H, m), 6.96-7.03 (2 H, m), 6.89-6.95 (1 H, m), 6.85 (1 H, d, J = 1.66 Hz), 6.50 (1 H, dd, J = 7.21, 1.94 Hz), 3.88 (3 H, s), 3.88 (2 H, s), 3.78-3.82 (1 H, m), 1.37 (6 H, s), 0.81-0.86 (4 H, m) |
| B-8 | CF₃CH₂ | OMe | #12 | #5 0.91 min | 448 | ¹H NMR (400 MHz, CHLOROFORM-d) δ ppm 7.63 (2 H, d, J = 8.14 Hz), 7.40-7.46 (3 H, m), 6.96-7.03 (2 H, m), 6.85-6.95 (2 H, m), 6.51 (1 H, dd, J = 7.26, 1.98 Hz), 3.89 (3 H, s), 3.88 (2 H, s), 3.45 (2 H, q, J = 10.64 Hz), 1.37 (6 H, s) |
| B-9 | CHF₂O | OMe | #13 | #5 0.87 min | 432 | ¹H NMR (400 MHz, CHLOROFORM-d) δ ppm 7.63 (2 H, d), 7.42 (1 H, d, J = 7.04 Hz), 7.24 (2 H, d, J = 8.58 Hz), 6.95-7.03 (2 H, m), 6.90-6.93 (1 H, m), 6.86 (1 H, s), 6.48 (1 H, d, J = 7.26 Hz), 6.40-6.78 (1 H, m), 3.88 (3 H, s), 3.87 (2 H, s), 1.37 (6 H, s) |
| B-10 | CHF₂O | Me | #13 | #5 0.93 min | 416 | ¹H NMR (400 MHz, CHLOROFORM-d) δ ppm 7.69 (2 H, d, J = 8.80 Hz), 7.52 (1 H, d, J = 7.04 Hz), 7.29 (2 H, s), 7.19-7.25 (2 H, m), 7.12 (1 H, d, J = 1.76 Hz), 6.91-6.97 (1 H, m), 6.71 (1 H, dd), 6.43-6.81 (1 H, m), 3.88 (2 H, s), 2.34 (3 H, s), 1.42 (6 H, s) |
| B-11 | CF₃O | Me | #9 | #5 1.00 min | 434 | ¹H NMR (400 MHz, CHLOROFORM-d) δ ppm 7.66 (2 H, d, J = 8.80 Hz), 7.44 (1 H, d), 7.35 (2 H, d), 7.17-7.24 (2 H, m), 6.89-6.95 (2 H, m), 6.49-6.54 (1 H, m), 3.86 (2 H, s), 2.32 (3 H, s), 1.40 (6 H, s) |
| B-12 | CF₃ | Me | #9 | #5 0.99 min | 418 | ¹H NMR (400 MHz, CHLOROFORM-d) δ ppm 7.76 (4 H, d, J = 1.98 Hz), 7.51 (1 H, d, J = 7.04 Hz), 7.18-7.23 (2 H, m), 7.07 (1 H, d, J = 1.54 Hz), 6.90-6.95 (1 H, m), 6.64 (1 H, dd), 3.86 (2 H, s), 2.32 (3 H, s), 1.40 (6 H, s) |
| B-13 | CF₃O | Et | #9 | #5 1.06 | 448 | ¹H NMR (500 MHz, CHLOROFORM-d) δ ppm 7.63-7.71 (2 H, m), 7.46 (1 H, d, J = 6.94 Hz), 7.36 (2 H, d, J = 8.05 Hz), 7.22-7.26 (2 H, m), 6.95 (1 H, d, J = 8.32 Hz), 6.92 (1 H, d, J = 1.66 Hz), 6.52 (1 H, dd, J = 7.07, 2.08 Hz), 3.87 (2 H, s), 2.75 (2 H, q, J = 7.49 Hz), 1.42 (6 H, s), 1.28 (3 H, t, J = 7.49 Hz) |

TABLE B-continued

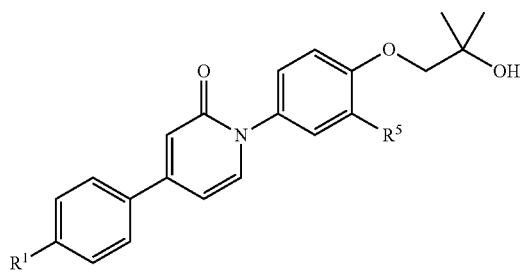

| Ex. No. | R¹ | R⁵ | Synthetic Procedure Used | HPLC Method ($t_R$ Min.) | MS (M + H) | NMR Data |
|---|---|---|---|---|---|---|
| B-14 | CF₃ | Et | #9 | #5 1.04 min | 432 | ¹H NMR (500 MHz, CHLOROFORM-d) δ ppm 7.69-7.80 (4 H, m), 7.45 (1 H, d, J = 7.21 Hz), 7.23-7.26 (2 H, m), 6.94 (1 H, d, J = 8.32 Hz), 6.90 (1 H, d, J = 1.66 Hz), 6.49 (1 H, dd, J = 7.21, 1.94 Hz), 3.86 (2 H, s), 2.74 (2 H, q, J = 7.49 Hz), 1.41 (6 H, s), 1.27 (3 H, t, J = 7.49 Hz) |
| B-15 | CF₃O | Cl | #9 | #5 1.01 min | 454 | ¹H NMR (400 MHz, CHLOROFORM-d) δ ppm 7.66 (2 H, d), 7.48 (1 H, d, J = 2.42 Hz), 7.41 (1 H, d, J = 7.26 Hz), 7.32-7.37 (2 H, m), 7.31 (1 H, d, J = 2.64 Hz), 7.04 (1 H, d, J = 8.80 Hz), 6.90 (1 H, d, J = 1.54 Hz), 6.53 (1 H, dd, J = 7.04, 1.98 Hz), 3.91 (2 H, s), 1.41 (6 H, s) |
| B-16 | CF₃ | CN | #9 | #5 0.93 | 429 | ¹H NMR (400 MHz, CHLOROFORM-d) δ ppm 7.77 (2 H, d, J = 8.36 Hz), 7.73 (2 H, d, J = 8.36 Hz), 7.63-7.69 (2 H, m, J = 4.79, 2.64, 2.45, 2.45 Hz), 7.42 (1 H, d, J = 6.60 Hz), 7.12 (1 H, d, J = 9.68 Hz), 6.92 (1 H, d, J = 1.54 Hz), 6.57 (1 H, dd, J = 7.04, 1.98 Hz), 3.98 (2 H, s), 1.43 (6 H, s) |
| B-17 | c-Pr | OMe | #12 | #5 0.94 min | 406 | ¹H NMR (400 MHz, CHLOROFORM-d) δ ppm 7.55 (2 H, d, J = 8.14 Hz), 7.44 (1 H, d, J = 7.26 Hz), 7.18 (2 H, d, J = 8.36 Hz), 6.87-7.03 (4 H, m), 6.64 (1 H, d, J = 7.04 Hz), 3.87 (5 H, s), 1.91-2.01 (1 H, m), 1.36 (6 H, s), 1.02-1.09 (2 H, m), 0.73-0.81 (2 H, m) |
| B-18 | Cl | OMe | #9 | #5 0.91 min | 400 | ¹H NMR (400 MHz, CHLOROFORM-d) δ ppm 7.54-7.59 (2 H, m), 7.45-7.49 (2 H, m), 7.42 (1 H, d, J = 7.28 Hz), 6.96-7.03 (2 H, m), 6.89-6.94 (1 H, m), 6.85 (1 H, d, J = 1.51 Hz), 6.48 (1 H, dd), 3.88 (3 H, s), 3.88 (2 H, s), 1.37 (6 H, s) |
| B-19 | F | OMe | #9 | #5 0.85 min | 384 | ¹H NMR (400 MHz, CHLOROFORM-d) δ ppm 7.59-7.64 (2 H, m), 7.41 (1 H, d), 7.18 (2 H, t), 6.96-7.03 (2 H, m), 6.90-6.94 (1 H, m), 6.84 (1 H, d), 6.47 (1 H, dd), 3.89 (3 H, s), 3.88 (2 H, s), 1.37 (6 H, s) |
| B-20 | H | OMe | #9 | #5 0.84 min | 366 | ¹H NMR (400 MHz, CHLOROFORM-d) δ ppm 7.62-7.67 (2 H, m), 7.46-7.54 (3 H, m), 7.42 (1 H, d), 6.97-7.04 (2 H, m), 6.91-6.95 (1 H, m), 6.89 (1 H, d), 6.53 (1 H, dd), 3.89 (3 H, s), 3.88 (2 H, s), 1.37 (6 H, s) |
| B-21 | CF₃O | MeSO₂ | #9 | #5 0.91 min | 498 | ¹H NMR (400 MHz, CHLOROFORM-d) δ ppm 7.97 (1 H, d, J = 2.42 Hz), 7.79 (1 H, dd, J = 8.80, 2.42 Hz), 7.66 (2 H, d, J = 8.80 Hz), 7.43 (1 H, d, J = 7.04 Hz), 7.35 (2 H, d, J = 7.92 Hz), 7.18 (1 H, d, J = 8.80 Hz), 6.88 (1 H, s), 6.55 (1 H, d, J = 6.60 Hz), 4.11 (2 H, s), 3.30 (3 H, s), 1.40 (6 H, s) |

TABLE C

| Ex. No. | Structure | Synthetic Procedure Used | HPLC Method ($t_R$ Min) | MS (M + H) | NMR Data |
|---|---|---|---|---|---|
| C-1 | 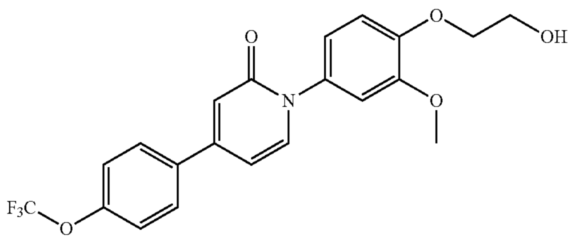 [SMILES: COc1cc(-n2ccc(-c3ccc(OC(F)(F)F)cc3)cc2=O)ccc1OCCO] | #9 | #5 0.88 min | 422 | $^1$H NMR (400 MHz, CHLOROFORM-d) δ ppm 7.62-7.67 (2 H, m), 7.43 (1 H, d, J = 7.04 Hz), 7.33 (2 H, d, J = 7.92 Hz), 7.01-7.06 (1 H, m), 6.98 (1 H, d, J = 2.42 Hz), 6.91-6.95 (1 H, m), 6.86 (1 H, d, J = 1.54 Hz), 6.48 (1 H, dd, J = 7.26, 1.98 Hz), 4.16-4.21 (2 H, m), 3.96-4.00 (2 H, m), 3.90 (3 H, s) |
| C-2 | 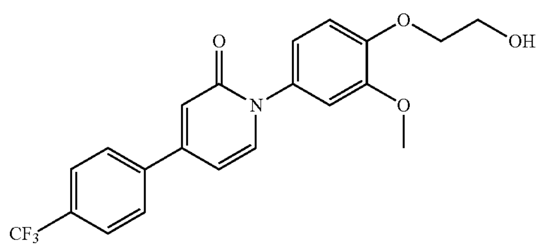 [SMILES: COc1cc(-n2ccc(-c3ccc(C(F)(F)F)cc3)cc2=O)ccc1OCCO] | #9 | #5 0.87 min | 406 | $^1$H NMR (400 MHz, CHLOROFORM-d) δ ppm 7.70-7.78 (4 H, m), 7.46 (1 H, d, J = 6.82 Hz), 7.04 (1 H, d, J = 8.36 Hz), 6.98 (1 H, d, J = 2.42 Hz), 6.88-6.96 (2 H, m), 6.50 (1 H, dd, J = 7.26, 1.98 Hz), 4.16-4.21 (2 H, m), 3.96-4.01 (2 H, m), 3.90 (3 H, s) |
| C-3 | 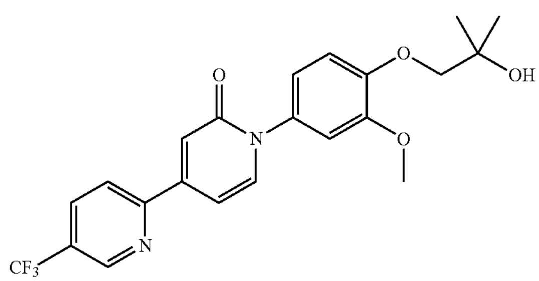 [SMILES: COc1cc(-n2ccc(-c3ccc(C(F)(F)F)cn3)cc2=O)ccc1OCC(C)(C)O] | #10 | #5 0.88 min | 435 | $^1$H NMR (400 MHz, CHLOROFORM-d) δ ppm 9.01 (1 H, s), 8.08 (1 H, d, J = 1.76 Hz), 7.92 (1 H, d, J = 8.36 Hz), 7.52 (1 H, d, J = 7.04 Hz), 7.29 (1 H, d, J = 1.54 Hz), 7.09 (1 H, dd, J = 7.04, 1.98 Hz), 7.00-7.03 (1 H, m), 6.98 (1 H, d, J = 2.42 Hz), 6.90-6.95 (1 H, m), 3.89 (3 H, s), 3.88 (2 H, s), 1.37 (6 H, s) |
| C-4 | 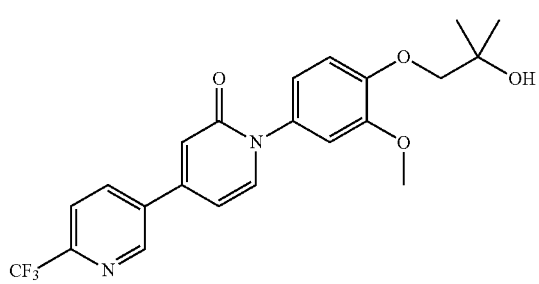 | #10 | #5 0.83 min | 435 | $^1$H NMR (400 MHz, CHLOROFORM-d) δ ppm 8.99 (1 H, d, J = 1.98 Hz), 8.09 (1 H, d, J = 6.60 Hz), 7.83 (1 H, d, J = 7.48 Hz), 7.49-7.55 (1 H, m), 6.99-7.05 (1 H, m), 6.97 (1 H, d, J = 2.42 Hz), 6.88-6.95 (2 H, m), 6.49 (1 H, dd, J = 7.04, 1.98 Hz), 3.89 (3 H, s), 3.88 (2 H, s), 1.37 (6 H, s) |

TABLE C-continued

| Ex. No. | Structure | Synthetic Procedure Used | HPLC Method ($t_R$ Min) | MS (M + H) | NMR Data |
|---|---|---|---|---|---|
| C-5 | 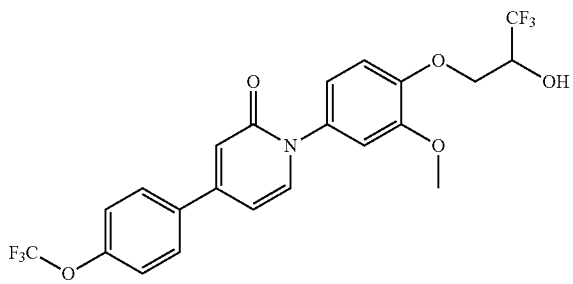 [SMILES: COc1cc(-n2ccc(-c3ccc(OC(F)(F)F)cc3)cc2=O)ccc1OCC(O)C(F)(F)F] | #9 | #5 0.98 min | 490 | $^1$H NMR (500 MHz, CHLOROFORM-d) δ ppm 7.66-7.69 (2 H, m), 7.46-7.49 (1 H, m), 7.36 (2 H, d, J = 8.05 Hz), 7.08 (1 H, d, J = 8.60 Hz), 7.02 (1 H, d, J = 2.50 Hz), 6.98 (1 H, d, J = 1.66 Hz), 6.95 (1 H, dd, J = 8.46, 2.36 Hz), 6.60 (1 H, dd, J = 7.21, 1.94 Hz), 4.37-4.44 (1 H, m, J = 6.80, 6.80, 6.80, 6.80, 3.33 Hz), 4.31-4.35 (1 H, m), 4.22-4.27 (1 H, m), 3.91 (3 H, s) |
| C-6 | 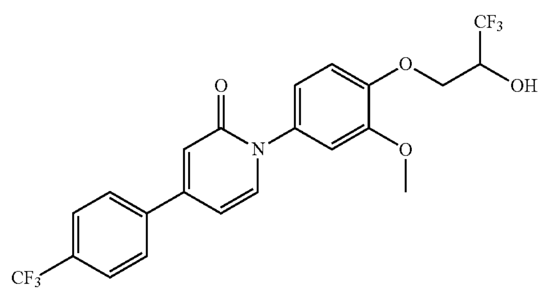 [SMILES: COc1cc(-n2ccc(-c3ccc(C(F)(F)F)cc3)cc2=O)ccc1OCC(O)C(F)(F)F] | #9 | #5 0.96 min | 474 | $^1$H NMR (500 MHz, CHLOROFORM-d) δ ppm 7.73-7.80 (4 H, m), 7.53 (1 H, d, J = 6.94 Hz), 7.06-7.11 (2 H, m), 7.02 (1 H, d, J = 2.50 Hz), 6.95 (1 H, dd, J = 8.46, 2.36 Hz), 6.67 (1 H, dd, J = 7.07, 2.08 Hz), 4.37-4.46 (1 H, m), 4.31-4.35 (1 H, m), 4.21-4.28 (1 H, m), 3.91 (3 H, s) |
| C-7 | 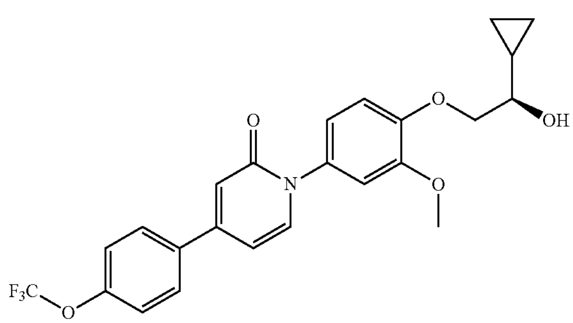 [SMILES: COc1cc(-n2ccc(-c3ccc(OC(F)(F)F)cc3)cc2=O)ccc1OC[C@H](O)C1CC1] | #9 | #5 1.08 min | 462 | $^1$H NMR (400 MHz, CHLOROFORM-d) δ ppm 7.62-7.70 (2 H, m), 7.43 (1 H, d, J = 7.04 Hz), 7.34 (2 H, d, J = 7.92 Hz), 7.04 (1 H, d, J = 8.58 Hz), 6.98 (1 H, d, J = 2.20 Hz), 6.91-6.96 (1 H, m), 6.86 (1 H, d, J = 1.76 Hz), 6.48 (1 H, dd, J = 7.26, 1.98 Hz), 4.22 (1 H, dd, J = 9.90, 2.86 Hz), 4.04 (1 H, dd, J = 9.79, 8.25 Hz), 3.89 (3 H, s), 3.37 (1 H, td, J = 8.36, 2.86 Hz), 0.89-1.05 (1 H, m), 0.51-0.68 (2 H, m), 0.41-0.52 (1 H, m), 0.28-0.37 (1 H, m) |
| C-8 | 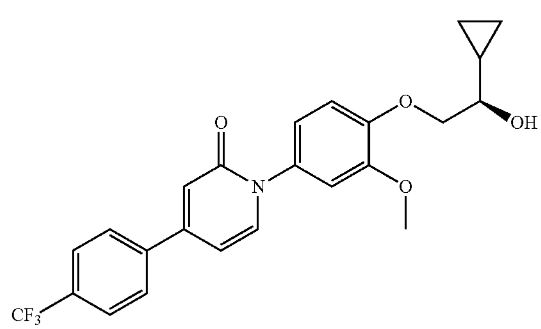 [SMILES: COc1cc(-n2ccc(-c3ccc(C(F)(F)F)cc3)cc2=O)ccc1OC[C@H](O)C1CC1] | #9 | #5 1.07 | 446 | $^1$H NMR (400 MHz, CHLOROFORM-d) δ ppm 7.71-7.79 (4 H, m), 7.46 (1 H, d, J = 7.26 Hz), 7.05 (1 H, d, J = 8.36 Hz), 6.98 (1 H, d, J = 2.20 Hz), 6.92-6.96 (1 H, m), 6.90 (1 H, d, J = 1.54 Hz), 6.50 (1 H, dd, J = 7.04, 1.98 Hz), 4.23 (1 H, dd, J = 9.68, 2.86 Hz), 4.05 (1 H, dd, J = 9.68, 8.36 Hz), 3.89 (3 H, s), 3.37 (1 H, td, J = 8.31, 2.75 Hz), 0.94-1.04 (1 H, m), 0.53-0.68 (2 H, m), 0.43-0.51 (1 H, m), 0.33 (1 H, ddd, J = 9.13, 4.73, 4.62 Hz) |

TABLE C-continued

| Ex. No. | Structure | Synthetic Procedure Used | HPLC Method ($t_R$ Min) | MS (M + H) | NMR Data |
|---|---|---|---|---|---|
| C-9 | 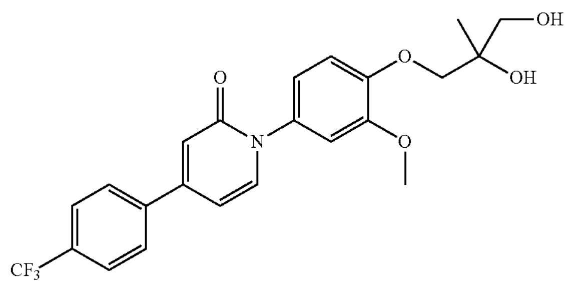 [SMILES: COc1cc(-n2ccc(-c3ccc(C(F)(F)F)cc3)cc2=O)ccc1OCC(C)(O)CO] | #14 | #5 0.86 min | 450 | $^1$H NMR (400 MHz, MeOD) δ ppm 7.93 (2 H, d, J = 8.14 Hz), 7.82 (2 H, d, J = 8.36 Hz), 7.73 (1 H, d, J = 7.04 Hz), 7.13 (1 H, d, J = 8.58 Hz), 7.08 (1 H, d, J = 2.42 Hz), 6.96 (1 H, dd, J = 8.47, 2.53 Hz), 6.92 (1 H, d, J = 1.54 Hz), 6.83 (1 H, dd, J = 7.26, 1.98 Hz), 3.97 (2 H, q, J = 9.24 Hz), 3.89 (3 H, s), 3.60 (2 H, q, J = 11.08 Hz), 1.29 (3 H, s) |
| C-10 | 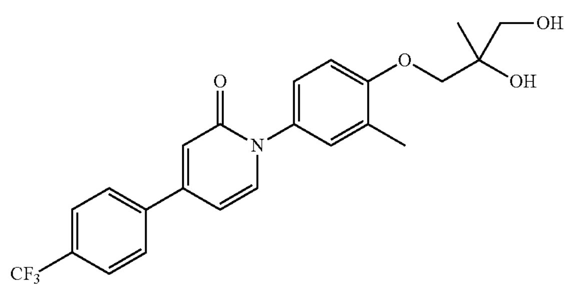 [SMILES: Cc1cc(-n2ccc(-c3ccc(C(F)(F)F)cc3)cc2=O)ccc1OCC(C)(O)CO] | #14 | #5 0.90 min | 434 | $^1$H NMR (400 MHz, CHLOROFORM-d) δ ppm 7.69-7.77 (4 H, m), 7.43 (1 H, d, J = 7.26 Hz), 7.18-7.26 (2 H, m), 6.93-7.01 (1 H, m), 6.89 (1 H, d, J = 1.76 Hz), 6.49 (1 H, dd, J = 7.04, 1.98 Hz), 3.99 (2 H, d, J = 1.54 Hz), 3.78 (1 H, d, J = 11.00 Hz), 3.63 (1 H, d, J = 10.34 Hz), 2.30 (3 H, s), 1.36 (3 H, s) |
| C-11 | 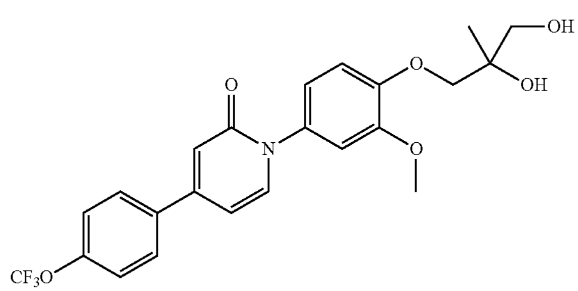 | #14 | #5 0.88 min | 466 | $^1$H NMR (400 MHz, CHLOROFORM-d) δ ppm 7.64-7.69 (2 H, m), 7.44 (1 H, d, J = 7.04 Hz), 7.35 (2 H, d, J = 7.92 Hz), 6.98-7.04 (2 H, m), 6.92-6.97 (1 H, m), 6.87 (1 H, d, J = 1.54 Hz), 6.50 (1 H, dd, J = 7.26, 1.98 Hz), 4.08-4.14 (1 H, m), 3.98-4.05 (1 H, m), 3.91 (3 H, s), 3.85 (1 H, dd, J = 11.44, 4.40 Hz), 3.54-3.63 (1 H, m), 3.27 (1 H, s), 2.93 (1 H, dd, J = 8.91, 4.51 Hz), 1.28 (3 H, s) |
| C-12 | 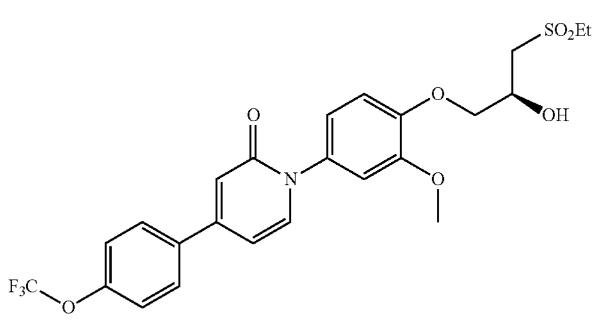 | #15 | #5 0.90 min | 528 | $^1$H NMR (400 MHz, CHLOROFORM-d) δ ppm 7.65-7.70 (2 H, m), 7.47 (1 H, d, J = 7.04 Hz), 7.35 (2 H, d, J = 8.14 Hz), 7.04 (1 H, d, J = 8.36 Hz), 7.00 (1 H, d, J = 2.42 Hz), 6.90-6.97 (2 H, m), 6.58 (1 H, dd, J = 7.15, 2.09 Hz), 4.61-4.68 (1 H, m), 4.11-4.16 (2 H, m), 3.89 (3 H, s), 3.30-3.38 (1 H, m), 3.27 (1 H, d, J = 2.64 Hz), 3.15-3.26 (2 H, m), 1.46 (3 H, t, J = 7.48 Hz) |

TABLE C-continued

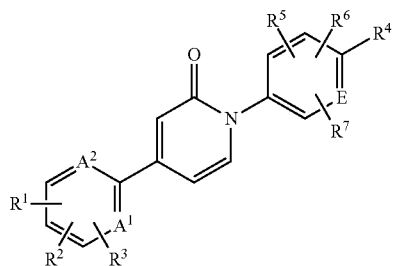

| Ex. No. | Structure | Synthetic Procedure Used | HPLC Method ($t_R$ Min) | MS (M + H) | NMR Data |
|---|---|---|---|---|---|
| C-13 | 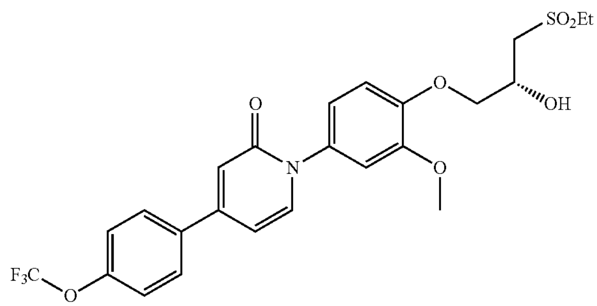 | #15 | #5 0.90 min | 528 | $^1$H NMR (400 MHz, CHLOROFORM-d) δ ppm 7.66-7.71 (2 H, m), 7.49 (1 H, d, J = 7.04 Hz), 7.36 (2 H, d, J = 8.14 Hz), 7.05 (1 H, d, J = 8.36 Hz), 6.99 (2 H, dd, J = 3.74, 2.20 Hz), 6.91-6.96 (1 H, m), 6.61 (1 H, dd, J = 7.26, 1.98 Hz), 4.62-4.69 (1 H, m), 4.11-4.17 (2 H, m), 3.89 (3 H, s), 3.30-3.40 (1 H, m), 3.27 (1 H, d, J = 2.64 Hz), 3.16-3.26 (2 H, m), 1.46 (3 H, t, J = 7.48 Hz) |
| C-14 | 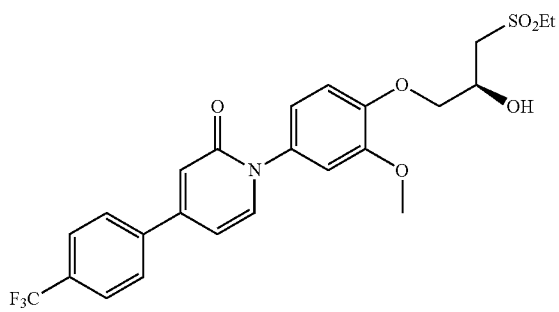 | #15 | #5 0.88 min | 512 | $^1$H NMR (400 MHz, CHLOROFORM-d) δ ppm 7.72-7.80 (4 H, m), 7.52 (1 H, d, J = 7.04 Hz), 7.01-7.08 (2 H, m), 7.00 (1 H, d, J = 2.20 Hz), 6.90-6.96 (1 H, m), 6.66 (1 H, dd, J = 7.15, 1.87 Hz), 4.60-4.69 (1 H, m), 4.09-4.16 (2 H, m), 3.89 (3 H, s), 3.31-3.38 (1 H, m), 3.28 (1 H, s), 3.15-3.25 (2 H, m), 1.46 (3 H, t, J = 7.48 Hz) |
| C-15 | 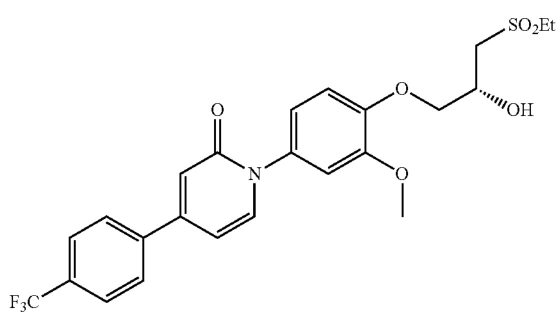 | #15 | #5 0.92 | 496 | $^1$H NMR (400 MHz, CHLOROFORM-d) δ ppm 7.73-7.80 (4 H, m), 7.50 (1 H, d, J = 6.60 Hz), 7.19-7.25 (2 H, m), 7.07 (1 H, d, J = 1.54 Hz), 6.92-6.96 (1 H, m), 6.64 (1 H, dd, J = 7.04, 1.98 Hz), 4.69-4.76 (1 H, m), 4.06-4.17 (2 H, m), 3.29-3.39 (2 H, m), 3.15-3.28 (2 H, m), 2.29 (3 H, s), 1.48 (3 H, t, J = 7.48 Hz) |
| C-16 | 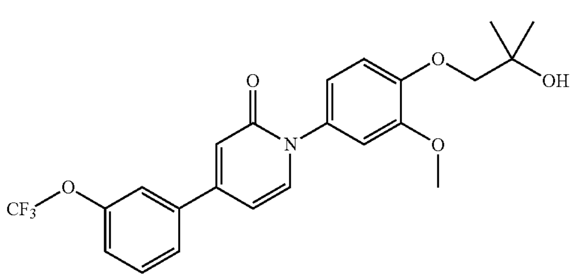 [SMILES: COc1cc(-n2ccc(-c3cccc(OC(F)(F)F)c3)cc2=O)ccc1OCC(C)(C)O] | #9 | #5 0.95 min | 450 | $^1$H NMR (400 MHz, CHLOROFORM-d) δ ppm 7.49-7.60 (3 H, m), 7.47 (1 H, s), 7.35 (1 H, d), 6.89-7.05 (4 H, m), 6.63 (1 H, d, J = 7.04 Hz), 3.89 (5 H, br. s.), 1.38 (6 H, s) |

TABLE D

| Ex. No. | R¹ | R² | D¹ | R⁵ | Synthetic Procedure Used | HPLC Method ($t_R$ Min) | MS (M + H) | NMR Data |
|---|---|---|---|---|---|---|---|---|
| D-1 | H | H | O | OMe | #7 | #5 0.87 min | 396 | 1H NMR (400 MHz, Chloroform-D) δ ppm 7.34-7.47 (5 H, m), 7.28 (1 H, d, J = 7.78 Hz), 6.96 (1 H, d, J = 8.53 Hz), 6.80-6.90 (2 H, m), 6.28 (1 H, d, J = 2.51 Hz), 6.16 (1 H, dd, J = 7.65, 2.64 Hz), 5.08 (2 H, s), 3.85 (5 H, s), 1.35 (6 H, s) |
| D-2 | 4-Cl | H | O | OMe | #7 | #5 0.93 min | 430 | ¹H NMR (400 MHz, Chloroform-D) δ ppm 7.32-7.44 (4 H, m), 7.24-7.28 (1 H, m), 6.96 (1 H, d, J = 8.53 Hz), 6.80-6.91 (2 H, m), 6.06-6.18 (2 H, m), 5.03 (2 H, s), 3.85 (5 H, d, J = 1.76 Hz), 1.35 (6 H, s) |
| D-3 | 4-F | H | O | OMe | #7 | #5 0.88 min | 414 | ¹H NMR (400 MHz, Chloroform-D) δ ppm 7.41 (2 H, dd, J = 8.53, 5.27 Hz), 7.27-7.31 (1 H, m), 7.11 (2 H, t, J = 8.66 Hz), 6.96 (1 H, d, J = 8.28 Hz), 6.80-6.91 (2 H, m), 6.23 (1 H, d, J = 2.76 Hz), 6.12 (1 H, dd, J = 7.53, 2.51 Hz), 5.03 (2 H, s), 3.85 (5 H, d, J = 1.51 Hz), 1.35 (6 H, s) |
| D-4 | 4-Cl | H | S | OMe | #8 | #5 0.96 min | 446 | ¹H NMR (400 MHz, Chloroform-D) δ ppm 7.29-7.40 (4 H, m), 7.21 (1 H, d, J = 7.28 Hz), 6.95 (1 H, d, J = 8.53 Hz), 6.79-6.90 (2 H, m), 6.55 (1 H, d, J = 2.01 Hz), 6.18 (1 H, dd, J = 7.28, 2.01 Hz), 4.16 (2 H, s), 3.85 (5 H, s), 1.35 (6 H, s) |
| D-5 | 4-F | H | S | OMe | #8 | #5 0.91 min | 430 | ¹H NMR (400 MHz, Chloroform-D) δ ppm 7.39 (2 H, dd, J = 8.78, 5.27 Hz), 7.20 (1 H, d, J = 7.28 Hz), 7.05 (2 H, t, J = 8.66 Hz), 6.95 (1 H, d, J = 8.53 Hz), 6.80-6.90 (2 H, m), 6.52 (1 H, d, J = 2.01 Hz), 6.17 (1 H, dd, J = 7.28, 2.01 Hz), 4.16 (2 H, s), 3.85 (5 H, s), 1.35 (6 H, s) |
| D-6 | H | H | S | OMe | #8 | #5 0.91 min | 412 | ¹H NMR (400 MHz, Chloroform-D) δ ppm 7.28-7.46 (5 H, m), 7.17 (1 H, d, J = 7.28 Hz), 6.96 (1 H, d, J = 8.53 Hz), 6.81-6.91 (2 H, m), 6.46 (1 H, d, J = 2.01 Hz), 6.11 (1 H, dd, J = 7.15, 2.13 Hz), 4.18 (2 H, s), 3.85 (5 H, s), 1.35 (6 H, s) |
| D-7 | H | 2-F | O | OMe | #7 | #5 0.87 | 414 | 1H NMR (400 MHz, MeOD) δ ppm 7.40-7.47 (2 H, m), 7.28-7.37 (1 H, m, J = 7.79, 7.79, 5.56, 1.76 Hz), 7.04-7.17 (2 H, m), 6.96 (1 H, d, J = 8.36 Hz), 6.90 (1 H, d, J = 2.42 Hz), 6.77 (1 H, dd, J = 8.36, 2.42 Hz), 6.15 (1 H, dd, J = 7.48, 2.64 Hz), 6.04 (1 H, d, J = 2.64 Hz), 5.11 (2 H, s), 3.77 (3 H, s), 3.74 (2 H, s), 1.23 (6 H, s) |
| D-8 | H | 2-Cl | O | OMe | #7 | #5 0.91 | 430 | 1H NMR (400 MHz, MeOD) δ ppm 7.42-7.51 (2 H, m), 7.35-7.41 (1 H, m), 7.25-7.31 (2 H, m), 6.97 (1 H, d, J = 8.58 Hz), 6.90 (1 H, d, J = 2.64 Hz), 6.78 (1 H, dd, J = 8.36, 2.42 Hz), 6.18 (1 H, dd, J = 7.48, 2.64 Hz), 6.01 (1 H, d, J = 2.64 Hz), 5.15 (2 H, s), 3.77 (3 H, s), 3.74 (2 H, s), 1.23 (6 H, s) |

TABLE D-continued

| Ex. No. | R¹ | R² | D¹ | R⁵ | Synthetic Procedure Used | HPLC Method ($t_R$ Min) | MS (M + H) | NMR Data |
|---|---|---|---|---|---|---|---|---|
| D-9 | H | 2-CN | O | OMe | #7 | #5 0.82 | 421 | 1H NMR (400 MHz, MeOD) δ ppm 7.73 (1 H, d, J = 7.48 Hz), 7.59-7.67 (2 H, m), 7.41-7.52 (2 H, m), 6.96 (1 H, d, J = 8.36 Hz), 6.91 (1 H, d, J = 2.42 Hz), 6.78 (1 H, dd, J = 8.58, 2.42 Hz), 6.18 (1 H, dd, J = 7.59, 2.75 Hz), 6.05 (1 H, d, J = 2.64 Hz), 5.22 (2 H, s), 3.77 (3 H, s), 3.73 (2 H, s), 1.23 (6 H, s) |
| D-10 | H | 3-F | O | OMe | #7 | #5 0.88 | 414 | 1H NMR (400 MHz, MeOD) δ ppm 7.43 (1 H, d, J = 7.70 Hz), 7.28-7.37 (1 H, m), 7.08-7.21 (2 H, m), 6.93-7.04 (2 H, m), 6.89 (1 H, d, J = 2.42 Hz), 6.77 (1 H, dd, J = 8.58, 2.42 Hz), 6.18 (1 H, dd, J = 7.59, 2.75 Hz), 5.98 (1 H, d, J = 2.64 Hz), 5.08 (2 H, s), 3.77 (3 H, s), 3.73 (2 H, s), 1.23 (6 H, s) |
| D-11 | H | 3-Cl | O | OMe | #7 | #5 0.93 | 430 | 1H NMR (400 MHz, MeOD) δ ppm 7.37-7.47 (2 H, m), 7.23-7.32 (3 H, m), 6.96 (1 H, d, J = 8.36 Hz), 6.89 (1 H, d, J = 2.64 Hz), 6.77 (1 H, dd, J = 8.58, 2.42 Hz), 6.18 (1 H, dd, J = 7.59, 2.75 Hz), 5.98 (1 H, d, J = 2.64 Hz), 5.07 (2 H, s), 3.77 (3 H, s), 3.73 (2 H, s), 1.23 (6 H, s) |
| D-12 | H | 3-CN | O | OMe | #7 | #5 0.82 | 421 | 1H NMR (400 MHz, MeOD) δ ppm 7.76 (1 H, s), 7.61-7.73 (2 H, m), 7.51 (1 H, t, J = 7.92 Hz), 7.44 (1 H, d, J = 7.70 Hz), 6.96 (1 H, d, J = 8.58 Hz), 6.90 (1 H, d, J = 2.42 Hz), 6.77 (1 H, dd, J = 8.36, 2.42 Hz), 6.20 (1 H, dd, J = 7.59, 2.75 Hz), 5.99 (1 H, d, J = 2.64 Hz), 5.13 (2 H, s), 3.76-3.80 (3 H, m), 3.74 (2 H, s), 1.23 (6 H, s) |
| D-13 | CF₃O | H | O | OMe | #7 | #5 0.97 | 480 | 1H NMR (400 MHz, CHLOROFORM-d) δ ppm 7.46 (2 H, d, J = 8.53 Hz), 7.25-7.32 (3 H, m), 6.96 (2 H, d, J = 8.53 Hz), 6.80-6.91 (2 H, m), 6.22 (1 H, d, J = 2.51 Hz), 6.13 (1 H, dd, J = 7.53, 2.51 Hz), 5.07 (2 H, s), 3.85 (5 H, s), 1.35 (6 H, s) |
| D-14 | CHF₂O | H | O | OMe | #8 | #5 0.89 min | 462 | ¹H NMR (400 MHz, CHLOROFORM-d) δ ppm 7.43 (2 H, d, J = 8.80 Hz), 7.23 (1 H, d, J = 8.14 Hz), 7.18 (2 H, d, J = 8.58 Hz), 6.97 (1 H, d, J = 8.58 Hz), 6.90 (1 H, d, J = 2.42 Hz), 6.83-6.87 (1 H, m), 6.34-6.73 (1 H, m), 6.03 (2 H, dd, J = 4.07, 1.65 Hz), 5.03 (2 H, s), 3.86 (3 H, s), 3.86 (2 H, s), 1.36 (6 H, s) |
| D-15 | CF₃ | H | O | OMe | #7 | #5 0.95 | 464 | 1H NMR (400 MHz, MeOD) ppm 7.61-7.69 (2 H, m), 7.54-7.61 (2 H, m), 7.46 (1 H, d, J = 7.70 Hz), 6.97 (1 H, d, J = 8.58 Hz), 6.90 (1 H, d, J = 2.42 Hz), 6.78 (1 H, dd, J = 8.58, 2.42 Hz), 6.21 (1 H, dd, J = 7.59, 2.75 Hz), 6.00 (1 H, d, J = 2.64 Hz), 5.18 (2 H, s), 3.78 (3 H, s), 3.74 (2 H, s), 1.24 (6 H, s) |
| D-16 | CN | H | O | OMe | #7 | #5 0.82 | 421 | 1H NMR (400 MHz, MeOD) δ ppm 7.64-7.73 (2 H, m), 7.56 (2 H, d, J = 8.58 Hz), 7.44 (1 H, d, J = 7.70 Hz), 6.96 (1 H, d, J = 8.58 Hz), 6.89 (1 H, d, J = 2.42 Hz), 6.77 (1 H, dd, J = 8.47, 2.53 Hz), 6.19 (1 H, dd, J = 7.59, 2.75 Hz), 5.97 (1 H, d, J = 2.64 Hz), 5.17 (2 H, s), 3.77 (3 H, s), 3.73 (2 H, s), 1.23 (6 H, s) |

TABLE D-continued

| Ex. No. | R¹ | R² | D¹ | R⁵ | Synthetic Procedure Used | HPLC Method ($t_R$ Min) | MS (M + H) | NMR Data |
|---|---|---|---|---|---|---|---|---|
| D-17 | c-Pr | H | O | OMe | #9 | #7 3.85 min | 436 | 1H NMR (CDCl₃, 400 MHz) δ 7.32 (m, 3 H), 7.11 (d, J = 8.2 Hz, 2 H), 6.94 (d, J = 7.7 Hz, 1 H), 6.84 (m, 3 H), 6.46 (d, J = 2.7 Hz, 1 H), 6.25 (m, 1 H), 5.06 (s, 2 H), 3.85 (s, 3 H), 1.92 (m, 1 H), 1.36 (s, 3 H), 0.98 (m, 2 H), 0.71 (m, 2 H) |
| D-18 | Ph | H | O | OMe | #7 | #8 3.80 min. | 472 | 1H NMR (500 MHz, DMSO) δ 7.69 (4 H, dd, J = 14.9, 7.7 Hz), 7.53 (3 H, t, J = 8.0 Hz), 7.47 (2 H, t, J = 7.7 Hz), 7.33-7.41 (1 H, m), 7.01 (1 H, d, J = 8.3 Hz), 6.94 (1 H, d, J = 2.2 Hz), 6.82 (1 H, dd, J = 8.5, 2.5 Hz), 6.08 (1 H, dd, J = 7.7, 2.8 Hz), 5.96 (1 H, d, J = 2.8 Hz), 5.18 (2 H, s), 3.76 (3 H, s), 3.72 (2 H, s), 1.20 (6 H, s). |
| D-19 | PhO | H | O | OMe | #7 | #8 3.77 min. | 488 | 1H NMR (500 MHz, CDCl3) δ 7.26-7.34 (4 H, m), 7.14 (1 H, d, J = 7.7 Hz), 7.06 (1 H, t, J = 7.4 Hz), 6.96 (4 H, dd, J = 8.8, 2.2 Hz), 6.88 (1 H, d, J = 8.3 Hz), 6.82 (1 H, d, J = 2.2 Hz), 6.77 (1 H, dd, J = 8.3, 2.2 Hz), 5.93-5.99 (2 H, m), 4.93 (2 H, s), 3.77-3.78 (5 H, m), 2.59 (1 H, s), 1.27 (6 H, s). |
| D-20 | F | 3-F | O | OMe | #7 | #5 0.89 | 432 | 1H NMR (400 MHz, MeOD) δ ppm 7.43 (1 H, d, J = 7.70 Hz), 7.28-7.37 (1 H, m), 7.08-7.21 (2 H, m), 6.93-7.04 (2 H, m), 6.89 (1 H, d, J = 2.42 Hz), 6.77 (1 H, dd, J = 8.58, 2.42 Hz), 6.18 (1 H, dd, J = 7.59, 2.75 Hz), 5.98 (1 H, d, J = 2.64 Hz), 5.08 (2 H, s), 3.77 (3 H, s), 3.73 (2 H, s), 1.23 (6 H, s) |
| D-21 | F | 2-F | O | OMe | #7 | #5 0.88 | 432 | 1H NMR (400 MHz, MeOD) δ ppm 7.39-7.54 (2 H, m), 6.88-7.01 (4 H, m), 6.77 (1 H, dd, J = 8.58, 2.42 Hz), 6.13 (1 H, dd, J = 7.48, 2.64 Hz), 6.04 (1 H, d, J = 2.64 Hz), 5.07 (2 H, s), 3.77 (3 H, s), 3.74 (2 H, s), 1.23 (6 H, s) |
| D-22 | H | 2,5-F₂ | O | OMe | #7 | #5 0.88 | 432 | 1H NMR (400 MHz, MeOD) δ ppm 7.71 (1 H, d, J = 7.48 Hz), 7.44-7.52 (1 H, m), 7.28-7.41 (2 H, m), 7.23 (1 H, d, J = 8.58 Hz), 7.17 (1 H, d, J = 2.42 Hz), 7.05 (1 H, dd, J = 8.58, 2.42 Hz), 6.45 (1 H, dd, J = 7.59, 2.75 Hz), 6.29 (1 H, d, J = 2.64 Hz), 5.38 (2 H, s), 4.04 (3 H, s), 4.01 (2 H, s), 1.50 (6 H, s) |
| D-23 | H | 3,5-F₂ | O | OMe | #7 | #5 0.90 | 432 | 1H NMR (400 MHz, MeOD) δ ppm 7.56 (1 H, d, J = 7.70 Hz), 7.05-7.17 (3 H, m), 6.93-7.04 (2 H, m), 6.89 (1 H, dd, J = 8.58, 2.42 Hz), 6.32 (1 H, dd, J = 7.59, 2.75 Hz), 6.09 (1 H, d, J = 2.64 Hz), 5.22 (2 H, s), 3.89 (3 H, s), 3.86 (2 H, s), 1.35 (6 H, s) |
| D-24 | F | 3,5-F₂ | O | OMe | #7 | #5 0.99 | 450 | 1H NMR (400 MHz, MeOD) δ ppm 7.56 (1 H, d, J = 7.70 Hz), 7.26-7.34 (2 H, m), 7.08 (1 H, d, J = 8.58 Hz), 7.01 (1 H, d, J = 2.64 Hz), 6.89 (1 H, dd, J = 8.36, 2.42 Hz), 6.31 (1 H, dd, J = 7.59, 2.75 Hz), 6.08 (1 H, d, J = 2.64 Hz), 5.17 (2 H, s), 3.89 (3 H, s), 3.86 (2 H, s), 1.35 (6 H, s) |
| D-25 | Cl | 3-F | O | OMe | #7 | #5 0.94 | 448 | 1H NMR (400 MHz, MeOD) δ ppm 7.42 (2 H, t, J = 8.36 Hz), 7.28 (1 H, dd, J = 10.01, 1.87 Hz), 7.19 (1 H, dd, J = |

TABLE D-continued

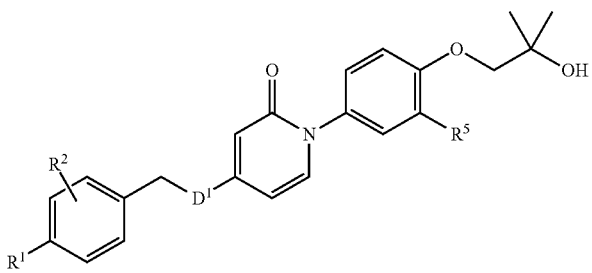

| Ex. No. | R¹ | R² | D¹ | R⁵ | Synthetic Procedure Used | HPLC Method ($t_R$ Min) | MS (M + H) | NMR Data |
|---|---|---|---|---|---|---|---|---|
| | | | | | | | | 8.14, 1.10 Hz), 6.96 (1 H, d, J = 8.58 Hz), 6.89 (1 H, d, J = 2.42 Hz), 6.77 (1 H, dd, J = 8.47, 2.53 Hz), 6.18 (1 H, dd, J = 7.59, 2.75 Hz), 5.97 (1 H, d, J = 2.64 Hz), 5.07 (2 H, s), 3.77 (3 H, s), 3.73 (2 H, s), 1.23 (6 H, s) |
| D-26 | MeO | 3-F | O | OMe | #7 | #5 0.86 | 444 | 1H NMR (400 MHz, MeOD) δ ppm 7.42 (1 H, d, J = 7.48 Hz), 7.12 (2 H, d, J = 9.90 Hz), 7.02 (1 H, t, J = 8.36 Hz), 6.96 (1 H, d, J = 8.58 Hz), 6.89 (1 H, d, J = 2.42 Hz), 6.77 (1 H, dd, J = 8.58, 2.42 Hz), 6.15 (1 H, dd, J = 7.59, 2.75 Hz), 5.98 (1 H, d, J = 2.64 Hz), 4.99 (2 H, s), 3.79 (3 H, s), 3.77 (3 H, s), 3.73 (2 H, s), 1.23 (6 H, s) |
| D-27 | CF₃O | 3-F | O | OMe | #7 | #5 0.98 | 498 | 1H NMR (400 MHz, MeOD) δ ppm 7.56 (1 H, d, J = 7.48 Hz), 7.46-7.53 (2 H, m), 7.37-7.43 (1 H, m), 7.08 (1 H, d, J = 8.58 Hz), 7.02 (1 H, d, J = 2.42 Hz), 6.89 (1 H, dd, J = 8.47, 2.53 Hz), 6.31 (1 H, dd, J = 7.59, 2.75 Hz), 6.10 (1 H, d, J = 2.64 Hz), 5.23 (2 H, s), 3.89 (3 H, s), 3.86 (2 H, s), 1.35 (6 H, s) |
| D-28 | Cl | 2-F | O | OMe | #7 | #8 3.55 min. | 448 | 1H NMR (500 MHz, DMSO) δ 7.57 (1 H, t, J = 8.3 Hz), 7.45-7.52 (2 H, m), 7.33 (1 H, d, J = 8.3 Hz), 6.97 (1 H, d, J = 8.3 Hz), 6.90 (1 H, s), 6.78 (1 H, dd, J = 8.5, 2.5 Hz), 6.00 (1 H, dd, J = 7.7, 2.8 Hz), 5.96 (1 H, d, J = 2.8 Hz), 5.11 (2 H, s), 3.72 (3 H, s), 3.68 (2 H, s), 2.03 (1 H, s), 1.17 (6 H, s). |
| D-29 | Cl | 3-Cl | O | OMe | #7 | #5 0.99 | 465 | 1H NMR (400 MHz, MeOD) δ ppm 7.41-7.51 (3 H, m), 7.31 (1 H, dd, J = 8.36, 1.98 Hz), 6.97 (1 H, d, J = 8.58 Hz), 6.90 (1 H, d, J = 2.42 Hz), 6.78 (1 H, dd, J = 8.58, 2.42 Hz), 6.17 (1 H, dd, J = 7.70, 2.64 Hz), 6.00 (1 H, d, J = 2.64 Hz), 5.13 (2 H, s), 3.77 (3 H, s), 3.74 (2 H, s), 1.23 (6 H, s) |
| D-30 | Cl | 2,6-F₂ | O | OMe | #7 | #8 3.55 min. | 466 | 1H NMR (500 MHz, CDCl3) δ 7.27 (1 H, d, J = 7.7 Hz), 7.01 (2 H, d, J = 7.2 Hz), 6.94 (1 H, d, J = 8.3 Hz), 6.86 (1 H, d, J = 2.2 Hz), 6.81 (1 H, dd, J = 8.3, 2.2 Hz), 6.35 (1 H, d, J = 2.8 Hz), 6.08 (1 H, dd, J = 7.4, 2.5 Hz), 5.07 (2 H, s), 3.84 (5 H, s), 1.34 (6 H, s). |
| D-31 | Cl | H | O | F | #17 | #5 0.95 | 418 | 1H NMR (400 MHz, MeOD) δ ppm 7.35-7.58 (5 H, m), 7.17-7.27 (2 H, m), 7.05-7.14 (1 H, m), 6.25 (1 H, dd, J = 7.78, 2.76 Hz), 6.06 (1 H, d, J = 2.51 Hz), 5.14 (2 H, s), 3.90 (2 H, s), 1.34 (6 H, s) |
| D-32 | F | H | O | Me | #17 | #5 0.93 | 398 | 1H NMR (400 MHz, MeOD) δ ppm 7.32-7.48 (3 H, m), 6.97-7.11 (4 H, m), 6.89 (1 H, d, J = 8.14 Hz), 6.13 (1 H, dd, J = 7.59, 2.75 Hz), 5.98 (1 H, d, J = 2.86 Hz), 5.03 (2 H, s), 3.73 (2 H, s), 2.20 (3 H, s), 1.26 (6 H, s) |
| D-33 | Cl | H | O | Me | #10 | #5 0.99 | 414 | 1H NMR (400 MHz, MeOD) δ ppm 7.36-7.54 (5 H, m), 7.06-7.20 (2 H, m), |

TABLE D-continued

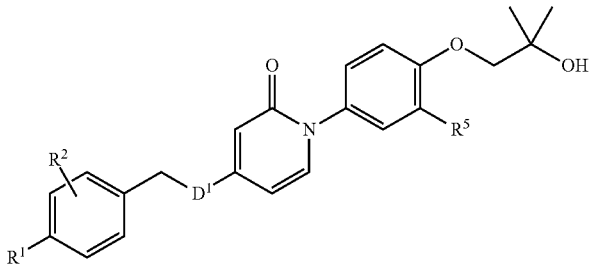

| Ex. No. | R[1] | R[2] | D[1] | R[5] | Synthetic Procedure Used | HPLC Method ($t_R$ Min) | MS (M + H) | NMR Data |
|---|---|---|---|---|---|---|---|---|
| D-34 | CHF$_2$O | H | O | Me | #8 | #5 0.95 | 446 | 6.98 (1 H, d, J = 8.28 Hz), 6.24 (1 H, dd, J = 7.65, 2.64 Hz), 6.07 (1 H, d, J = 2.51 Hz), 5.14 (2 H, s), 3.83 (2 H, s), 2.29 (3 H, s), 1.35 (6 H, s) <br> $^1$H NMR (400 MHz, CHLOROFORM-d) δ ppm 7.44 (2 H, d, J = 8.58 Hz), 7.30 (1 H, d, J = 7.48 Hz), 7.18 (2 H, d, J = 8.58 Hz), 7.10-7.14 (2 H, m), 6.86-6.90 (1 H, m), 6.38 (1 H, d, J = 2.64 Hz), 6.36-6.74 (1 H, m), 6.19 (1 H, dd, J = 7.48, 2.64 Hz), 5.08 (2 H, s), 3.84 (2 H, s), 2.30 (3 H, s), 1.39 (6 H, s) |
| D-35 | CF$_3$O | H | O | Me | #17 | 1.02; method 5 | 464 | $^1$H NMR (400 MHz, CHLOROFORM-d) δ ppm 7.45 (2 H, d, J = 8.78 Hz), 7.26 (2 H, d, J = 7.78 Hz), 7.21 (1 H, dd, J = 7.03, 0.75 Hz), 7.08-7.16 (2 H, m), 6.87 (1 H, d, J = 8.28 Hz), 5.94-6.10 (2 H, m), 5.03 (2 H, s), 3.82 (2 H, s), 2.29 (2 H, s), 1.37 (6 H, s) |
| D-36 | F | H | O | Et | #17 | #5 0.97 | 412 | 1H NMR (400 MHz, MeOD) δ ppm 7.35-7.45 (3 H, m), 6.98-7.09 (4 H, m), 6.87-6.95 (1 H, m), 6.14 (1 H, dd, J = 7.59, 2.75 Hz), 5.98 (1 H, d, J = 2.64 Hz), 5.03 (2 H, s), 3.73 (2 H, s), 2.64 (2 H, q, J = 7.48 Hz), 1.26 (6 H, s), 1.13 (3 H, t, J = 7.48 Hz) |
| D-37 | Cl | H | O | Et | #17 | #5 1.03 | 428 | 1H NMR (400 MHz, MeOD) δ ppm 7.40-7.57 (5 H, m), 7.11-7.18 (2 H, m), 7.00-7.06 (1 H, m), 6.27 (1 H, dd, J = 7.53, 2.76 Hz), 6.09 (1 H, d, J = 2.76 Hz), 5.17 (2 H, s), 3.85 (2 H, s), 2.76 (2 H, q, J = 7.36 Hz), 1.38 (6 H, s), 1.25 (3 H, t, J = 7.53 Hz) |
| D-38 | CF$_3$O | H | O | Et | #17 | 1.05; method 5 | 478 | $^1$H NMR (400 MHz, CHLOROFORM-d) δ ppm 7.45 (2 H, d, J = 8.53 Hz), 7.26 (2 H, d, J = 8.03 Hz), 7.23 (1 H, d, J = 8.03 Hz), 7.11-7.17 (2 H, m), 6.88 (1 H, d, J = 9.03 Hz), 5.94-6.11 (2 H, m), 5.03 (2 H, s), 3.82 (2 H, s), 2.70 (2 H, q, J = 7.53 Hz), 1.37 (6 H, s), 1.23 (3 H, t, J = 7.53 Hz) |
| D-39 | F | H | O | Cl | #17 | #5 0.94 | 418 | 1H NMR (400 MHz, MeOD) δ ppm 7.31-7.46 (4 H, m), 7.13-7.22 (1 H, m), 6.96-7.12 (3 H, m), 6.14 (1 H, dd, J = 7.59, 2.75 Hz), 5.98 (1 H, d, J = 2.64 Hz), 5.03 (2 H, s), 3.80 (2 H, s), 1.27 (6 H, s) |
| D-40 | Cl | H | O | Cl | #17 | #5 0.99 | 435 | 1H NMR (400 MHz, MeOD) δ ppm 7.36-7.58 (6 H, m), 7.24-7.32 (1 H, m), 7.16-7.24 (1 H, m), 6.28 (1 H, dd, J = 7.53, 2.76 Hz), 6.09 (1 H, d, J = 2.51 Hz), 5.16 (2 H, s), 3.92 (2 H, s), 1.39 (6 H, s) |

TABLE D-continued

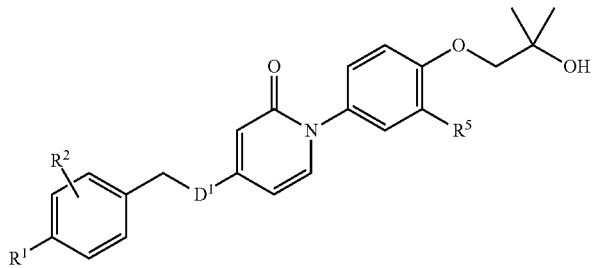

| Ex. No. | R¹ | R² | D¹ | R⁵ | Synthetic Procedure Used | HPLC Method ($t_R$ Min) | MS (M + H) | NMR Data |
|---|---|---|---|---|---|---|---|---|
| D-41 | CF₃O | H | O | Cl | #17 | 0.89; method 5 | 478 | ¹H NMR (400 MHz, CHLOROFORM-d) δ ppm 7.82 (1 H, d, J = 2.64 Hz), 7.62 (1 H, dd, J = 8.80, 2.64 Hz), 7.33 (2 H, d, J = 8.80 Hz), 7.29 (2 H, d, J = 8.58 Hz), 7.17 (1 H, d, J = 7.70 Hz), 7.07 (1 H, d, J = 8.80 Hz), 6.03-6.12 (2 H, m), 4.97 (2 H, s), 4.01 (2 H, s), 3.20 (3 H, s), 1.32 (6 H, s) |
| D-42 | Cl | H | O | CN | #17 | 1.02; method 5 | 484 | ¹H NMR (400 MHz, CHLOROFORM-d) δ ppm 7.45 (2 H, d, J = 8.53 Hz), 7.40 (1 H, d, J = 2.51 Hz), 7.26 (2 H, d, J = 8.03 Hz), 7.23 (1 H, dd, J = 8.78, 2.51 Hz), 7.20 (1 H, d, J = 7.53 Hz), 6.99 (1 H, d, J = 8.78 Hz), 5.98-6.08 (2 H, m), 5.03 (2 H, s), 3.88 (2 H, s), 1.39 (6 H, s) |
| D-43 | Cl | H | O | Me—SO₂ | #17 | 0.93; method 5 | 425 | ¹H NMR (400 MHz, CHLOROFORM-d) δ ppm 7.53-7.61 (2 H, m), 7.40 (2 H, d, J = 8.80 Hz), 7.36 (2 H, d, J = 8.80 Hz), 7.19 (1 H, d, J = 7.70 Hz), 7.07 (1 H, d, J = 9.68 Hz), 6.09 (1 H, dd, J = 7.59, 2.75 Hz), 6.03 (1 H, d, J = 2.64 Hz), 5.02 (2 H, s), 3.95 (2 H, s), 1.42 (6 H, s) |
| D-44 | Cl | 2-F | S | OMe | #8 | #5 0.98 | 464 | 1H NMR (400 MHz, CHLOROFORM-d) δ ppm 7.39 (1 H, t, J = 8.28 Hz), 7.20 (1 H, d, J = 7.28 Hz), 7.11-7.17 (2 H, m), 6.96 (1 H, d, J = 8.53 Hz), 6.79-6.92 (2 H, m), 6.47 (1 H, d, J = 2.01 Hz), 6.13 (1 H, dd, J = 7.15, 2.13 Hz), 4.17 (2 H, s), 3.85 (5 H, s), 1.35 (6 H, s) |
| D-45 | Cl | H | O | MeO—CH₂O | #17 | 0.94; method 5 | 460 | ¹H NMR (500 MHz, CHLOROFORM-d) δ ppm 7.31 (2 H, d, J = 8.60 Hz), 7.28 (2 H, d, J = 8.60 Hz), 7.14 (1 H, dd, J = 7.21, 0.83 Hz), 7.03 (1 H, d, J = 2.22 Hz), 6.90 (1 H, d, J = 8.32 Hz), 6.88 (1 H, dd, J = 8.60, 2.22 Hz), 5.91-5.99 (2 H, m), 5.14 (2 H, s), 4.93 (2 H, s), 3.78 (2 H, s), 3.44 (3 H, s), 1.28 (6 H, s) |

TABLE E

| Ex. No. | Structure | Synthetic Procedure Used | HPLC Method ($t_R$ Min) | MS (M + H) | NMR Data |
|---|---|---|---|---|---|
| E-1 | 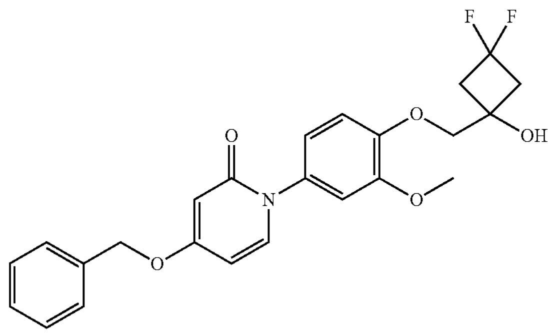 [SMILES: COc1cc(-n2ccc(OCc3ccccc3)cc2=O)ccc1OCC1(O)CC(F)(F)C1] | #7 | 0.91; method 5 | 444 | $^1$H NMR (400 MHz, MeOD) δ ppm 7.19-7.47 (6 H, m), 7.01 (1 H, d, J = 8.53 Hz), 6.91 (1 H, d, J = 2.26 Hz), 6.78 (1 H, dd, J = 8.53, 2.51 Hz), 6.16 (1 H, dd, J = 7.53, 2.76 Hz), 5.99 (1 H, d, J = 2.76 Hz), 5.06 (2 H, s), 3.95 (2 H, s), 3.77 (3 H, s), 2.72-2.87 (2 H, m), 2.44-2.59 (2 H, m) |
| E-2 | 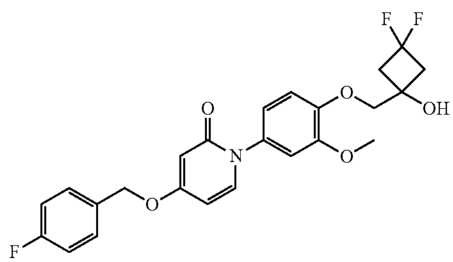 [SMILES: COc1cc(-n2ccc(OCc3ccc(F)cc3)cc2=O)ccc1OCC1(O)CC(F)(F)C1] | #17 | 0.92; method 5 | 462 | 1H NMR (400 MHz, CHLOROFORM-d) δ ppm 7.37-7.45 (2 H, m), 7.27 (1 H, s), 7.07-7.15 (2 H, m), 7.02 (1 H, d, J = 8.53 Hz), 6.91 (1 H, d, J = 2.26 Hz), 6.86 (1 H, dd, J = 8.53, 2.51 Hz), 6.19 (1 H, d, J = 2.76 Hz), 6.11 (1 H, dd, J = 7.65, 2.64 Hz), 5.03 (2 H, s), 4.10 (2 H, s), 3.86 (3 H, s), 2.71-2.88 (4 H, m) |
| E-3 | 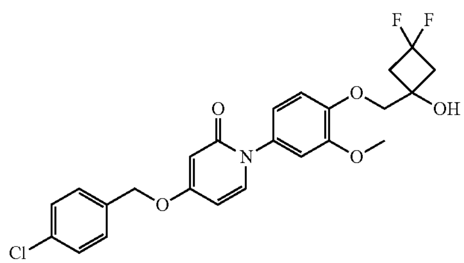 [SMILES: COc1cc(-n2ccc(OCc3ccc(Cl)cc3)cc2=O)ccc1OCC1(O)CC(F)(F)C1] | #17 | 0.96; method 5 | 478 | 1H NMR (400 MHz, CHLOROFORM-d) δ ppm 7.31-7.47 (4 H, m), 7.18-7.31 (1 H, m), 7.02 (1 H, d, J = 8.53 Hz), 6.80-6.96 (2 H, m), 5.97-6.10 (2 H, m), 5.01 (2 H, s), 4.09 (2 H, s), 3.86 (3 H, s), 2.67-2.88 (4 H, m) |
| E-4 | 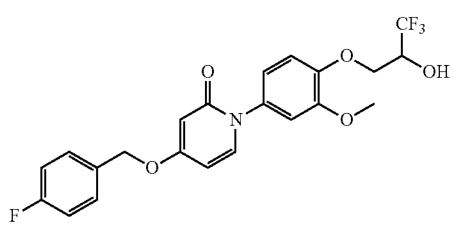 [SMILES: COc1cc(-n2ccc(OCc3ccc(F)cc3)cc2=O)ccc1OCC(O)C(F)(F)F] | #17 | 0.91; method 5 | 454 | 1H NMR (400 MHz, MeOD) δ ppm 7.33-7.45 (3 H, m), 6.98-7.10 (3 H, m), 6.91 (1 H, d, J = 2.42 Hz), 6.78 (1 H, dd, J = 8.58, 2.42 Hz), 6.15 (1 H, dd, J = 7.59, 2.75 Hz), 5.99 (1 H, d, J = 2.64 Hz), 5.04 (2 H, s), 4.28 (1 H, dt, J = 7.21, 3.55 Hz), 4.15-4.22 (1 H, m), 4.02-4.09 (1 H, m), 3.76 (3 H, s) |
| E-5 | 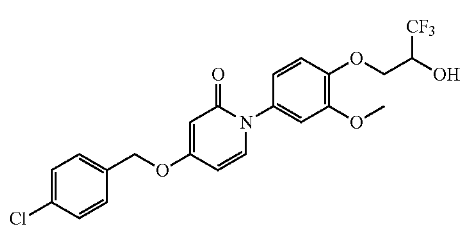 [SMILES: COc1cc(-n2ccc(OCc3ccc(Cl)cc3)cc2=O)ccc1OCC(O)C(F)(F)F] | #17 | 0.96; method 5 | 470 | 1H NMR (400 MHz, MeOD) δ ppm 7.42 (1 H, d, J = 7.70 Hz), 7.28-7.39 (4 H, m), 7.01 (1 H, d, J = 8.58 Hz), 6.91 (1 H, d, J = 2.42 Hz), 6.78 (1 H, dd, J = 8.36, 2.42 Hz), 6.16 (1 H, dd, J = 7.70, 2.64 Hz), 5.98 (1 H, d, J = 2.64 Hz), 5.05 (2 H, s), 4.23-4.35 (1 H, m), 4.15-4.23 (1 H, m), 4.00-4.11 (1 H, m), 3.76 (3 H, s) |

TABLE E-continued

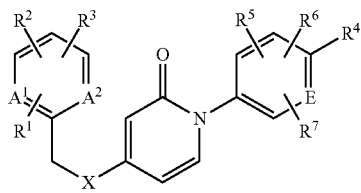

| Ex. No. | Structure | Synthetic Procedure Used | HPLC Method ($t_R$ Min) | MS (M + H) | NMR Data |
| --- | --- | --- | --- | --- | --- |
| E-6 | 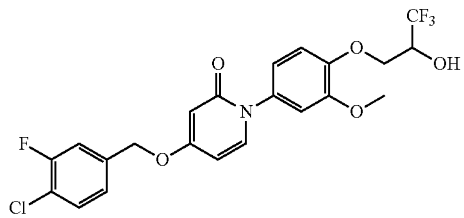 [SMILES: COc1cc(-n2ccc(OCc3ccc(Cl)c(F)c3)cc2=O)ccc1OCC(O)C(F)(F)F] | #17 | 0.97; method 5 | 488 | 1H NMR (400 MHz, MeOD) δ ppm 7.42 (2 H, t, J = 8.36 Hz), 7.28 (1 H, dd, J = 10.01, 1.87 Hz), 7.19 (1 H, dd, J = 8.25, 1.21 Hz), 7.01 (1 H, d, J = 8.58 Hz), 6.92 (1 H, d, J = 2.42 Hz), 6.78 (1 H, dd, J = 8.58, 2.42 Hz), 6.18 (1 H, dd, J = 7.59, 2.75 Hz), 5.97 (1 H, d, J = 2.64 Hz), 5.07 (2 H, s), 4.28 (1 H, td, J = 7.15, 3.74 Hz), 4.15-4.22 (1 H, m), 4.02-4.10 (1 H, m), 3.76 (3 H, s) |
| E-7 | 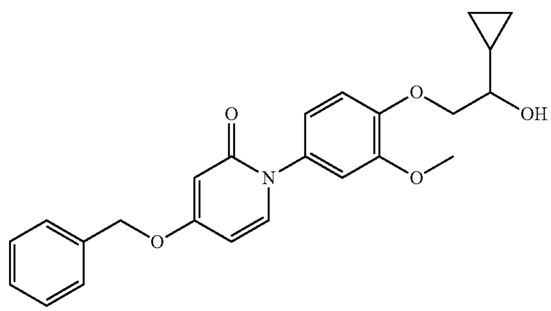 [SMILES: COc1cc(-n2ccc(OCc3ccccc3)cc2=O)ccc1OCC(O)C1CC1] | #17 | 0.88; method 5 | 408 | 1H NMR (400 MHz, CHLOROFORM-d) δ ppm 7.35-7.49 (5 H, m), 7.30 (1 H, d, J = 7.53 Hz), 7.00 (1 H, d, J = 8.53 Hz), 6.81-6.92 (2 H, m), 6.32 (1 H, d, J = 2.76 Hz), 6.18 (1 H, dd, J = 7.53, 2.76 Hz), 5.09 (2 H, s), 4.20 (1 H, dd, J = 9.79, 2.76 Hz), 3.97-4.09 (1 H, m), 3.86 (3 H, s), 3.35 (1 H, td, J = 8.34, 2.89 Hz), 0.91-1.07 (1 H, m), 0.50-0.67 (2 H, m), 0.40-0.50 (1 H, m), 0.24-0.36 (1 H, m) |
| E-8 | 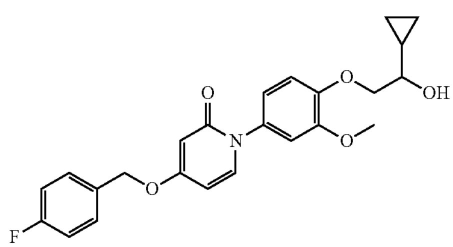 [SMILES: COc1cc(-n2ccc(OCc3ccc(F)cc3)cc2=O)ccc1OCC(O)C1CC1] | #7 | 0.89; method 5 | 426 | 1H NMR (400 MHz, CHLOROFORM-d) δ ppm 7.36-7.45 (2 H, m), 7.26-7.30 (1 H, m), 7.06-7.15 (2 H, m), 7.00 (1 H, d, J = 8.57 Hz), 6.82-6.91 (2 H, m), 6.21 (1 H, d, J = 2.64 Hz), 6.11 (1 H, dd, J = 7.69, 2.64 Hz), 5.03 (2 H, s), 4.20 (1 H, dd, J = 9.89, 2.86 Hz), 4.02 (1 H, dd, J = 9.78, 8.24 Hz), 3.86 (3 H, s), 3.35 (1 H, td, J = 8.35, 2.86 Hz), 0.90-1.06 (1 H, m), 0.50-0.68 (2 H, m), 0.40-0.50 (1 H, m), 0.31 (1 H, ddd, J = 9.17, 4.83, 4.67 Hz) |
| E-9 | 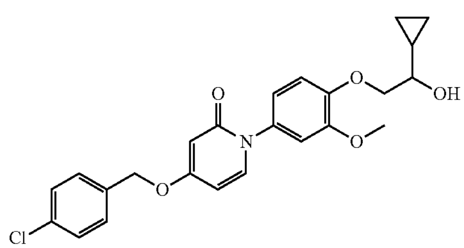 [SMILES: COc1cc(-n2ccc(OCc3ccc(Cl)cc3)cc2=O)ccc1OC[C@@H](O)C1CC1] | #7 | 0.94; method 5 | 442 | 1H NMR (400 MHz, CHLOROFORM-d) δ ppm 7.32-7.44 (4 H, m), 7.24 (1 H, d, J = 7.28 Hz), 7.00 (1 H, d, J = 8.53 Hz), 6.81-6.91 (2 H, m), 6.02-6.13 (2 H, m), 5.02 (2 H, s), 4.20 (1 H, dd, J = 9.79, 2.76 Hz), 3.96-4.08 (1 H, m), 3.86 (3 H, s), 3.35 (1 H, td, J = 8.34, 2.89 Hz), 0.97 (1 H, dt, J = 8.28, 4.77 Hz), 0.50-0.67 (2 H, m), 0.40-0.49 (1 H, m), 0.25-0.36 (1 H, m) |

TABLE E-continued

| Ex. No. | Structure | Synthetic Procedure Used | HPLC Method ($t_R$ Min) | MS (M + H) | NMR Data |
|---|---|---|---|---|---|
| E-10 | 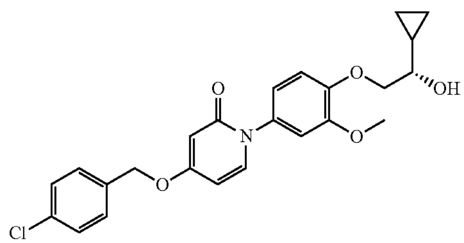 | #7 | 0.94; method 5 | 442 | 1H NMR (500 MHz, MeOD) δ ppm 7.42 (1 H, d, J = 7.77 Hz), 7.27-7.38 (4 H, m), 6.99 (1 H, d, J = 8.60 Hz), 6.89 (1 H, d, J = 2.50 Hz), 6.77 (1 H, dd, J = 8.32, 2.50 Hz), 6.15 (1 H, dd, J = 7.49, 2.77 Hz), 5.98 (1 H, d, J = 2.77 Hz), 5.05 (2 H, s), 4.03 (1 H, dd, J = 9.85, 3.47 Hz), 3.93 (1 H, dd, J = 9.99, 6.94 Hz), 3.76 (3 H, s), 3.18-3.25 (1 H, m), 0.92 (1 H, dt, J = 8.25, 4.89 Hz), 0.37-0.51 (2 H, m), 0.27-0.36 (1 H, m), 0.19-0.28 (1 H, m) |
| E-11 | 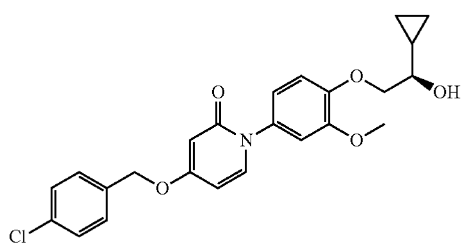 [SMILES: COc1cc(-n2ccc(OCc3ccc(Cl)cc3)cc2=O)ccc1OC[C@H](O)C1CC1] | #17 | 0.94; method 5 | 442 | 1H NMR (500 MHz, MeOD) δ ppm 7.42 (1 H, d, J = 7.77 Hz), 7.27-7.38 (4 H, m), 6.99 (1 H, d, J = 8.60 Hz), 6.89 (1 H, d, J = 2.50 Hz), 6.77 (1 H, dd, J = 8.32, 2.50 Hz), 6.15 (1 H, dd, J = 7.49, 2.77 Hz), 5.98 (1 H, d, J = 2.77 Hz), 5.05 (2 H, s), 4.03 (1 H, dd, J = 9.85, 3.47 Hz), 3.93 (1 H, dd, J = 9.99, 6.94 Hz), 3.76 (3 H, s), 3.18-3.25 (1 H, m), 0.92 (1 H, dt, J = 8.25, 4.89 Hz), 0.37-0.51 (2 H, m), 0.27-0.36 (1 H, m), 0.19-0.28 (1 H, m) |
| E-12 | 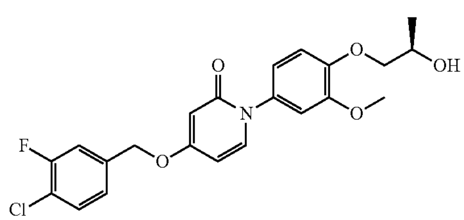 [SMILES: COc1cc(-n2ccc(OCc3ccc(Cl)c(F)c3)cc2=O)ccc1OC[C@@H](C)O] | #17 | 0.92; method 5 | 434 | 1H NMR (500 MHz, CHLOROFORM-d) δ ppm 7.44 (1 H, t, J = 7.91 Hz), 7.26-7.29 (1 H, m), 7.23 (1 H, dd, J = 9.57, 1.80 Hz), 7.14 (1 H, d, J = 8.32 Hz), 6.98 (1 H, d, J = 8.60 Hz), 6.89 (1 H, d, J = 2.50 Hz), 6.85 (1 H, dd, J = 8.32, 2.50 Hz), 6.04-6.11 (2 H, m), 5.02 (2 H, s), 4.22 (1 H, ddd, J = 8.25, 6.45, 2.77 Hz), 4.03 (1 H, dd, J = 9.57, 2.91 Hz), 3.78-3.89 (4 H, m), 1.26 (3 H, d, J = 6.38 Hz) |
| E-13 | 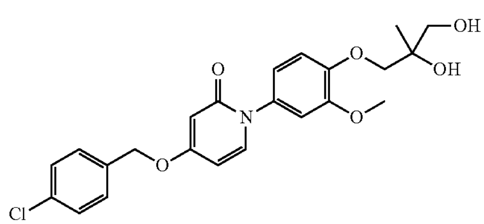 [SMILES: COc1cc(-n2ccc(OCc3ccc(Cl)cc3)cc2=O)ccc1OCC(C)(O)CO] | #11 | #7 3.50 min | 446 | ¹H NMR (CDCl₃, 400 MHz) δ 7.39 (m, 4 H), 7.23 (d, J = 7.7 Hz, 1 H), 6.90 (m, 3 H), 6.02 (m, 2 H), 5.00 (s, 2 H), 4.00 (m, 2 H), 3.85 (s, 3 H), 3.81 (m, 1 H), 3.54 (m, 1 H), 1.24 (s, 3 H) |

TABLE E-continued

| Ex. No. | Structure | Synthetic Procedure Used | HPLC Method ($t_R$ Min) | MS (M + H) | NMR Data |
|---|---|---|---|---|---|
| E-14 | 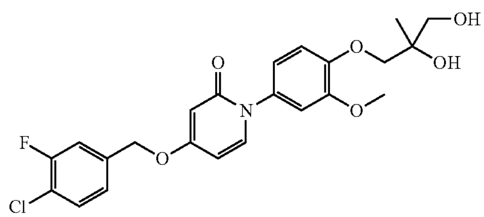 [SMILES: COc1cc(-n2ccc(OCc3ccc(Cl)c(F)c3)cc2=O)ccc1OCC(C)(O)CO] | #11 | #5 0.88 min | 464 | $^1$H NMR (500 MHz, MeOD) δ ppm 7.49-7.56 (2 H, m), 7.38 (1 H, dd, J = 9.99, 1.94 Hz), 7.27-7.31 (1 H, m), 7.08 (1 H, d, J = 8.60 Hz), 6.99 (1 H, d, J = 2.50 Hz), 6.87 (1 H, dd, J = 8.32, 2.50 Hz), 6.28 (1 H, dd, J = 7.49, 2.77 Hz), 6.07 (1 H, d, J = 2.77 Hz), 5.17 (2 H, s), 3.91-3.99 (2 H, m), 3.86 (3 H, s), 3.53-3.65 (2 H, m), 1.28 (3 H, s) |
| E-15 | 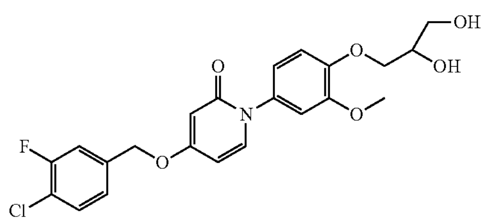 [SMILES: COc1cc(-n2ccc(OCc3ccc(Cl)c(F)c3)cc2=O)ccc1OCC(O)CO] | #11 | #5 0.83 min | 450 | $^1$H NMR (400 MHz, MeOD) δ ppm 7.49-7.55 (2 H, m), 7.38 (1 H, dd, J = 10.12, 1.76 Hz), 7.28 (1 H, dd, J = 8.36, 1.10 Hz), 7.08 (1 H, d, J = 8.58 Hz), 6.99 (1 H, d, J = 2.42 Hz), 6.87 (1 H, dd, J = 8.58, 2.42 Hz), 6.27 (1 H, dd, J = 7.59, 2.75 Hz), 6.06 (1 H, d, J = 2.64 Hz), 5.17 (2 H, s), 4.08-4.16 (1 H, m), 3.96-4.06 (2 H, m), 3.86 (3 H, s), 3.62-3.73 (2 H, m) |
| E-16 | 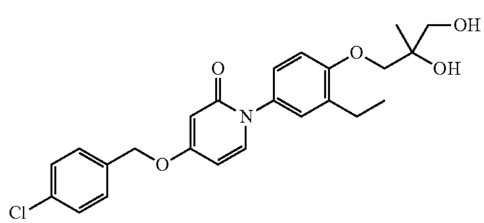 [SMILES: CCc1cc(-n2ccc(OCc3ccc(Cl)cc3)cc2=O)ccc1OCC(C)(O)CO] | #11 | #7 3.87 min | 444 | $^1$H NMR (CDCl$_3$, 400 MHz) δ 7.37 (m, 4 H), 7.21 (d, J = 7.7 Hz, 1 H), 7.15 (m, 2 H), 6.87 (d, J = 8.2 Hz, 1 H), 6.03 (m, 2 H), 5.00 (s, 2 H), 3.90 (m, 2 H), 3.68 (m, 1 H), 3.56 (m, 1 H), 2.64 (q, J = 7.7 Hz, 2 H), 1.29 (s, 3 H), 1.20 (t, J = 7.7 Hz, 3 H) |
| E-17 | 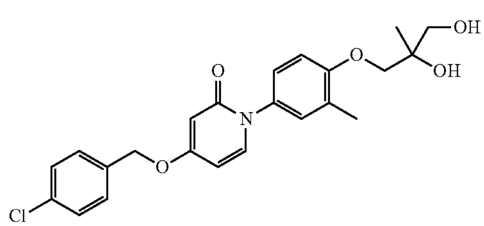 [SMILES: Cc1cc(-n2ccc(OCc3ccc(Cl)cc3)cc2=O)ccc1OCC(C)(O)CO] | #11 | #7 3.74 min | 430 | $^1$H NMR (CDCl$_3$, 400 MHz) δ 7.36 (m, 4 H), 7.20 (d, J = 7.7 Hz, 1 H), 7.11 (m, 2 H), 6.86 (d, J = 8.2 Hz, 1 H), 6.02 (m, 2 H), 5.01 (s, 2 H), 3.90 (m, 2 H), 3.68 (m, 1 H), 3.56 (m, 1 H), 2.24 (s, 3 H), 1.30 (s, 3 H) |
| E-18 | 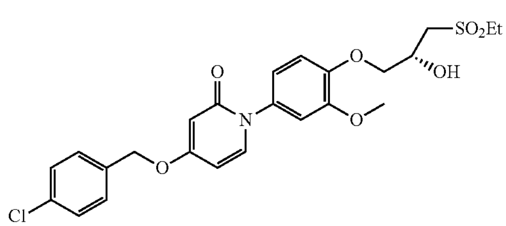 | #10 | #7 3.47 min | 508 | $^1$H NMR (CDCl$_3$, 400 MHz) δ 7.36 (m, 4 H), 7.22 (d, J = 7.7 Hz, 1 H), 6.96 (d, J = 8.2 Hz, 1 H), 6.89 (d, J = 2.2 Hz, 1 H), 6.85 (m, 1 H), 6.03 (m, 2 H), 5.01 (s, 2 H), 4.56 (m, 1 H), 4.05 (m, 2 H), 3.87 (s, 3 H), 3.20 (m, 4 H), 1.43 (t, J = 7.7 Hz, 3 H) |

TABLE E-continued

| Ex. No. | Structure | Synthetic Procedure Used | HPLC Method ($t_R$ Min) | MS (M + H) | NMR Data |
|---|---|---|---|---|---|
| E-19 | 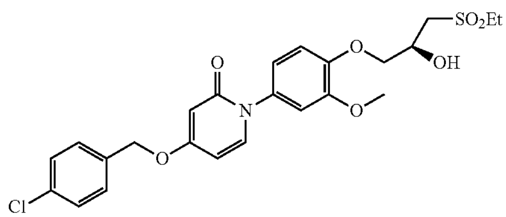 | #10 | #7 3.47 min | 508 | $^1$H NMR (CDCl$_3$, 400 MHz) δ 7.36 (m, 4 H), 7.22 (d, J = 7.7 Hz, 1 H), 6.96 (d, J = 8.2 Hz, 1 H), 6.89 (d, J = 2.2 Hz, 1 H), 6.85 (m, 1 H), 6.03 (m, 2 H), 5.01 (s, 2 H), 4.56 (m, 1 H), 4.05 (m, 2 H), 3.87 (s, 3 H), 3.20 (m, 4 H), 1.43 (t, J = 7.7 Hz, 3 H) |
| E-20 | 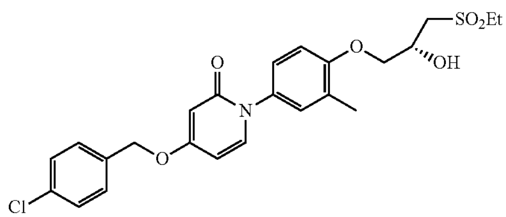 | #10 | #7 3.66 min | 492 | $^1$H NMR (CDCl$_3$, 400 MHz) δ 7.36 (m, 4 H), 7.22 (d, J = 7.7 Hz, 1 H), 7.10 (m, 2 H), 6.75 (d, J = 8.2 Hz, 1 H), 6.03 (m, 2 H), 5.01 (s, 2 H), 4.49 (m, 1 H), 3.84 (m, 2 H), 3.22 (m, 4 H), 2.24 (s, 3 H), 1.42 (t, J = 7.7 Hz, 3 H) |
| E-21 | 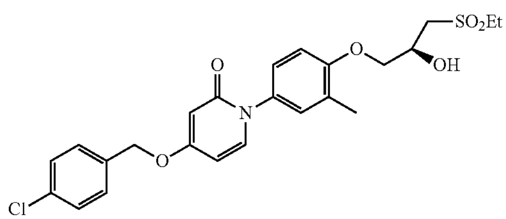 | #10 | #7 3.66 min | 492 | $^1$H NMR (CDCl$_3$, 400 MHz) δ 7.36 (m, 4 H), 7.22 (d, J = 7.7 Hz, 1 H), 7.10 (m, 2 H), 6.75 (d, J = 8.2 Hz, 1 H), 6.03 (m, 2 H), 5.01 (s, 2 H), 4.49 (m, 1 H), 3.84 (m, 2 H), 3.22 (m, 4 H), 2.24 (s, 3 H), 1.42 (t, J = 7.7 Hz, 3 H) |
| E-22 | 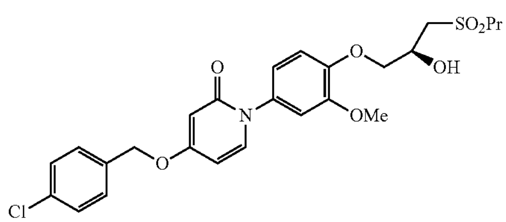 | #10 | #7 3.61 min | 522 | $^1$H NMR (CDCl$_3$, 400 MHz) δ 7.36 (m, 4 H), 7.22 (d, J = 7.7 Hz, 1 H), 6.94 (d, J = 8.2 Hz, 1 H), 6.89 (d, J = 2.2 Hz, 1 H), 6.83 (m, 1 H), 6.04 (m, 2 H), 5.01 (s, 2 H), 4.54 (m, 1 H), 4.01 (m, 2 H), 3.83 (s, 3 H), 3.23 (m, 4 H), 1.90 (m, 2 H), 1.08 (t, J = 7.7 Hz, 3 H) |
| E-23 | 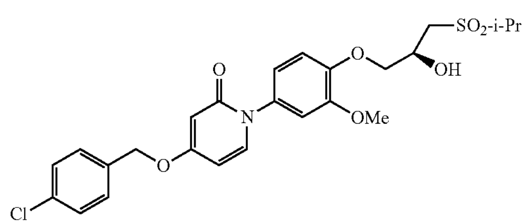 | #10 | #7 3.54 min | 522 | $^1$H NMR (CDCl$_3$, 400 MHz) δ 7.36 (m, 4 H), 7.22 (d, J = 7.7 Hz, 1 H), 6.94 (d, J = 8.2 Hz, 1 H), 6.89 (d, J = 2.2 Hz, 1 H), 6.83 (m, 1 H), 6.04 (m, 2 H), 5.01 (s, 2 H), 4.58 (m, 1 H), 4.03 (m, 2 H), 3.83 (s, 3 H), 3.29 (m, 3 H), 1.41 (m, 6 H) |
| E-24 | 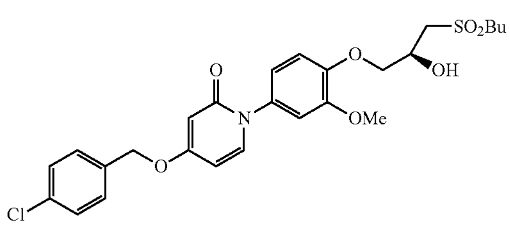 | #10 | #7 3.73 min | 536 | $^1$H NMR (CDCl$_3$, 400 MHz) δ 7.38 (m, 4 H), 7.22 (d, J = 7.7 Hz, 1 H), 6.96 (d, J = 8.2 Hz, 1 H), 6.89 (d, J = 2.2 Hz, 1 H), 6.84 (m, 1 H), 6.05 (m, 2 H), 5.01 (s, 2 H), 4.58 (m, 1 H), 4.05 (m, 2 H), 3.84 (s, 3 H), 3.23 (m, 4 H), 1.86 (m, 2 H), 1.47 (m, 2 H), 0.97 (t, J = 7.7 Hz, 3 H) |

TABLE E-continued
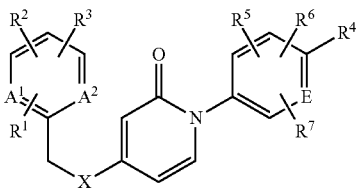
| Ex. No. | Structure | Synthetic Procedure Used | HPLC Method ($t_R$ Min) | MS (M + H) | NMR Data |
|---|---|---|---|---|---|
| E-25 | 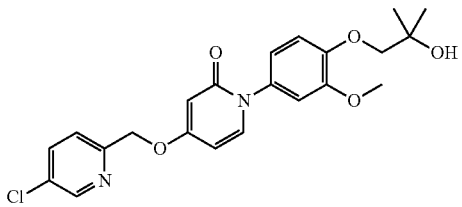 [SMILES: COc1cc(-n2ccc(OCc3ccc(Cl)cn3)cc2=O)ccc1OCC(C)(C)O] | #16 | #8 3.04 min. | 431 | 1H NMR (400 MHz, CDCl3) δ 8.52 (1 H, d, J = 2.6 Hz), 7.66 (1 H, dd, J = 8.4, 2.6 Hz), 7.37 (1 H, d, J = 8.4 Hz), 7.18 (1 H, d, J = 7.9 Hz), 6.89 (1 H, d, J = 8.8 Hz), 6.82 (1 H, d, J = 2.2 Hz), 6.73-6.79 (1 H, m), 6.01 (1 H, dd, J = 7.9, 2.6 Hz), 5.95 (1 H, d, J = 2.6 Hz), 5.08 (2 H, s), 3.78 (5 H, s), 2.53 (1 H, s), 1.28 (6 H, s). |
| E-26 | 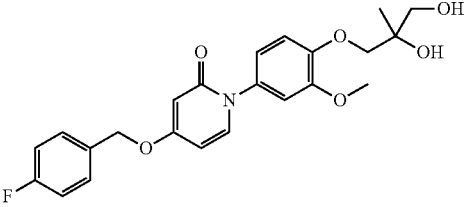 [SMILES: COc1cc(-n2ccc(OCc3ccc(F)cc3)cc2=O)ccc1OCC(C)(O)CO] | #11 | #7 3.25 min | 430 | $^1$H NMR (CDCl$_3$, 400 MHz) δ 7.39 (m, 2 H), 7.21 (m, 1 H), 7.09 (m, 2 H), 6.93 (d, J = 8.2 Hz, 1 H), 6.88 (d, J = 2.2 Hz, 1 H), 6.82 (m, 1 H), 6.02 (m, 2 H), 5.00 (s, 2 H), 4.99 (m, 2 H), 3.84 (s, 3 H), 3.77 (m, 1 H), 3.54 (m, 1 H), 1.24 (s, 3 H) |
| E-27 | 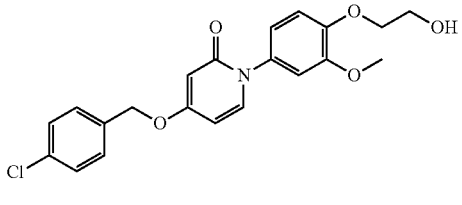 [SMILES: COc1cc(-n2ccc(OCc3ccc(Cl)cc3)cc2=O)ccc1OCCO] | #17 | 0.87; method 5 | 402 | 1H NMR (400 MHz, MeOD) δ ppm 7.54 (1 H, d, J = 7.70 Hz), 7.40-7.51 (4 H, m), 7.10 (1 H, d, J = 8.58 Hz), 7.01 (1 H, d, J = 2.42 Hz), 6.89 (1 H, dd, J = 8.58, 2.42 Hz), 6.27 (1 H, dd, J = 7.59, 2.75 Hz), 6.10 (1 H, d, J = 2.64 Hz), 5.17 (2 H, s), 4.13 (2 H, t), 3.84-3.99 (5 H, m) |

TABLE F

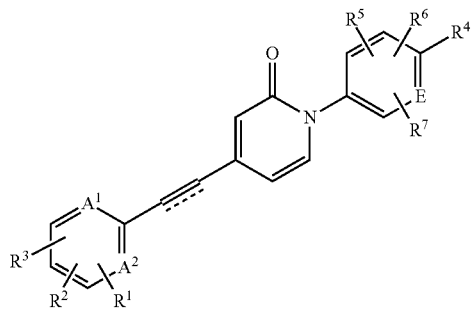

| Ex. No. | Structure | Experimental Procedure Used | HPLC Method ($t_R$ Min) | MS (M + H) | NMR Data |
|---|---|---|---|---|---|
| F-1 | 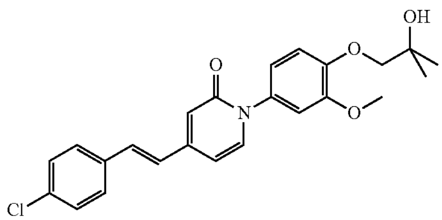 [SMILES: COc1cc(-n2ccc(/C=C/c3ccc(Cl)cc3)cc2=O)ccc1OCC(C)(C)O] | #6 | #7 3.90 min | 426 | $^1$H NMR (CDCl$_3$, 400 MHz) δ 7.50 (d, J = 8.4 Hz, 2 H), 7.46 (d, J = 7.0 Hz, 1 H), 7.38 (d, J = 8.4 Hz, 2 H), 7.25 (d, J = 16 Hz, 1 H), 6.94 (m, 4 H), 6.88 (m, 1 H), 6.76 (dd, J = 7.0 and 1.8 Hz, 1 H), 3.87 (s, 2 H), 3.86 (s, 3 H), 1.35 (s, 6 H). |
| F-2 | 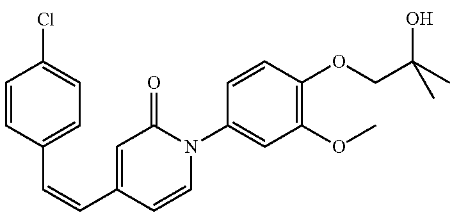 [SMILES: COc1cc(-n2ccc(/C=C\c3ccc(Cl)cc3)cc2=O)ccc1OCC(C)(C)O] | #6 | #7 3.81 min | 426 | $^1$H NMR (CDCl$_3$, 400 MHz) δ 7.30 (d, J = 8.8 Hz, 2 H), 7.24 (m, 3 H), 6.96 (d, J = 8.8 Hz, 1 H), 6.90 (d, J = 2.2 Hz, 1 H), 6.87 (m, 2 H), 6.80 (s, 1 H), 6.47 (d, J = 12 Hz, 1 H), 6.21 (dd, J = 7.0 and 1.8 Hz, 1 H), 3.87 (s, 2 H), 3.86 (s, 3 H), 1.37 (s, 6 H). |
| F-3 | 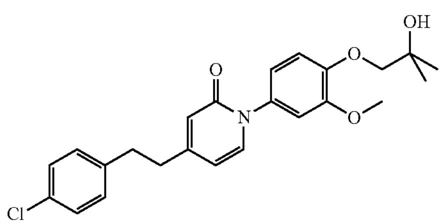 [SMILES: COc1cc(-n2ccc(CCc3ccc(Cl)cc3)cc2=O)ccc1OCC(C)(C)O] | Prepared from F-2 by reduction with H$_2$/Pd/C in EtOAc | #7 3.75 min | 428 | $^1$H NMR (CDCl$_3$, 400 MHz) δ 7.27 (d, J = 8.5 Hz, 2 H), 7.23 (d, J = 7.0 Hz, 1 H), 7.13 (d, J = 8.5 Hz, 2 H), 6.96 (d, J = 8.4 Hz, 1 H), 6.90 (d, J = 2.6 Hz, 1 H), 6.86 (m, 1 H), 6.46 (s, 1 H), 6.06 (m, 1 H), 3.86 (m, 5 H), 2.90 (m, 2 H), 2.77 (m, 2 H). |
| F-4 | 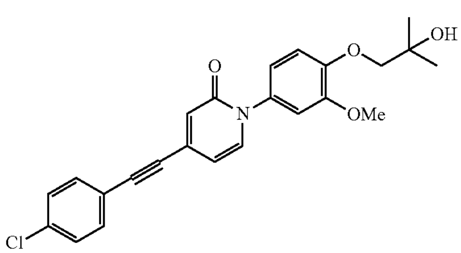 | #18 | #5 1.00 min | 424 | $^1$H NMR (400 MHz, CHLOROFORM-d) δ ppm 7.49-7.54 (2 H, m), 7.37-7.44 (3 H, m), 6.96-7.02 (2 H, m), 6.93 (1 H, d, J = 2.26 Hz), 6.89 (1 H, dd), 6.50 (1 H, d, J = 7.03 Hz), 3.88 (5 H, s), 1.38 (6 H, s) |
| F-5 | 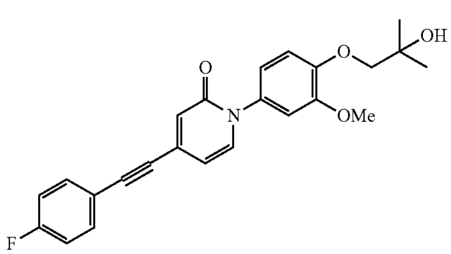 | #18 | #5 0.94 min | 408 | $^1$H NMR (400 MHz, CHLOROFORM-d) δ ppm 7.53-7.60 (2 H, m), 7.36 (1 H, d), 7.11 (2 H, t), 6.96-7.02 (1 H, m), 6.92-6.95 (1 H, m), 6.85-6.91 (2 H, m), 6.39 (1 H, dd), 3.88 (3 H, s), 3.87 (2 H, s), 1.37 (6 H, s) |

TABLE F-continued

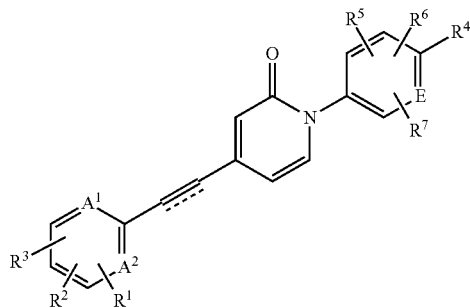

| Ex. No. | Structure | Experimental Procedure Used | HPLC Method ($t_R$ Min) | MS (M + H) | NMR Data |
|---|---|---|---|---|---|
| F-6 | 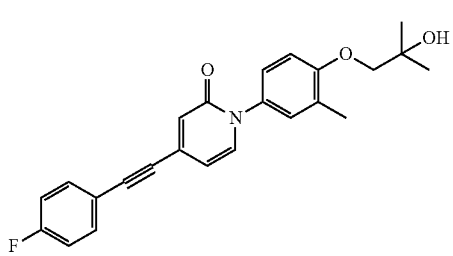 | #18 | #5 0.99 min | 392 | $^1$H NMR (400 MHz, CHLOROFORM-d) δ ppm 7.52-7.59 (2 H, m), 7.29 (1 H, d, J = 7.04 Hz), 7.15-7.20 (2 H, m), 7.06-7.12 (2 H, m), 6.90 (1 H, d), 6.80 (1 H, s), 6.28 (1 H, dd), 3.85 (2 H, s), 2.31 (3 H, s), 1.39 (6 H, s) |
| F-7 | 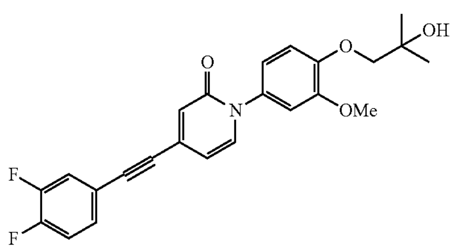 | #18 | #5 0.94 min | 426 | $^1$H NMR (400 MHz, CHLOROFORM-d) δ ppm 7.51-7.57 (1 H, m), 7.33 (1 H, d, J = 7.04 Hz), 6.99 (1 H, d, J = 8.36 Hz), 6.94 (2 H, d, J = 2.20 Hz), 6.91 (1 H, s), 6.86-6.90 (1 H, m), 6.84 (1 H, d, J = 1.32 Hz), 6.34 (1 H, d, J = 1.76 Hz), 3.88 (3 H, s), 3.87 (2 H, s), 1.37 (6 H, s) |
| F-8 | 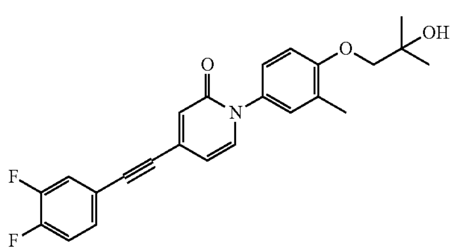 | #18 | #5 1.00 min | 410 | $^1$H NMR (400 MHz, CHLOROFORM-d) δ ppm 7.48-7.58 (1 H, m), 7.31 (1 H, d, J = 7.04 Hz), 7.13-7.20 (2 H, m), 6.87-6.96 (3 H, m), 6.83 (1 H, d, J = 1.32 Hz), 6.31 (1 H, dd, J = 7.04, 1.54 Hz), 3.85 (2 H, s), 2.31 (3 H, s), 1.39 (6 H, s) |

Analytical HPLC Methods

Method 1. Phenomenex S5 C18, 4.6×30 mm column; 2 min gradient at 4 mL/min, 10:90:0.1 to 90:10:0.1 MeOH—$H_2O$-TFA with 1 min hold at the end of the gradient.

Method 2. Phenomenex Luna S5 C18, 4.6×30 mm column; 2 min gradient at 4 mL/min, 10 mM ammonium acetate in 90:10 water-acetonitrile to 10 mM ammonium acetate in 10:90 water-acetonitrile with 1 min hold at the end of the gradient.

Method 3. Phenomenex S5 C18, 4.6×30 mm column; 4 min gradient at 4 mL/min, 10:90:0.1 to 90:10:0.1 MeOH—$H_2O$-TIF with 2 min hold at the end of the gradient.

Method 4. Phenomenex S5 C18, 4.6×30 mm column; 2 min gradient at 4 mL/min, 10:90:0.1 to 90:10:0.1 acetonitrile-$H_2O$-TFA with 1 min hold at the end of the gradient.

Method 5. BEH C18, 2.1×50 mm column; 1 min gradient at 0.8 mL/min, 2:98:0.05 to 98:2:0.05 acetonitrile-$H_2O$-TFA with 0.5 min hold at the end of the gradient.

Method 6. Zorbax Column SB C18, 4.6×75 mm; Gradient Time: 8 min; Flow Rate: 2.5 mL/min.; Solvent Gradient: 50-100% B; Detector Wavelength: 220 nm. (Solvent A=10% MeOH –90% $H_2O$-0.2% $H_3PO_4$; Solvent B 90% MeOH-10% $H_2O$-0.2% $H_3PO_4$).

Method 7. Phenomenex Onyx Monolithic C18, 4.6×100 mm column; 4 min gradient at 4 mL/min, 10:90:0.1 to 90:10: 0.1 MeOH—$H_2O$—$H_3PO_4$ with 1 min hold at the end of the gradient.

Procedure 1

Example A-1

4-((4-Chlorophenoxy)methyl)-1-(4-(2-hydroxy-2-methylpropoxy)-3-methoxyphenyl)pyridin-2(1H)-one

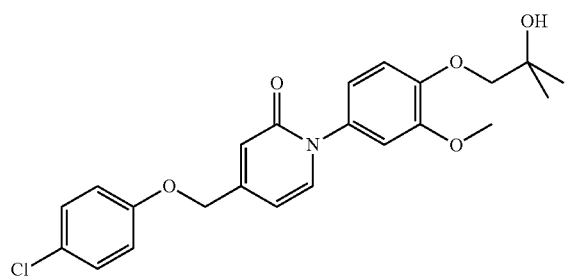

A. Methyl 2-oxo-1,2-dihydropyridine-4-carboxylate

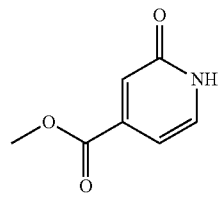

To MeOH (80 mL) at 0° C. was slowly added acetyl chloride (20.45 mL, 288 mmol) while stirring. The resulting solution was allowed to warm to RT and stirred for 30 min. To the resulting HCl/MeOH/MeOAc solution was added 2-hydroxyisonicotinic acid (4.00 g, 28.8 mmol) in one portion, and the mixture was stirred at ambient temperature for 16 h. The mixture was concentrated and the residue was stripped from MeOH (10 mL). The crude product was purified by chromatography (silica gel 230-400 mesh, solvent gradient 0-20% MeOH/CH$_2$Cl$_2$) to afford 1A (3.40 g, 22.20 mmol, 77% yield) as a yellow solid. LC-MS, [M+H]$^+$=154.

B. (2-((2-Methoxy-4-(4,4,5,5-tetramethyl-1,3,2-dioxaborolan-2-yl)phenoxy)methoxy)ethyl)trimethylsilane

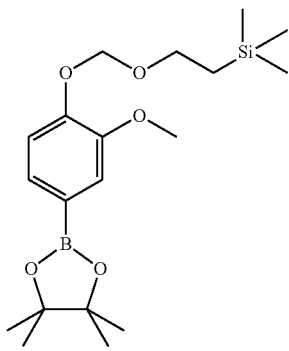

To a stirred solution of 2-methoxy-4-(4,4,5,5-tetramethyl-1,3,2-dioxaborolan-2-yl)phenol (4.00 g, 15.99 mmol) in CH$_2$Cl$_2$ (50 mL) at 0° C. was slowly added N,N-diisopropylethylamine (11.17 mL, 64.0 mmol) and (2-(chloromethoxy)ethyl)trimethylsilane (4.21 mL, 23.99 mmol). The resulting mixture was stirred at ambient temperature for 30 min, then allowed to warm to RT and stirred for 16 h. The mixture was concentrated and the residue was chromatographed on silica gel (230-400 mesh, solvent gradient 0-10% EtOAc/Hex) to give 1B (5.91 g, 15.54 mmol, 97% yield) as a clear liquid. LC-MS, [M+Na]$^+$=403.

C. 3-Methoxy-4-((2-(trimethylsilyl)ethoxy)methoxy)phenylboronic acid

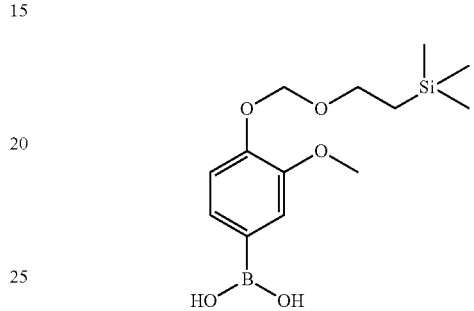

To a solution of Part B (14.35 g, 37.7 mmol) in acetone (400 mL) and water (400 mL) was added ammonium acetate (11.63 g, 151 mmol) and sodium periodate (32.3 g, 151 mmol). The white solution was stirred at ambient temperature for 16 h. The mixture was evaporated to remove most of the acetone and the residue was diluted with water. The aqueous mixture was extracted with EtOAc (3×200 mL) and, the combined organic extracts were dried over sodium sulfate and concentrated. Chromatography (silica gel 230-400 mesh, solvent gradient 0-70% EtOAc/Hex) of the crude furnished 1C (11.15 g, 37.4 mmol, 82% yield) as a slightly yellow liquid. LC-MS, [M+Na]$^+$=321.

D. Methyl 1-(3-methoxy-4-((2-(trimethylsilyeethoxy)methoxy)phenyl)-2-oxo-1,2-dihydropyridine-4-carboxylate

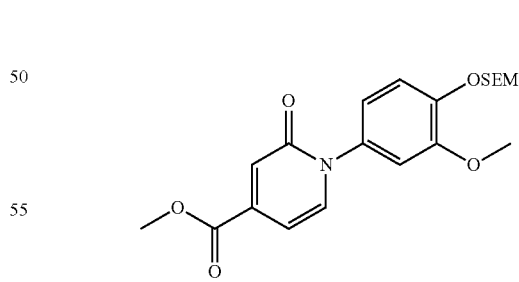

To a suspension of Part A (1.16 g, 7.57 mmol), Part C (2.71 g, 9.09 mmol) and copper (II) acetate (2.06 g, 11.36 mmol) in CH$_2$Cl$_2$ (75 mL) was added triethylamine (2.11 mL, 15.15 mmol), pyridine (1.23 mL, 15.15 mmol) and Molecular Sieves (4 Å, 1.0 g). The mixture was stirred at ambient temperature for 16 h and then filtered through Celite. The filter cake was rinsed with CH$_2$Cl$_2$ (2×50 mL) and the combined filtrates were evaporated. Chromatography (silica gel 230-

400 mesh, solvent gradient 0-100% EtOAc/Hex) of the crude gave 1D (2.61 g, 6.43 mmol, 85% yield) as a slight brown solid. LC-MS, [M+H]$^+$=406.

E. 4-(Hydroxymethyl)-1-(3-methoxy-4-((2-(trimethylsilyl)ethoxy)methoxy)phenyl)pyridin-2(1H)-one

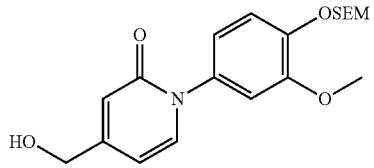

To a solution of Part D (2.61 g, 6.43 mmol) in THF (25 mL) at ambient temperature was added 2.0M lithium borohydride/THF (4.82 mL, 9.64 mmol). The mixture was stirred at ambient temperature for 16 h. and then concentrated. The residue was dissolved in MeOH and stirred for 30 min. The resulting solution was evaporated and the remnant was passed through a silica gel column (230-400 mesh) eluting with MeOH/CH$_2$Cl$_2$ (0-10% gradient) to provide 1E (2.33 g, 6.18 mmol, 96% yield) as a brown solid. LC-MS, [M+H]$^+$=378.

F. 4-(Bromomethyl)-1-(3-methoxy-4-4-((2-(trimethylsilyl)ethoxy)methoxy)phenyl)pyridin-2(1H)-one

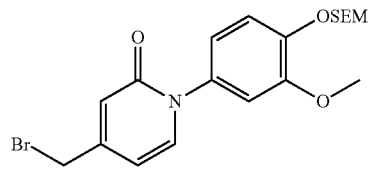

To a solution of Part E (740 mg, 1.960 mmol) in CH$_2$Cl$_2$ (5 mL) at 0° C. was added carbon tetrabromide (845 mg, 2.55 mmol) and triphenylphosphine (668 mg, 2.55 mmol). After warming to ambient temperature and stirring for 16 h, the volatiles were removed under vacuum. The resulting residue was chromatographed (silica gel 230-400 mesh, solvent gradient 0-50% EtOAc/Hex) to afford 1F (502 mg, 1.140 mmol, 58.1% yield) as a white solid. LC-MS, [M+H]$^+$=442.

G. 4-((4-Chlorophenoxy)methyl)-1-(3-methoxy-4-((2-(trimethylsilyl)ethoxy)methoxy)phenyl)pyridin-2(1H)-one

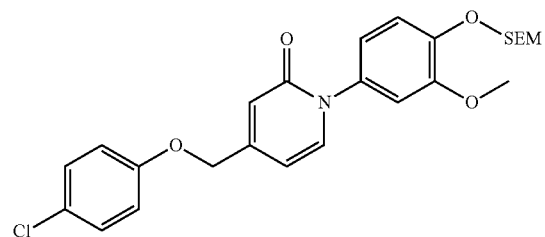 [SMILES: COc1cc(-n2ccc(COc3ccc(Cl)cc3)cc2=O)ccc1OCOCC[Si](C)(C)C]

To a solution of Part F (200 mg, 0.454 mmol) in acetonitrile (2 mL) at ambient temperature was added 4-chlorophenol (64.2 mg, 0.500 mmol) and potassium carbonate (188 mg, 1.362 mmol). The suspension was stirred at ambient temperature for 3 h and then diluted with water. The aqueous mixture was extracted with EtOAc (3×20 mL) and the combined organic extracts were dried over sodium sulfate and concentrated. Chromatography (silica gel 230-400 mesh, solvent gradient 0-80% EtOAc/hexane) of the crude gave 1G (200 mg, 0.410 mmol, 90% yield) as a white solid. LC-MS, [M+H]$^+$=488.

H. 4-((4-Chlorophenoxy)methyl)-1-(4-(2-hydroxy-2-methylpropoxy)-3-methoxyphenyl)pyridin-2(1H)-one

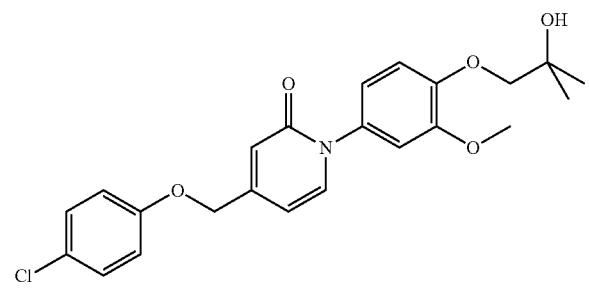 [SMILES: COc1cc(-n2ccc(COc3ccc(Cl)cc3)cc2=O)ccc1OCC(C)(C)O]

To a solution of Part G (87 mg, 0.178 mmol) in CH$_2$Cl$_2$ (1.0 mL) and MeOH (2.0 mL) was added 4M HCl/Dioxane (0.5 mL, 0.2 mmol). The mixture was stirred at RT for 16 h. and then evaporated. Drying under vacuum provided the crude phenol as a white solid. LC-MS, [M+H]$^+$=358.

To a solution of the above phenol in acetonitrile (1.5 mL) and water (0.5 mL) was added 2,2-dimethyloxirane (0.179 mL, 1.783 mmol) and potassium carbonate (73.9 mg, 0.535 mmol). The mixture was heated at 125° C. for 30 min in a microwave reactor. After cooling to RT, the mixture was diluted with water and extracted with EtOAc (3×30 mL). The combined organic extracts were concentrated and the residue was purified by Prep-HPLC (MeOH/H$_2$O/TFA) to afford the title compound A-1 as a white solid (67 mg, 0.153 mmol, 86% yield). LC-MS, [M+H]$^+$=430. $^1$H NMR (CDCl$_3$, 400 MHz) δ 1.36 (s, 6H), 3.86 (2s, 5H), 4.95 (s, 2H), 6.36 (dd, J=7.0, 1.8 Hz, 1H), 6.78 (s, 1H), 6.84-6.93 (m, 4H), 6.97 (d, J=8.4 Hz, 1H), 7.26 (d, J=2.6 Hz, 2H), 7.38 (d, J=7.0 Hz, 1H).

HPLC-(Zorbax): Rt 5.00 min, purity=99%.

Procedure 2

Example A-2

4((4-Chlorophenoxy)methyl)-1-(4-(2-hydroxy-2-methylpropoxy)-3-methylphenyl)pyridin-2(1H)-one

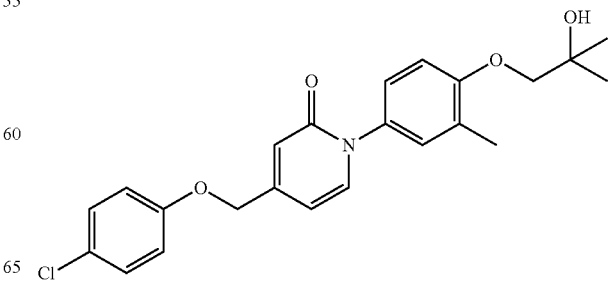

A. Methyl 1-(4-methoxy-3-methylphenyl)-2-oxo-1,2-dihydropyridine-4-carboxylate

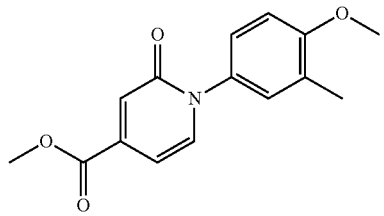

To a solution of Part A of Procedure 1 (2.37 g, 15.48 mmol) in CH$_2$Cl$_2$ (20 mL) was added 4-methoxy-3-methylphenylboronic acid (3.85 g, 23.21 mmol), copper (II) acetate (4.22 g, 23.21 mmol), Et$_3$N (4.31 mL, 31.0 mmol), pyridine (2.50 mL, 31.0 mmol) and Molecular Sieves (4 Å, 1.5 g). The mixture was stirred at RT overnight and then filtered through Celite. After rinsing the filter cake with 1/1 CH$_2$Cl$_2$/MeOH (200 mL), the combined filtrates were evaporated. Chromatography (silica gel 230-400 mesh, solvent gradient 0-50% EtOAc/Hex followed by 20% MeOH/CH$_2$Cl$_2$) afforded 2A (1.54 g, 5.64 mmol, 36.4% yield) as a yellowish solid. LC-MS, [M+H]$^+$=274.

B. Methyl 1-(4-hydroxy-3-methylphenyl)-2-oxo-1,2-dihydropyridine-4-carboxylate

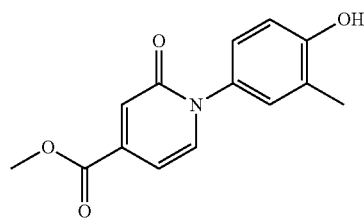

To a solution of Part A (700 mg, 2.56 mmol) in CH$_2$Cl$_2$ (10 mL) at 0° C. was added BF$_3$-SMe$_2$ (1.62 mL, 15.37 mmol) dropwise. The mixture was stirred for 16 h while slowly warming up to RT. The mixture was concentrated and the residue was dissolved in MeOH (10 mL). After stirring for 30 min at RT, the resulting solution was concentrated and the reaction crude was chromatographed (silica gel 230-400 mesh, solvent gradient 0-80% EtOAc/Hex) to give 2B (378 mg, 0.88 mmol, 34.2% yield) as a yellow solid. LC-MS, [M+H]$^+$=260.

C. Methyl 1-(3-methyl-4-((2-(trimethylsilyl)ethoxy)methoxy)phenyl)-2-oxo-1,2-dihydropyridine-4-carboxylate

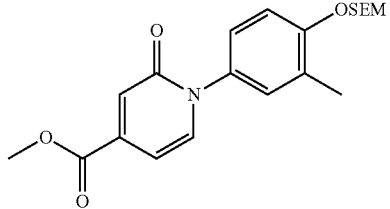

To a solution of Part B (38 mg, 0.15 mmol) in CH$_2$Cl$_2$ (2.0 mL) at 0° C. was added N,N'-diisopropylethylamine (0.10 mL, 0.60 mmol) and (2-(chloromethoxy)ethyl)trimethylsilane (39 μL, 0.22 mmol) dropwise. The mixture was stirred for 5 h while warming up to RT. After concentration, the residue was chromatographed on silica gel (230-400 mesh, solvent gradient 0-100% EtOAc/Hex) to yield 2C (64 mg, 0.16 mmol, quantitative) as a yellow solid. LC-MS, [M+H]$^+$=390.

D. 4-(Hydroxymethyl)-1-(3-methyl-4-((2-(trimethylsilyl)ethoxy)methoxy)phenyl)pyridin-2(1H)-one

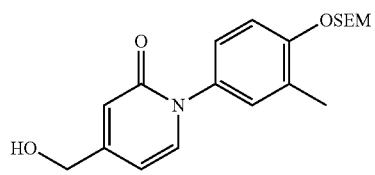

To a solution of Part C (130 mg, 0.33 mmol) in THF (5 mL) was added a 2.0 M lithium borohydride/THF solution (0.25 mL, 0.50 mmol). After stirring at RT for 16 h, the mixture was concentrated to give a white solid which was dissolved in MeOH (10 mL). After stirring at RT for 30 min, the resulting solution was evaporated and the residue was chromatographed (silica gel 230-400 mesh, solvent gradient 0-15% MeOH/CH$_2$Cl$_2$) to afford 2D (122 mg, 0.34 mmol, quantitative) as a thick colorless oil. LC-MS, [M+H]$^+$=362.

E. 4-(Bromomethyl)-1-(3-methyl-4-((2-(trimethylsilyl)ethoxy)methoxy)phenyl)pyridin-2(1H)-one

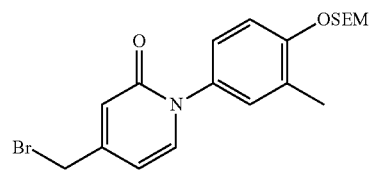

To a solution of Part D (122 mg, 0.34 mmol) in CH$_2$Cl$_2$ (2.0 mL) at 0° C. was added carbon tetrabromide (145 mg, 0.44 mmol) and triphenylphosphine (115 mg, 0.44 mmol). After stirring the mixture for 1 h while warming up to RT, the volatiles were removed under vacuum. The residue was chromatographed (silica gel 230-400 mesh, solvent gradient 0-50% EtOAc/Hex) to furnish 2E (100 mg, 0.236 mmol, 70% yield) as a white solid. LC-MS, [M+H]$^+$=426.

F. 4-((4-Chlorophenoxy)methyl)-1-(3-methyl-4-((2-(trimethylsilyl)ethoxy)methoxy)phenyl)pyridin-2(1H)-one

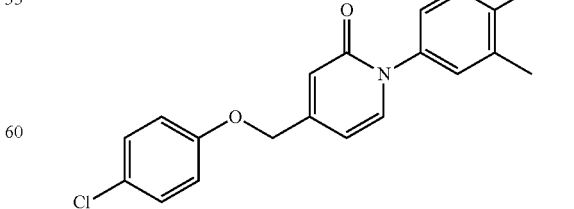

A mixture of Part E (50 mg, 0.118 mmol), 4-chlorophenol (18.17 mg, 0.141 mmol), and K$_2$CO$_3$ (48.8 mg, 0.353 mmol) in DMF (2 mL) was stirred at RT for 3 h. The mixture was passed through a silica gel column (230-400 mesh) eluting with 70% EtOAc/Hexane) to give 2F (54 mg, 0.11 mmol, 97% yield) as a white solid. LC-MS, [M+H]⁺=472.

G. 4-((4-Chlorophenoxy)methyl)-1-(4-(2-hydroxy-2-methylpropoxy)-3-methylphenyl)pyridin-2(1H)-one

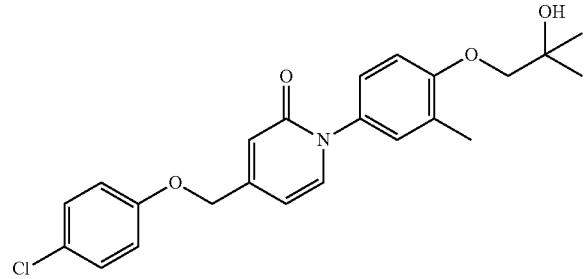 [SMILES: Cc1cc(-n2ccc(COc3ccc(Cl)cc3)cc2=O)ccc1OCC(C)(C)O]

To a solution of Part F (54 mg, 0.114 mmol) in CH₂Cl₂ (2 mL) and MeOH (2 mL) at RT was added 4N HCl in dioxane (0.5 mL, 2.0 mmol). The resulting solution was stirred for 3 h and then concentrated under vacuum. Following dissolution of the residue in acetonitrile (1.5 mL) and water (0.5 mL), K₂CO₃ (47 mg, 0.34 mmol) and 2,2-dimethyloxirane (0.12 mL, 1.14 mmol) was added. The resulting suspension was heated to 125° C. for 30 min in a microwave reactor. After cooling to RT, the mixture was diluted with water and extracted with EtOAc (3×20 mL). The combined organic extracts were concentrated and the crude was purified by preparative HPLC (MeOH/H₂O/TFA) to afford the title compound A-2 (6 mg, 0.014 mmol, 12% yield) as a white solid. LC-MS, [M+H]⁺=414. ¹H NMR (CDCl₃, 400 MHz) δ 1.38 (s, 6H), 2.30 (s, 3H), 3.84 (s, 2H), 4.96 (s, 2H), 6.41 (dd, J=7.0, 1.8 Hz, Hz, 1H). HPLC-(Zorbax): Rt 6.02 min, purity=96%.

Procedure 3

Example A-3

4-((4-Chlorophenoxy)methyl)-1-(4-(2-cyclopropyl-2-hydroxyethoxy)-3-methoxyphenyl)pyridin-2(1H)-one

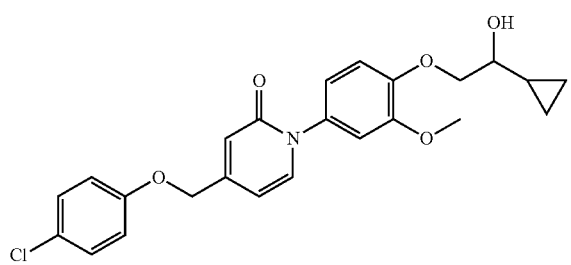 [SMILES: COc1cc(-n2ccc(COc3ccc(Cl)cc3)cc2=O)ccc1OCC(O)C1CC1]

A. 4-((4-Chlorophenoxy)methyl)-1-(4-(2-cyclopropyl-2-oxoethoxy)-3-methoxyphenyl)pyridin-2(1H)-one

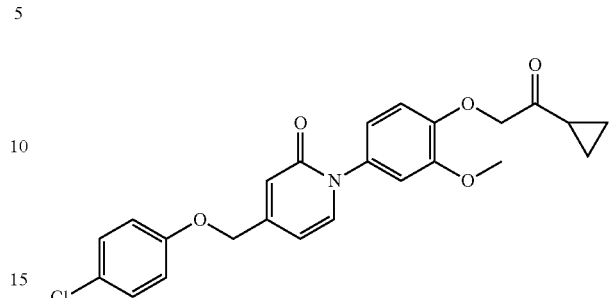

After addition of 4N HCl in dioxane (0.5 mL, 2.0 mmol) to a solution of Part G of procedure 1 (70 mg, 0.143 mmol) in CH₂Cl₂ (2 mL) and MeOH (2 mL) at RT, the resulting solution was stirred at for 3 h prior to being concentrated to give a white solid. To a suspension of this solid in acetonitrile (2 mL) was added Cs₂CO₃ (140 mg, 0.430 mmol) and 2-cyclopropyl-2-oxoethyl 4-methylbenzenesulfonate (55 mg, 0.22 mmol). The resulting mixture was stirred at RT for 16 h, diluted with water (10 mL) and extracted with EtOAc (3×10 mL). The combined organic extracts were dried over Na₂SO₄, and concentrated. The crude residue was chromatographed on silica gel (230-400 mesh, solvent gradient 0-80% EtOAc/Hex) to afford 3A (110 mg, 0.130 mmol, 91% yield) as a white solid. LC-MS, [M+H]⁺=440.

B. 4-((4-Chlorophenoxy)methyl)-1-(4-(2-cyclopropyl-2-hydroxyethoxy)-3-methoxyphenyl)pyridin-2(1H)-one

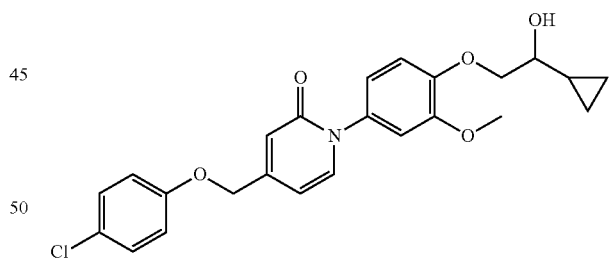

To a solution of Part A (110 mg, 0.13 mmol) in EtOH (1.5 mL) at 0° C. was added sodium borohydride (49 mg, 1.30 mmol). After warming to RT and stirring for 16 h, the reaction was quenched with 1N HCl solution (10 mL) After extracting the aqueous mixture with CH₂Cl₂. (3×30 mL), the combined organic extracts were dried over Na₂SO₄, concentrated and the residue was purified by Prep-HPLC (MeOH/H₂O/TFA) to furnish the title compound A-3 (22 mg, 0.05 mmol, 37% yield) as a white solid. LC-MS, [M+H]⁺=442. ¹H NMR (CDCl₃, 400 MHz) δ 0.24-0.36 (m, 1H), 0.40-0.49 (m, 1H), 0.50-0.68 (m, 2H), 0.90-1.04 (m, 1H), 3.35 (m, 1H), 3.86 (s, 3H), 4.03 (d, J=8.4 Hz, 1H), 4.20 (dd, J=9.7, 3.1 Hz, 1H), 4.93 (s, 2H), 6.30 (d, J=7.0 Hz, 1H), 6.72 (s, 1H), 6.83-6.95 (m, 4H), 7.01 (d, J=8.4 Hz, 1H), 7.26 (d, J=9.2 Hz, 2H), 7.35 (d, J=7.0 Hz, 1H). HPLC-(Zorbax): Rt 5.18 min, purity=96%.

Procedure 4

Example A-4

1-(4-(2-Hydroxy-2-methylpropoxy)-3-methoxyphenyl)-4-((pyridin-2-yloxy)methyl)pyridin-2(1H)-one

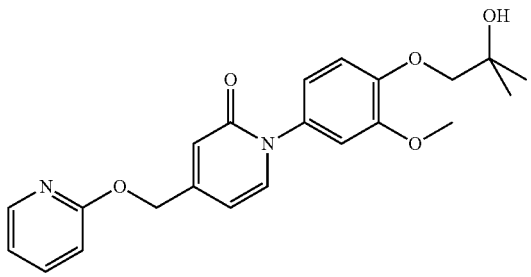

A. 1-(4-Hydroxy-3-methoxyphenyl)-4-(hydroxymethyl)pyridin-2(1H)-one

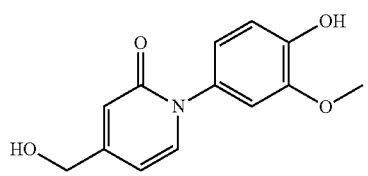 [SMILES: COc1cc(-n2ccc(CO)cc2=O)ccc1O]

To a solution of 4-(hydroxymethyl)-1-(3-methoxy-4-((2-(trimethylsilyl)ethoxy)-methoxy)phenyl)pyridin-2(1H)-one Part E of Procedure 1 (900 mg, 2.38 mmol) in CH$_2$Cl$_2$ (10 mL) and MeOH (10 mL) was added 4M HCl/Dioxane (10.7 mL, 43 mmol). After stirring at RT for 1 h, concentration under vacuum provided the crude phenol as a white solid. LC-MS, [M+H]$^+$=428.

B. 1-(4-(2-Hydroxy-2-methylpropoxy)-3-methoxyphenyl)-4-(hydroxymethyl)pyridin-2(1H)-one

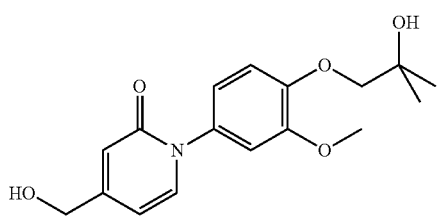 [SMILES: COc1cc(-n2ccc(CO)cc2=O)ccc1OCC(C)(C)O]

To a solution of 1-(4-hydroxy-3-methoxyphenyl)-4-(hydroxymethyl)pyridin-2(1H)-one Part A (589 mg, 2.38 mmol) in acetonitrile (7.5 mL) and water (7.50 mL) was added 2,2-dimethyloxirane (3.17 mL, 35.7 mmol) and K$_2$CO$_3$ (988 mg, 7.15 mmol). The mixture was heated at 145° C. for 30 min in a microwave reactor. After cooling to RT, the mixture was diluted with water and extracted with EtOAc. The combined organic extracts were dried (MgSO$_4$), concentrated and the residue was purified by chromatography on silica gel (solvent gradient: 5-10% MeOH/CH$_2$Cl$_2$) to obtain alcohol 4B (461 mg, 61% yield) as a white solid. LC-MS, [M+H]$^+$=320.

C. 1-(4-(2-Hydroxy-2-methylpropoxy)-3-methoxyphenyl)-4-((pyridin-2-yloxy)methyl)pyridin-2(1H)-one

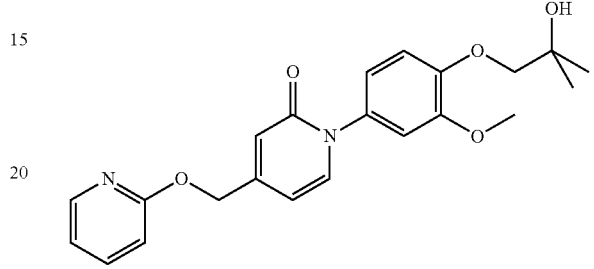

A solution of 1-(4-(2-hydroxy-2-methylpropoxy)-3-methoxyphenyl)-4-(hydroxymethyl)pyridin-2(1H)-one Part B (50 mg, 0.16 mmol) and 2-chloropyridine (0.059 mL, 0.63 mmol) in DMF (0.6 mL) was added to a mixture of Pd(OAc)$_2$ (7.0 mg, 0.03 mmol), racemic-2-(di-t-butylphosphino)-1,1'-binaphthyl (19 mg, 0.05 mmol), and Cs$_2$CO$_3$ (128 mg, 0.39 mmol) in 0.4 ml DMF. The mixture was stirred 15 min prior to heating at 80° C. for 6 h. After cooling to RT, the mixture was diluted with EtOAc and was filtered. The filtrate was concentrated and the residue was purified by Prep-HPLC (MeOH/H$_2$O/TFA) to afford the title compound A-4 as a white solid (24 mg, 37% yield). LC-MS, [M+H]$^+$=397. $^1$H NMR (CDCl$_3$, 400 MHz) δ 8.16 (m, 1H), 7.62 (m, 1H), 7.31 (d, J=7.1 Hz, 1H), 6.91 (m, 5H), 6.72 (s, 1H), 6.28 (dd, J=7.1 and 2.2 Hz, 1H), 5.29 (s, 2H), 3.85 (s, 5H), 1.33 (s, 6H), HPLC-Method 6; 3.07 min.

Procedure 5

Example A-5

4-(94-Fluorophenylthio)methyl)-1-(4-(2-hydroxy-2-methylpropoxy)-3-methoxyphenyl)pyridin-2(1H)-one

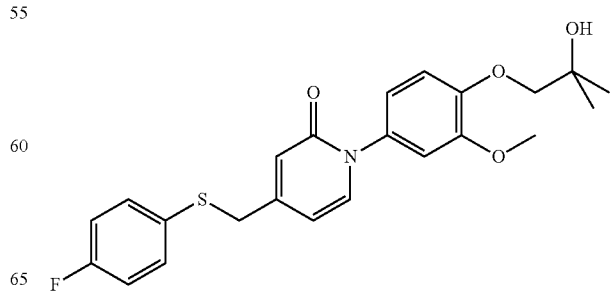

A. 4-((4-Fluorophenylthio)methyl)-1-(3-methoxy-4-((2-(trimethylsilyl)ethoxy)methoxy)phenyl)pyridin-2(1H)-one

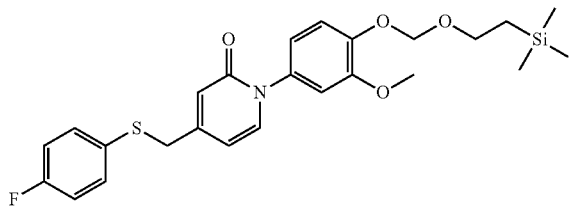 [SMILES: COc1cc(-n2ccc(CSc3ccc(F)cc3)cc2=O)ccc1OCOCC[Si](C)(C)C]

To a solution of 4-(bromomethyl)-1-(3-methoxy-4-((2-(trimethylsilyl)ethoxy)methoxy)phenyl)pyridin-2(1H)-one Part F of Procedure 1 (75 mg, 0.17 mmol) in acetonitrile (1.5 mL) at ambient temperature was added 4-fluorobenzenethiol (0.020 mL, 0.187 mmol) and $K_2CO_3$ (71 mg, 0.51 mmol). After stirring at ambient temperature for 12 h, the suspension was diluted with water and extracted with EtOAc. The combined organic extracts were dried over $MgSO_4$ and concentrated. Chromatography (silica gel solvent gradient 50-100% EtOAc/hexane) yielded the thioether 5A (64 mg, 77% yield) as a white solid. LC-MS, $[M+H]^+=488$.

B. 4-((4-Fluorophenylthio)methyl)-1-(4-(2-hydroxy-2-methylpropoxy)-3-methoxyphenyl)pyridin-2(1H)-one

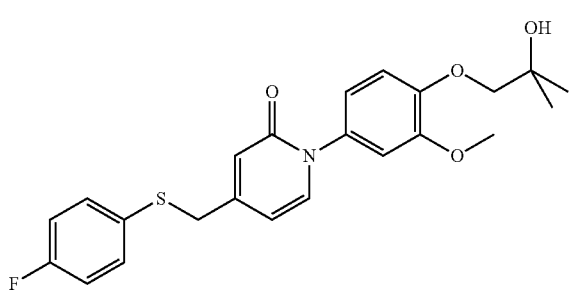

To a solution of 4-((4-fluorophenylthio)methyl)-1-(3-methoxy-4-((2-(trimethylsilyl)ethoxy)methoxy)phenyl)pyridin-2(1H)-one Part A (64 mg, 0.13 mmol) in $CH_2Cl_2$ (1.0 mL) and MeOH (1.0 mL) was added 4M HCl/Dioxane (2 mL, 8M mmol). After stirring at RT for 2 h, concentration under vacuum provided the crude phenol as a white solid. LC-MS, $[M+H]^+=358$.

To a solution of the above phenol in acetonitrile (1.0 mL) and water (1.0 mL) was added 2,2-dimethyloxirane (0.16 mL, 1.80 mmol) and $K_2CO_3$ (50 mg, 0.36 mmol). The mixture was heated at 145° C. for 1 h in a microwave reactor. After cooling to RT, the mixture was diluted with water and extracted with EtOAc. The combined organic extracts were dried ($MgSO_4$), concentrated and the residue was purified by Prep-HPLC (MeOH/$H_2O$/TFA) to afford the title compound A-5 as a white solid (32 mg, 59% yield). LC-MS, $[M+H]^+=430$. $^1H$ NMR ($CDCl_3$, 400 MHz) δ 7.34 (m, 2H), 7.31 (d, J=7.1 Hz, 1H), 7.01 (m, 2H), 6.95 (d, J=8.8 Hz, 1H), 6.88 (d, J=2.6 Hz, 1H), 6.83 (m, 1H), 6.46 (s, 1H), 6.32 (dd, J=7.1 and 2.2 Hz, 1H), 3.84 (m, 7H), 1.33 (s, 6H). HPLC-Method 6; 3.52 min.

Procedure 6

Example F-1

(E)-4-(4-Chlorostyryl)-1-(4-(2-hydroxy-2-methyl-propoxy)-3-methoxyphenyl)pyridin-2(1H)-one

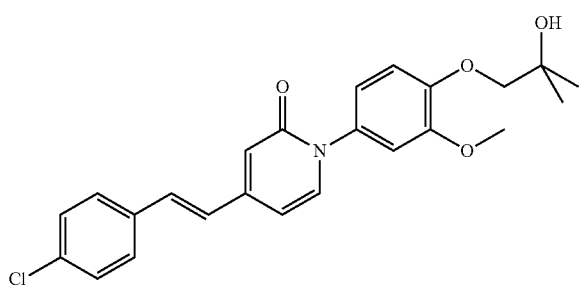 [SMILES: COc1cc(-n2ccc(/C=C/c3ccc(Cl)cc3)cc2=O)ccc1OCC(C)(C)O]

Example F-2

(Z)-4-(4-Chlorostyryl)-1-(4-(2-hydroxy-2-methylpropoxy)-3-methoxyphenyl)pyridin-2(III)-one

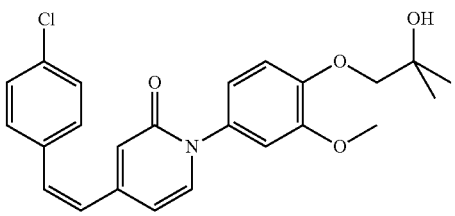 [SMILES: COc1cc(-n2ccc(/C=C\c3ccc(Cl)cc3)cc2=O)ccc1OCC(C)(C)O]

A. ((1-(3-Methoxy-4-((2-(trimethylsilyl)ethoxy)methoxy)phenyl)-2-oxo-1,2-dihydropyridin-4-yl)methyl)triphenylphosphonium, bromide salt

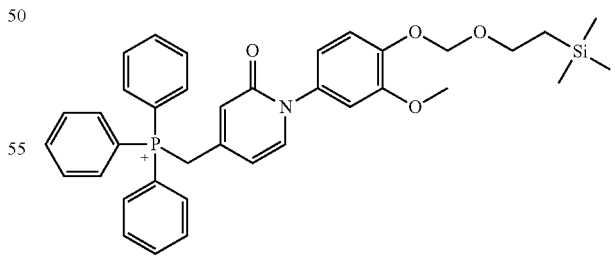

To a solution of 4-(bromomethyl)-1-(3-methoxy-4-4-((2-(trimethylsilyl)ethoxy)methoxy)phenyl)pyridin-2(1H)-one Part F of Procedure 1 (250 mg, 0.57 mmol) in toluene (6 mL) was added triphenylphosphine (179 mg, 0.681 mmol). The suspension was stirred at 100° C. for 2 h and then cooled to rt.

The solid was filtered and rinsed with hexanes to give the phosphonium salt (257 mg, 64% yield) as a white solid. LC-MS, [M+H]⁺=622.

B. (E) and (Z)-4-(4-Chlorostyryl)-1-(3-methoxy-4-((2-(trimethylsilyl)ethoxy)methoxy)phenyl)pyridin-2(1H)-one

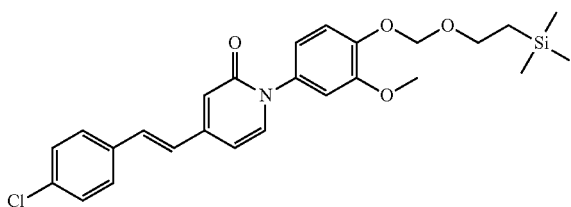 [SMILES: COc1cc(-n2ccc(/C=C/c3ccc(Cl)cc3)cc2=O)ccc1OCOCC[Si](C)(C)C]

To a solution of Part A ((1-(3-methoxy-4-((2-(trimethylsilyl)ethoxy)methoxy)phenyl)-2-oxo-1,2-dihydropyridin-4-yl)methyl)triphenylphosphonium, bromide salt (325 mg, 0.46 mmol) in THF (5 mL) at −78° C. was added n-BuLi (2M, 0.231 mL, 0.463 mmol). The solution was stirred 5 min prior to addition of 4-chlorobenzaldehyde (81 mg, 0.58 mmol) in 0.5 ml THF. The resulting solution was stirred 2 h after warming to RT. The reaction mixture was quenched with methanol, concentrated and the residue was purified by chromatography (silica gel solvent gradient 50-100% EtOAc/hexanes) gave the vinyl pyridones as a mixture of the cis and trans isomers (146 mg, 65% yield) as a white solid. LC-MS, [M+]⁺=484.

C. (E) and (Z)-4-(4-Chlorostyryl)-1-(4-(2-hydroxy-2-methylpropoxy)-3-methoxyphenyl)pyridin-2(1H)-one To a solution of E and Z isomers of 4-(4-chlorostyryl)-1-(3-methoxy-4-((2-(trimethylsilyl)ethoxy)methoxy)phenyl)pyridin-2(1H)-one Part B (146 mg, 0.30 mmol) in CH₂Cl₂ (5 mL) and MeOH (5 mL) was added HCl in dioxane (4M, 5.31 mL, 21.26 mmol). The mixture was stirred at RT for 2 h. and was then evaporated under vacuum to provide a mixture of the crude phenols as a white solid. LC-MS, [M+H]⁺=354.

To a solution of the above solid in acetonitrile (1.0 mL) and water (1.0 mL) was added 2,2-dimethyloxirane (0.16 mL, 1.80 mmol) and K₂CO₃ (123 mg, 0.89 mmol). The mixture was heated at 145° C. for 1 h in a microwave reactor. After cooling to RT, the mixture was diluted with water and extracted with EtOAc. The combined organic extracts were dried (MgSO₄), concentrated and the residue was purified by Prep-HPLC (MeOH/H₂O/TFA) to afford F-1 and F-2.

(E)-4-(4-Chlorostyryl)-1-(4-(2-hydroxy-2-methylpropoxy)-3-methoxyphenyl)-pyridin-2(1H)-one F-1

LC-MS, [M+H]⁺=426. ¹H NMR (CDCl₃, 400 MHz) δ 7.50 (d, J=8.4 Hz, 2H), 7.46 (d, J=7.0 Hz, 1H), 7.38 (d, J=8.4 Hz, 2H), 7.25 (d, J=16 Hz, 1H), 6.94 (m, 4H), 6.88 (m, 1H), 6.76 (dd, J=7.0 and 1.8 Hz, 1H), 3.87 (s, 2H), 3.86 (s, 3H), 1.35 (s, 6H). HPLC-Method 6; 3.90 min.

(Z)-4-(4-Chlorostyryl)-1-(4-(2-hydroxy-2-methylpropoxy)-3-methoxyphenyl)-pyridin-2(1H)-one F-2

LC-MS, [M+H]⁺=426. ¹H NMR (CDCl₃, 400 MHz) δ 7.30 (d, J=8.8 Hz, 2H), 7.24 (m, 3H), 6.96 (d, J=8.8 Hz, 1H), 6.90 (d, J=2.2 Hz, 1H), 6.87 (m, 2H), 6.80 (s, 1H), 6.47 (d, J=12 Hz, 1H), 6.21 (dd, J=7.0 and 1.8 Hz, 1H), 3.87 (s, 2H), 3.86 (s, 3H), 1.37 (s, 6H). HPLC-Method 6; 3.81 min.

Procedure 7

Example D-2

4-(4-Chlorobenzyloxy)-1-(4-(2-hydroxy-2-methylpropoxy)-3-methoxyphenyl)pyridin-2(1H)-one

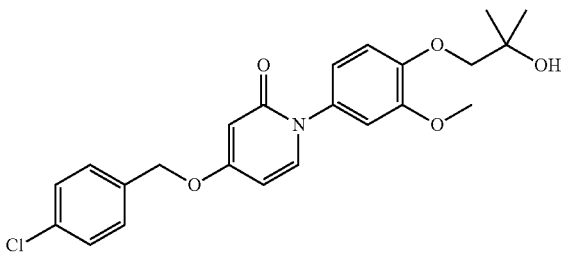

A. 1-(4-Bromo-2-methoxyphenoxy)-2-methylpropan-2-ol

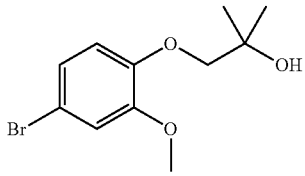

A mixture of 4-bromo-2-methoxyphenol (8 g, 39.4 mmol), 2,2-dimethyloxirane (14 mL, 158 mmol), potassium carbonate (4.3 g, 35.5 mmol), and sodium phosphate, monobasic (4.25 g, 35.5 mmol) in acetonitrile and water (85:15, 100 mL) was stirred in a steel bomb at 150-165° C. for 8 h. The reaction was cooled to RT, diluted with ether and EtOAc (1:1), washed with 1N NaOH, dried (Na₂SO₄), and concentrated. The crude was passed through a pad of silica gel using EtOAc for elution to afford the desired product 1-(4-bromo-2-methoxyphenoxy)-2-methylpropan-2-ol 7A (10 g, 36.3 mmol, 92% yield) as a brown oil. ¹H NMR (400 MHz, CHLOROFORM-d) δ6.95-7.08 (2H, m), 6.77 (1H, d, J=8.28 Hz), 3.85 (3H, s), 3.79 (2H, s), 1.34 (6H, s).

B. 4-(Benzyloxy)-1-(4-(2-hydroxy-2-methylpropoxy)-3-methoxyphenyl)pyridin-2(1H)-one: Example D-1

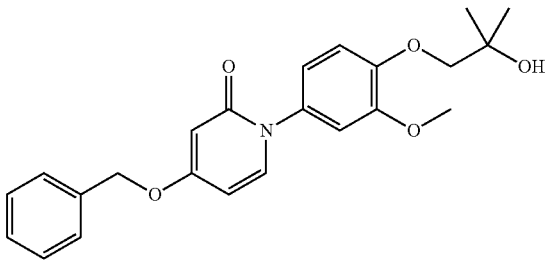 [SMILES: COc1cc(-n2ccc(OCc3ccccc3)cc2=O)ccc1OCC(C)(C)O]

A mixture of potassium phosphate tribasic (633 mg, 2.98 mmol), N1,N2-dimethylcyclohexane-1,2-diamine (141 mg, 0.99 mmol), copper(i) iodide (189 mg, 0.99 mmol), 1-(4-bromo-2-methoxyphenoxy)-2-methylpropan-2-ol (328 mg, 1.19 mmol) Part A and commercially available 4-(benzyloxy)pyridin-2(1H)-one (200 mg, 0.99 mmol) in dioxane (1.0 mL) was stirred in a sealed tube at 110° C. for 60 min. After removal of the solids by filtration and concentration of the filtrate, the crude product was subjected to flash chromatography (silica gel/CH$_2$Cl$_2$-10% MeOH/CH$_2$Cl$_2$ 100:0 to 0:100 gradient employing LC-MS to identify fractions containing the desired product). The semi-pure product thus obtained was further purified by prep-HPLC (C18 column/Water:MeOH:TFA 90:10:0.1 to 10:90:0.1 gradient) to obtain 4-(benzyloxy)-1-(4-(2-hydroxy-2-methylpropoxy)-3-methoxyphenyl)pyridin-2(1H)-one D-1 (298 mg, 74.3% yield) as a white foam. LC/MS 396 (M+H)$^+$, t$_R$ 0.87 min (method 5); $^1$H NMR (400 MHz, Chloroform-D) δ ppm 7.34-7.47 (5H, m), 718 (1H, d, J=7.78 Hz), 6.96 (1H, d, J=8.53 Hz), 6.80-6.90 (2H, m), 6.28 (1H, d, J=2.51 Hz), 6.16 (1H, dd, J=7.65, 2.64 Hz), 5.08 (2H, s), 3.85 (5H, s), 1.35 (6H, s).

C. 4-Hydroxy-1-(4-(2-hydroxy-2-methylpropoxy)-3-methoxyphenyl)pyridin-2(1H)-one

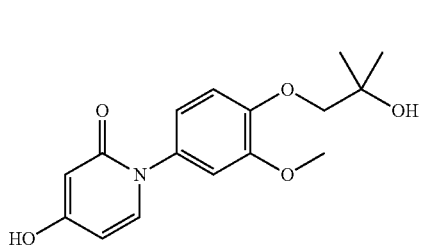 [SMILES: COc1cc(-n2ccc(O)cc2=O)ccc1OCC(C)(C)O]

A mixture of 4-(benzyloxy)-1-(4-(2-hydroxy-2-methylpropoxy)-3-methoxyphenyl)pyridin-2(1H)-one Part B (287 mg, 0.73 mmol) and 10% Pd/C (7.72 mg, 0.073 mmol) in MeOH (15 mL) was hydrogenated at 50 PSI of H$_2$ for 4 hours. Pd/C was filtered off and the filtrate was concentrated giving 4-hydroxy-1-(4-(2-hydroxy-2-methylpropoxy)-3-methoxyphenyl)pyridin-2(1H)-one 7C (228 mg, 98% yield).

D. 4-(4-Chlorobenzyloxy)-1-(4-(2-hydroxy-2-methylpropoxy)-3-methoxyphenyl)pyridin-2(1H)-one

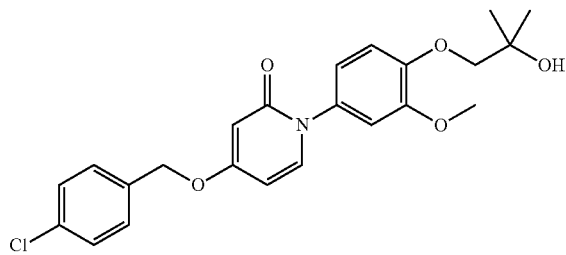 [SMILES: COc1cc(-n2ccc(OCc3ccc(Cl)cc3)cc2=O)ccc1OCC(C)(C)O]

A mixture of 1-chloro-4-(chloromethyl)benzene (26.4 mg, 0.16 mmol), 4-hydroxy-1-(4-(2-hydroxy-2-methylpropoxy)-3-methoxyphenyl)pyridin-2(1H)-one Part C (50 mg, 0.16 mmol) and K$_2$CO$_3$ (67.9 mg, 0.49 mmol) in DMF (1.0 mL) was stirred at 100° C. for 90 min The mixture was cooled to RT, filtered and the filtrate was concentrated. The crude product was purified by prep-HPLC (C18 column/Water:MeOH:TFA 90:10:0.1 to 10:90:0.1 gradient) yielding the title compound D-2-4-(4-chlorobenzyloxy)-1-(4-(2-hydroxy-2-methylpropoxy)-3-methoxyphenyl)pyridin-2(1H)-one D-2 (30 mg, 41.2% yield) as white solid. LC/MS 430 (M+H)$^+$, t$_R$ 0.93 min (method 5); $^1$H NMR (400 MHz, Chloroform-D) δ ppm 7.32-7.44 (4H, m), 7.24-7.28 (1H, m), 6.96 (1H, d, J=8.53 Hz), 6.80-6.91 (2H, m), 6.06-6.18 (2H, m), 5.03 (2H, s), 3.85 (5H, d, J=1.76 Hz), 1.35 (6H, s).

Procedure 8

Example D-4

4-(4-Chlorobenzylthio)-1-(4-(2-hydroxy-2-methylpropoxy)-3-methoxyphenyl)pyridin-2(1H)one

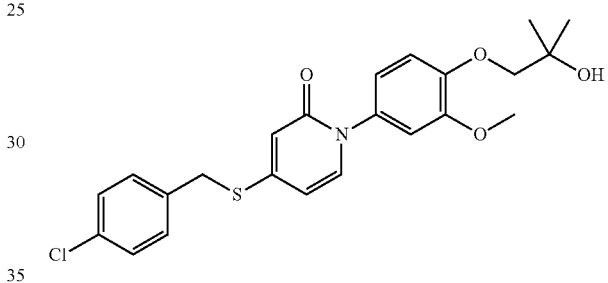

A. 4-(4-Chlorobenzylthio)pyridin-2(1H)-one

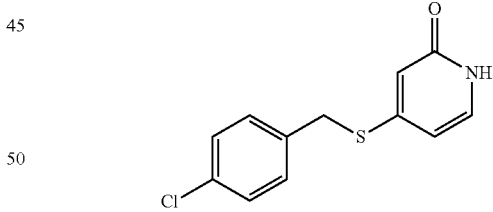

A mixture of 4-chloropyridin-2(1H)-one (100 mg, 0.77 mmol), K$_2$CO$_3$ (320 mg, 2.32 mmol) and (4-chlorophenyl)methanethiol (612 mg, 3.86 mmol) was stirred at 100° C. for 18 hours. After cooling the reaction to RT and was dilution with CH$_2$Cl$_2$ (5 mL), the crude product was subjected to flash chromatography (silica gel/hexane-EtOAc 100:0 to 0:100 gradient, employing LC-MS to identify the fractions containing the desired product) to afford 4-(4-chlorobenzylthio)pyridin-2(1H)-one 8A (96 mg, 46.9% yield). $^1$H NMR (400 MHz, Chloroform-D) δ ppm 12.30 (1H, br. s.), 7.28-7.43 (4H, m), 7.15 (1H, d, J=7.03 Hz), 6.28 (1H, d, J=1.51 Hz), 6.11 (1H, dd, J=6.90, 1.88 Hz), 4.11 (2H, s).

B. 4-(4-Chlorobenzylthio)-1-(4-(2-hydroxy-2-methylpropoxy)-3-methoxyphenyl)pyridin-2(1H)-one

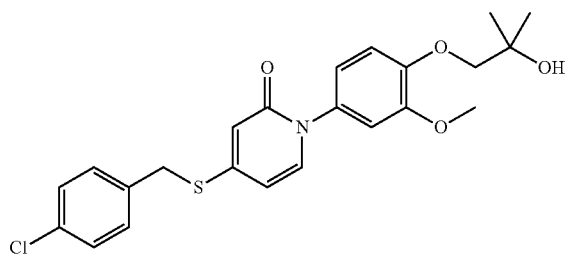 [SMILES: COc1cc(-n2ccc(SCc3ccc(Cl)cc3)cc2=O)ccc1OCC(C)(C)O]

Following the procedure for N-arylation and purification described in Part B of procedure 7, part A was converted to the title compound D-4. LC/MS 446 (M+H)[1], $t_R$ 0.96 min (method 5); $^1$H NMR (400 MHz, Chloroform-D) δ ppm 7.29-7.40 (4H, m), 7.21 (1H, d, J=7.28 Hz), 6.95 (1H, d, J=8.53 Hz), 6.79-6.90 (2H, m), 6.55 (1H, d, J=2.01 Hz), 6.18 (1H, dd, J=7.28, 2.01 Hz), 4.16 (2H, s), 3.85 (5H, s), 1.35 (6H, s).

Procedure 9

Example B-1

1-(4-(2-Hydroxy-2-methylpropoxy)-3-methoxyphenyl)-4-(4-(trifluoromethoxy)phenyl)pyridin-2(1H)-one

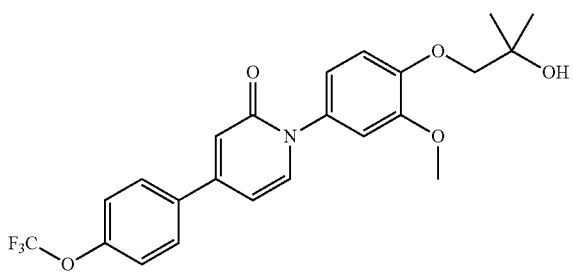 [SMILES: COc1cc(-n2ccc(-c3ccc(OC(F)(F)F)cc3)cc2=O)ccc1OCC(C)(C)O]

A.
1-(4-Bromo-2-methoxyphenoxy)-2-methylpropan-2-ol

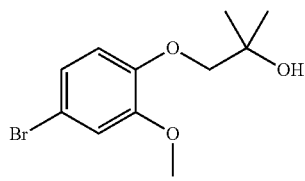

A mixture of 4-bromo-2-methoxyphenol (8 g, 39.4 mmol), 2,2-dimethyloxirane (14 mL, 158 mmol), potassium carbonate (4.3 g, 35.5 mmol), and sodium phosphate, monobasic (4.25 g, 35.5 mmol) in acetonitrile and water (85:15, 100 mL) was stirred in a steel bomb at 150-165° C. for 8 h. The reaction was cooled to RT, diluted with ether and EtOAc (1:1), washed with 1N NaOH, dried ($Na_2SO_4$), and concentrated. The crude was passed through a pad of silica gel using EtOAc for elution to afford the desired product 1-(4-bromo-2-methoxyphenoxy)-2-methylpropan-2-ol 9A (10 g, 36.3 mmol, 92% yield) as a brown oil. $^1$H NMR (400 MHz, Chloroform-d) δ6.95-7.08 (2H, m), 6.77 (1H, d, J=8.28 Hz), 3.85 (3H, s), 3.79 (2H, s), 1.34 (6H, s).

B. 1-(2-Methoxy-4-(4,4,5,5-tetramethyl-1,3,2-dioxaborolan-2-yl)phenoxy)-2-methylpropan-2-ol

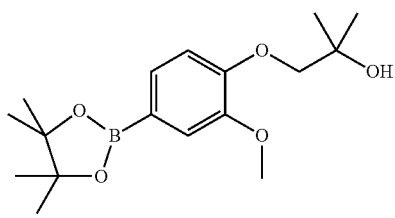 [SMILES: COc1cc(B2OC(C)(C)C(C)(C)O2)ccc1OCC(C)(C)O]

1-(4-Bromo-2-methoxyphenoxy)-2-methylpropan-2-ol Part A (1 g, 3.63 mmol) was dissolved in DMF (10 mL) under $N_2$ and potassium acetate (1 g, 10.90 mmol), bis(pinacolato)diboron (1 g, 3.82 mmol), and $PdCl_2$(dppf)-$CH_2Cl_2$ (0.15 g, 0.182 mmol) were added. The reaction mixture was heated at 90° C. for 1 h. (Terranova, Eric; Pascal, Jean Claude. (Galderma Research & Development, Fr.). WO 2004-FR3192; US 2007/001593). The reaction was diluted with EtOAc, washed sat $NH_4Cl$, brine, dried ($MgSO_4$), and concentrated to afford the crude product. The residue was purified using ISCO flash chromatography (silica gel/hexanes/ethyl acetate 100:0 to 0:100 gradient) to afford the desired product 1-(2-methoxy-4-4,4,5,5-tetramethyl-1,3,2-dioxaborolan-2-yl)phenoxy)-2-methylpropan-2-ol 9B (1.05 g, 3.26 mmol, 90% yield) as a yellow oil.

C. 4-(2-Hydroxy-2-methylpropoxy)-3-methoxyphenylboronic acid

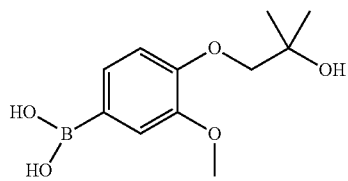 [SMILES: COc1cc(B(O)O)ccc1OCC(C)(C)O]

To a solution of 1-(2-methoxy-4-(4,4,5,5-tetramethyl-1,3,2-dioxaborolan-2-yl)phenoxy)-2-methylpropan-2-ol Part B (0.880 g, 2.73 mmol) in acetone (20 mL) and water (20 mL) was added sodium periodate (2.3 g, 10.92 mmol) and ammonium acetate (0.84 g, 10.92 mmol). The mixture stirred at RT overnight. Filtered the white solids, washed the filter cake with acetone and removed the acetone. The product was then extracted with EtOAc, and brine, and, dried ($MgSO_4$), concentrated to afford the crude product. Residue was purified using ISCO flash chromatography (silica gel/methylene chloride-methanol 100:0 to 85:15 gradient) to afford the desired product 4-(2-hydroxy-2-methylpropoxy)-3-methoxyphenylboronic acid 9C (0.443 g, 1.845 mmol, 67.6% yield) as a light brown solid.

D. 4-Chloro-1-(4-(2-hydroxy-2-methylpropoxy)-3-methoxyphenyl)pyridin-2(1H)-one

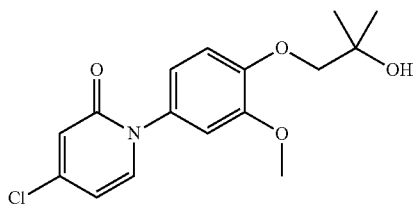 [SMILES: COc1cc(-n2ccc(Cl)cc2=O)ccc1OCC(C)(C)O]

Pyridine (1.2 mL, 15.4 mmol) was added to a stirred solution of commercially available 4-chloropyridin-2(1H)-one (100 mg, 0.77 mmol), 4-(2-hydroxy-2-methylpropoxy)-3-methoxyphenylboronic acid Part C (278 mg, 1.16 mmol), and copper (II) acetate, monohydrate (154 mg, 0.77 mmol) in $CH_2Cl_2$ (7 mL) and MeOH (0.7 mL). The reaction mixture stirred at RT under the presence of air overnight (21 hours). The reaction mixture was diluted with $CH_2Cl_2$, washed with 1N HCl, sat. $NaHCO_3$, dried ($Na_2SO_4$), and concentrated. The crude product was purified using preparative HPLC (C18 column/10:90:0.1 to 90:10:0.1 MeOH—$H_2O$-TFA) to afford the desired product 4-chloro-1-(4-(2-hydroxy-2-methylpropoxy)-3-methoxyphenyl)pyridin-2(1H)-one 9D (169 mg, 0.49 mmol, 62.8% yield) as a brown gum. LC/MS 324 $(M+H)^+$, $t_R$ 0.75 min (method 5)

E. 1-(4-(2-Hydroxy-2-methylpropoxy)-3-methoxyphenyl)-4-(4-(trifluoromethoxy)-phenyl)pyridin-2(1H)-one

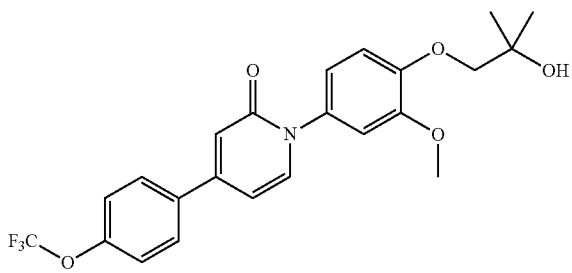 [SMILES: COc1cc(-n2ccc(-c3ccc(OC(F)(F)F)cc3)cc2=O)ccc1OCC(C)(C)O]

A mixture of 4-chloro-1-(4-(2-hydroxy-2-methylpropoxy)-3-methoxyphenyl)pyridin-2(1H)-one Part D (25 mg, 0.08 mmol), 4-(trifluoromethoxy)phenylboronic acid (28 mg, 0.14 mmol), tribasic potassium phosphate (49 mg, 0.23 mmol), and palladium tetrakis (9 mg, 7.7 μmol) in DMF (0.4 mL) was stirred at 60° C. under nitrogen for 17 hours. The reaction mixture was diluted with $CH_2Cl_2$, filtered and concentrated. The crude was purified using preparative HPLC (C18 column/10:90:0.1 to 90:10:0.1 MeOH—$H_2O$-TFA). This material further purified by ISCO flash chromatography (silica gel/hexanes-ethyl acetate 100:0 to 0:100 gradient) to afford the title compound 1-(4-(2-hydroxy-2-methylpropoxy)-3-methoxyphenyl)-4-(4-(trifluoromethoxy)-phenyl)pyridin-2(1H)-one B-1 (23.2 mg, 0.049 mmol, 63.6% yield) as a light yellow solid. LC/MS 450 $(M+H)^+$, $t_R$ 0.95 min (method 5). $^1H$ NMR (500 MHz, chloroform-d) δ 7.65 (2H, d, J=8.88 Hz), 7.43 (1H, d, J=7.49 Hz), 7.34 (2H, d, J=8.05 Hz), 6.97-7.02 (2H, m), 6.93 (1H, dd), 6.85 (1H, s), 6.48 (1H, dd), 3.89 (3H, s), 3.88 (2H, s), 1.37 (6H, s).

Procedure 10

Example A-34

(S)-4-((4-chlorophenoxy)methyl)-1-(4-(3-(ethylsulfonyl)-2-hydroxypropoxy)-3-methoxyphenyl)pyridin-2(1H)-one

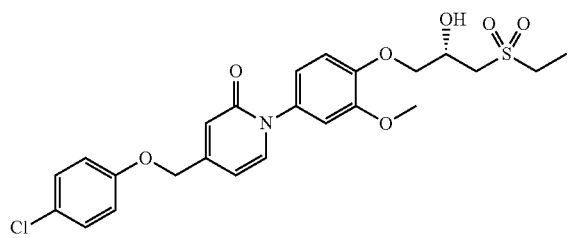 [SMILES: CCS(=O)(=O)C[C@@H](O)COc1ccc(-n2ccc(COc3ccc(Cl)cc3)cc2=O)cc1OC]

A. (R)-4-((4-chlorophenoxy)methyl)-1-(3-methoxy-4-(oxiran-2-ylmethoxy)phenyl)pyridin-2(1H)-one

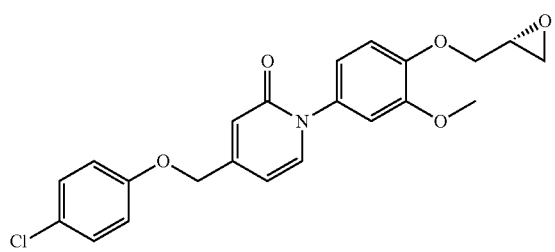 [SMILES: COc1cc(-n2ccc(COc3ccc(Cl)cc3)cc2=O)ccc1OC[C@H]1CO1]

4-((4-chlorophenoxy)methyl)-1-(4-hydroxy-3-methoxyphenyl)pyridin-2(1H)-one can be prepared by treatment of a solution of Part G of Procedure 1 with HCl/dioxane as described in Part H of Procedure 1. To a solution of 4-((4-chlorophenoxy)methyl)-1-(4-hydroxy-3-methoxyphenyl)pyridin-2(1H)-one (50 mg, 0.14 mmol) in DMF (2 mL) was added cesium fluoride (64 mg, 0.42 mmol). After stirring 1 h, (R)-oxiran-2-ylmethyl-3-nitrobenzenesulfonate (47 mg, 0.18 mmol) was added and the mixture was stirred 2 days. The mixture was partially concentrated, diluted with water and extracted with EtOAc. The combined organic extracts were washed with water, dried ($MgSO_4$), concentrated and the residue was purified by Chromatography ($SiO_2$ solvent gradient 33-60% EtOAc/Hexanes) to give the desired epoxide 10A (43 mg, 74% yield) as a white solid. LC-MS, $[M+H]^+$=414.

B. (S)-4-((4-chlorophenoxy)methyl)-1-(4-(3-(ethylthio)-2-hydroxypropoxy)-3-methoxyphenyl)pyridin-2(1H)-one

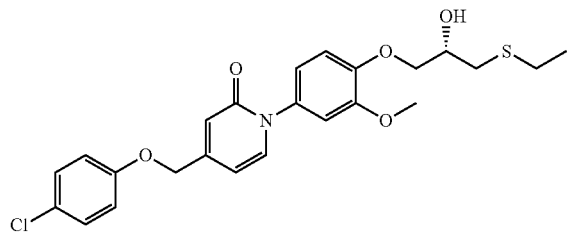 [SMILES: CCSC[C@@H](O)COc1ccc(-n2ccc(COc3ccc(Cl)cc3)cc2=O)cc1OC]

To a solution of ethanethiol (0.08 mL, 1.04 mmol) in 25% aqueous KOH (233 mg, 1.04 mmol) was added (R)-4-((4-chlorophenoxy)methyl)-1-(3-methoxy-4-(oxiran-2-ylmethoxy)phenyl)pyridin-2(1H)-one Part A (43 mg, 0.104 mmol) in THF (2 mL). Tetrabutylammonium bromide (3.3 mg, 10.4 μmol) was added and the mixture was stirred overnight. The mixture was diluted with water and extracted with EtOAc. The combined organic extracts were washed with water, dried (MgSO$_4$), concentrated and the residue was purified by Chromatography (SiO$_2$ solvent gradient 33-60% EtOAc/Hexanes) to give thioether 10B (47 mg, 95% yield) as a white solid. LC-MS, [M+H]$^+$=476.

C. (S)-4-((4-chlorophenoxy)methyl)-1-(4-(3-(ethylsulfonyl)-2-hydroxypropoxy)-3-methoxyphenyl)pyridin-2(1H)-one To a solution of (S)-4-((4-chlorophenoxy)methyl)-1-(4-(3-(ethylthio)-2-hydroxypropoxy)-3-methoxyphenyl)pyridin-2(1H)-one (47 mg, 0.10 mmol) Part B in methylene chloride (5 mL) at 0° C. was added m-CPBA (55 mg, 0.25 mmol) in portions. The mixture was warmed to rt and was stirred overnight. The mixture was diluted with methylene chloride, washed sat. NaHCO$_3$, dried (MgSO$_4$) and concentrated. The residue was purified by reverse phase HPLC 30-100% MeOH/H$_2$O to give the desired chiral sulphone A-34 (7 mg, 13% yield) as a white solid.

Procedure 11

Example A-35

4-((4-chlorophenoxy)methyl)-1-(4-(2,3-dihydroxy-2-methylpropoxy)-3-methoxyphenyl)pyridin-2(1H)-one

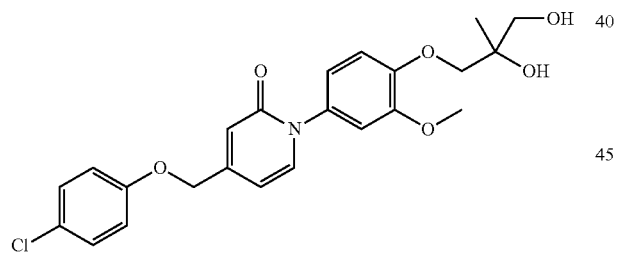

A. 4-((4-chlorophenoxy)methyl)-1-(3-methoxy-4-(2-methylallyloxy)phenyl)pyridin-2(1H)-one

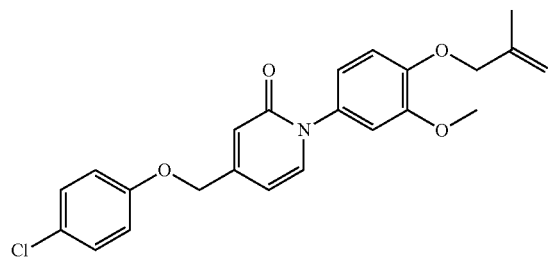 [SMILES: C=C(C)COc1ccc(-n2ccc(COc3ccc(Cl)cc3)cc2=O)cc1OC]

To a solution of 4-((4-chlorophenoxy)methyl)-1-(4-hydroxy-3-methoxyphenyl)pyridin-2(1H)-one (125 mg, 0.35 mmol), preparation described in Part A of Procedure 10, in DMF (3 mL) was added K$_2$CO$_3$ (145 mg, 1.0 mmol) and 3-bromo-2-methylpropene (0.07 mL, 0.70 mmol) and the mixture was heated to 70° C. After stirring 4 h, the mixture was diluted with water and extracted with EtOAc. The combined organic extracts were washed with water, dried (MgSO$_4$), concentrated and the residue was purified by Chromatography (SiO$_2$ solvent gradient 50-100% EtOAc/Hexanes) to give the desired methallylether 11A (119 mg, 83% yield) as a white solid. LC-MS, [M+H]$^+$=412.

B. 4-((4-chlorophenoxy)methyl)-1-(4-(2,3-dihydroxy-2-methylpropoxy)-3-methoxyphenyl)pyridin-2(1H)-one To a solution of 4-((4-chlorophenoxy)methyl)-1-(3-methoxy-4-(2-methylallyloxy)phenyl)pyridin-2(1H)-one (119 mg, 0.29 mmol) Part A in acetone (2 mL) and water (1 mL) was added 4-methylmorpholine-N-oxide (40 mg, 0.35 mmol) and osmium tetroxide (0.09 mL, 0.014 mmol, 4% in water). After stirring overnight the mixture was diluted with water and 10% aqueous sodium bisulfite and was extracted with EtOAc. The combined organic extracts were washed with water, dried (MgSO$_4$), concentrated and the residue was purified by Chromatography (SiO$_2$ solvent gradient 5-10% MeOH/CH$_2$Cl$_2$) to give the desired racemic diol A-35 (104 mg, 79% yield) as a white solid.

Proceudure 12

Example B-6

1-(4-(2-hydroxy-2-methylpropoxy)-3-methoxyphenyl)-4-(4-(1,1,2,2-tetrafluoroethoxy)phenyl)pyridin-2(1H)-one

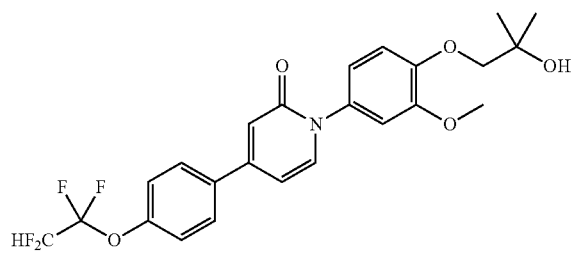

A. 1-(4-(2-hydroxy-2-methylpropoxy)-3-methoxyphenyl)-2-oxo-1,2-dihydropyridin-4-ylboronic acid

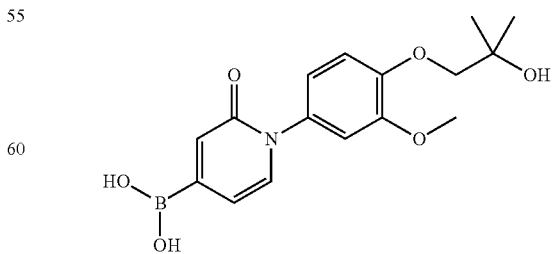

A mixture of 4-chloro-1-(4-(2-hydroxy-2-methylpropoxy)-3-methoxyphenyl)pyridin-2(1H)-one Part D of procedure 9 (300 mg, 0.93 mmol), 4,4,4',4',5,5,5',5'-octamethyl-2,2'-bi(1,3,2-dioxaborolane) (706 mg, 2.78 mmol), potassium acetate (273 mg, 2.78 mmol), TRIS(DIBENZYLIDENEACETONE)-DIPALLADIUM(0)-CHLOROFORM ADDUCT (67 mg, 0.06 mmol), and X-Phos (133 mg, 0.28 mmol) in Dioxane (6 mL) was stirred at 90° C. for 18 hours (Mullen et al, JOC, 2008, 73 (23) 9207-9213). The reaction was filtered and concentrated. The crude was purified using ISCO flash chromatography (silica gel/methylene chloride/methanol 100:0 to 90:10 gradient) to afford the desired product 1-(4-(2-hydroxy-2-methylpropoxy)-3-methoxyphenyl)-2-oxo-1,2-dihydropyridin-4-ylboronic acid 12A (112 mg, 0.336 minol, 36.3% yield) as a brown solid. LC/MS 334 (M+H)$^+$, $t_R$ 0.59 min (method 5)

B. 1-(4-(2-hydroxy-2-methylpropoxy)-3-methoxyphenyl)-4-(4-(1,1,2,2-tetrafluoroethoxy)phenyl)pyridin-2(1H)-one

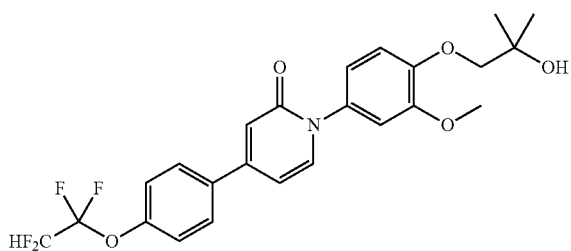

A mixture of 1-(4-(2-hydroxy-2-methylpropoxy)-3-methoxyphenyl)-2-oxo-1,2-dihydropyridin-4-ylboronic acid Part A (20 mg, 0.06 mmol), 1-bromo-4-(1,1,2,2-tetrafluoroethoxy)benzene (24.6 mg, 0.09 mmol), potassium phosphate, tribasic (32 mg, 0.15 mmol), and PalladiumTetrakis (4 mg, 3.00 μmol) in DMF (0.6 mL) was stirred under nitrogen at 80° C. overnight. The mixture was filtered, concentrated, and was purified using HPLC (Phen Luna Axia C18 5μ 10:90:0.1 to 90:10:0.1 MeOH—H$_2$O-TFA). The product was repurified using ISCO flash chromatography (silica gel/hexanes/ethyl acetate/methanol 100:0 to 0:90:10 gradient) to afford the desired product 1-(4-(2-hydroxy-2-methylpropoxy)-3-methoxyphenyl)-4-(4-(1,1,2,2-tetrafluoroethoxy)phenyl)pyridin-2(1H)-one B-6 (16.43 mg, 0.032 mmol, 54.0% yield) as a light yellow solid. LC/MS 482 (M+H)$^+$, $t_R$ 0.92 min (method 5). $^1$H NMR (400 MHz, CHLOROFORM-d) δ ppm 7.63-7.67 (2H, m), 7.43 (1H, d, J=7.26 Hz), 7.34 (2H, d, J=8.58 Hz), 6.97-7.03 (2H, m), 6.90-6.96 (1H, m), 6.87 (1H, d, J=1.76 Hz), 6.49 (1H, dd, J=7.26, 1.98 Hz), 5.80-6.11 (1H, m), 3.89 (3H, s), 3.88 (2H, s), 1.37 (6H, s)

Procedure 13

Example B-9

4-(4-(difluoromethoxy)phenyl)-1-(4-(2-hydroxy-2-methylpropoxy)-3-methoxyphenyl)pyridin-2(1H)-one

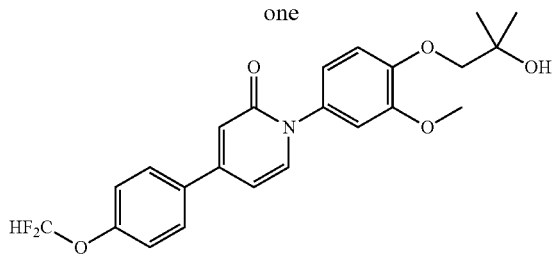

A. 2-(4-(difluoromethoxy)phenyl)-4,4,5,5-tetramethyl-1,3,2-dioxaborolane

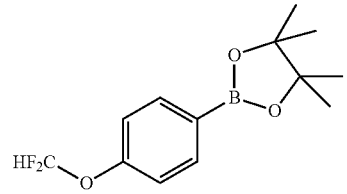

A mixture of commercially available 1-bromo-4-(difluoromethoxy)benzene (1 g, 4.48 mmol), 4,4,4',4',5,5,5',5'-octamethyl-2,2'-bi(1,3,2-dioxaborolane) (1.2 g, 4.71 mmol), potassium acetate (1.3 g, 13.4 mmol), and PdCl$_2$(dppf)-CH$_2$Cl$_2$ Adduct (0.18 g, 0.22 mmol) in DMF (15 mL) was stirred under nitrogen at 90° C. for 1 hour. Diluted with DCM, washed with water, sat. NaHCO$_3$, brine, dried (MgSO$_4$), and concentrated. The crude was purified using ISCO flash chromatography (silica gel hexanes/ethyl acetate 100:0 to 50:50 gradient) to afford the desired product 2-(4-(difluoromethoxy)phenyl)-4,4,5,5-tetramethyl-1,3,2-dioxaborolane 13A (1.12 g, 3.32 mmol, 74.0% yield) as a brown oil.

B. 4-(4-(difluoromethoxy)phenyl)-1-(4-(2-hydroxy-2-methylpropoxy)-3-methoxyphenyl)pyridin-2(1H)-one

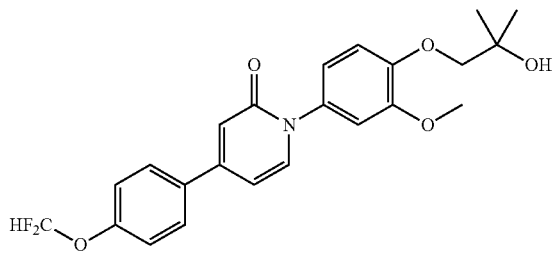

A mixture of 2-(4-(difluoromethoxy)phenyl)-4,4,5,5-tetramethyl-1,3,2-dioxaborolane Part A (62.6 mg, 0.23 mmol), 4-chloro-1-(4-(2-hydroxy-2-methylpropoxy)-3-methoxyphenyl)pyridin-2(1H)-one Part D of Procedure 9 (50 mg, 0.15 mmol), Potassium phosphate tribasic (65.6 mg, 0.31 mmol), Palladium (II) acetate (1.7 mg, 7.7 μmol), and 2-DICYCLOHEXYLPHOSPHINO-2',6'-DIMETHOXY-1,1'-BIPHENYL (3.1 mg, 7.72 μmol) in Toluene (1.4 mL) and Water (0.15 mL) was stirred at 100° C. for 16 h. The mixture was filtered, diluted with EtOAc, washed with sat. NaHCO$_3$, dired (MgSO$_4$), and concentrated. The crude was purified using HPLC (Phen Luna Axia C18 5μ 10:90:0.1 to 90:10:0.1 MeOH—H$_2$O-TFA to afford 4-(4-(difluoromethoxy)phenyl)-1-(4-(2-hydroxy-2-methylpropoxy)-3-methoxyphenyl)pyridin-2(1H)-one B-9 (26.26 mg, 0.057 mmol, 36.7% yield) as a white solid. LC/MS 432 (M+H)$^+$, $t_R$ 0.87 min (method 5). $^1$H NMR (400 MHz, CHLOROFORM-d) δ ppm 7.63 (2H, d), 7.42 (1H, d, J=7.04 Hz), 7.24 (2H, d, J=8.58 Hz), 6.95-7.03 (2H, m), 6.90-6.93 (1H, m), 6.86 (1H, s), 6.48 (1H, d, J=7.26 Hz), 6.40-6.78 (1H, m), 3.88 (3H, s), 3.87 (2H, s), 1.37 (6H, s)

Procedure 14

Example C-9

1-(4-(2,3-dihydroxy-2-methylpropoxy)-3-methoxyphenyl)-4-(4-(trifluoromethyl)phenyl)pyridin-2(1H)-one

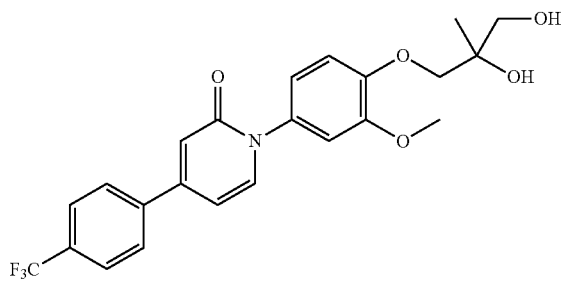 [SMILES: COc1cc(-n2ccc(-c3ccc(C(F)(F)F)cc3)cc2=O)ccc1OCC(C)(O)CO]

A. 4-chloro-1-(3-methoxy-4-((2-(trimethylsilyl)ethoxy)methoxy)phenyl)pyridin-2(1H)-one

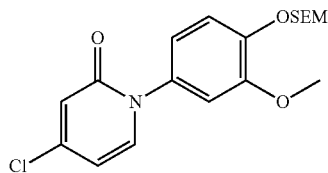

N1,N2-dimethylcyclohexane-1,2-diamine (140 µL, 0.81 mmol) was added to a mixture of commercially available 4-chloropyridin-2(1H)-one (150 mg, 1.16 mmol), (2-((4-bromo-2-methoxyphenoxy)methoxy)ethyl)trimethylsilane (463 mg, 1.39 mmol), preparation described in Part G of Procedure 1, K₃PO₄ (737 mg, 3.47 mmol), and Copper (I) Iodide (154 mg, 0.81 mmol) in Dioxane (6 mL). The mixture was stirred at 100° C. overnight. The reaction was diluted with DCM, washed with sat. NaHCO₃, dried (Na₂SO₄), and concentrated. The crude was subjected to ISCO flash chromatography (silica gel/hexanes/ethyl acetate 100:0 to 0:100 gradient) to afford the desired product 4-chloro-1-(3-methoxy-4-((2-(trimethylsilyl)ethoxy)methoxy)phenyl)pyridin-2(1H)-one 14A (358 mg, 0.94 mmol, 81% yield) as a light yellow solid. LC/MS 382 (M+H)⁺, t$_R$ 1.06 min (method 5).

B. 1-(4-hydroxy-3-methoxyphenyl)-4-(4-(trifluoromethyl)phenyl)pyridin-2(1H)-one

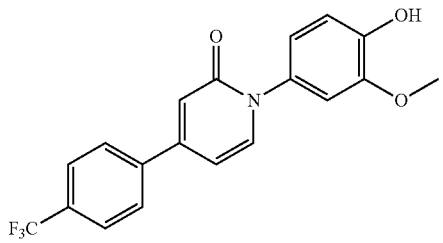 [SMILES: COc1cc(-n2ccc(-c3ccc(C(F)(F)F)cc3)cc2=O)ccc1O]

A mixture of 4-chloro-1-(3-methoxy-4-((2-(trimethylsilyl)ethoxy)methoxy)phenyl)-pyridin-2(1H)-one Part A (118 mg, 0.31 mmol), 4-(trifluoromethoxy)phenylboronic acid (95 mg, 0.463 mmol), Potassium phosphate tribasic (197 mg, 0.93 mmol), and PalladiumTetrakis (18 mg, 0.02 mmol) in DMF (1.5 mL) was stirred under nitrogen at 90° C. overnight. The mixture was diluted with DCM, filtered, and concentrated. The crude was dissolved in 10:90 MeOH/CH₂Cl₂ (5 mL) and 4N HCl in dioxane (1 mL) was added. The mixture was stirred for 30 min at RT. Concentrated and the residue was purified using ISCO flash chromatography (silica gel/hexanes/ethyl acetate/methanol 100:0 to 0:90:10 gradient) to afford the desired product 1-(4-hydroxy-3-methoxyphenyl)-4-(4-(trifluoromethoxy)phenyl)pyridin-2(1H)-one 14B (99 mg, 0.26 mmol, 85% yield) as a yellow solid. LC/MS 362 (M+H)⁺, t$_R$ 0.89 min (method 5).

C. 1-(3-methoxy-4-(2-methylallyloxy)phenyl)-4-(4-(trifluoromethyl)phenyl)pyridin-2(1H)-one

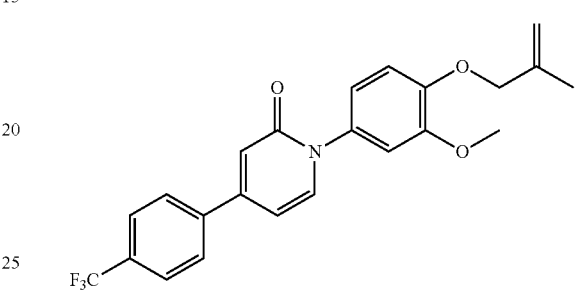

A mixture of 1-(4-hydroxy-3-methoxyphenyl)-4-(4-(trifluoromethoxy)phenyl)pyridin-2(1H)-one Part B (55 mg, 0.15 mmol), 3-chloro-2-methylprop-1-ene (19.80 mg, 0.219 mmol), and potassium carbonate (60.4 mg, 0.437 mmol) in DMF (1.5 mL) was stirred at 70° C. overnight. Diluted with DCM, washed with water, sat. NaHCO₃, dried (Na₂SO₄), and concentrated. The crude was purified using ISCO flash chromatography (silica gel/hexanes/ethyl acetate 100:0 to 50:50 gradient) to afford the desired product 1-(3-methoxy-4-(2-methylallyloxy)phenyl)-4-(4-(trifluoromethoxy)phenyl)pyridin-2(1H)-one 14C (55.3 mg, 0.13 mmol, 88% yield) as a white solid. LC/MS 416 (M+H)⁺, t$_R$ 1.04 min (method 5).

D. 1-(4-(2,3-dihydroxy-2-methylpropoxy)-3-methoxyphenyl)-4-(4-(trifluoromethyl)phenyl)pyridin-2(1H)-one

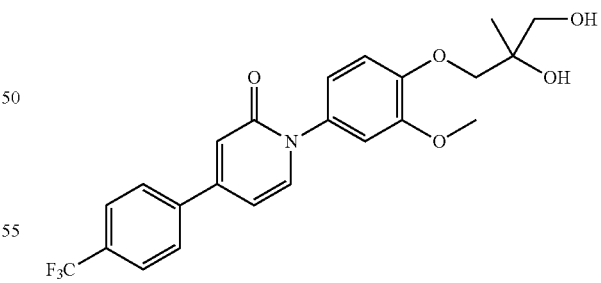

A mixture of 1-(3-methoxy-4-(2-methylallyloxy)phenyl)-4-(4-(trifluoromethoxy)phenyl)pyridin-2(1H)-one Part C (55 mg, 0.13 mmol), 4-methylmorpholine 4-oxide (18 mg, 0.15 mmol), and osmium tetraoxide (2.0 µL, 6.4 µmol) in Acetone (1 ML) and Water (0.4 mL) was stirred at RT for 2.5 h. Diluted with DCM, washed with 5% sodium sulfite, dried (Na₂SO₄), and concentrated. The residue was purified using ISCO flash chromatography (silica gel/CH₂Cl₂/methanol 100:0 to 90:10 gradient) to afford the desired product 1-(4-(2,3-dihydroxy- 2-methylpropoxy)-3-mnethoxyphenyl)-4-(4-(trifluoromethoxy)phenyl)-pyridin-2(1H)-one C-9 (46.2 mg, 0.1 mmol, 76% yield) as an off-white solid. LC/MS 466 (M+H)+, $t_R$ 0.88 min (method 5). $^1$H NMR (400 MHz, CHLOROFORM-d) δ ppm 7.64-7.69 (2H, m), 7.44 (1H, d, J=7.04 Hz), 7.35 (2H, d, J=7.92 Hz), 6.98-7.04 (2H, m), 6.92-6.97 (1H, m), 6.87 (1H, d, J=1.54 Hz), 6.50 (1H, dd, J=7.26, 1.98 Hz), 4.08-4.14 (1H, m), 3.98-4.05 (1H, m), 3.91 (3H, s), 3.85 (1H, dd, J=11.44, 4.40 Hz), 3.54-3.63 (1H, m), 3.27 (1H, s), 2.93 (1H, dd, J=8.91, 4.51 Hz), 1.28 (3H, s)

Procedure 15

Example C-14

(S)-1-(4-(3-(ethylsulfonyl)-2-hydroxypropoxy)-3-methoxyphenyl)-4-(4-(trifluoromethyl)phenyl)pyridin-2(1H)-one

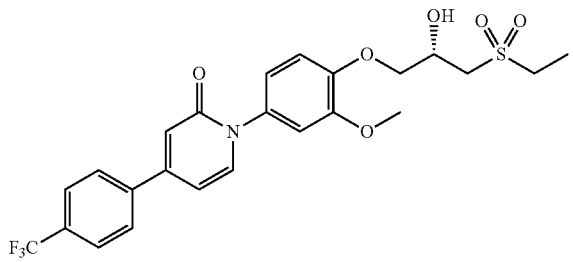 [SMILES: CCS(=O)(=O)C[C@@H](O)COc1ccc(-n2ccc(-c3ccc(C(F)(F)F)cc3)cc2=O)cc1OC]

A. (R)-1-(3-methoxy-4-(oxiran-2-ylmethoxy)phenyl)-4-(4-(trifluoromethyl)phenyl)pyridin-2(1H)-one

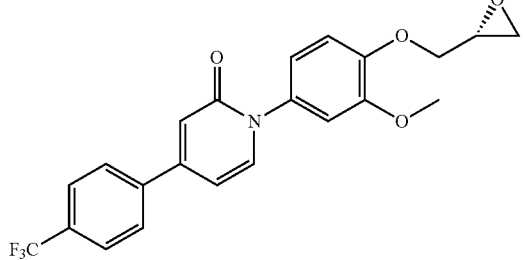

A mixture of 1-(4-hydroxy-3-methoxyphenyl)-4-(4-(trifluoromethyl)phenyl)pyridin-2(1H)-one Part B of Procedure 14 (38 mg, 0.105 mmol) and cesium fluoride (48 mg, 0.32 mmol) in DMF (1 mL) was stirred at RT for 30 min. Then, (R)-oxiran-2-ylmethyl 3-nitrobenzenesulfonate (35 mg, 0.13 mmol) was added and stirred overnight at RT. Diluted with DCM, washed with water, sat. NaHCO$_3$, dried (Na$_2$SO$_4$), and concentrated. The crude was purified using ISCO flash chromatography (silica gel/hexanes/ethyl acetate 100:0 to 0:100 gradient) to afford the desired product (R)-1-(3-methoxy-4-(oxiran-2-ylmethoxy)phenyl)-4-(4-(trifluoromethyl)phenyl) pyridin-2(1H)-one 15A (32.1 mg, 0.08 mmol, 73.1% yield) as a light yellow solid. LC/MS 418 (M+H)+, $t_R$ 0.93 min (method 5).

B. (S)-1-(4-(3-(ethylthio)-2-hydroxypropoxy)-3-methoxyphenyl)-4-(4-(trifluoromethyl)phenyl)pyridin-2(1H)-one

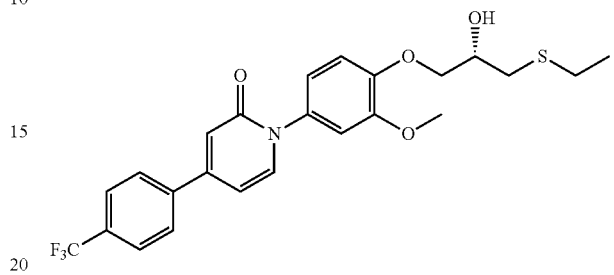

Ethanethiol (47.6 mg, 0.76 mmol) and 25% aq. potassium hydroxide (172 mg, 0.77 mmol) were added to a solution of (R)-1-(3-methoxy-4-(oxiran-2-ylmethoxy)phenyl)-4-(4-(trifluoromethyl)phenyl)pyridin-2(1H)-one (32 mg, 0.08 mmol) Part A in THF (1.5 mL). The mixture was stirred overnight at RT. Diluted with EtOAc, washed with sat. NaHCO$_3$, dried (Na$_2$SO$_4$), and concentrated. The residue was purified using ISCO flash chromatography (silica gel/hexanes/ethyl acetate 100:0 to 0:100 gradient) to afford the desired product (S)-1-(4-(3-(ethylthio)-2-hydroxypropoxy)-3-methoxyphenyl)-4-(4-(trifluoromethyl)phenyl)pyridin-2(1H)-one 15B (28 mg, 0.06 mmol, 76% yield) as a light yellow solid. LC/MS 480 (M+H)+, $t_R$ 0.97 min (method 5).

C. (S)-1-(4-(3-(ethylsulfonyl)-2-hydroxypropoxy)-3-methoxyphenyl)-4-(4-(trifluoromethyl)phenyl)pyridin-2(1H)-one

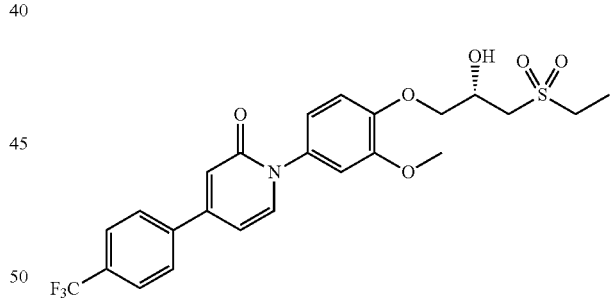

mCPBA (43 mg, 0.17 mmol) was added to a solution of (S)-1-(4-(3-(ethylthio)-2-hydroxypropoxy)-3-methoxyphenyl)-4-(4-(trifluoromethyl)phenyl)pyridin-2(1H)-one Part B (28 mg, 0.06 mmol) in DCM (1.2 mL) and stirred at RT for 1 hour. Diluted with DCM, washed with 5% sodium thiosulfate, dried (Na$_2$SO$_4$), and concentrated. Crude was purified using HPLC (Phen Luna Axia C18 5μ 10:90:0.1 to 90:10:0.1 MeOH—H$_2$O-TFA) to afford the desired product (S)-1-(4-(3-(ethylsulfonyl)-2-hydroxypropoxy)-3-methoxyphenyl)-4-(4-(trifluoromethyl)phenyl)pyridin-2(1H)-one C-14 (24.03 mg, 0.045 mmol, 76% yield) as a light yellow solid. LC/MS 512 (M+H)+, $t_R$ 0.88 min (method 5). $^1$H NMR (400 MHz, CHLOROFORM-d) δ ppm 7.72-7.80 (4H, m), 7.52 (1H, d, J=7.04 Hz), 7.01-7.08 (2H, m), 7.00 (1H, d, J=2.20 Hz), 6.90-6.96 (1H, m), 6.66 (1H, dd, J=7.15, 1.87 Hz), 4.60-4.69 (1H, m), 4.09-4.16 (2H, m), 3.89 (3H, s), 3.31-3.38 (1H, m), 3.28 (1H, s), 3.15-3.25 (2H, m), 1.46 (3H, t, J=7.48 Hz)

Procedure 16

Example E-25

4-((5-Chloropyridin-2-yl)methoxy)-1-(4-(2-hydroxy-2-methylpropoxy)-3-methoxyphenyl)pyridin-2(1H)-one

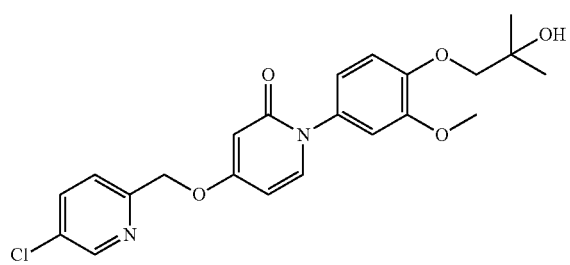 [SMILES: COc1cc(-n2ccc(OCc3ccc(Cl)cn3)cc2=O)ccc1OCC(C)(C)O]

A. Iodomethyl benzoate

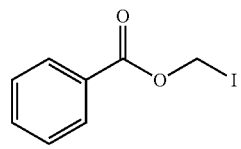 [SMILES: O=C(OCI)c1ccccc1]

Title compound was prepared according to the procedure described in: Iyer, R. P; Yu, D.; Ho, N.-H.; Agrawal, S. *Synth. Commun.* 1995, 25, 2739. A solution of chloromethyl benzoate (1.00 g, 5.86 mmol) and sodium iodide (1.76 g, 11.72 mmol) in acetonitrile (7.00 mL) was stirred at RT for 24 h. The acetonitrile was removed in vacua and ether was added. The solid formed was filtered, washed well with ether, air dried under vacuum and subjected to flash chromatography (silica gel/hexanes-EtOAc 100:0 to 85:15 gradient) to afford iodomethyl benzoate 16A (1.21 g, 79% yield) as a clear oil. LC-MS, [M+H]⁺=263. ¹H NMR (400 MHz, CDCl3) δ 8.03 (2H, d, J=7.0 Hz), 7.60 (1H, t, J=7.5 Hz), 7.45 (2H, t, J=7.9 Hz), 6.15 (2H, s).
HPLC-Method 8; 3.20 min.

B. (Benzoyloxymethyl)zinc(II) iodide

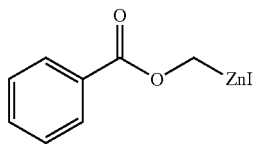

Title compound was prepared according to the procedure described in: Silhar, P.; Pohl, R.; Votruba, I.; Hocek, M. *Org. Lett.* 2004, 6, 3225. To a 10° C. solution of zinc (dust) (0.604 g, 9.24 mmol) in THF (1.7 mL) was added a solution of iodomethyl benzoate Part A (1.21 g, 4.62 mmol) in THF (2.1 mL) and the reaction was stirred at 10° C. 1.5 h. Reaction monitored by LCMS by observing the formation of hydrolyzed product (methyl benzoate). Material was used in the next step without purification as a 0.9 M THF solution.

C. (5-Chloropyridin-2-yl)methyl benzoate

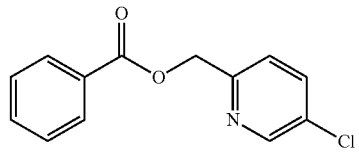 [SMILES: O=C(OCc1ccc(Cl)cn1)c1ccccc1]

Title compound was prepared according to the procedure described in: Hasnik, Z.; Silhar, P.; Hocek, M. *Synlett* 2008, 4, 543. A solution of (benzoyloxymethyl)zinc(II) iodide Part B (2.17 mL, 1.949 mmol) was added to a solution of 2-bromo-5-chloropyridine (125 mg, 0.650 mmol) and Pd(PPh3)4 (37.5 mg, 0.032 mmol) in THF (1.30 mL). The reaction mixture was stirred at RT for 5 h at which point it was quenched with 1M NaH2PO4 (30 mL) The solid formed was filtered and washed well with water. The filtrate was extracted with DCM (3×25 mL) and the combined organic layers were dried over anhydrous Na2SO4 and concentrated. The crude product was subjected to flash chromatography (silica gel/hexanes-EtOAc 100:0 to 50:50 gradient) to afford (5-chloropyridin-2-yl)methyl benzoate 16C (101 mg, 63% yield) as an off-white solid. LC-MS, [M+H]⁺=248. HPLC-Method 8; 3.30 min.

D. (5-Chloropyridin-2-yl)methanol

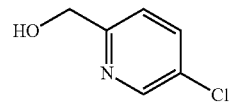

Sodium methoxide (1M in MeOH) (0.162 mL, 0.162 mmol) was added to a solution of (5-chloropyridin-2-yl)methyl benzoate Part C (200 mg, 0.808 mmol) in MeOH (47.5 mL) and stirred at RT for 2.0 h. The solvent was removed in vacuo and the crude product was subjected to flash chromatography (silica gel/DCM-MeOH 100:0 to 90:10 gradient) to afford (5-chloropyridin-2-yl)methanol 16D (68 mg, 59% yield) as an off-white solid. LC-MS, [M+H]⁺=144. ¹H NMR (400 MHz, DMSO) δ 8.51 (1H, d, J=2.2 Hz), 7.91 (1H, dd, J=8.4, 2.6 Hz), 7.49 (1H, d, J=8.4 Hz), 5.53 (1H, t, J=5.9 Hz), 4.54 (2H, d, J=6.2 Hz). HPLC-Method 8; 0.76 min.

E. 2-(Bromomethyl)-5-chloropyridine

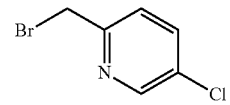

To a 0° C. solution of (5-chloropyridin-2-yl)methanol Part D (10 mg, 0.070 mmol) and triphenylphosphine (32.9 mg, 0.125 mmol) in DCM (0.170 mL) was added a solution of carbon tetrabromide (31.4 mg, 0.095 mmol) in DCM (0.084 mL) dropwise. The mixture was stirred at RT for 2.0 h at which point the solvent was removed in vacuo and the crude product was subjected to flash chromatography (silica gel/DCM-EtOAc 100:0 to 0:100 gradient) to afford 2-(bromomethyl)-5-chloropyridine 16E (2.4 mg, 16.8% yield) as a light brown oil. LC-MS, [M+H]+208. $^1$H NMR (400 MHz, CDCl3) δ 8.47 (1H, d, J=2.2 Hz), 7.61 (1H, dd, J=8.4, 2.2 Hz), 7.33 (1H, d, J=8.4 Hz), 4.46 (2H, s). HPLC-Method 8; 2.42 min.

F. 4-((5-Chloropyridin-2-yl)methoxy)-1-(4-(2-hydroxy-2-methylpropoxy)-3-methoxyphenyl)pyridin-2(1H)-one

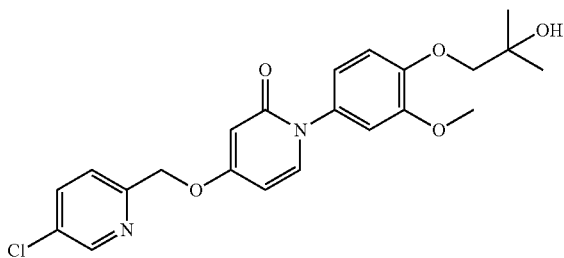 [SMILES: COc1cc(-n2ccc(OCc3ccc(Cl)cn3)cc2=O)ccc1OCC(C)(C)O]

Following the procedure described in Part D of Example 7, Part E 16E was converted to the title compound E-25. LC-MS, [M+H]+–431. $^1$H NMR (400 MHz, CDCl3) δ 8.52 (1H, d, J=2.6 Hz), 7.66 (1H, dd, J=8.4, 2.6 Hz), 7.37 (1H, d, J=8.4 Hz), 7.18 (1H, d, J=7.9 Hz), 6.89 (1H, d, J=8.8 Hz), 6.82 (1H, d, J=2.2 Hz), 6.73-6.79 (1H, m), 6.01 (1H, dd, J=7.9, 2.7 Hz), 5.95 (1H, d, J=2.6 Hz), 5.08 (2H, s), 3.78 (5H, s), 2.53 (1H, s), 1.28 (6H, s). HPLC-Method 8; 3.04 min Procedure 17

Example D-32

4-(4-fluorobenzyloxy)-1-(4-(2-hydroxy-2-methylpropoxy)-3-methylphenyl)pyridin-2(1H)-one

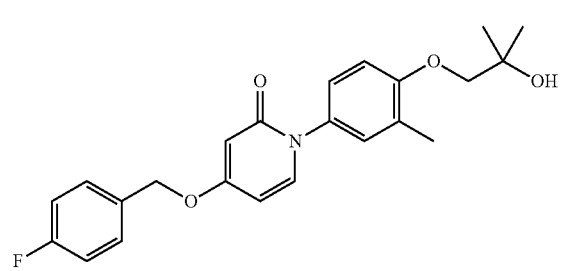 [SMILES: Cc1cc(-n2ccc(OCc3ccc(F)cc3)cc2=O)ccc1OCC(C)(C)O]

A. 4-(4-fluorobenzyloxy)pyridin-2(1H)-one

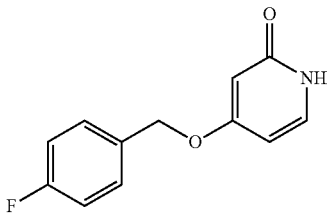 [SMILES: O=c1cc(OCc2ccc(F)cc2)cc[nH]1]

A mixture of potassium carbonate (12.44 g, 90 mmol), 4-hydroxypyridin-2(1H)-one (10 g, 90 mmol) in DMF (500 mL) was stirred at 140° C. for 60 min prior to addition of a solution of 1-(chloromethyl)-4-fluorobenzene (13.01 g, 90 mmol) in DMF (5.0 mL). After stirring at 140° C. for 60 min, the reaction was cooled to RT prior to dilution with water (1.0 L). The resulting suspension was stirred at RT for 60 min prior to collection of precipitate by filtration. The filter cake was washed with water (250 mL), suspended with stirring in ethyl ether (500 mL) for 15 min and collected by filtration. After air-drying, 4-(4-fluorobenzyloxy)pyridin-2(1H)-one 17A was obtained as a white solid (6.67 g, 28.9 mmol, 32.1% yield). 1H NMR (400 MHz, MeOD) δ ppm 7.42-7.56 (2H, m), 7.34 (1H, d, J=7.26 Hz), 7.03-7.25 (2H, m), 6.12-6.24 (1H, m), 6.01 (1H, br. s.), 5.10 (2H, s).

B. 4-(4-fluorobenzyloxy)-1-(4-(2-hydroxy-2-methylpropoxy)-3-methylphenyl)pyridin-2(1H)-one

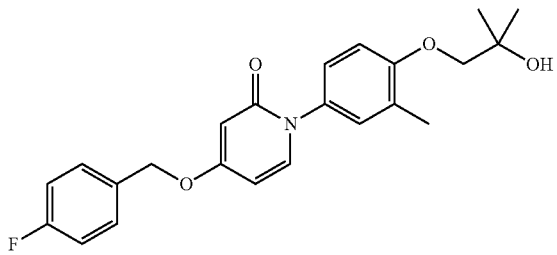

Following the procedure for N-arylation and purification described in Part B of Procedure 7, 17A was converted to the title compound D-32. LC/MS 398 (M+H)$^+$, t$_g$ 0.93 min (method 5); 1H NMR (400 MHz, MeOD) δ ppm 7.32-7.48 (3H, m), 6.97-7.11 (4H, m), 6.89 (1H, d, J=8.14 Hz), 6.13 (1H, dd, J=7.59, 2.75 Hz), 5.98 (1H, d, J=2.86 Hz), 5.03 (2H, s), 3.73 (2H, s), 2.20 (3H, s), 1.26 (6H, s)

Procedure 18

Example F-4

4-((4-chlorophenyl)ethynyl)-1-(4-(2-hydroxy-2-methylpropoxy)-3-methoxyphenyl)pyridin-2(1H)-one

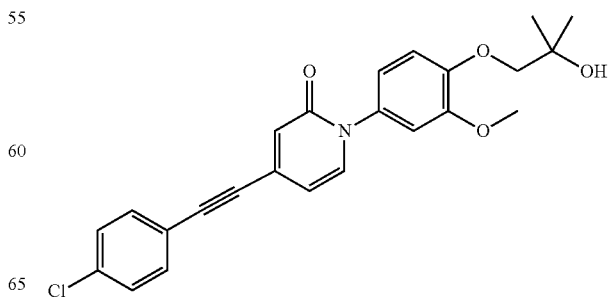

121

A. Tributyl((4-chlorophenyl)ethynyl)stannane

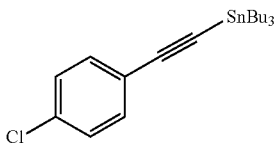

A mixture of commercially available 1-chloro-4-ethynylbenzene (4 g, 29 mmol) and 1,1,1-tributyl-N,N-dimethylstannanamine (9.79 g, 29.3 mmol) was stirred at RT for 2 hours. The reaction was concentrated to afford the desired product tributyl((4-chlorophenyl)ethynyl)stannane 18A (13.1 g, 27.7 mmol, 95% yield) as a light yellow oil.

B. 4-((4-chlorophenyl)-ethynyl)-1-(4-(2-hydroxy-2-methylpropoxy)-3-methoxyphenyl)pyridin-2(1H)-one

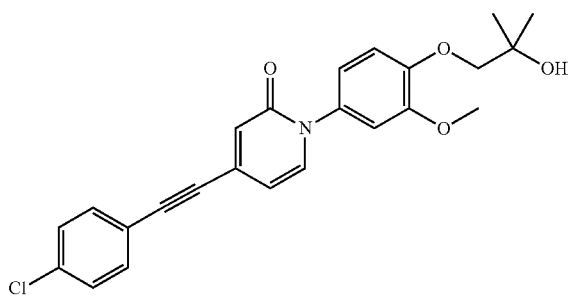 [SMILES: COc1cc(-n2ccc(C#Cc3ccc(Cl)cc3)cc2=O)ccc1OCC(C)(C)O]

122

A mixture of 4-chloro-1-(4-(2-hydroxy-2-methylpropoxy)-3-methoxyphenyl)pyridin-2(1H)-one Part D of Procedure 9 (100 mg, 0.31 mmol), tributyl((4-chlorophenyl)ethynyl)stannane Part A (237 mg, 0.56 mmol), copper (I) iodide (17.6 mg, 0.09 mmol), and PalladiumTetrakis (54 mg, 0.05 mmol) in DMF (1.5 mL) was stirred under nitrogen at 70° C. overnight. The reaction was diluted with DCM, filtered, washed with 1N HCl, sat. NaHCO$_3$, dried (MgSO$_4$), and concentrated. The residue was purified using ISCO flash chromatography (silica gel/hexanes/ethyl acetate 100:0 to 0:100 gradient). The product was repurified using HPLC (Phen Luna Axia C18 5μ 10:90:0.1 to 90:100.1 MeOH—H$_2$O-TFA) to afford the desired product 4-((4-chlorophenyl)ethynyl)-1-(4-(2-hydroxy-2-methylpropoxy)-3-methoxyphenyepyridin-2(1H)-one F-4 (90 mg, 0.21 mmol, 66.7% yield) as a light yellow solid. LC/MS 424 (M+H)$^+$, $t_R$ 1.00 min (method 5). $^1$H NMR (400 MHz, CHLOROFORM-d) δ ppm 7.49-7.54 (2H, m), 7.37-7.44 (3H, m), 6.96-7.02 (2H, m), 6.93 (1H, d, J=2.26 Hz), 6.89 (1H, dd), 6.50 (1H, d, Hz), 3.88 (5H, s), 1.38 (6H, s)

Prodrug Examples P-1 TO P-4

Prodrugs were prepared of selected secondary and tertiary alcohols to improve solubility and exposure. Preparation of the glycine ester of the tertiary alcohols is exemplified below. Examples P-2-P-4 were prepared in a similar manner to that described for P-1 using the appropriate alcohol and BOC glycine followed by TFA removal of the BOC group.

TABLE P

Prodrug Esters

| Ex. No. | Ester of Example No. | Structure | HPLC Method ($t_R$ Min.) | LC MS | $^1$H-NMR (CDCl$_3$) |
|---|---|---|---|---|---|
| P-1 | A-1 | 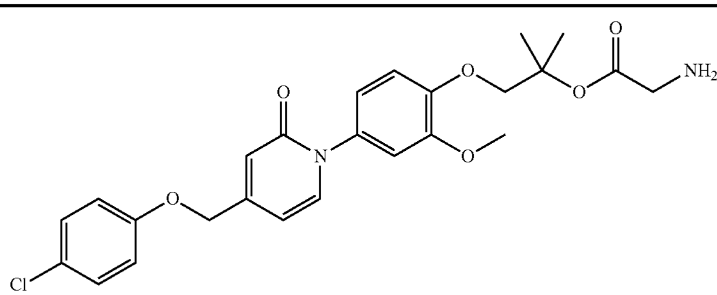 | 3.24 method 7 | 487 | $^1$H NMR (400 MHz, CDCl$_3$) 7.35 (d, J = 7.0 Hz, 1H), 7.27 (m, 2H), 6.97 (d, J = 8.8 Hz, 1H), 6.88 (m, 3H), 6.83 (dd, J = 8.3 and 2.2 Hz, 1H), 6.70 (s, 1H), 6.27 (m, 1H), 4.92 (s, 2H), 4.19 (s, 2H), 3.85 (s, 3H), 3.76 (d, J = 5.7 Hz, 2H), 1.58 (s, 6H), 1.02 (s, 9H). |
| P-2 | D-1 | 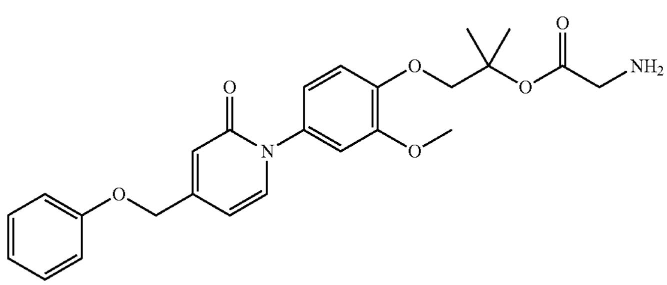 [SMILES: COc1cc(-n2ccc(COc3ccccc3)cc2=O)ccc1OCC(C)(C)OC(=O)CN] | 0.76 method 5 | 453 | $^1$H NMR (400 MHz, MeOD) δ ppm 7.52 (1 H, d, J = 7.53 Hz), 7.25-7.45 (5 H, m), 7.02 (1 H, d, J = 8.53 Hz), 6.95 (1 H, d, J = 2.26 Hz), 6.82 (1 H, dd, J = 8.41, 2.38 Hz), 6.30 (1 H, dd, J = 7.53, 2.76 Hz), 6.10 (1 H, d, J = 2.76 Hz), 5.13 (2 H, s), 4.22 (2 H, s), 3.79 (3 H, s), 3.64 (2 H, s), 1.58 (6 H, s) |

TABLE P-continued

Prodrug Esters

| Ex. No. | Ester of Example No. | Structure | HPLC Method ($t_R$ Min.) | LC MS | $^1$H-NMR (CDCl$_3$) |
|---|---|---|---|---|---|
| P-3 | D-2 | 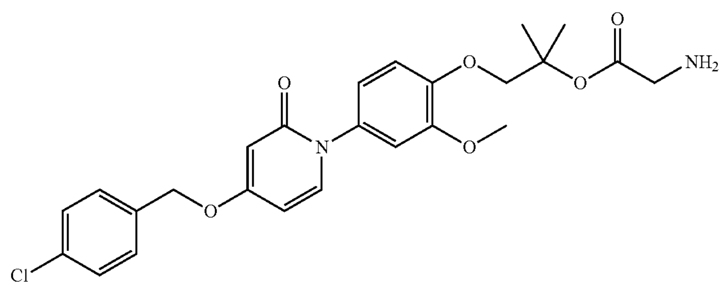 [SMILES: COc1cc(-n2ccc(OCc3ccc(Cl)cc3)cc2=O)ccc1OCC(C)(C)OC(=O)CN] | 0.83 method 5 | 487 | $^1$H NMR (400 MHz, MeOD) δ ppm 7.65 (1 H, d, J = 7.53 Hz), 7.47 (4 H, q, J = 8.53 Hz), 7.11 (1 H, d, J = 8.53 Hz), 7.05 (1 H, d, J = 2.26 Hz), 6.91 (1 H, dd, J = 8.53, 2.26 Hz), 6.43 (1 H, dd, J = 7.53, 2.76 Hz), 6.21 (1 H, d, J = 2.51 Hz), 5.22 (2 H, s), 4.31 (2 H, s), 3.88 (3 H, s), 3.74 (2 H, s), 1.67 (6 H, s) |
| P-4 | D-3 | 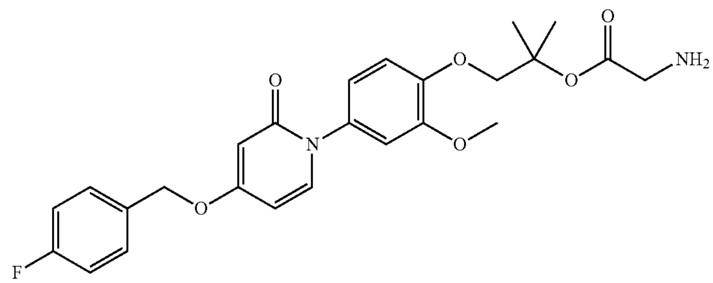 [SMILES: COc1cc(-n2ccc(OCc3ccc(F)cc3)cc2=O)ccc1OCC(C)(C)OC(=O)CN] | 0.78 method 5 | 471 | $^1$H NMR (400 MHz, MeOD) δ ppm 7.62 (1 H, d, J = 7.53 Hz), 7.35-7.47 (2 H, m), 6.91-7.13 (4 H, m), 6.82 (1 H, dd, J = 8.41, 2.38 Hz), 6.41 (1 H, dd, J = 7.53, 2.76 Hz), 6.20 (1 H, d, J = 2.51 Hz), 5.13 (2 H, s), 4.18 (2 H, s), 3.76 (3 H, s), 3.63 (2 H, s), 1.55 (6 H, s) |

Example P-1

1-(4-(4-((4-Chlorophenoxy)methyl)-2-oxopyridin-1 (2H)-yl)-2-methoxyphenoxy)-2-methylpropan-2-yl 2-aminoacetate hydrochloride

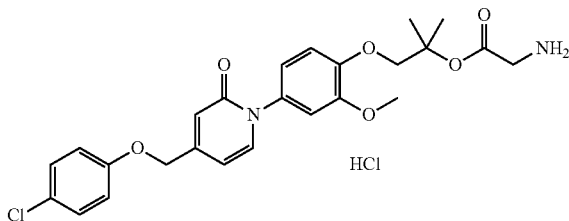 [SMILES: COc1cc(-n2ccc(COc3ccc(Cl)cc3)cc2=O)ccc1OCC(C)(C)OC(=O)CN ; Cl]

A. 1-(4-(4-((4-Chlorophenoxy)methyl)-2-oxopyridin-1(2H)-yl)-2-methoxyphenoxy)-2-methylpropan-2-yl 2-(tert-butoxycarbonylamino)acetate To a stirred suspension of the alcohol prepared in Example A-1 (1.15 g, 2.7 mmol), 4-pyrrolidinopyridine (0.40 g, 2.7 mmol) and BOC-glycine (1.4 g, 8.0 mmol) in CH$_2$Cl$_2$ (30 mL) at 42° C. was added N,N-diisopropylcarbodiimide (1.14 mL, 7.4 mmol) over 30 min. HPLC analysis showed 40% alcohol still remained. More BOC-glycine (1.4 g, 8.0 mmol) was added followed by additional N,N'-diisopropylcarbodiimide (1.14 mL, 7.4 mmol) which was slowly added over 30 min. The reaction was allowed to cool to RT and was stirred overnight. Hydrazine (0.42 mL, 13.4 mmol) was added and the reaction mixture was stirred 1 h. The reaction mixture was diluted with cold water, acidified with cold 1M HCl (3×20 mL) and was extracted with methylene chloride. The combined organic extracts washed with water and sat. NaHCO$_3$, prior to drying over MgSO$_4$ and concentrating under vacuum. Chromatography (silica gel 230-400 mesh, 75% EtOAc/hexane) of the residue afforded the desired ester (1.45 g, 92% yield). HPLC-Method 6; 4.07 min: LC MS (M+1–587): $^1$H NMR (400 MHz, CDCl$_3$) 7.35 (d, J=7.0 Hz, 1H), 7.27 (m, 2H), 6.97 (d, J'8.8 Hz, 1H), 6.88 (m, 3H), 6.83 (dd, J=8.3 and 2.2 Hz, 1H), 6.70 (s, 1H), 6.27 (m, 1H), 4.92 (s, 2H), 4.19 (s, 2H), 3.85 (s, 3H), 3.76 (d, J=5.7 Hz, 2H), 1.58 (s, 6H), 1.02 (s, 9H).

B. 1-(2-Methoxy-4-(2-oxo-3-(4-(trifluoromethyl) phenylthio)pyrazin-1(2H)-yl)phenoxy)-2-methylpropan-2-yl2-aminoacetate hydrochloride The BOC glycinate ester described in Part A (1.25 g, 2.13 mmol) was treated with 4M HCl in dioxane (60 mL) at 40° C. for 30 min. The volatiles were removed under vacuum and the residue was under further dried under vacuum at 40° C. The resulting solid was triturated with ether/EtOAc followed by trituration with ether to give the title compound P-1 as the amine hydrochloride salt (0.92 g, 83%) as a white solid. HPLC-Method 6; 3.24 min: LC MS (M+1=487): $^1$H NMR (400 MHz, CD$_3$OD) 7.63 (d, J=7.0 Hz, 1H), 7.29 (m, 2H), 7.09 (d, J=8.8 Hz, 1H), 7.04 (d, J=2.6 Hz, 1H), 7.01 (m, 2H), 6.92 (m, 1H), 6.71 (s, 1H), 6.56 (m, 1H), 5.09 (s, 2H), 4.29 (s, 2H), 3.85 (s, 3H), 3.69 (s, 2H), 1.64 (s, 6H).

Biological Assays

Radioligand Binding Assay for Assessment of MCHR1 Activity
Assay and Biological Evaluation Compounds of Formula I were initially characterized in an in vitro binding assay to determine their Ki or ability to antagonize binding of a peptide agonist to the human melanin concentrating hormone receptor (MCHR1). Representative compounds of the present invention had the following Ki values:

| Example No. | Ki (nM) |
|---|---|
| A-6 | 2341 |
| A-29 | 29 |
| A-33 | 500 |
| B-2 | 7 |
| C-1 | 3 |
| D-4 | 4 |

Radioligand Binding Assay for Assessment of MCHR1 Activity

Membranes from stably transfected HEK-293 cells expressing a mutated (E4Q, AST) hMCHR1 receptor were prepared by dounce homogenization and differential centrifugation. Binding experiments were carried out with 0.5-1.0 ug of membrane protein incubated in a total of 0.2 ml in 25 mM HEPES (pH 7.4) with 10 mM $MgCl_2$, 2 mM EGTA, and 0.1% BSA (Binding Buffer) for 90 min. For competition binding assays, reactions were carried out in the presence of with 0.06-0.1 nM [Phe$^{13}$, [$^{125}$I]Tyr$^{19}$]-MCH and increasing concentrations of unlabeled test molecules. Reactions were terminated by rapid vacuum filtration over 96 well-GFC Unifilter plates pre-coated with 0.075 ml binding buffer containing 1% BSA, and washed 3 times with 0.4 ml of Phospho-buffered Saline (pH 7.4) containing 0.01% TX-100. Filters were dried; 0.05 ml microscint 20 was added to each well and radioactivity was subsequently quantified by scintillation counting on a TOPCOUNT® microplate scintillation counter (Packard). Inhibitory constants were determined by nonlinear least squares analysis using a four parameter logistic equation.

Evaluation of Prodrug

The relative ability of the prodrug to enhance exposure (bioavailability) was assessed in an eight hour PK study using cannulated SPRAGUE DAWLEY® (CD, Charles River Breeding Laboratory) rats. The compounds (parent and prodrug esters) were administered p.o. at 2.0 ml/kg as a suspension in 0.5% methyl cellulose, 0.1% Tween 80 in water at 10 mg/kg p.o. Blood samples were taken at 1, 2, 4 and 8 hr. After determination of parent concentration, an AUC was calculated for the eight hour study.

Assessment of In Vivo MCHR1 Activity

Male SPRAGUE DAWLEY® (CD, Charles River Breeding Laboratory) rats weighing approximately 240 grams were placed in individual plastic cages with ALPHADRI® bedding. The room was maintained at 72° F. and 50% humidity, and a 12/12 light dark cycle with lights out at 1600 hours. The rats were conditioned for 5 days prior to the start of the study to having a choice of foods. A normal chow (Harlan Teklad, 2018) that contains 18% protein, 5% fat and 73% carbohydrate and a high fat high sugar diet (Research Diets (D2327) that contains 20% protein, 40% fat and 40% carbohydrate where the carbohydrate is entirely sucrose and the fat is soybean and coconut oil. Studies have revealed that rats exhibit a high preference for the high fat/high sucrose diet (80% preference). Body weight and consumption of both kinds of food as well as water intake were measured daily. Water was available ad lib throughout the study. Food consumption is presented as daily caloric consumption which is the sum of grams of chow multiplied by the Kcal per gram (3.5) plus grams of high fat high sugar multiplied by Kcal per gram (4.59).

Baseline body weight was measured prior to drug treatment on day 0 of the study. Baseline food consumption was the average of the 3 days prior to the first drug treatment. Drug was administered daily p.o. at 2.0 ml/kg at 1500 hours beginning on day 0 and continuing daily through day 4 as a suspension in 0.5% methyl cellulose, 0.1% Tween 80 in water at 3.0, 10 and 30 mg/kg p.o. All data were evaluated using ANOVA and Fishers PLSD statistics.

| Compound Administered to SPRAGUE DAWLEY ® Rats | % Weight change versus Control after daily Administration of drug at 30 mg/kg for four days |
|---|---|
| P-1 | 3.4% |
| P-3 | 6.1% |

The assessment of activity of the compounds of Formula I of the invention in treating intestinal inflammation such as caused by inflammatory bowel disease, colitis and/or Crohn's disease, as described above, may be carried out employing the various assays as disclosed in Kokkotou, E. et al., "Melanin-concentrating hormone as a mediator of intestinal inflammation", *PNAS*, 105(30):10613-10618 (Jul. 29, 2008).

What is claimed is:
1. A compound having the following formula:

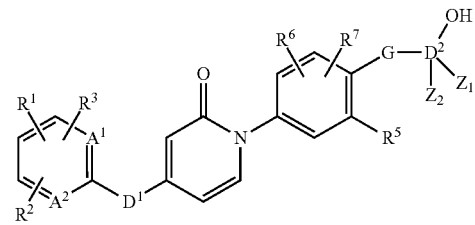

or a pharmaceutically acceptable salt or prodrug thereof; wherein,
$A^1$ and $A^2$ are independently C or N;
$D^1$ is a bond, —$CR^8R^9X$—, —$XCR^8R^9$—, —$CHR^8CHR^9$—, —$CR^{10}$=$CR^{10'}$—, —C≡C—, or 1,2-cyclopropyl;
X is O, S, $SO_2$ or —$NR^{11}$;
$R^1$, $R^2$, and $R^3$ are independently selected from the group consisting of hydrogen, halogen, —CN, substituted or unsubstituted $C_1$ to $C_4$ alkyl, substituted or unsubstituted $C_3$ to $C_5$ cycloalkyl, substituted or unsubstituted $C_3$ to $C_5$ cycloalkoxy, —$CF_3$, —$OCF_3$, —$OCHF_2$, —$OCF_2CHF_2$, —$OR^{12}$, substituted or unsubstituted phenyl and —$SR^{12}$;
G is O or S;
$D^2$ is substituted or unsubstituted $C_2$ to $C_4$ alkyl, substituted or unsubstituted $C_3$ to $C_5$ cycloalkyl, substituted or unsubstituted $C_3$ to $C_5$ cycloalkoxy, substituted or unsubstituted $C_2$ to $C_3$ alkyl-$C_3$ to $C_5$ cycloalkyl, substituted or unsubstituted $C_1$ to $C_3$ alkyl-$C_3$ to $C_5$ cycloalkoxy;
$Z_1$ and $Z_2$ are independently hydrogen, halogen, substituted or unsubstituted $C_1$ to $C_3$ alkyl, substituted or unsubstituted $C_3$ to $C_5$ cycloalkyl, —$OCH_3$, substituted or unsubstituted $C_3$ to $C_5$ cycloalkoxy, halo, —$CH_2SO_2$-alkyl, hydroxyalkyl, —$CF_3$, —$OCONR^{14}R^{14'}$, —CN, —CONR$^{14}$R$^{14'}$, —SOR$^{12}$, —SO$_2$R$^{12}$, —NR$^{14}$COR$^{14'}$, —NR$^{14}$CO$_2$R$^{14'}$, —CO$_2$R$^{12}$, NR$^{14}$SO$_2$R$^{12}$ or —COR$^{12}$ provided that if Z$_1$ is —CH$_3$ and one of R$_1$, R$_2$, or R$_3$ is F, then Z$_2$ cannot be H;

R$^5$ is independently selected from the group consisting of halogen, substituted or unsubstituted C$_1$ to C$_4$ alkyl, substituted or unsubstituted C$_3$ to C$_5$ cycloalkyl, substituted or unsubstituted C$_3$ to C$_5$ cycloalkoxy, —CF$_3$, —SR$^{12}$, —OCH$_3$, —OCH$_2$CH$_3$, —OCH$_2$OMe, —CN, —CONR$^{14}$R$^{14'}$, SOR$^{12}$, SO$_2$R$^{12}$, NR$^{14}$COR$^{14'}$, NR$^{14}$CO$_2$R$^{12}$, CO$_2$R$^{12}$, NR$^{14}$SO$_2$R$^{12}$ and —COR$^{12}$;

R$^6$, and R$^7$ are independently selected from the group consisting of hydrogen, halogen, substituted or unsubstituted C$_1$ to C$_4$ alkyl, substituted or unsubstituted C$_3$ to C$_5$ cycloalkyl, substituted or unsubstituted C$_3$ to C$_5$ cycloalkoxy, —CF$_3$, —SR$^{12}$, —OCH$_3$, —OCH$_2$CH$_3$, —OCH$_2$OMe, —CN, —CONR$^{14}$R$^{14'}$, SOR$^{12}$, SO$_2$R$^{12}$, NR$^{14}$COR$^{14'}$, NR$^{14}$CO$_2$R$^{12}$, CO$_2$R$^{12}$, NR$^{14}$SO$_2$R$^{12}$ and —COR$^{12}$;

R$^8$, R$^9$, R$^{10}$, R$^{10'}$, R$^{11}$ are independently hydrogen or —CH$_3$;

R$^{12}$ is substituted or unsubstituted C$_1$ to C$_4$ alkyl, substituted or unsubstituted C$_3$ to C$_5$ cycloalkyl or phenyl;

R$^{14}$ and R$^{14'}$ are independently H, substituted or unsubstituted C$_1$ to C$_3$ alkyl, substituted or unsubstituted C$_3$ to C$_5$ cycloalkyl or R$^{14}$ and R$^{14'}$ together with the N to which they are attached form a ring having 4 to 7 atoms; and wherein the prodrugs of the compounds of said formula are selected from the group consisting of amino acid esters, monoesters of dicarboxylic acids and monoesters of phosphoric acid and incorporate the hydroxyl group that is attached to D$^2$.

2. The compound according to claim 1 wherein R$^1$, R$^2$, and R$^3$ are each independently H, Cl, —CF$_3$, —C$_2$F$_5$, or —OCF$_3$.

3. The compound according to claim 1 wherein G is O.

4. The compound according to claim 1 wherein D$^2$ is —CH$_2$C— or —CH$_2$-cyclobutyl.

5. The compound according to claim 1 wherein D$^1$ a bond, —CR$^8$R$^9$X—, —XCR$^8$R$^9$—, —CHR$^8$CHR$^9$—, —CR$^{10}$═CR$^{10}$—, or —C≡C— and X is O, S, —SO$_2$ or —NR$^{11}$.

6. The compound according to claim 1 wherein Z$^1$ and Z$^2$ are —CH$_3$.

7. The compound according to claim 1 wherein Z$^1$ is H and Z$^2$ is cyclopropyl.

8. The compound according to claim 1,
wherein,
R$^1$, R$^2$, and R$^3$ are independently H, halo, or CF$_3$;
A$^1$ is C or N;
A$^2$ is C;
D$^1$ is a bond, —CR$^8$R$^9$X—, —XCR$^8$R$^9$—, —CHR$^8$CHR$^9$—, or —CR$^{10}$═CR$^{10'}$—;
X is O, S, SO$_2$, NH;
R$^5$ is independently —CH$_3$ or —OCH$_3$; R$^6$, and R$^7$ are independently H, —CH$_3$ or —OCH$_3$;
R$^8$, R$^9$, R$^{10}$, and R$^{11}$, are independently H;
G is O;
D$^2$ is —CH$_2$C— or —CH$_2$-cyclobutyl;
Z$_1$ and Z$_2$ are both —CH$_3$ or Z$_1$ is H and Z$_2$ is cyclopropyl, or Z$_1$ and Z$_2$ are both F; and
wherein the prodrugs of the compounds of said formula are selected from the group consisting of amino acid esters, monoesters of dicarboxylic acids and monoesters of phosphoric acid and incorporate the hydroxyl group that is attached to D$^2$.

9. The compound according to claim 8 wherein D$^1$ is —CH$_2$X— or —XCH$_2$—.

10. The compound according to claim 8 wherein Z$_1$ and Z$_2$ are both —CH$_3$.

11. A compound is selected from the group consisting of:

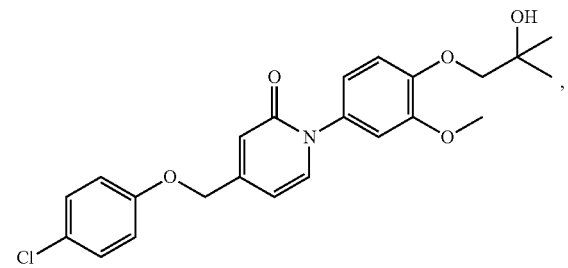
,

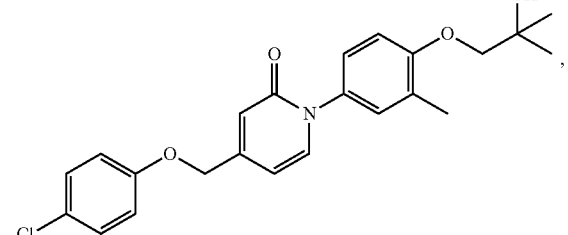
,

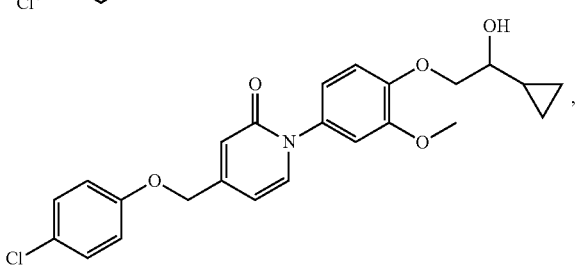
,

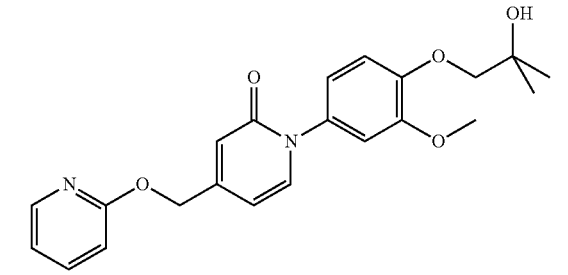
,

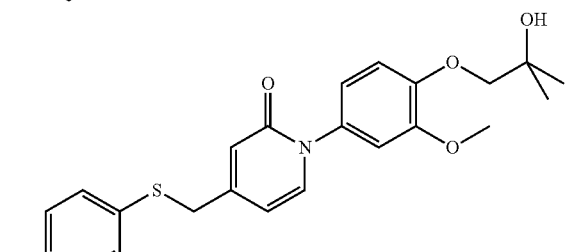
,

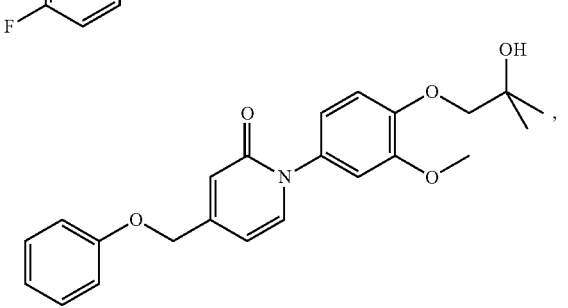
,

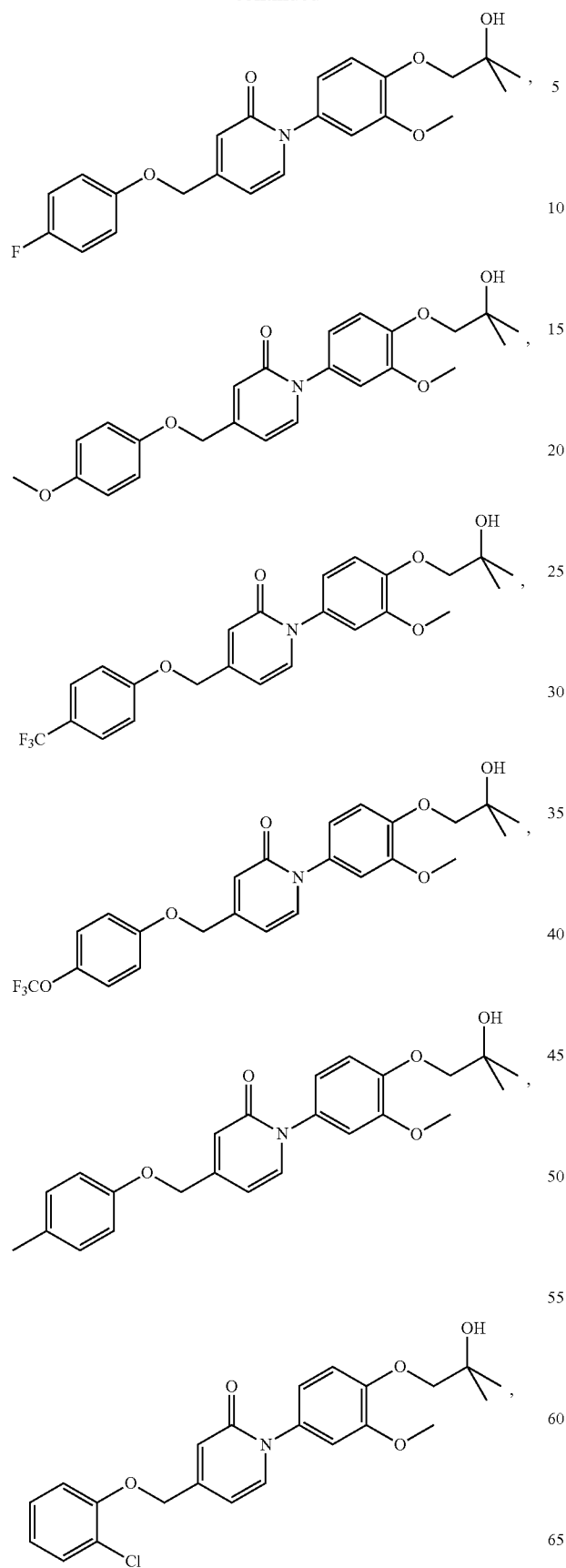
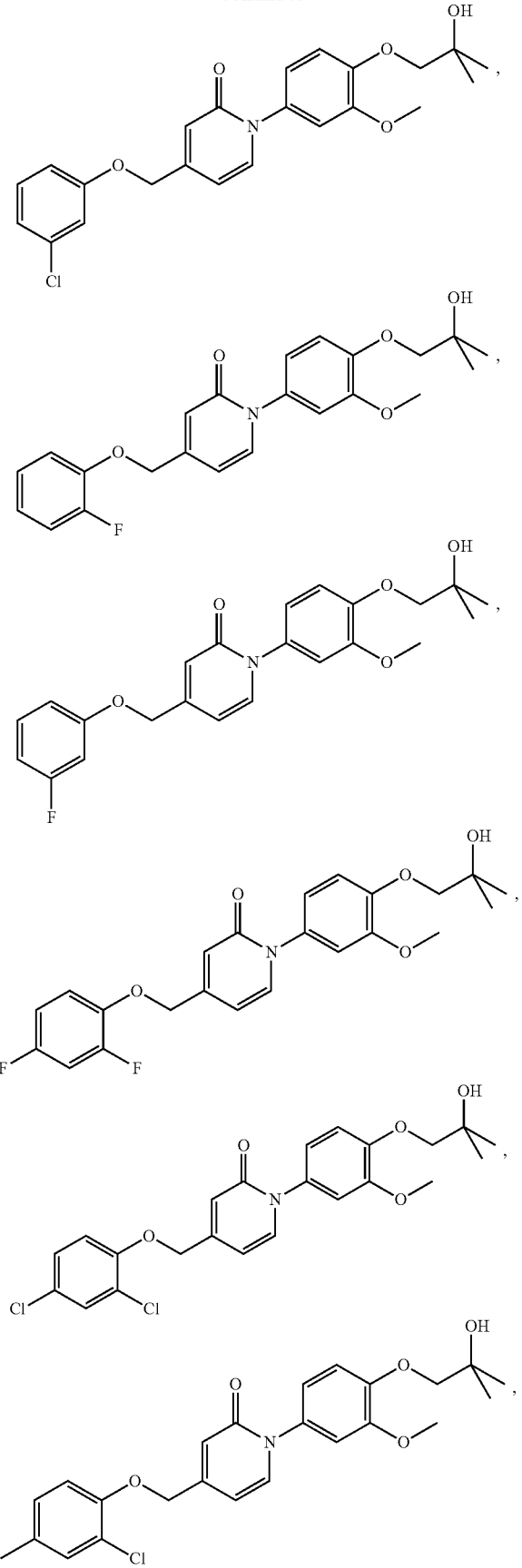

131
-continued
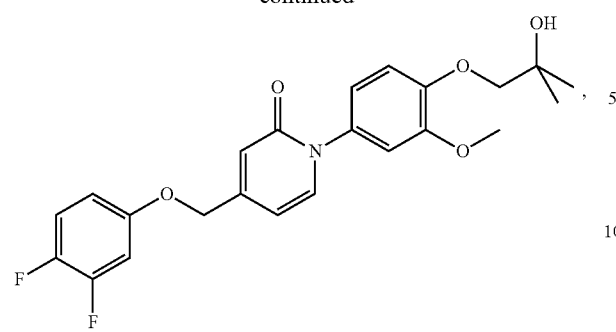
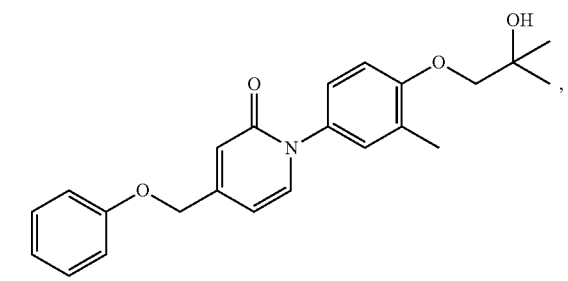
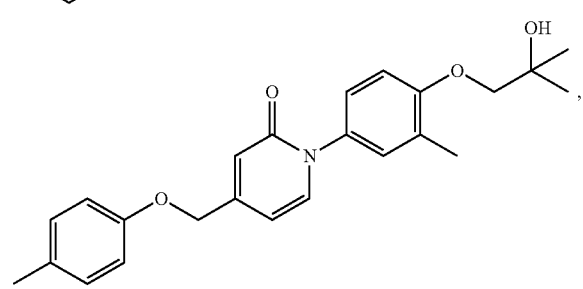
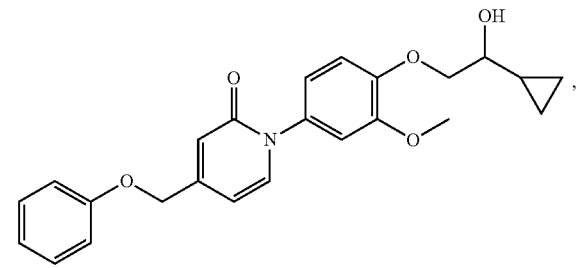
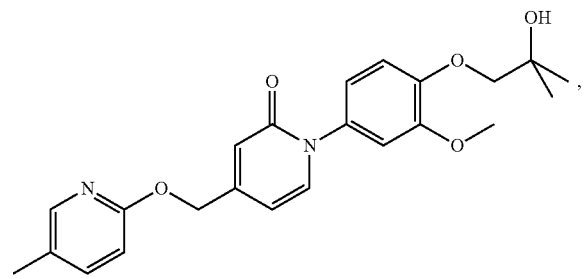
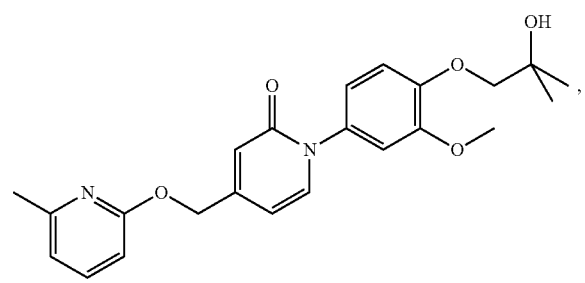
132
-continued
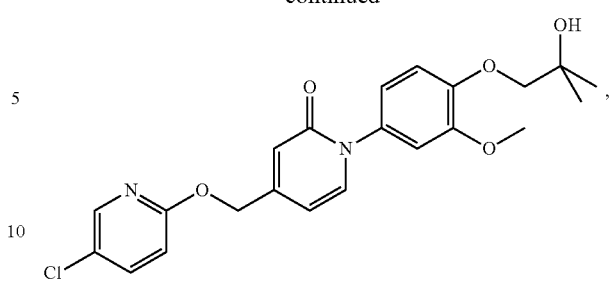
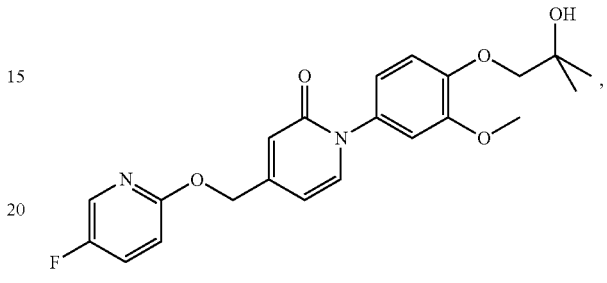
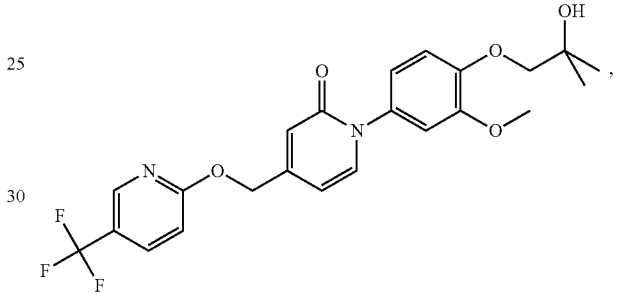
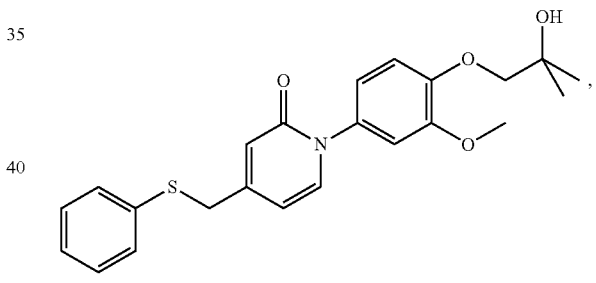
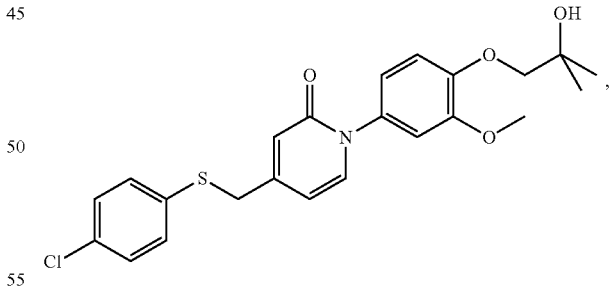
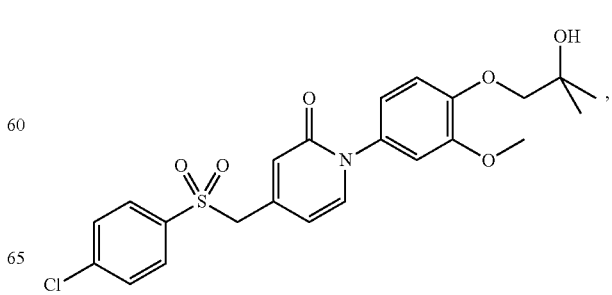

133
-continued
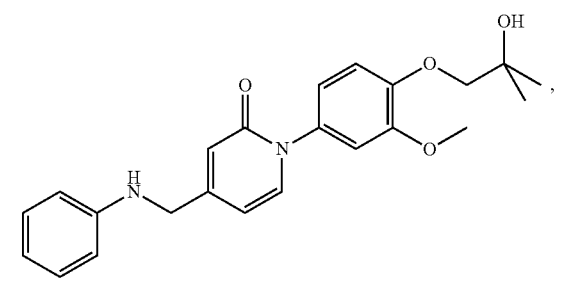
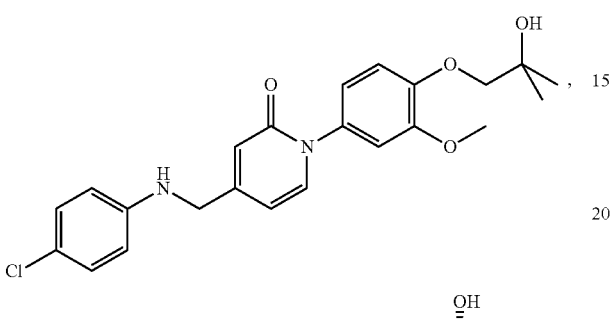
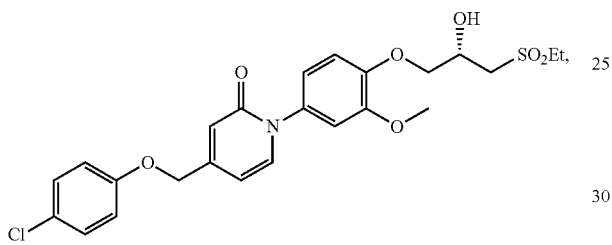
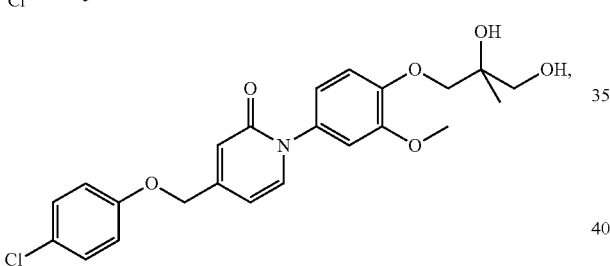
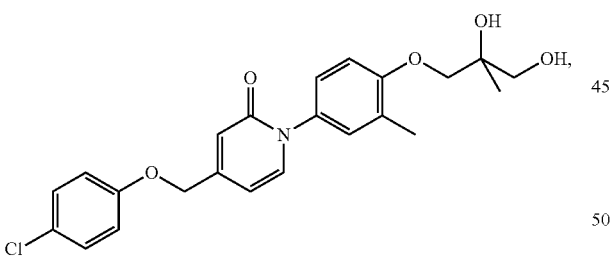
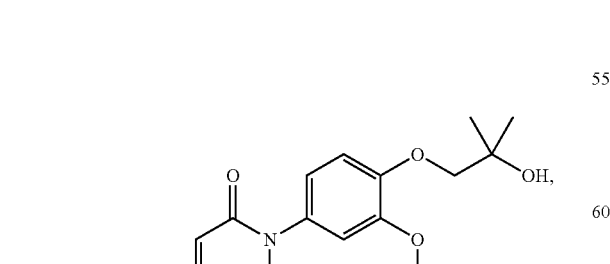
134
-continued
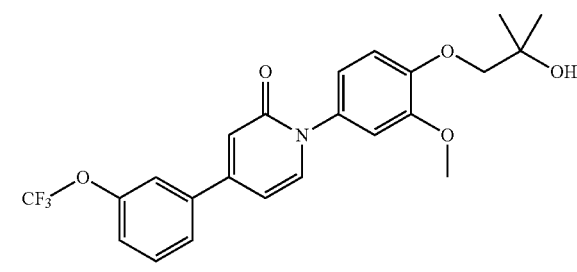
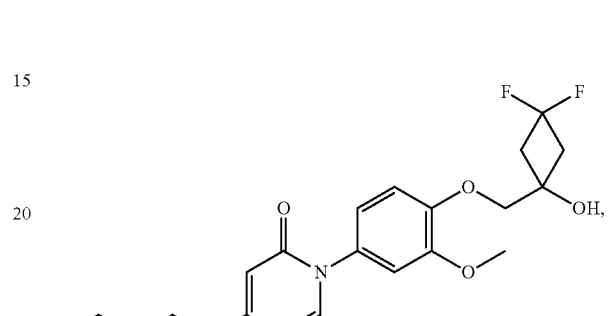
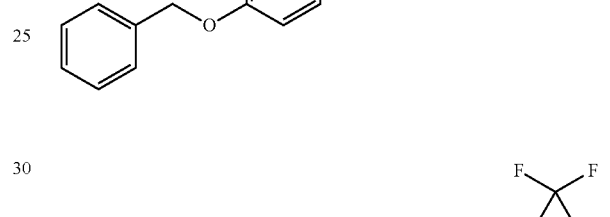
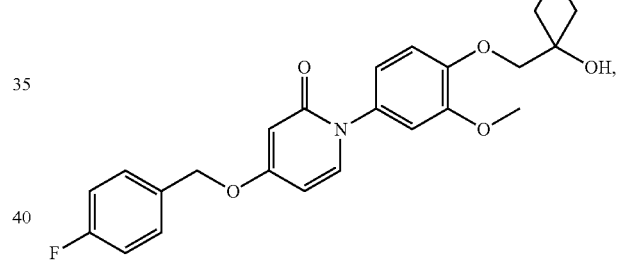
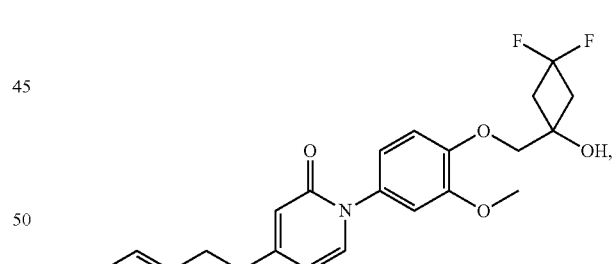
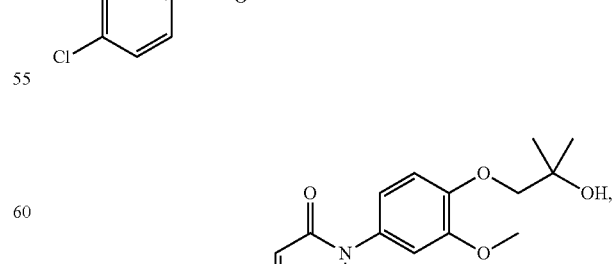
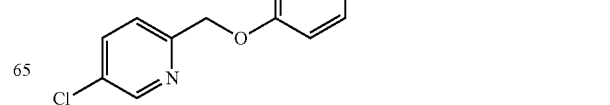

135
-continued
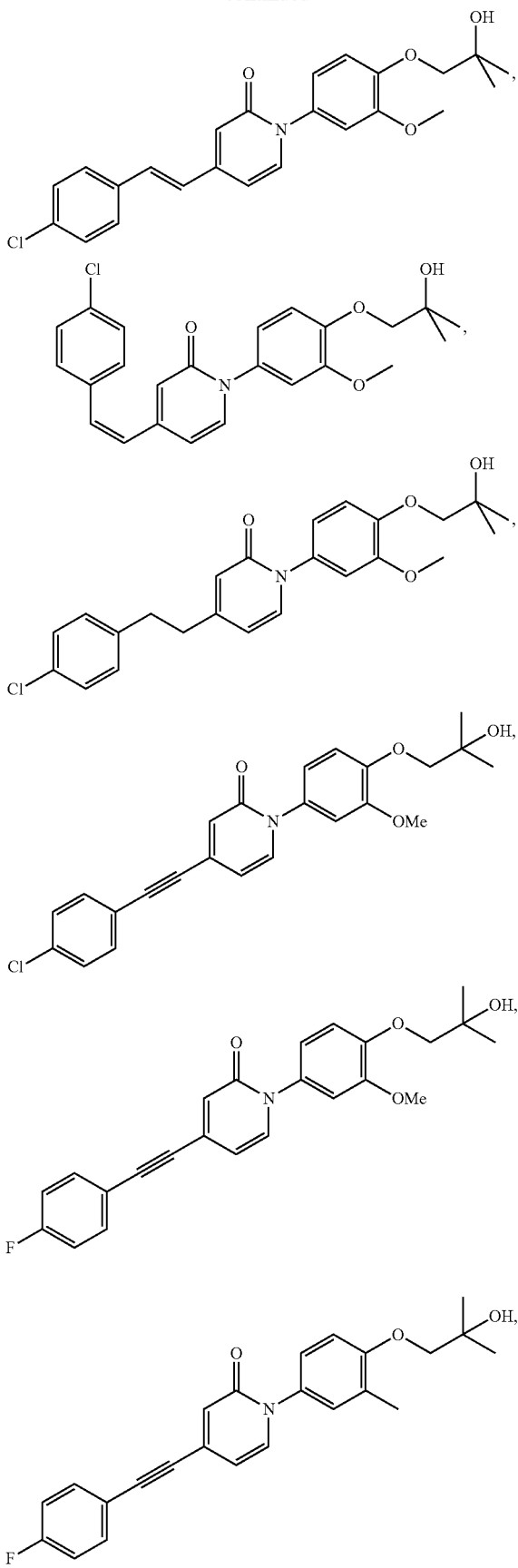
136
-continued
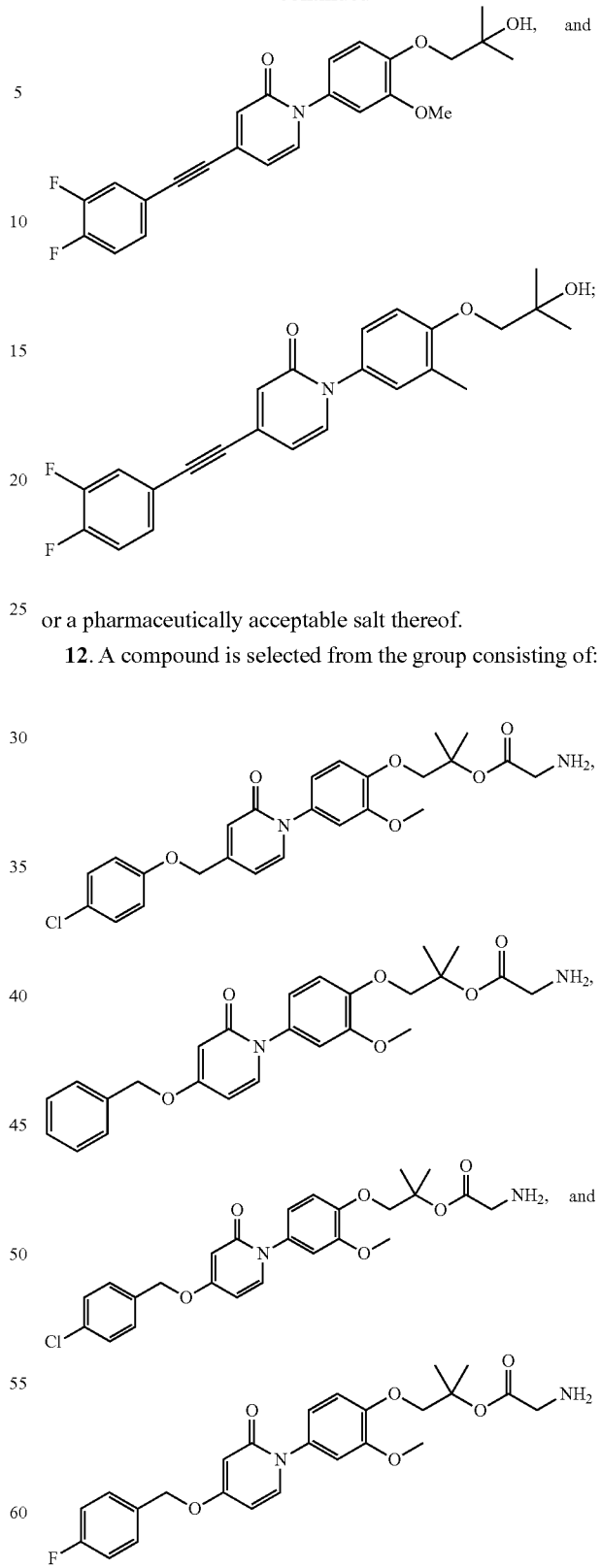
or a pharmaceutically acceptable salt thereof.
12. A compound is selected from the group consisting of:
or a pharmaceutically acceptable salt thereof.
13. A pharmaceutical composition comprising a compound according to claim 1 in an amount effective to treat obesity in a patient in need of such treatment together with a pharmaceutically acceptable carrier.

14. The pharmaceutical combination of claim 13 further comprising at least one additional therapeutic agent selected from the group consisting of an anti-obesity agent, an anti-diabetic agent, an anti-anxiety agent, an anti-inflammatory or an anti-depressant.

15. A method for treating obesity comprising administering to a patient in need of such treatment a therapeutically effective amount of a compound according to claim 1.

16. A method for treating diabetes comprising administering to a patient in need of such treatment a therapeutically effective amount of a compound according to claim 1.

17. A method for treating depression comprising administering to a patient in need of such treatment a therapeutically effective amount of a compound according to claim 1.

18. A method for treating anxiety comprising administering to a patient in need of such treatment a therapeutically effective amount of a compound according to claim 1.

19. A method for treating inflammatory bowel disease comprising administering to a patient in need of such treatment a therapeutically effective amount of a compound according to claim 1.

20. A pharmaceutical composition comprising a compound according to claim 11 in an amount effective to treat obesity in a patient in need of such treatment together with a pharmaceutically acceptable carrier.

21. A pharmaceutical composition comprising a compound according to claim 12 in an amount effective to treat obesity in a patient in need of such treatment together with a pharmaceutically acceptable carrier.

* * * * *

UNITED STATES PATENT AND TRADEMARK OFFICE
CERTIFICATE OF CORRECTION

PATENT NO.       : 8,563,583 B2
APPLICATION NO.  : 13/255129
DATED            : October 22, 2013
INVENTOR(S)      : Saleem Ahmad et al.

It is certified that error appears in the above-identified patent and that said Letters Patent is hereby corrected as shown below:

In the Claims

Column 127
Line 3, "$R_1$, $R_2$, or $R_3$," should read -- $R^1$, $R^2$, or $R^3$, --;
Line 38, "$D^1$" should read -- $D^1$ is --;
Line 42, "$Z^1$ and $Z^2$" should read -- $Z_1$ and $Z_2$ --;
Line 44, "$Z^1$" should read -- $Z_1$ --; and
Line 45, "$Z^2$" should read -- $Z_2$ --.

Column 133

Lines 45-50 (approx.), after " 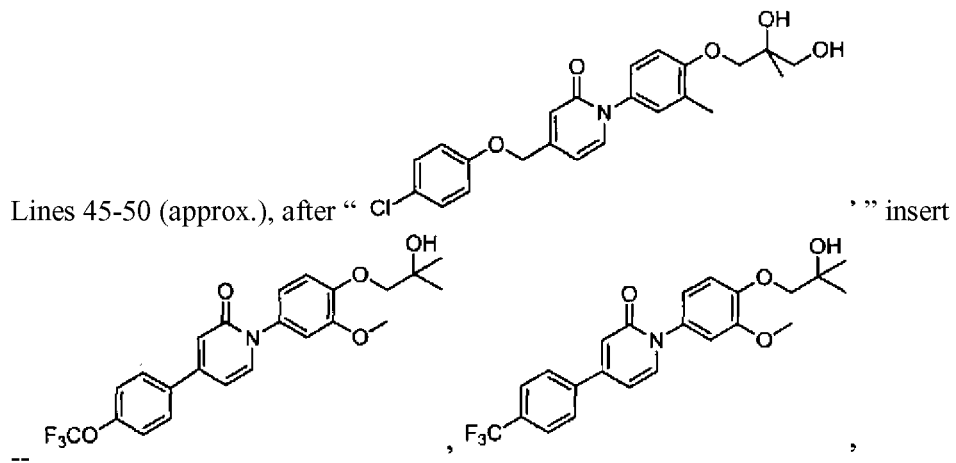 ' " insert --

,

,

--

Signed and Sealed this
Third Day of June, 2014

Michelle K. Lee
*Deputy Director of the United States Patent and Trademark Office*

CERTIFICATE OF CORRECTION (continued)
U.S. Pat. No. 8,563,583 B2

Column 133 (Cont'd)

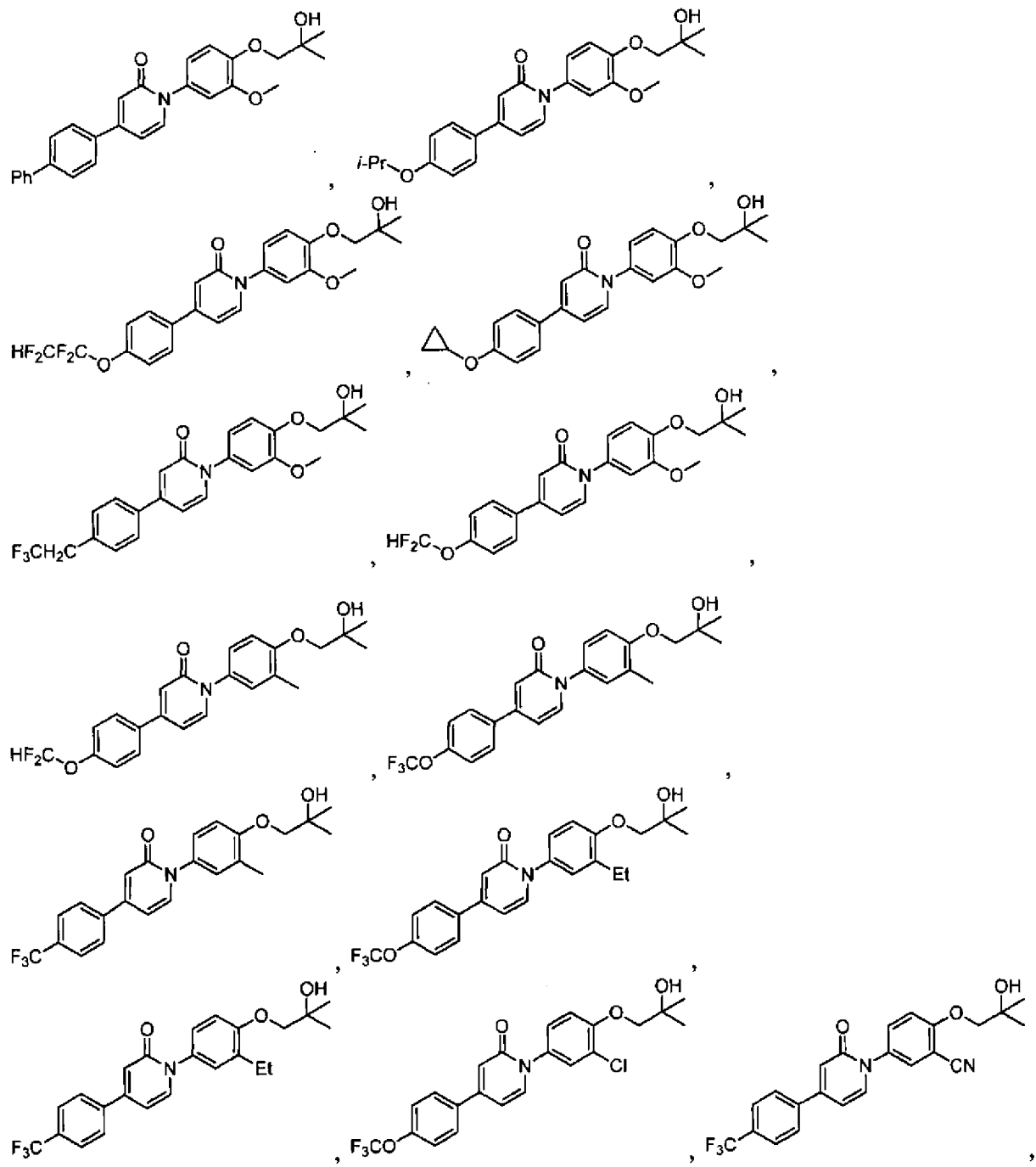

CERTIFICATE OF CORRECTION (continued)
U.S. Pat. No. 8,563,583 B2

Column 133 (Cont'd)

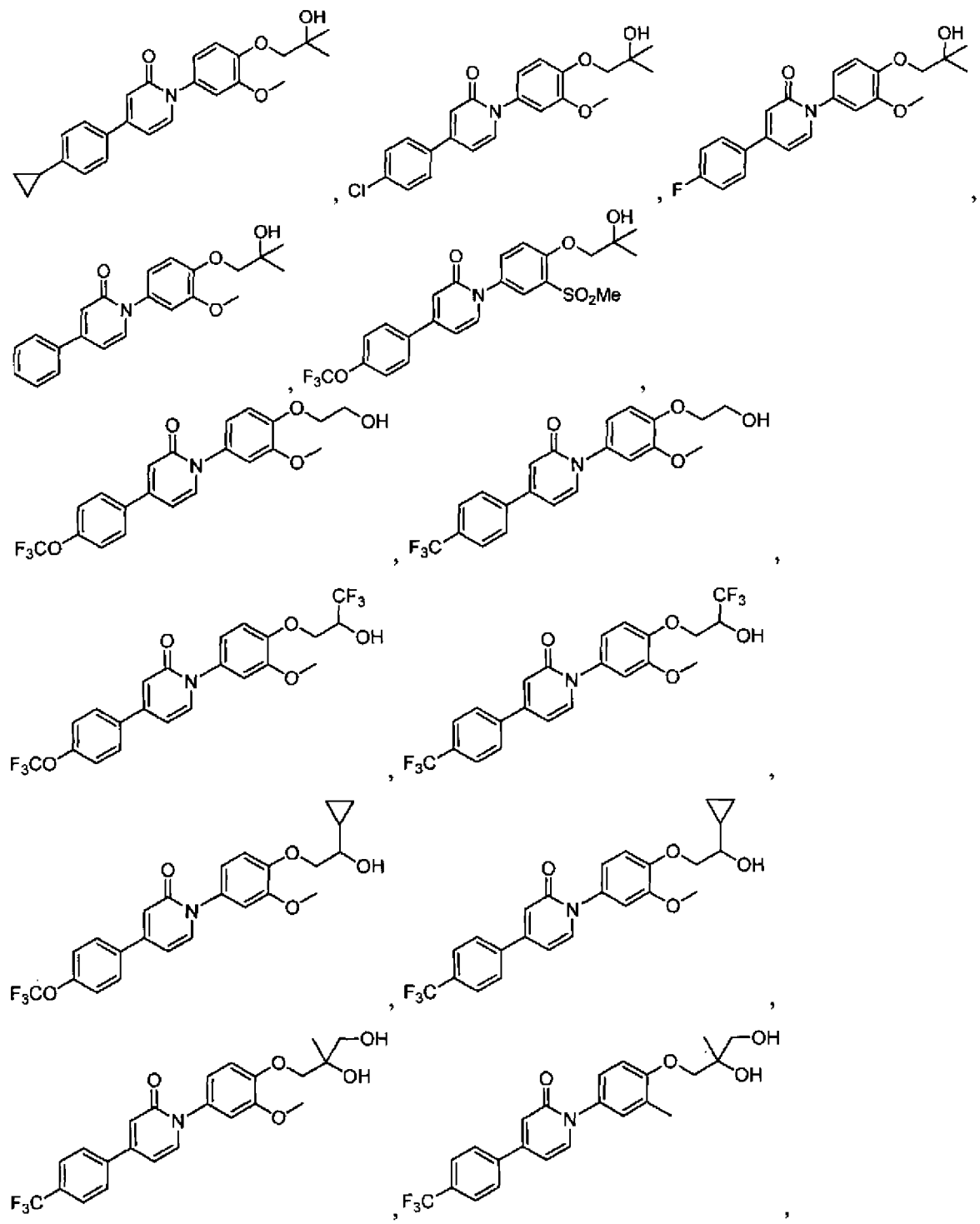

CERTIFICATE OF CORRECTION (continued)
U.S. Pat. No. 8,563,583 B2

Page 4 of 9

Column 133 (Cont'd)

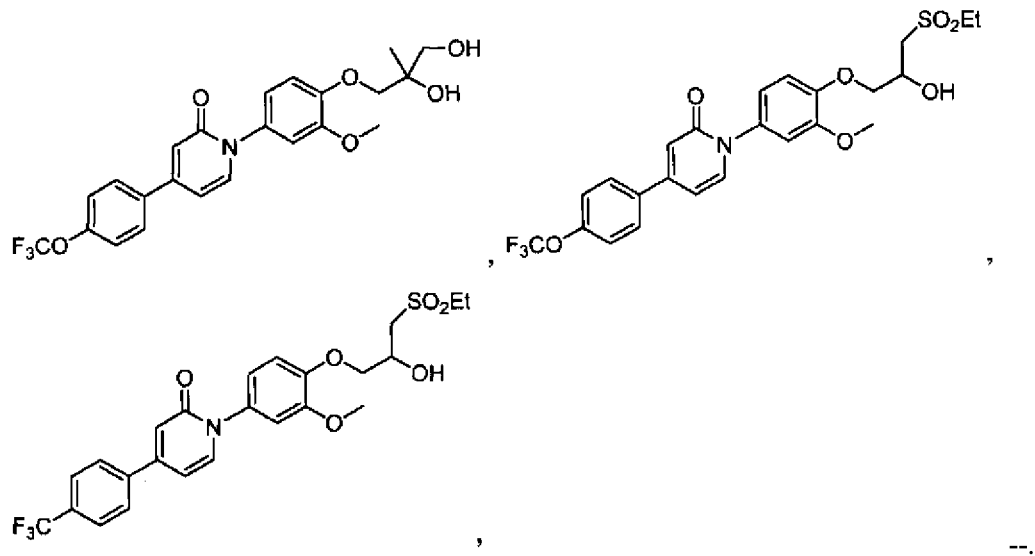

Column 134

Lines 5-10 (approx.), after " 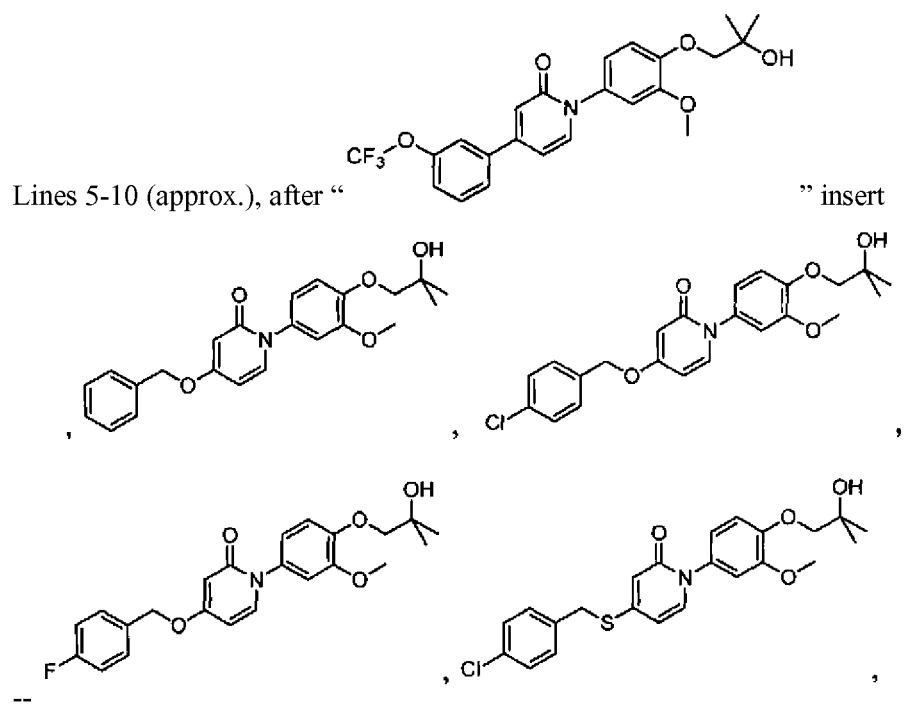 " insert

CERTIFICATE OF CORRECTION (continued)
U.S. Pat. No. 8,563,583 B2

Column 134 (Cont'd)

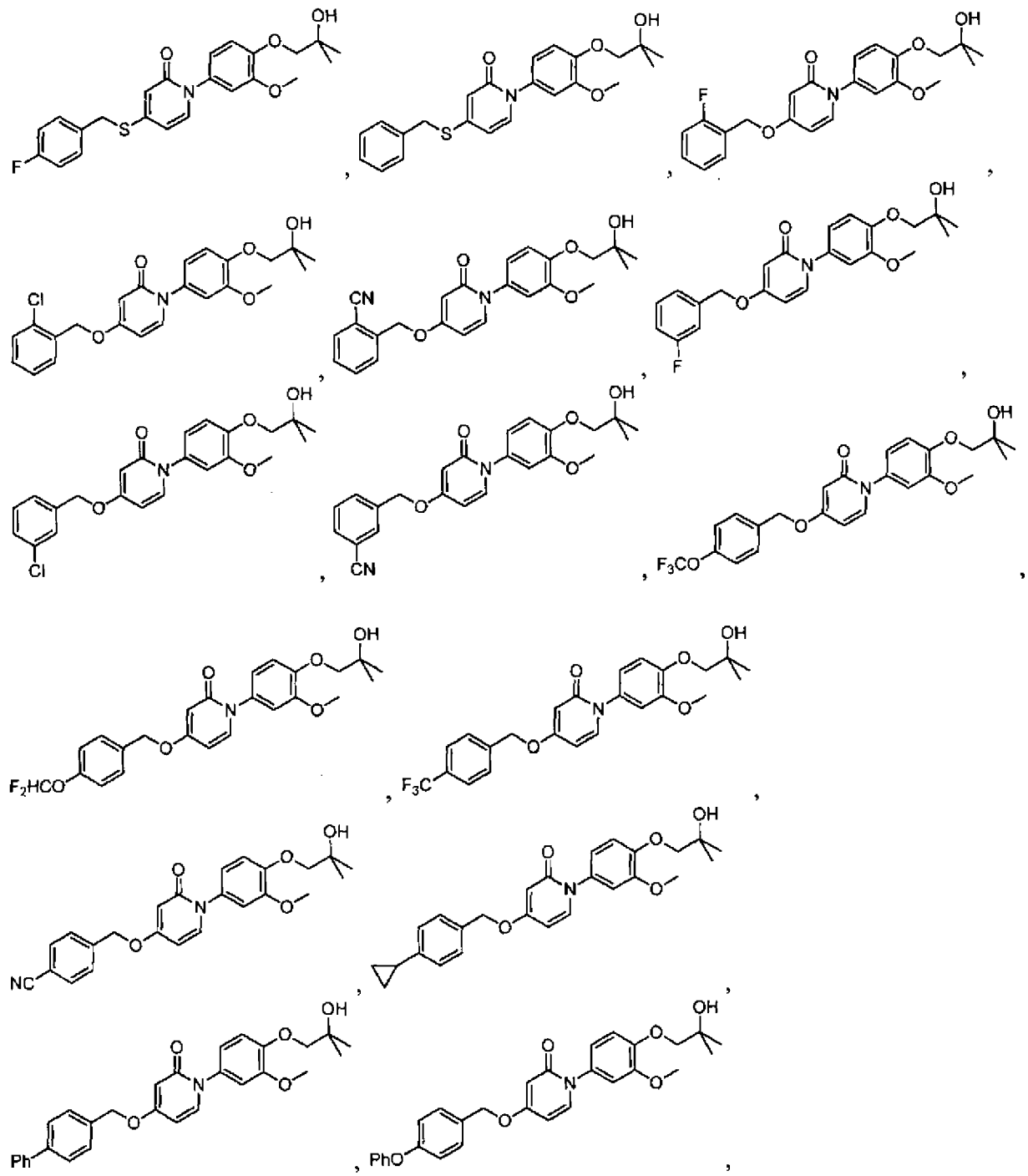

Column 134 (Cont'd)
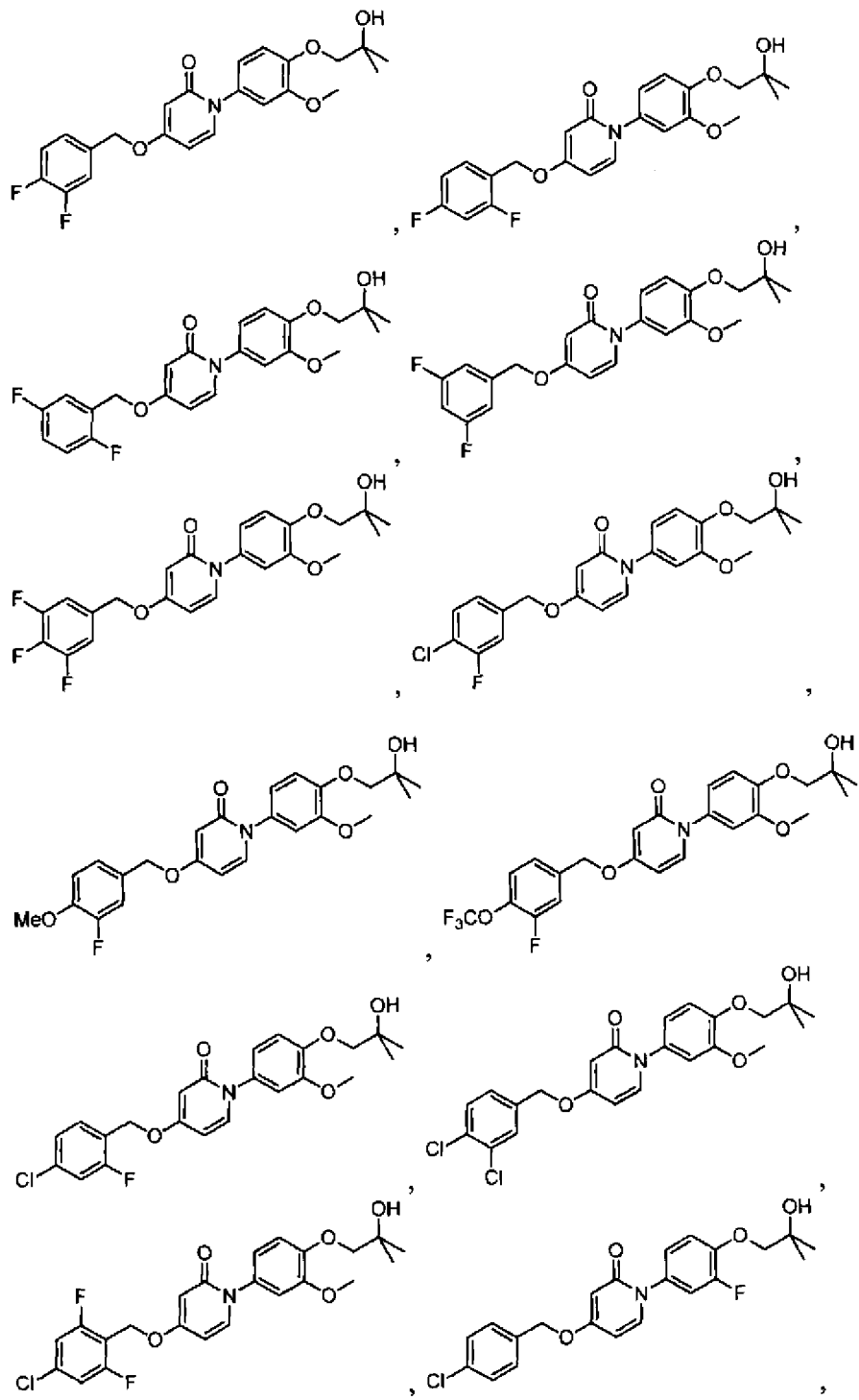

CERTIFICATE OF CORRECTION (continued)

U.S. Pat. No. 8,563,583 B2

Column 134 (Cont'd)

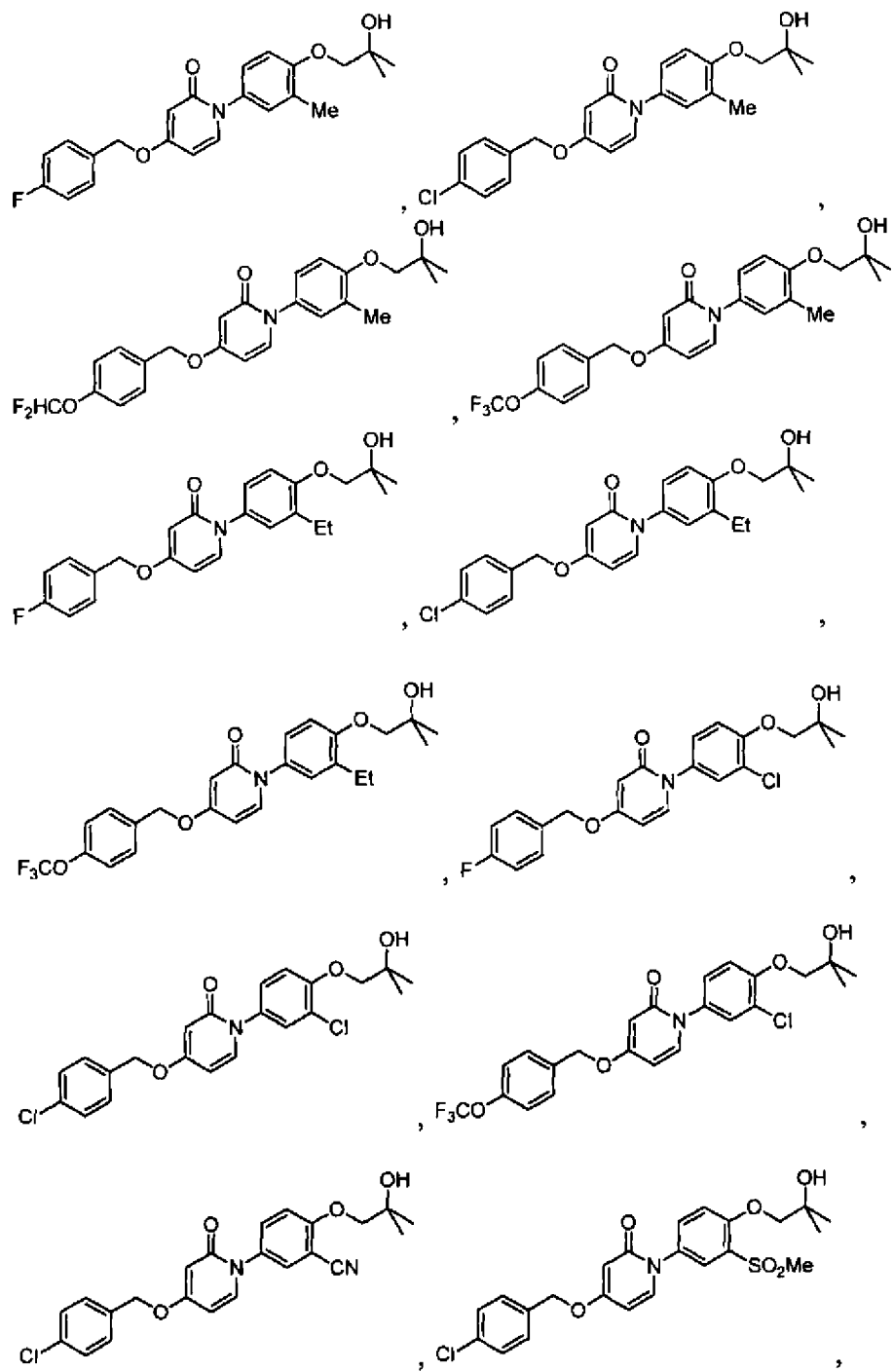

Column 134 (Cont'd)
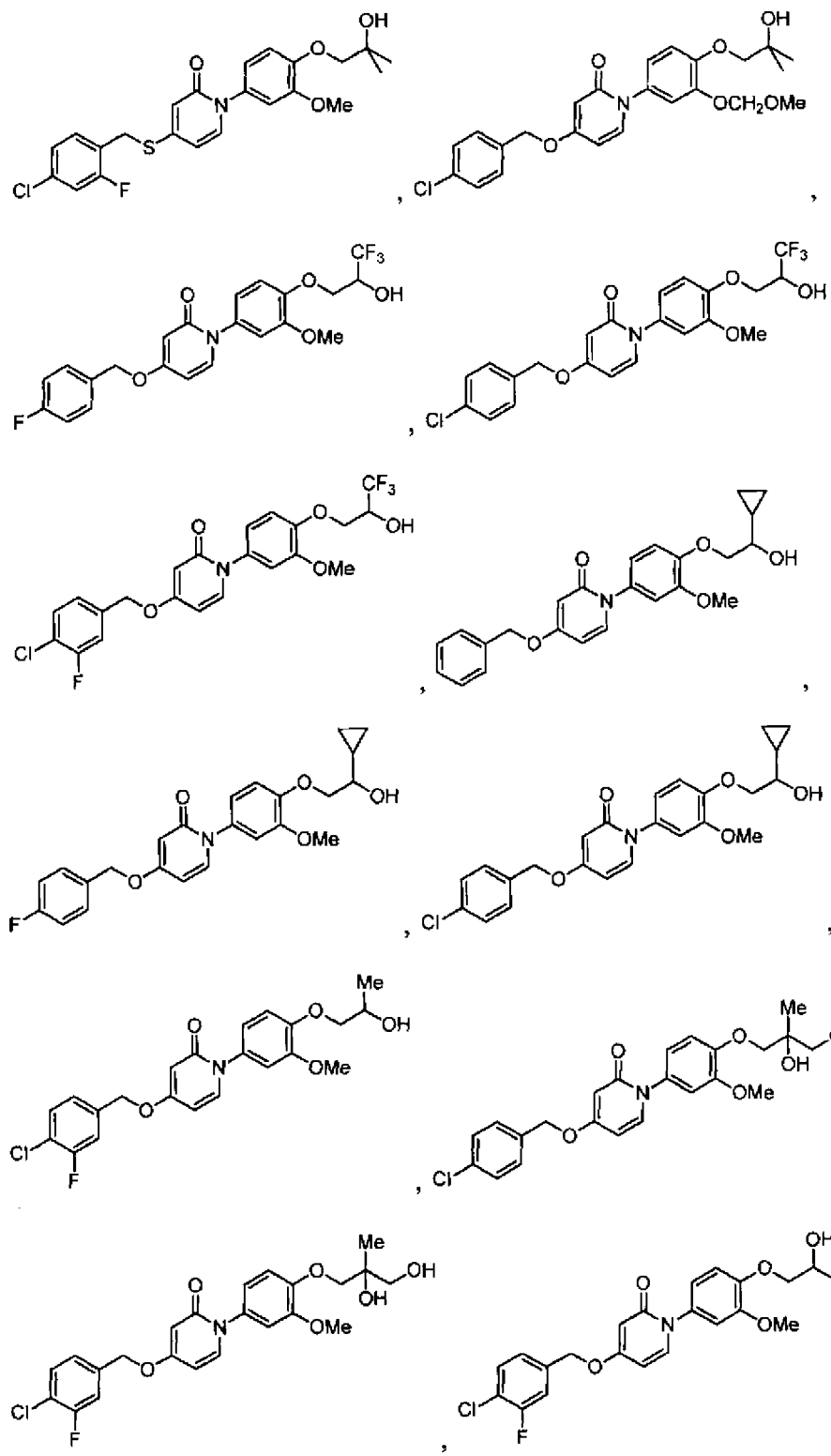

Column 134 (Cont'd)
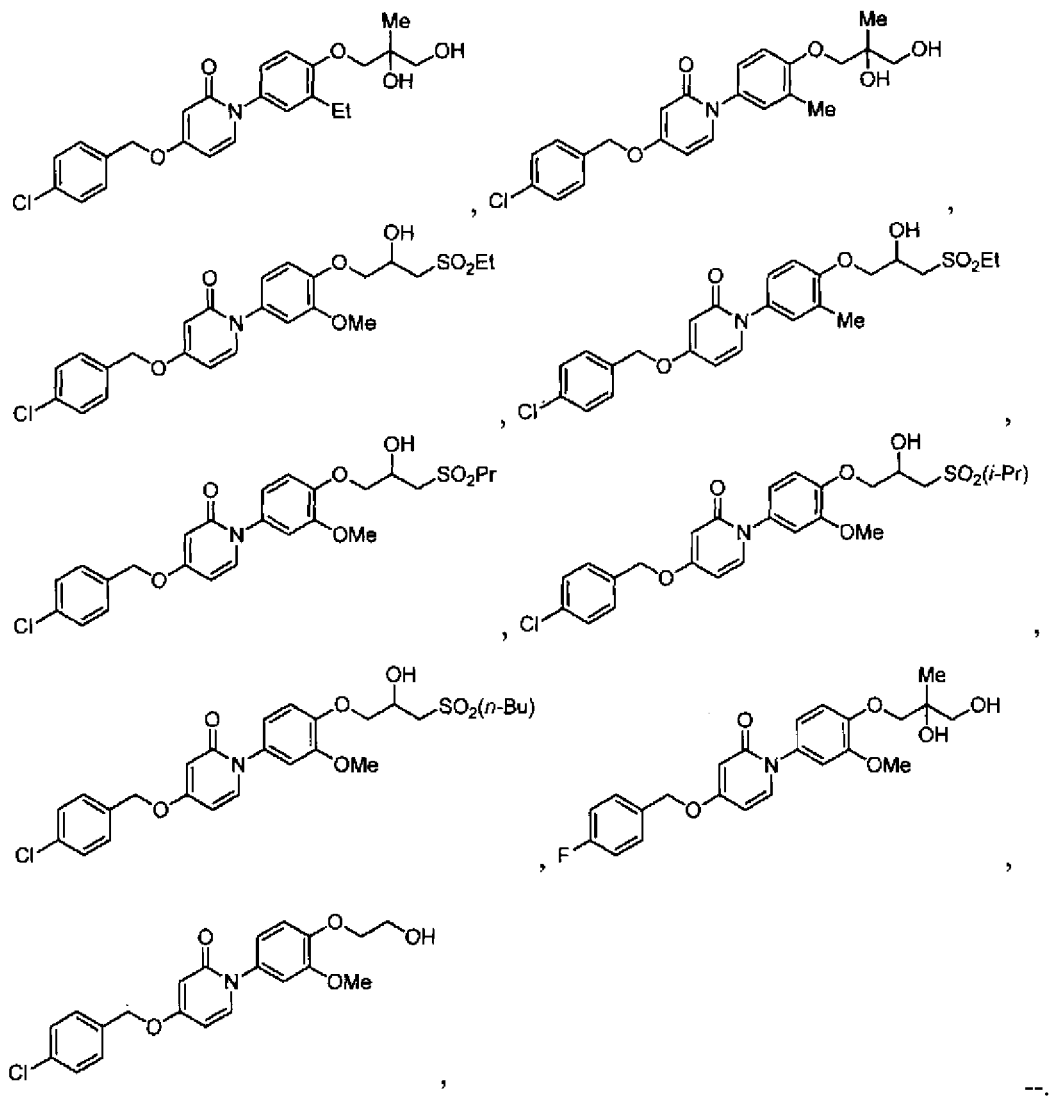
Column 137
Line 3, "combination" should read -- composition --.